(12) United States Patent
Steward et al.

(10) Patent No.: US 8,021,859 B2
(45) Date of Patent: Sep. 20, 2011

(54) MODIFIED CLOSTRIDIAL TOXINS WITH ALTERED TARGETING CAPABILITIES FOR CLOSTRIDIAL TOXIN TARGET CELLS

(75) Inventors: Lance E. Steward, Irvine, CA (US); Ester Fernandez-Salas, Fullerton, CA (US); Joseph Francis, Aliso Viejo, CA (US); Shengwen Li, Irvine, CA (US); Marcella A. Gilmore, Santa Ana, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 352 days.

(21) Appl. No.: 12/192,934

(22) Filed: Aug. 15, 2008

(65) Prior Publication Data

US 2010/0041098 A1    Feb. 18, 2010

Related U.S. Application Data

(63) Continuation-in-part of application No. 11/817,937, filed as application No. PCT/US2006/009831 on Mar. 14, 2006.

(60) Provisional application No. 60/662,151, filed on Mar. 15, 2005, provisional application No. 60/661,953, filed on Mar. 15, 2005.

(51) Int. Cl.
C07K 14/33    (2006.01)
C12N 15/62    (2006.01)
C12P 21/02    (2006.01)

(52) U.S. Cl. ............ 435/69.7; 435/69.1; 435/252.7; 424/239.1; 424/236.1; 424/9.1; 514/2; 514/12; 530/350

(58) Field of Classification Search ............ 424/239.1, 424/236.1, 9.1; 514/2, 12; 530/350; 435/252.7, 435/69.7, 69.1
See application file for complete search history.

(56) References Cited

U.S. PATENT DOCUMENTS

| | | | |
|---|---|---|---|
| 5,668,255 A | 9/1997 | Murphy | |
| 5,939,070 A | 8/1999 | Johnson et al. | |
| 6,461,617 B1 | 10/2002 | Shone et al. | |
| 6,500,436 B2 | 12/2002 | Donovan | |
| 6,632,440 B1 | 10/2003 | Quinn et al. | |
| 6,641,820 B1 | 11/2003 | Donovan | |
| 6,843,998 B1 | 1/2005 | Steward et al. | |
| 6,962,703 B2 | 11/2005 | Foster et al. | |
| 7,052,702 B1 | 5/2006 | Duggan et al. | |
| 7,056,729 B2 | 6/2006 | Donovan | |
| 7,132,259 B1 | 11/2006 | Dolly et al. | |
| 7,138,127 B1 | 11/2006 | Donovan | |
| 7,192,596 B2 | 3/2007 | Shone et al. | |
| 7,244,436 B2 | 7/2007 | Donovan | |
| 7,244,437 B2 | 7/2007 | Donovan | |
| 7,262,291 B2 | 8/2007 | Donovan | |
| 7,419,676 B2 * | 9/2008 | Dolly et al. ............ 424/239.1 |
| 7,709,228 B2 * | 5/2010 | Dolly et al. ............ 435/69.7 |
| 2003/0180289 A1 | 9/2003 | Foster | |
| 2004/0071736 A1 | 4/2004 | Quinn et al. | |
| 2006/0099672 A1 | 5/2006 | Dolly | |
| 2006/0110410 A1 | 5/2006 | Shone et al. | |
| 2006/0121056 A1 | 6/2006 | Chaddock | |
| 2008/0032931 A1 | 2/2008 | Steward et al. | |
| 2008/0081355 A1 | 4/2008 | Dolly et al. | |
| 2008/0161226 A1 | 7/2008 | Steward et al. | |
| 2008/0161543 A1 | 7/2008 | Steward et al. | |

FOREIGN PATENT DOCUMENTS

| | | |
|---|---|---|
| WO | WO 94/21300 | 9/1994 |
| WO | WO 00/57897 | 10/2000 |
| WO | WO 01/14570 | 3/2001 |
| WO | WO 2004/024909 | 3/2004 |
| WO | WO 2005/023309 | 3/2005 |
| WO | WO 2006/027207 | 3/2006 |
| WO | WO 2006/059093 | 6/2006 |
| WO | WO 2006/059105 | 6/2006 |
| WO | WO2006/059113 | 6/2006 |

OTHER PUBLICATIONS

U.S. Appl. No. 11/466,244, filed Aug. 22, 2006, Donovan.
U.S. Appl. No. 11/610,440, filed Dec. 13, 2006, Dolly et al.
U.S. Appl. No. 11/765,863, filed Jun. 20, 2007, Donovan.
U.S. Appl. No. 11/765,878, filed Jun. 20, 2007, Donovan.
U.S. Appl. No. 11/781,359, filed Jul. 23, 2007, Dolly et al.
U.S. Appl. No. 11/782,112, filed Jul. 24, 2007, Dolly et al.
U.S. Appl. No. 11/829,475, filed Jul. 27, 2007, Steward et al.
U.S. Appl. No. 11/832,108, filed Aug. 1, 2007, Steward et al.
U.S. Appl. No. 11/832,173, filed Aug. 1, 2007, Steward et al.
U.S. Appl. No. 11/833,142, filed Aug. 2, 2007, Steward et al.
U.S. Appl. No. 11/833,720, filed Aug. 3, 2007, Steward et al.
U.S. Appl. No. 11/834,068, filed Aug. 6, 2007, Steward et al.
U.S. Appl. No. 11/844,780, filed Aug. 24, 2007, Steward et al.
U.S. Appl. No. 11/844,850, filed Aug. 24, 2007, Steward et al.
U.S. Appl. No. 11/844,885, filed Aug. 24, 2007, Steward et al.
U.S. Appl. No. 11/844,929, filed Aug. 24, 2007, Steward et al.
U.S. Appl. No. 11/844,919, filed Aug. 24, 2007, Steward et al.
U.S. Appl. No. 11/844,899, filed Aug. 24, 2007, Steward et al.
U.S. Appl. No. 11/844,517, filed Aug. 24, 2007, Steward et al.
U.S. Appl. No. 11/817,937, filed Sep. 6, 2007, Steward et al.
U.S. Appl. No. 11/844,546, filed Aug. 24, 2007, Steward et al.
U.S. Appl. No. 11/845,167, filed Aug. 27, 2007, Steward et al.
U.S. Appl. No. 11/845,252, filed Aug. 27, 2007, Steward et al.
U.S. Appl. No. 11/845,284, filed Aug. 27, 2007, Steward et al. U.S. Appl. No. 11/845,320, filed Aug. 27, 2007, Steward et al.
U.S. Appl. No. 11/845,345, filed Aug. 27, 2007, Steward et al.
U.S. Appl. No. 11/845,466, filed Aug. 27, 2007, Steward et al.
Chaddock, J. A., et al., A conjugate composed of nerve growth factor coupled to a non-toxic derivative of Clostridium botulinum neurotoxin type A can inhibit neurotransmitter release in vitro, 18(2) Growth Factors 147-155 (2000).
Gozes, I., Furman, S., Potential clinical applications of vasoactive intestinal peptide: a selected update, 18(4) Best Prac. Res. Clinical Endocrin. Metab. 623-640 (2004).

(Continued)

Primary Examiner — Chih-Min Kam
(74) Attorney, Agent, or Firm — Kenton Abel; Debra Condino

(57) ABSTRACT

The specification discloses modified Clostridial toxins comprising a Clostridial toxin enzymatic domain, a Clostridial toxin translocation domain and an enhanced Clostridial toxin binding domain; polynucleotide molecules encoding such modified Clostridial toxins; and method of producing such modified Clostridial toxins.

13 Claims, 6 Drawing Sheets

OTHER PUBLICATIONS

Duggan, M. J., et al., Inhibition of release of neurotransmitters from rat dorsal root ganglia by a novel conjugate of a Clostridium botulinum toxin A endopeptidase fragment and Erythrina cristagalli lectin, 277(38) J. Biol. Chem. 34846-34852 (2002).

Herreros et al, "C-Terminal Half of Tetanus Toxin Fragment C is Sufficient for Neuronal Binding and Interaction with a Putative Protein Receptor", Biochemical Journal, vol. 347, No. Part 1, pp. 199-204, Apr. 1, 2001.

Rummel et al, "The Hcc-domain of botulinum neurotoxins A and B exhibits a singular ganglioside binding site displaying serotype specific carbohydrate interation", Molecular Microbiology, pp. 631-643, Dec. 15, 2003.

Halpern et al, "Characterization of the receptor-binding domain of tetanus toxin", Journal of Biological Chemistry, pp. 11188-11192, May 5, 1993.

* cited by examiner

FIG. 1B.

Toxin

1. Heavy Chain Binding Domain — Receptor System
2. Heavy Chain Translocation Domain
3. ATP → ADP, H⁺
4. Light Chain

MODIFIED CLOSTRIDIAL TOXINS WITH ALTERED TARGETING CAPABILITIES FOR CLOSTRIDIAL TOXIN TARGET CELLS

This is a continuation-in-part application and claims priority pursuant to 35 U.S.C. §120 to U.S. patent application Ser. No. 11/817,937, filed Sep. 6, 2007, a national stage patent application under 35 U.S.C. §371 of PCT application PCT/2006/009831 filed on Mar. 14, 2006, which claims priority pursuant to 35 U.S.C. §19(e) to U.S. Provisional Patent Application Ser. No. 60/662,151 filed on Mar. 15, 2005 and U.S. Provisional Patent Application Ser. No. 60/661,953 filed on Mar. 15, 2005, each of which is hereby incorporated by reference in its entirety.

All of the patents and publications cited in this application are hereby incorporated by reference in their entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. In addition, Clostridial toxin therapies are proposed for treating neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May 7, 2004); and Kei Roger Aoki, et al., Method for Treating Dystonia with Botulinum Toxin C to G, U.S. Pat. No. 6,319,505 (Nov. 20, 2001); eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004); pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, Botulinum Toxin Therapy for Fibromyalgia, U.S. Patent Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004); muscle injuries, see e.g., Gregory F. Brooks, Methods for Treating Muscle Injuries, U.S. Pat. No. 6,423,319 (Jul. 23, 2002); headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998); cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004); neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001); neuropsychiatric disorders, see e.g., Stephen Donovan, Botulinum Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003); endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000); cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005); otic disorders, see e.g., Stephen Donovan, Neurotoxin Therapy for Inner Ear Disorders, U.S. Pat. No. 6,358,926 (Mar. 19, 2002); and Stephen Donovan, Method for Treating Otic Disorders, U.S. Pat. No. 6,265,379 (Jul. 24, 2001); autonomic disorders, see, e.g., Pankaj J. Pasricha and Anthony N. Kalloo, Method for Treating Gastrointestinal Muscle Disorders and Other Smooth Muscle Dysfunction, U.S. Pat. No. 5,437,291 (Aug. 1, 1995); as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R. First, Application of Botulinum Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of Botulinum Toxin for Treatment of Downturned Mouth, U.S. Pat. No. 6,358,917 (Mar. 19, 2002); Stephen Donovan, Use of a Clostridial Toxin to Reduce Appetite, U.S. Patent Publication No. 2004/40253274 (Dec. 16, 2004); and Howard I. Katz and Andrew M. Blumenfeld, Botulinum Toxin Dental Therapies and Procedures, U.S. Patent Publication No. 2004/0115139 (Jun. 17, 2004); Kei Roger Aoki, et al., Treatment of Neuromuscular Disorders and Conditions with Different Botulinum, U.S. Patent Publication No. 2002/0010138 (Jan. 24, 2002); and Kei Roger Aoki, et al., Use of Botulinum Toxins for Treating Various Disorders and Conditions and Associated Pain, U.S.

Patent Publication No. 2004/0013692 (Jan. 22, 2004). In addition, the expected use of Clostridial toxins, such as, e.g., BoNTs and TeNT, in therapeutic and cosmetic treatments of humans and other mammals is anticipated to expand to an ever widening range of diseases and ailments that can benefit from the properties of these toxins.

Clostridial toxin therapies are successfully used for many indications. Generally, administration of a Clostridial toxin treatment is well tolerated. However, toxin administration in some applications can be challenging because of the larger doses required to achieve a beneficial effect. Larger doses can increase the likelihood that the toxin may move through the interstitial fluids and the circulatory systems, such as, e.g., the cardiovascular system and the lymphatic system, of the body, resulting in the undesirable dispersal of the toxin to areas not targeted for toxin treatment. Such dispersal can lead to undesirable side effects, such as, e.g., inhibition of neurotransmitter release in neurons not targeted for treatment or paralysis of a muscle not targeted for treatment. For example, a patient administered a therapeutically effective amount of a BoNT/A treatment into the neck muscles for torticollis may develop dysphagia because of dispersal of the toxin into the oropharynx. Thus, there remains a need for improved Clostridial toxins that are effective at the site of treatment, but have negligible to minimal effects in areas not targeted for a toxin treatment.

The growing clinical, therapeutic and cosmetic use of Clostridial toxins in therapies requiring larger doses necessitates the pharmaceutical industry to develop modified Clostridial toxins that are effective at the target site of the application, but reduce or prevent the undesirable side-effects associated with the dispersal of the toxins to an unwanted location or locations. The present invention provides novel Clostridial toxins that reduce or prevent unwanted side-effects associated with toxin dispersal into non-targeted areas. These and related advantages are useful for various clinical, therapeutic and cosmetic applications, such as, e.g., the treatment of neuromuscular disorders, neuropathic disorders, eye disorders, pain, muscle injuries, headache, cardiovascular diseases, neuropsychiatric disorders, endocrine disorders, cancers, otic disorders and hyperkinetic facial lines, as well as, other disorders where a Clostridial toxin administration to a mammal can produce a beneficial effect.

BRIEF DESCRIPTION OF THE DRAWINGS

FIG. 1 shows a schematic of the current paradigm of neurotransmitter release and Clostridial toxin intoxication in a central and peripheral neuron. FIG. 1B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the $H_N$ domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

FIG. 3 shows modified Clostridial toxins with an enhanced targeting domain located at the amino terminus of the modified toxin.

FIG. 4 shows modified Clostridial toxins with an enhanced targeting domain located between the other two domains.

FIG. 5 shows modified Clostridial toxins with an enhanced targeting domain located at the carboxyl terminus of the modified toxin.

DETAILED DESCRIPTION

Figure 1A:
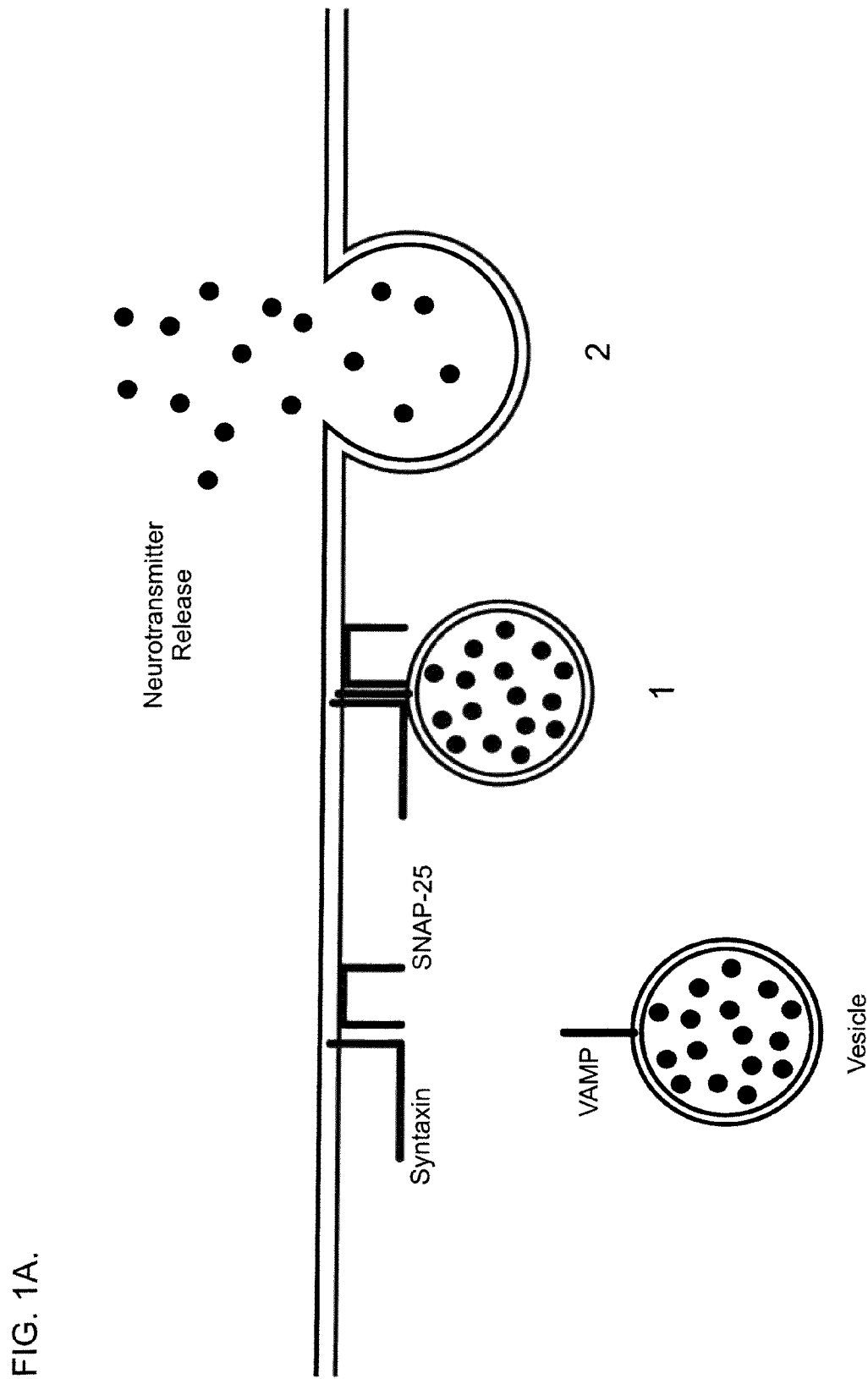
FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

The present invention discloses modified Clostridial toxins that exhibit enhanced binding activity for cells targeted by naturally-occurring Clostridial toxins. Enhanced binding activity is achieved by replacing a naturally-occurring binding domain of a Clostridial toxin with a binding domain for a non-Clostridial toxin receptor system present on a Clostridial toxin target cell. This enhanced binding activity for a target cell should allow lower effective doses of a modified Clostridial toxin to be administered to an individual because more toxin will be delivered to a target cell. Thus modified Clostridial toxins with enhanced binding activity will reduce the undesirable dispersal of the toxin to areas not targeted for treatment, thereby reducing or preventing the undesirable side-effects associated with diffusion of a Clostridial toxin to an unwanted location.

Aspects of the present invention provide modified Clostridial toxins comprising a Clostridial toxin enzymatic domain, a Clostridial toxin translocation domain and an enhanced targeting domain, wherein the modified Clostridial toxin exhibits a binding activity for a non-Clostridial toxin receptor system present on a Clostridial toxin target cell relative to a naturally-occurring Clostridial toxin. It is envisioned that the location of the enhanced targeting domain in the modified Clostridial toxins of the present specification can be located at the amino terminus of the toxin, between the enzymatic and translocation domains or at the carboxyl terminus of the toxin. Thus, a modified Clostridial toxins disclosed in the present specification can comprise an amino to carboxyl domain arrangement of, e.g., an enhanced targeting domain, a Clostridial toxin translocation domain and a Clostridial toxin enzymatic domain; an enhanced targeting domain, a Clostridial toxin enzymatic domain and a Clostridial toxin translocation domain; a Clostridial toxin enzymatic domain, an enhanced targeting domain and a Clostridial toxin translocation domain; a Clostridial toxin translocation domain, an enhanced targeting domain and a Clostridial toxin enzymatic domain; a Clostridial toxin enzymatic domain, a Clostridial toxin translocation domain and an enhanced targeting domain; and a Clostridial toxin translocation domain, a Clostridial toxin enzymatic domain and an enhanced targeting domain.

Other aspects of the present invention provide polynucleotide molecules encoding modified Clostridial toxins comprising a Clostridial toxin enzymatic domain, a Clostridial toxin translocation domain and an enhanced targeting domain, wherein the modified Clostridial toxin exhibits an enhanced binding activity for a non-Clostridial toxin receptor system present on a Clostridial toxin target cell relative to a naturally-occurring Clostridial toxin. It is envisioned that the location of the enhanced targeting domain of the modified Clostridial toxins encoded by polynucleotide molecules of the present specification can be located at the amino terminus of the toxin, between the enzymatic and translocation domains or at the carboxyl terminus of the toxin. Thus, polynucleotide molecules disclosed in the present specification can encoded modified Clostridial toxins comprising an amino to carboxyl domain arrangement of, e.g., an enhanced targeting domain, a Clostridial toxin translocation domain and a Clostridial toxin enzymatic domain; an enhanced targeting domain, a Clostridial toxin enzymatic domain and a Clostridial toxin translocation domain; a Clostridial toxin enzymatic domain, an enhanced targeting domain and a Clostridial toxin translocation domain; a Clostridial toxin translocation domain, an enhanced targeting domain and a Clostridial toxin enzymatic domain; a Clostridial toxin enzymatic domain, a Clostridial toxin translocation domain and an enhanced targeting domain; and a Clostridial toxin translocation domain, a Clostridial toxin enzymatic domain and an enhanced targeting domain.

Other aspects of the present invention provide methods of producing a modified Clostridial toxin disclosed in the present specification, the method comprising the step of expressing in a cell a polynucleotide molecule encoding a modified Clostridial toxin comprising a Clostridial toxin enzymatic domain, a Clostridial toxin translocation domain and an enhanced targeting domain, wherein the modified Clostridial toxin exhibits an enhanced targeting activity for a Clostridial toxin target cell relative to a naturally-occurring Clostridial toxin. Other aspects of the present invention provide methods of producing a modified Clostridial toxin disclosed in the present specification, the method comprising the steps of introducing in a cell an expression construct comprising a polynucleotide molecule encoding a modified Clostridial toxin comprising a Clostridial toxin enzymatic domain, a Clostridial toxin translocation domain and an enhanced targeting domain, wherein the modified Clostridial toxin exhibits an enhanced targeting activity for a Clostridial toxin target cell relative to a naturally-occurring Clostridial toxin and expressing the expression construct in the cell.

The toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). While all seven botulinum toxins (BoNT) serotypes have similar structure and pharmacological properties, each also displays heterogeneous bacteriological characteristics. In contrast, tetanus toxin (TeNT) is produced by a uniform group of *C. tetani*. Two other species of Clostridia, *C. baratii* and *C. butyricum*, also produce toxins similar to BoNT/F and BoNT/E, respectively.

Figure 2:
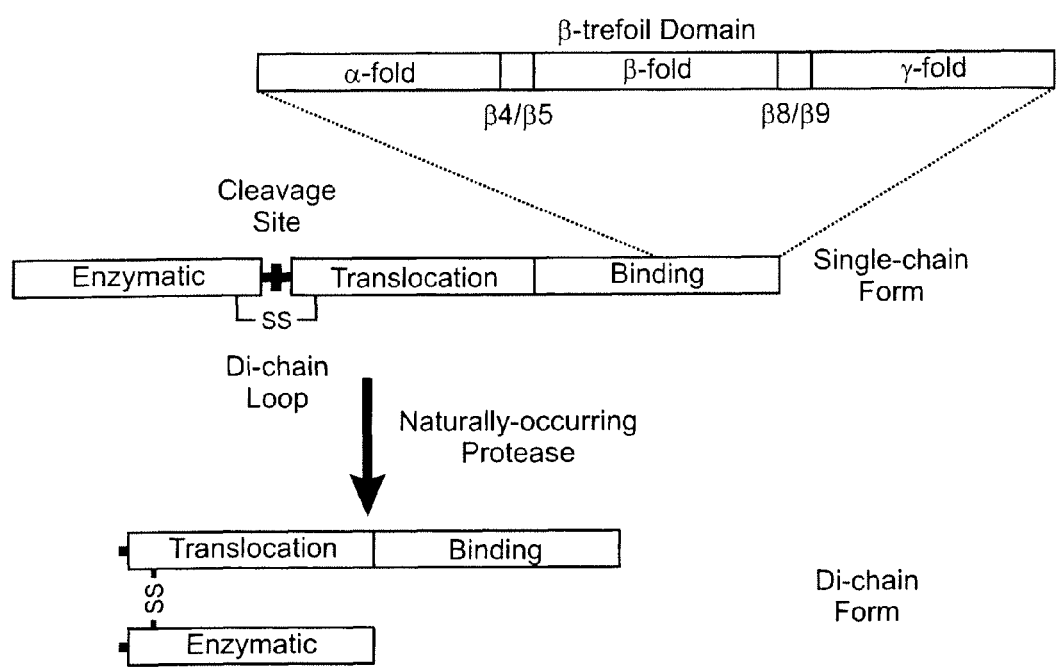
FIG. 2 shows the domain organization of naturally-occurring Clostridial toxins. The single chain form depicts the amino to carboxyl linear organization comprising an an enzymatic domain, a translocation domain, and a binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single chain form of the toxin into the di-chain form. Above the single-chain form, the $H_{CC}$ region of the Clostridial toxin binding domain is depicted. This region comprises the β-trefoil domain which comprises in a amino to carboxyl linear organization an α-fold, a β4/β5 hairpin turn, a β-fold, a β8/β9 hairpin turn and a γ-fold.

Clostridia toxins possess approximately 35% amino acid identity with each other and share the same functional domain organization and overall structural architecture. Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring proteases produced in the environment (FIG. 2). This posttranslational processing yields a di-chain molecule comprising an approximately 50 kDa light chain (LC) and an approximately 100 kDa heavy chain (HC) held together by a single disulfide bond and non-covalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus (Table 1); 2) a translocation domain contained within the amino-terminal half of the HC ($H_N$) that facilitates release of the LC from intracellular vesicles into the cytoplasm of the target cell (Table 1); and 3) a binding domain found within the carboxyl-terminal half of the HC ($H_C$) that determines the binding activity and binding specificity of the toxin to the receptor complex located at the surface of the target cell (Table 1).

TABLE 1

Clostridial Toxin Reference Sequences and Regions

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-K445 | D446-N862 | S863-E1276 |
| BoNT/E | 5 | M1-R422 | K423-R845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (see FIG. 1). The process is initiated when the $H_C$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it appears to specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); Giovanna Lalli et al., *The Journey of Tetanus and Botulinum Neurotoxins in Neurons*, 11(9) Trends Microbiol. 431-437, (2003).

Aspects of the present invention provide, in part, a modified Clostridial toxin. As used herein, the term "modified Clostridial toxin" means any polypeptide that can execute the overall cellular mechanism whereby a Clostridial toxin enters a neuron and inhibits neurotransmitter release and encompasses the binding of a Clostridial toxin to a low or high affinity receptor complex, the internalization of the toxin, the translocation of the Clostridial toxin light chain into the cytoplasm and the enzymatic modification of a Clostridial toxin substrate. A modified Clostridial toxin disclosed in the present specification is distinguished from a naturally-occurring Clostridial toxin by the fact that a modified Clostridial toxin lacks the cell binding activity of a naturally-occurring binding domain found in a Clostridial toxin. Instead, a modified Clostridial toxin disclosed in the present specification comprises an enhanced targeting domain that determines the binding activity of the modified Clostridial toxin to an endogenous Clostridial toxin receptor system located at the surface of the target cell. By definition, a naturally-occurring Clostridial toxin lacks an enhanced targeting domain.

Aspects of the present invention provide, in part, a Clostridial toxin enzymatic domain. As used herein, the term "Clostridial toxin enzymatic domain" means any Clostridial toxin polypeptide that can execute the enzymatic target modification step of the intoxication process. Thus, a Clostridial toxin enzymatic domain specifically targets a Clostridial toxin substrate and encompasses the proteolytic cleavage of a Clostridial toxin substrate, such as, e.g., SNARE proteins like a SNAP-25 substrate, a VAMP substrate and a Syntaxin substrate. Non-limiting examples of a Clostridial toxin enzymatic domain include, e.g., a Clostridial toxin light chain region such as, e.g., a BoNT/A light chain region, a BoNT/B light chain region, a BoNT/C1 light chain region, a BoNT/D light chain region, a BoNT/E light chain region, a BoNT/F light chain region, a BoNT/G light chain region, and a TeNT light chain region.

A Clostridial toxin enzymatic domain includes, without limitation, naturally occurring Clostridial toxin light chain variants, such as, e.g., Clostridial toxin light chain isoforms and Clostridial toxin light chain subtypes; non-naturally occurring Clostridial toxin light chain variants, such as, e.g., conservative Clostridial toxin light chain variants, non-conservative Clostridial toxin light chain variants, Clostridial toxin light chain chimerics, active Clostridial toxin light chain fragments thereof, or any combination thereof.

As used herein, the term "Clostridial toxin light chain variant," whether naturally-occurring or non-naturally-occurring, means a Clostridial toxin light chain that has at least one amino acid change from the corresponding region of the disclosed reference sequences (see Table 1) and can be described in percent identity to the corresponding region of that reference sequence. Unless expressly indicated, all Clostridial toxin light chain variants disclosed in the present specification are capable of executing the enzymatic target modification step of the intoxication process. As non-limiting examples, a BoNT/A light chain variant comprising amino acids 1-448 of SEQ ID NO: 1 will have at least one amino acid difference, such as, e.g., an amino acid substitution, deletion or addition, as compared to the amino acid region 1-448 of SEQ ID NO: 1; a BoNT/B light chain variant comprising amino acids 1-441 of SEQ ID NO: 2 will have at least one amino acid difference, such as, e.g., an amino acid substitution, deletion or addition, as compared to the amino acid region 1-441 of SEQ ID NO: 2; a BoNT/C1 light chain variant comprising amino acids 1-449 of SEQ ID NO: 3 will have at least one amino acid difference, such as, e.g., an amino acid substitution, deletion or addition, as compared to the amino acid region 1-449 of SEQ ID NO: 3; a BoNT/D light chain variant comprising amino acids 1-445 of SEQ ID NO: 4 will have at least one amino acid difference, such as, e.g., an amino acid substitution, deletion or addition, as compared to the amino acid region 1-445 of SEQ ID NO: 4; a BoNT/E light chain variant comprising amino acids 1-422 of SEQ ID NO: 5 will have at least one amino acid difference, such as, e.g., an amino acid substitution, deletion or addition, as compared to the amino acid region 1-422 of SEQ ID NO: 5; a BoNT/F light chain variant comprising amino acids 1-439 of SEQ ID NO: 6 will have at least one amino acid difference, such as, e.g., an amino acid substitution, deletion or addition, as compared to the amino acid region 1-439 of SEQ ID NO: 6; a BoNT/G light chain variant comprising amino acids 1-446 of SEQ ID NO: 7 will have at least one amino acid difference, such as, e.g., an amino acid substitution, deletion or addition, as compared to the amino acid region 1-446 of SEQ ID NO: 7; and a TeNT light chain variant comprising amino acids 1-457 of SEQ ID NO: 8 will have at least one amino acid difference, such as, e.g., an amino acid substitution, deletion or addition, as compared to the amino acid region 1-457 of SEQ ID NO: 8.

It is recognized by those of skill in the art that within each serotype of Clostridial toxin there can be naturally occurring Clostridial toxin light chain variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific light chain subtypes showing approximately 95% amino acid identity when compared to another BoNT/A light chain subtype. As used herein, the term "naturally occurring Clostridial toxin light chain variant" means any Clostridial toxin light chain produced by a naturally-occurring process, including, without limitation, Clostridial toxin light chain isoforms produced from alternatively-spliced transcripts, Clostridial toxin light chain isoforms produced by spontaneous mutation and Clostridial toxin light chain subtypes. A naturally occurring Clostridial toxin light chain variant can function in substantially the same manner as the reference Clostridial toxin light chain on which the naturally occurring Clostridial toxin light chain variant is based, and can be substituted for the reference Clostridial toxin light chain in any aspect of the present invention. A naturally occurring Clostridial toxin light chain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin light chain on which the naturally occurring Clostridial toxin light chain variant is based. A naturally occurring Clostridial toxin light chain variant can also substitute at least 10 contiguous amino acids, at least 15 contiguous amino acids, at least 20 contiguous amino acids, or at least 25 contiguous amino acids from the reference Clostridial toxin light chain on which the naturally occurring Clostridial toxin light chain variant is based, that possess at least 50% amino acid identity, 65% amino acid identity, 75% amino acid identity, 85% amino acid identity or 95% amino acid identity to the reference Clostridial toxin light chain on which the naturally occurring Clostridial toxin light chain variant is based.

A non-limiting examples of a naturally occurring Clostridial toxin light chain variant is a Clostridial toxin light chain isoform such as, e.g., a BoNT/A light chain isoform, a BoNT/B light chain isoform, a BoNT/C1 light chain isoform, a BoNT/D light chain isoform, a BoNT/E light chain isoform, a BoNT/F light chain isoform, a BoNT/G light chain isoform, and a TeNT light chain isoform. A Clostridial toxin light chain isoform can function in substantially the same manner as the reference Clostridial toxin light chain on which the Clostridial toxin light chain isoform is based, and can be substituted for the reference Clostridial toxin light chain in any aspect of the present invention.

Another non-limiting examples of a naturally occurring Clostridial toxin light chain variant is a Clostridial toxin light chain subtype such as, e.g., a light chain from subtype BoNT/A1, BoNT/A2, BoNT/A3 and BoNT/A4; a light chain from subtype BoNT/B1, BoNT/B2, BoNT/B bivalent and BoNT/B nonproteolytic; a light chain from subtype BoNT/C1-1 and BoNT/C1-2; a light chain from subtype BoNT/E1, BoNT/E2 and BoNT/E3; and a light chain from subtype BoNT/F1, BoNT/F2, BoNT/F3 and BoNT/F4. A Clostridial toxin light chain subtype can function in substantially the same manner as the reference Clostridial toxin light chain on which the Clostridial toxin light chain subtype is based, and can be substituted for the reference Clostridial toxin light chain in any aspect of the present invention.

As used herein, the term "non-naturally occurring Clostridial toxin light chain variant" means any Clostridial toxin light chain produced with the aid of human manipulation, including, without limitation, Clostridial toxin light chains produced by genetic engineering using random mutagenesis or rational design and Clostridial toxin light chains produced by chemical synthesis. Non-limiting examples of non-naturally occurring Clostridial toxin light chain variants include, e.g., conservative Clostridial toxin light chain variants, non-conservative Clostridial toxin light chain variants, Clostridial toxin light chain chimeric variants and active Clostridial toxin light chain fragments.

As used herein, the term "conservative Clostridial toxin light chain variant" means a Clostridial toxin light chain that has at least one amino acid substituted by another amino acid or an amino acid analog that has at least one property similar to that of the original amino acid from the reference Clostridial toxin light chain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin light chain variant can function in substantially the same manner as the reference Clostridial toxin light chain on which the conservative Clostridial toxin light chain variant is based, and can be substituted for the reference Clostridial toxin light chain in any aspect of the present invention. A conservative Clostridial toxin light chain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin light chain on which the conservative Clostridial toxin light chain variant is based. A conservative Clostridial toxin light chain variant can also substitute at least 10 contiguous amino acids, at least 15 contiguous amino acids, at least 20 contiguous amino acids, or at least 25 contiguous amino acids from the reference Clostridial toxin light chain on which the conservative Clostridial toxin light chain variant is based, that possess at least 50% amino acid identity, 65% amino acid identity, 75% amino acid identity, 85% amino acid identity or 95% amino acid identity to the reference Clostridial toxin light chain on which the conservative Clostridial toxin light chain variant is based. Non-limiting examples of a conservative Clostridial toxin light chain variant include, e.g., conservative BoNT/A light chain variants, conservative BoNT/B light chain variants, conservative BoNT/C1 light chain variants, conservative BoNT/D light chain variants, conservative BoNT/E light chain variants, conservative BoNT/F light chain variants, conservative BoNT/G light chain variants, and conservative TeNT light chain variants.

As used herein, the term "non-conservative Clostridial toxin light chain variant" means a Clostridial toxin light chain in which 1) at least one amino acid is deleted from the reference Clostridial toxin light chain on which the non-conservative Clostridial toxin light chain variant is based; 2) at least one amino acid added to the reference Clostridial toxin light chain on which the non-conservative Clostridial toxin light chain is based; or 3) at least one amino acid is substituted by another amino acid or an amino acid analog that does not share any property similar to that of the original amino acid from the reference Clostridial toxin light chain sequence (Table 1). A non-conservative Clostridial toxin light chain variant can function in substantially the same manner as the reference Clostridial toxin light chain on which the non-conservative Clostridial toxin light chain variant is based, and can be substituted for the reference Clostridial toxin light chain in any aspect of the present invention. A non-conservative Clostridial toxin light chain variant can delete one or more amino acids, two or more amino acids, three or more amino acids, four or more amino acids, five or more amino acids, and ten or more amino acids from the reference Clostridial toxin light chain on which the non-conservative Clostridial toxin light chain variant is based. A non-conservative Clostridial toxin light chain variant can add one or more amino acids, two or more amino acids, three or more amino acids, four or more amino acids, five or more amino acids, and ten or more amino acids to the reference Clostridial toxin light chain on which the non-conservative Clostridial toxin light chain variant is based. A non-conservative Clostridial toxin light chain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin light chain on which the non-conservative Clostridial toxin light chain variant is based. A non-conservative Clostridial toxin light chain variant can also substitute at least 10 contiguous amino acids, at least 15 contiguous amino acids, at least 20 contiguous amino acids, or at least 25 contiguous amino acids from the reference Clostridial toxin light chain on which the non-conservative Clostridial toxin light chain variant is based, that possess at least 50% amino acid identity, 65% amino acid identity, 75% amino acid identity, 85% amino acid identity or 95% amino acid identity to the reference Clostridial toxin light chain on which the non-conservative Clostridial toxin light chain variant is based. Non-limiting examples of a non-conservative Clostridial toxin light chain variant include, e.g., non-conservative BoNT/A light chain variants, non-conservative BoNT/B light chain variants, non-conservative BoNT/C1 light chain variants, non-conservative BoNT/D light chain variants, non-conservative BoNT/E light chain variants, non-conservative BoNT/F light chain variants, non-conservative BoNT/G light chain variants, and non-conservative TeNT light chain variants.

As used herein, the term "Clostridial toxin light chain chimeric" means a polypeptide comprising at least a portion of a Clostridial toxin light chain and at least a portion of at least one other polypeptide to form a toxin light chain with at least one property different from the reference Clostridial toxin light chains of Table 1, with the proviso that this Clostridial toxin light chain chimeric is still capable of specifically targeting the core components of the neurotransmitter release apparatus and thus participate in executing the overall cellular mechanism whereby a Clostridial toxin proteolytically cleaves a substrate. Such Clostridial toxin light chain chimerics are described in, e.g., Lance E. Steward et al., Leucine-based Motif and Clostridial Toxins, U.S. Patent Publication 2003/0027752 (Feb. 6, 2003); Lance E. Steward et al., Clostridial Neurotoxin Compositions and Modified Clostridial Neurotoxins, U.S. Patent Publication 2003/0219462 (Nov. 27, 2003); and Lance E. Steward et al., Clostridial Neurotoxin Compositions and Modified Clostridial Neurotoxins, U.S. Patent Publication 2004/0220386 (Nov. 4, 2004).

As used herein, the term "active Clostridial toxin light chain fragment" means any of a variety of Clostridial toxin fragments comprising the light chain can be useful in aspects of the present invention with the proviso that these light chain fragments can specifically target the core components of the neurotransmitter release apparatus and thus participate in executing the overall cellular mechanism whereby a Clostridial toxin proteolytically cleaves a substrate. The light chains of Clostridial toxins are approximately 420-460 amino acids in length and comprise an enzymatic domain (Table 1). Research has shown that the entire length of a Clostridial toxin light chain is not necessary for the enzymatic activity of the enzymatic domain. As a non-limiting example, the first eight amino acids of the BoNT/A light chain (residues 1-8 of SEQ ID NO: 1) are not required for enzymatic activity. As another non-limiting example, the first eight amino acids of the TeNT light chain (residues 1-8 of SEQ ID NO: 8) are not required for enzymatic activity. Likewise, the carboxyl-terminus of the light chain is not necessary for activity. As a non-limiting example, the last 32 amino acids of the BoNT/A light chain (residues 417-448 of SEQ ID NO: 1) are not required for enzymatic activity. As another non-limiting example, the last 31 amino acids of the TeNT light chain (residues 427-457 of SEQ ID NO: 8) are not required for enzymatic activity. Thus, aspects of this embodiment can include Clostridial toxin light chains comprising an enzymatic domain having a length of, e.g., at least 350 amino acids, at least 375 amino acids, at least 400 amino acids, at least 425 amino acids and at least 450 amino acids. Other aspects of this embodiment can include Clostridial toxin light chains comprising an enzymatic domain having a length of, e.g., at most 350 amino acids, at most 375 amino acids, at most 400 amino acids, at most 425 amino acids and at most 450 amino acids.

Any of a variety of sequence alignment methods can be used to determine percent identity of naturally-occurring Clostridial toxin light chain variants and non-naturally-occurring Clostridial toxin light chain variants, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics, 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

Thus, in an embodiment, a modified Clostridial toxin disclosed in the present specification comprises a Clostridial toxin enzymatic domain. In an aspect of this embodiment, a Clostridial toxin enzymatic domain comprises a naturally occurring Clostridial toxin light chain variant, such as, e.g., a Clostridial toxin light chain isoform or a Clostridial toxin light chain subtype. In another aspect of this embodiment, a Clostridial toxin enzymatic domain comprises a non-naturally occurring Clostridial toxin light chain variant, such as, e.g., a conservative Clostridial toxin light chain variant, a non-conservative Clostridial toxin light chain variant, a Clostridial toxin chimeric light chain, an active Clostridial toxin light chain fragment, or any combination thereof.

In another embodiment, a Clostridial toxin enzymatic domain comprises a BoNT/A light chain. In an aspect of this embodiment, a BoNT/A light chain comprises amino acids 1-448 of SEQ ID NO: 1. In another aspect of this embodiment, a BoNT/A light chain comprises a naturally occurring BoNT/A light chain variant, such as, e.g., a light chain from a BoNT/A isoform or a light chain from a BoNT/A subtype. In another aspect of this embodiment, a BoNT/A light chain comprises amino acids 1-448 of a naturally occurring BoNT/A light chain variant of SEQ ID NO: 1, such as, e.g., amino acids 1-448 of a BoNT/A isoform of SEQ ID NO: 1 or amino acids 1-448 of a BoNT/A subtype of SEQ ID NO: 1. In still another aspect of this embodiment, a BoNT/A light chain comprises a non-naturally occurring BoNT/A light chain variant, such as, e.g., a conservative BoNT/A light chain variant, a non-conservative BoNT/A light chain variant, a BoNT/A chimeric light chain, an active BoNT/A light chain fragment, or any combination thereof. In still another aspect of this embodiment, a BoNT/A light chain comprises amino acids 1-448 of a non-naturally occurring BoNT/A light chain variant of SEQ ID NO: 1, such as, e.g., amino acids 1-448 of a conservative BoNT/A light chain variant of SEQ ID NO: 1, amino acids 1-448 of a non-conservative BoNT/A light chain variant of SEQ ID NO: 1, amino acids 1-448 of an active BoNT/A light chain fragment of SEQ ID NO: 1, or any combination thereof.

In other aspects of this embodiment, a BoNT/A light chain comprises a polypeptide having, e.g., at least 70% amino acid identity with amino acids 1-448 of SEQ ID NO: 1, at least 75% amino acid identity with amino acids 1-448 of SEQ ID NO: 1, at least 80% amino acid identity with amino acids 1-448 of SEQ ID NO: 1, at least 85% amino acid identity with amino acids 1-448 of SEQ ID NO: 1, at least 90% amino acid identity with amino acids 1-448 of SEQ ID NO: 1 or at least 95% amino acid identity with amino acids 1-448 of SEQ ID NO: 1. In yet other aspects of this embodiment, a BoNT/A light chain comprises a polypeptide having, e.g., at most 70% amino acid identity with amino acids 1-448 of SEQ ID NO: 1, at most 75% amino acid identity with amino acids 1-448 of SEQ ID NO: 1, at most 80% amino acid identity with amino acids 1-448 of SEQ ID NO: 1, at most 85% amino acid identity with amino acids 1-448 of SEQ ID NO: 1, at most 90% amino acid identity with amino acids 1-448 of SEQ ID NO: 1 or at most 95% amino acid identity with amino acids 1-448 of SEQ ID NO: 1.

In other aspects of this embodiment, a BoNT/A light chain comprises a polypeptide having, e.g., at most one, two, three, four, five, six, seven, eight, nine, 10, 20, 30, 40, 50, 100, or 200 non-contiguous amino acid substitutions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 non-contiguous amino acid substitutions relative to amino acids 1-448 of SEQ ID NO: 1. In yet other aspects of this embodiment, a BoNT/A light chain comprises a polypeptide having, e.g., at most one, two, three, four, five, six, seven, eight, nine, 10, 20, 30, 40, 50, 100 or 200 non-contiguous amino acid deletions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 non-contiguous amino acid deletions relative to amino acids 1-448 of SEQ ID NO: 1. In still other aspects of this embodiment, a BoNT/A light chain comprises a polypeptide having, e.g., at most one, two, three, four, five, six, seven, eight, nine, 10, 20, 30, 40, 50, 100 or 200 non-contiguous amino acid additions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 non-contiguous amino acid additions relative to amino acids 1-448 of SEQ ID NO: 1.

In other aspects of this embodiment, a BoNT/A light chain comprises a polypeptide having, e.g., at most one, two, three, four, five, six, seven, eight, nine, 10, 20, 30, 40, 50, 100 or 200 contiguous amino acid substitutions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 contiguous amino acid substitutions relative to amino acids 1-448 of SEQ ID NO: 1. In yet other aspects of this embodiment, a BoNT/A light chain comprises a polypeptide having, e.g., at most one, two, three, four, five, six, seven, eight, nine, 10, 20, 30, 40, 50, 100 or 200 contiguous amino acid deletions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 contiguous amino acid deletions relative to amino acids 1-448 of SEQ ID NO: 1. In still other aspects of this embodiment, a BoNT/A light chain comprises a polypeptide having, e.g., at most one, two, three, four, five, six, seven, eight, nine, 10, 20, 30, 40, 50, 100 or 200 contiguous amino acid additions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 contiguous amino acid additions relative to amino acids 1-448 of SEQ ID NO: 1.

In another embodiment, a Clostridial toxin enzymatic domain comprises a BoNT/B light chain. In an aspect of this embodiment, a BoNT/B light chain comprises amino acids 1-441 of SEQ ID NO: 2. In another aspect of this embodiment, a BoNT/B light chain comprises a naturally occurring BoNT/B light chain variant, such as, e.g., a light chain from a BoNT/B isoform or a light chain from a BoNT/B subtype. In another aspect of this embodiment, a BoNT/B light chain comprises amino acids 1-441 of a naturally occurring BoNT/B light chain variant of SEQ ID NO: 2, such as, e.g., amino acids 1-441 of a BoNT/B isoform of SEQ ID NO: 2 or amino acids 1-441 of a BoNT/B subtype of SEQ ID NO: 2. In still another aspect of this embodiment, a BoNT/B light chain comprises a non-naturally occurring BoNT/B light chain variant, such as, e.g., a conservative BoNT/B light chain variant, a non-conservative BoNT/B light chain variant, a BoNT/B chimeric light chain, an active BoNT/B light chain fragment, or any combination thereof. In still another aspect of this embodiment, a BoNT/B light chain comprises amino acids 1-441 of a non-naturally occurring BoNT/B light chain variant of SEQ ID NO: 2, such as, e.g., amino acids 1-441 of a conservative BoNT/B light chain variant of SEQ ID NO: 2, amino acids 1-441 of a non-conservative BoNT/B light chain variant of SEQ ID NO: 2, amino acids 1-441 of an active BoNT/B light chain fragment of SEQ ID NO: 2, or any combination thereof.

In other aspects of this embodiment, a BoNT/B light chain comprises a polypeptide having, e.g., at least 70% amino acid identity with amino acids 1-441 of SEQ ID NO: 2, at least 75% amino acid identity with amino acids 1-441 of SEQ ID NO: 2, at least 80% amino acid identity with amino acids 1-441 of SEQ ID NO: 2, at least 85% amino acid identity with amino acids 1-441 of SEQ ID NO: 2, at least 90% amino acid identity with amino acids 1-441 of SEQ ID NO: 2 or at least 95% amino acid identity with amino acids 1-441 of SEQ ID NO: 2. In yet other aspects of this embodiment, a BoNT/B light chain comprises a polypeptide having, e.g., at most 70% amino acid identity with amino acids 1-441 of SEQ ID NO: 2, at most 75% amino acid identity with amino acids 1-441 of SEQ ID NO: 2, at most 80% amino acid identity with amino acids 1-441 of SEQ ID NO: 2, at most 85% amino acid identity with amino acids 1-441 of SEQ ID NO: 2, at most 90% amino acid identity with amino acids 1-441 of SEQ ID NO: 2 or at most 95% amino acid identity with amino acids 1-441 of SEQ ID NO: 2.

In other aspects of this embodiment, a BoNT/B light chain comprises a polypeptide having, e.g., at most one, two, three, four, five, six, seven, eight, nine, 10, 20, 30, 40, 50, 100, or 200 non-contiguous amino acid substitutions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 non-contiguous amino acid substitutions relative to amino acids 1-441 of SEQ ID NO: 2. In yet other aspects of this embodiment, a BoNT/B light chain comprises a polypeptide having, e.g., at most one, two, three, four, five, six, seven, eight, nine, 10, 20, 30, 40, 50, 100 or 200 non-contiguous amino acid deletions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 non-contiguous amino acid deletions relative to amino acids 1-441 of SEQ ID NO: 2. In still other aspects of this embodiment, a BoNT/B light chain comprises a polypeptide having, e.g., at most one, two, three, four, five, six, seven, eight, nine, 10, 20, 30, 40, 50, 100 or 200 non-contiguous amino acid additions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 non-contiguous amino acid additions relative to amino acids 1-441 of SEQ ID NO: 2.

In other aspects of this embodiment, a BoNT/B light chain comprises a polypeptide having, e.g., at most one, two, three, four, five, six, seven, eight, nine, 10, 20, 30, 40, 50, 100 or 200 contiguous amino acid substitutions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 contiguous amino acid substitutions relative to amino acids 1-441 of SEQ ID NO: 2. In yet other aspects of this embodiment, a BoNT/B light chain comprises a polypeptide having, e.g., at most one, two, three, four, five, six, seven, eight, nine, 10, 20, 30, 40, 50, 100 or 200 contiguous amino acid deletions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 contiguous amino acid deletions relative to amino acids 1-441 of SEQ ID NO: 2. In still other aspects of this embodiment, a BoNT/B light chain comprises a polypeptide having, e.g., at most one, two, three, four, five, six, seven, eight, nine, 10, 20, 30, 40, 50, 100 or 200 contiguous amino acid additions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 contiguous amino acid additions relative to amino acids 1-441 of SEQ ID NO: 2.

In another embodiment, a Clostridial toxin enzymatic domain comprises a BoNT/C1 light chain. In an aspect of this embodiment, a BoNT/C1 light chain comprises amino acids 1-449 of SEQ ID NO: 3. In another aspect of this embodiment, a BoNT/C1 light chain comprises a naturally occurring BoNT/C1 light chain variant, such as, e.g., a light chain from a BoNT/C1 isoform or a light chain from a BoNT/C1 subtype. In another aspect of this embodiment, a BoNT/C1 light chain comprises amino acids 1-449 of a naturally occurring BoNT/C1 light chain variant of SEQ ID NO: 3, such as, e.g., amino acids 1-449 of a BoNT/C1 isoform of SEQ ID NO: 3 or amino acids 1-449 of a BoNT/C1 subtype of SEQ ID NO: 3. In still another aspect of this embodiment, a BoNT/C1 light chain comprises a non-naturally occurring BoNT/C1 light chain variant, such as, e.g., a conservative BoNT/C1 light chain variant, a non-conservative BoNT/C1 light chain variant, a BoNT/C1 chimeric light chain, an active BoNT/C1 light chain fragment, or any combination thereof. In still another aspect of this embodiment, a BoNT/C1 light chain comprises amino acids 1-449 of a non-naturally occurring BoNT/C1 light chain variant of SEQ ID NO: 3, such as, e.g., amino acids 1-449 of a conservative BoNT/C1 light chain variant of SEQ ID NO: 3, amino acids 1-449 of a non-conservative BoNT/C1 light chain variant of SEQ ID NO: 3, amino acids 1-449 of an active BoNT/C1 light chain fragment of SEQ ID NO: 3, or any combination thereof.

In other aspects of this embodiment, a BoNT/C1 light chain comprises a polypeptide having, e.g., at least 70% amino acid identity with amino acids 1-449 of SEQ ID NO: 3, at least 75% amino acid identity with amino acids 1-449 of SEQ ID NO: 3, at least 80% amino acid identity with amino acids 1-449 of SEQ ID NO: 3, at least 85% amino acid identity with amino acids 1-449 of SEQ ID NO: 3, at least 90% amino acid identity with amino acids 1-449 of SEQ ID NO: 3 or at least 95% amino acid identity with amino acids 1-449 of SEQ ID NO: 3. In yet other aspects of this embodiment, a BoNT/C1 light chain comprises a polypeptide having, e.g., at most 70% amino acid identity with amino acids 1-449 of SEQ ID NO: 3, at most 75% amino acid identity with amino acids 1-449 of SEQ ID NO: 3, at most 80% amino acid identity with amino acids 1-449 of SEQ ID NO: 3, at most 85% amino acid identity with amino acids 1-449 of SEQ ID NO: 3, at most 90% amino acid identity with amino acids 1-449 of SEQ ID NO: 3 or at most 95% amino acid identity with amino acids 1-449 of SEQ ID NO: 3.

In other aspects of this embodiment, a BoNT/C1 light chain comprises a polypeptide having, e.g., at most one, two, three, four, five, six, seven, eight, nine, 10, 20, 30, 40, 50, 100, or 200 non-contiguous amino acid substitutions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 non-contiguous amino acid substitutions relative to amino acids 1-449 of SEQ ID NO: 3. In yet other aspects of this embodiment, a BoNT/C1 light chain comprises a polypeptide having, e.g., at most one, two, three, four, five, six, seven, eight, nine, 10, 20, 30, 40, 50, 100 or 200 non-contiguous amino acid deletions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 non-contiguous amino acid deletions relative to amino acids 1-449 of SEQ ID NO: 3. In still other aspects of this embodiment, a BoNT/C1 light chain comprises a polypeptide having, e.g., at most one, two, three, four, five, six, seven, eight, nine, 10, 20, 30, 40, 50, 100 or 200 non-contiguous amino acid additions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 non-contiguous amino acid additions relative to amino acids 1-449 of SEQ ID NO: 3.

In other aspects of this embodiment, a BoNT/C1 light chain comprises a polypeptide having, e.g., at most one, two, three, four, five, six, seven, eight, nine, 10, 20, 30, 40, 50, 100 or 200 contiguous amino acid substitutions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 contiguous amino acid substitutions relative to amino acids 1-449 of SEQ ID NO: 3. In yet other aspects of this embodiment, a BoNT/C1 light chain comprises a polypeptide having, e.g., at most one, two, three, four, five, six, seven, eight, nine, 10, 20, 30, 40, 50, 100 or 200 contiguous amino acid deletions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 contiguous amino acid deletions relative to amino acids 1-449 of SEQ ID NO: 3. In still other aspects of this embodiment, a BoNT/C1 light chain comprises a polypeptide having, e.g., at most one, two, three, four, five, six, seven, eight, nine, 10, 20, 30, 40, 50, 100 or 200 contiguous amino acid additions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 contiguous amino acid additions relative to amino acids 1-449 of SEQ ID NO: 3.

In another embodiment, a Clostridial toxin enzymatic domain comprises a BoNT/D light chain. In an aspect of this embodiment, a BoNT/D light chain comprises amino acids 1-445 of SEQ ID NO: 4. In another aspect of this embodiment, a BoNT/D light chain comprises a naturally occurring BoNT/D light chain variant, such as, e.g., a light chain from a BoNT/D isoform or a light chain from a BoNT/D subtype. In another aspect of this embodiment, a BoNT/D light chain comprises amino acids 1-445 of a naturally occurring BoNT/D light chain variant of SEQ ID NO: 4, such as, e.g., amino acids 1-445 of a BoNT/D isoform of SEQ ID NO: 4 or amino acids 1-445 of a BoNT/D subtype of SEQ ID NO: 4. In still another aspect of this embodiment, a BoNT/D light chain comprises a non-naturally occurring BoNT/D light chain variant, such as, e.g., a conservative BoNT/D light chain variant, a non-conservative BoNT/D light chain variant, a BoNT/D chimeric light chain, an active BoNT/D light chain fragment, or any combination thereof. In still another aspect of this embodiment, a BoNT/D light chain comprises amino acids 1-445 of a non-naturally occurring BoNT/D light chain variant of SEQ ID NO: 4, such as, e.g., amino acids 1-445 of a conservative BoNT/D light chain variant of SEQ ID NO: 4, amino acids 1-445 of a non-conservative BoNT/D light chain variant of SEQ ID NO: 4, amino acids 1-445 of an active BoNT/D light chain fragment of SEQ ID NO: 4, or any combination thereof.

In other aspects of this embodiment, a BoNT/D light chain comprises a polypeptide having, e.g., at least 70% amino acid identity with amino acids 1-445 of SEQ ID NO: 4, at least 75% amino acid identity with amino acids 1-445 of SEQ ID NO: 4, at least 80% amino acid identity with amino acids 1-445 of SEQ ID NO: 4, at least 85% amino acid identity with amino acids 1-445 of SEQ ID NO: 4, at least 90% amino acid identity with amino acids 1-445 of SEQ ID NO: 4 or at least 95% amino acid identity with amino acids 1-445 of SEQ ID NO: 4. In yet other aspects of this embodiment, a BoNT/D light chain comprises a polypeptide having, e.g., at most 70% amino acid identity with amino acids 1-445 of SEQ ID NO: 4, at most 75% amino acid identity with amino acids 1-445 of SEQ ID NO: 4, at most 80% amino acid identity with amino acids 1-445 of SEQ ID NO: 4, at most 85% amino acid identity with amino acids 1-445 of SEQ ID NO: 4, at most 90% amino acid identity with amino acids 1-445 of SEQ ID NO: 4 or at most 95% amino acid identity with amino acids 1-445 of SEQ ID NO: 4.

In other aspects of this embodiment, a BoNT/D light chain comprises a polypeptide having, e.g., at most one, two, three, four, five, six, seven, eight, nine, 10, 20, 30, 40, 50, 100, or 200 non-contiguous amino acid substitutions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 non-contiguous amino acid substitutions relative to amino acids 1-445 of SEQ ID NO: 4. In yet other aspects of this embodiment, a BoNT/D light chain comprises a polypeptide having, e.g., at most one, two, three, four, five, six, seven, eight, nine, 10, 20, 30, 40, 50, 100 or 200 non-contiguous amino acid deletions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 non-contiguous amino acid deletions relative to amino acids 1-445 of SEQ ID NO: 4. In still other aspects of this embodiment, a BoNT/D light chain comprises a polypeptide having, e.g., at most one, two, three, four, five, six, seven, eight, nine, 10, 20, 30, 40, 50, 100 or 200 non-contiguous amino acid additions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 non-contiguous amino acid additions relative to amino acids 1-445 of SEQ ID NO: 4.

In other aspects of this embodiment, a BoNT/D light chain comprises a polypeptide having, e.g., at most one, two, three, four, five, six, seven, eight, nine, 10, 20, 30, 40, 50, 100 or 200 contiguous amino acid substitutions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 contiguous amino acid substitutions relative to amino acids 1-445 of SEQ ID NO: 4. In yet other aspects of this embodiment, a BoNT/D light chain comprises a polypeptide having, e.g., at most one, two, three, four, five, six, seven, eight, nine, 10, 20, 30, 40, 50, 100 or 200 contiguous amino acid deletions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 contiguous amino acid deletions relative to amino acids 1-445 of SEQ ID NO: 4. In still other aspects of this embodiment, a BoNT/D light chain comprises a polypeptide having, e.g., at most one, two, three, four, five, six, seven, eight, nine, 10, 20, 30, 40, 50, 100 or 200 contiguous amino acid additions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 contiguous amino acid additions relative to amino acids 1-445 of SEQ ID NO: 4.

In another embodiment, a Clostridial toxin enzymatic domain comprises a BoNT/E light chain. In an aspect of this embodiment, a BoNT/E light chain comprises amino acids 1-422 of SEQ ID NO: 5. In another aspect of this embodiment, a BoNT/E light chain comprises a naturally occurring BoNT/E light chain variant, such as, e.g., a light chain from a BoNT/E isoform or a light chain from a BoNT/E subtype. In another aspect of this embodiment, a BoNT/E light chain comprises amino acids 1-422 of a naturally occurring BoNT/E light chain variant of SEQ ID NO: 5, such as, e.g., amino acids 1-422 of a BoNT/E isoform of SEQ ID NO: 5 or amino acids 1-422 of a BoNT/E subtype of SEQ ID NO: 5. In still another aspect of this embodiment, a BoNT/E light chain comprises a non-naturally occurring BoNT/E light chain variant, such as, e.g., a conservative BoNT/E light chain variant, a non-conservative BoNT/E light chain variant, a BoNT/E chimeric light chain, an active BoNT/E light chain fragment, or any combination thereof. In still another aspect of this embodiment, a BoNT/E light chain comprises amino acids 1-422 of a non-naturally occurring BoNT/E light chain variant of SEQ ID NO: 5, such as, e.g., amino acids 1-422 of a conservative BoNT/E light chain variant of SEQ ID NO: 5, amino acids 1-422 of a non-conservative BoNT/E light chain variant of SEQ ID NO: 5, amino acids 1-422 of an active BoNT/E light chain fragment of SEQ ID NO: 5, or any combination thereof.

In other aspects of this embodiment, a BoNT/E light chain comprises a polypeptide having, e.g., at least 70% amino acid identity with amino acids 1-422 of SEQ ID NO: 5, at least 75% amino acid identity with amino acids 1-422 of SEQ ID NO: 5, at least 80% amino acid identity with amino acids 1-422 of SEQ ID NO: 5, at least 85% amino acid identity with amino acids 1-422 of SEQ ID NO: 5, at least 90% amino acid identity with amino acids 1-422 of SEQ ID NO: 5 or at least 95% amino acid identity with amino acids 1-422 of SEQ ID NO: 5. In yet other aspects of this embodiment, a BoNT/E light chain comprises a polypeptide having, e.g., at most 70% amino acid identity with amino acids 1-422 of SEQ ID NO: 5, at most 75% amino acid identity with amino acids 1-422 of SEQ ID NO: 5, at most 80% amino acid identity with amino acids 1-422 of SEQ ID NO: 5, at most 85% amino acid identity with amino acids 1-422 of SEQ ID NO: 5, at most 90% amino acid identity with amino acids 1-422 of SEQ ID NO: 5 or at most 95% amino acid identity with amino acids 1-422 of SEQ ID NO: 5.

In other aspects of this embodiment, a BoNT/E light chain comprises a polypeptide having, e.g., at most one, two, three, four, five, six, seven, eight, nine, 10, 20, 30, 40, 50, 100, or 200 non-contiguous amino acid substitutions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 non-contiguous amino acid substitutions relative to amino acids 1-422 of SEQ ID NO: 5. In yet other aspects of this embodiment, a BoNT/E light chain comprises a polypeptide having, e.g., at most one, two, three, four, five, six, seven, eight, nine, 10, 20, 30, 40, 50, 100 or 200 non-contiguous amino acid deletions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 non-contiguous amino acid deletions relative to amino acids 1-422 of SEQ ID NO: 5. In still other aspects of this embodiment, a BoNT/E light chain comprises a polypeptide having, e.g., at most one, two, three, four, five, six, seven, eight, nine, 10, 20, 30, 40, 50, 100 or 200 non-contiguous amino acid additions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 non-contiguous amino acid additions relative to amino acids 1-422 of SEQ ID NO: 5.

In other aspects of this embodiment, a BoNT/E light chain comprises a polypeptide having, e.g., at most one, two, three, four, five, six, seven, eight, nine, 10, 20, 30, 40, 50, 100 or 200 contiguous amino acid substitutions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 contiguous amino acid substitutions relative to amino acids 1-422 of SEQ ID NO: 5. In yet other aspects of this embodiment, a BoNT/E light chain comprises a polypeptide having, e.g., at most one, two, three, four, five, six, seven, eight, nine, 10, 20, 30, 40, 50, 100 or 200 contiguous amino acid deletions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 contiguous amino acid deletions relative to amino acids 1-422 of SEQ ID NO: 5. In still other aspects of this embodiment, a BoNT/E light chain comprises a polypeptide having, e.g., at most one, two, three, four, five, six, seven, eight, nine, 10, 20, 30, 40, 50, 100 or 200 contiguous amino acid additions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 contiguous amino acid additions relative to amino acids 1-422 of SEQ ID NO: 5.

In another embodiment, a Clostridial toxin enzymatic domain comprises a BoNT/F light chain. In an aspect of this embodiment, a BoNT/F light chain comprises amino acids 1-439 of SEQ ID NO: 6. In another aspect of this embodiment, a BoNT/F light chain comprises a naturally occurring BoNT/F light chain variant, such as, e.g., a light chain from a BoNT/F isoform or a light chain from a BoNT/F subtype. In another aspect of this embodiment, a BoNT/F light chain comprises amino acids 1-439 of a naturally occurring BoNT/F light chain variant of SEQ ID NO: 6, such as, e.g., amino acids 1-439 of a BoNT/F isoform of SEQ ID NO: 6 or amino acids 1-439 of a BoNT/F subtype of SEQ ID NO: 6. In still another aspect of this embodiment, a BoNT/F light chain comprises a non-naturally occurring BoNT/F light chain variant, such as, e.g., a conservative BoNT/F light chain variant, a non-conservative BoNT/F light chain variant, a BoNT/F chimeric light chain, an active BoNT/F light chain fragment, or any combination thereof. In still another aspect of this embodiment, a BoNT/F light chain comprises amino acids 1-439 of a non-naturally occurring BoNT/F light chain variant of SEQ ID NO: 6, such as, e.g., amino acids 1-439 of a conservative BoNT/F light chain variant of SEQ ID NO: 6, amino acids 1-439 of a non-conservative BoNT/F light chain variant of SEQ ID NO: 6, amino acids 1-439 of an active BoNT/F light chain fragment of SEQ ID NO: 6, or any combination thereof.

In other aspects of this embodiment, a BoNT/F light chain comprises a polypeptide having, e.g., at least 70% amino acid identity with amino acids 1-439 of SEQ ID NO: 6, at least 75% amino acid identity with amino acids 1-439 of SEQ ID NO: 6, at least 80% amino acid identity with amino acids 1-439 of SEQ ID NO: 6, at least 85% amino acid identity with amino acids 1-439 of SEQ ID NO: 6, at least 90% amino acid identity with amino acids 1-439 of SEQ ID NO: 6 or at least 95% amino acid identity with amino acids 1-439 of SEQ ID NO: 6. In yet other aspects of this embodiment, a BoNT/F light chain comprises a polypeptide having, e.g., at most 70% amino acid identity with amino acids 1-439 of SEQ ID NO: 6, at most 75% amino acid identity with amino acids 1-439 of SEQ ID NO: 6, at most 80% amino acid identity with amino acids 1-439 of SEQ ID NO: 6, at most 85% amino acid identity with amino acids 1-439 of SEQ ID NO: 6, at most 90% amino acid identity with amino acids 1-439 of SEQ ID NO: 6 or at most 95% amino acid identity with amino acids 1-439 of SEQ ID NO: 6.

In other aspects of this embodiment, a BoNT/F light chain comprises a polypeptide having, e.g., at most one, two, three, four, five, six, seven, eight, nine, 10, 20, 30, 40, 50, 100, or 200 non-contiguous amino acid substitutions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 non-contiguous amino acid substitutions relative to amino acids 1-439 of SEQ ID NO: 6. In yet other aspects of this embodiment, a BoNT/F light chain comprises a polypeptide having, e.g., at most one, two, three, four, five, six, seven, eight, nine, 10, 20, 30, 40, 50, 100 or 200 non-contiguous amino acid deletions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 non-contiguous amino acid deletions relative to amino acids 1-439 of SEQ ID NO: 6. In still other aspects of this embodiment, a BoNT/F light chain comprises a polypeptide having, e.g., at most one, two, three, four, five, six, seven, eight, nine, 10, 20, 30, 40, 50, 100 or 200 non-contiguous amino acid additions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 non-contiguous amino acid additions relative to amino acids 1-439 of SEQ ID NO: 6.

In other aspects of this embodiment, a BoNT/F light chain comprises a polypeptide having, e.g., at most one, two, three, four, five, six, seven, eight, nine, 10, 20, 30, 40, 50, 100 or 200 contiguous amino acid substitutions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 contiguous amino acid substitutions relative to amino acids 1-439 of SEQ ID NO: 6. In yet other aspects of this embodiment, a BoNT/F light chain comprises a polypeptide having, e.g., at most one, two, three, four, five, six, seven, eight, nine, 10, 20, 30, 40, 50, 100 or 200 contiguous amino acid deletions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 contiguous amino acid deletions relative to amino acids 1-439 of SEQ ID NO: 6. In still other aspects of this embodiment, a BoNT/F light chain comprises a polypeptide having, e.g., at most one, two, three, four, five, six, seven, eight, nine, 10, 20, 30, 40, 50, 100 or 200 contiguous amino acid additions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 contiguous amino acid additions relative to amino acids 1-439 of SEQ ID NO: 6.

In another embodiment, a Clostridial toxin enzymatic domain comprises a BoNT/G light chain. In an aspect of this embodiment, a BoNT/G light chain comprises amino acids 1-446 of SEQ ID NO: 7. In another aspect of this embodiment, a BoNT/G light chain comprises a naturally occurring BoNT/G light chain variant, such as, e.g., a light chain from a BoNT/G isoform or a light chain from a BoNT/G subtype. In another aspect of this embodiment, a BoNT/G light chain comprises amino acids 1-446 of a naturally occurring BoNT/G light chain variant of SEQ ID NO: 7, such as, e.g., amino acids 1-446 of a BoNT/G isoform of SEQ ID NO: 7 or amino acids 1-446 of a BoNT/G subtype of SEQ ID NO: 7. In still another aspect of this embodiment, a BoNT/G light chain comprises a non-naturally occurring BoNT/G light chain variant, such as, e.g., a conservative BoNT/G light chain variant, a non-conservative BoNT/G light chain variant, a BoNT/G chimeric light chain, an active BoNT/G light chain fragment, or any combination thereof. In still another aspect of this embodiment, a BoNT/G light chain comprises amino acids 1-446 of a non-naturally occurring BoNT/G light chain variant of SEQ ID NO: 7, such as, e.g., amino acids 1-446 of a conservative BoNT/G light chain variant of SEQ ID NO: 7, amino acids 1-446 of a non-conservative BoNT/G light chain variant of SEQ ID NO: 7, amino acids 1-446 of an active BoNT/G light chain fragment of SEQ ID NO: 7, or any combination thereof.

In other aspects of this embodiment, a BoNT/G light chain comprises a polypeptide having, e.g., at least 70% amino acid identity with amino acids 1-446 of SEQ ID NO: 7, at least 75% amino acid identity with amino acids 1-446 of SEQ ID NO: 7, at least 80% amino acid identity with amino acids 1-446 of SEQ ID NO: 7, at least 85% amino acid identity with amino acids 1-446 of SEQ ID NO: 7, at least 90% amino acid identity with amino acids 1-446 of SEQ ID NO: 7 or at least 95% amino acid identity with amino acids 1-446 of SEQ ID NO: 7. In yet other aspects of this embodiment, a BoNT/G light chain comprises a polypeptide having, e.g., at most 70% amino acid identity with amino acids 1-446 of SEQ ID NO: 7, at most 75% amino acid identity with amino acids 1-446 of SEQ ID NO: 7, at most 80% amino acid identity with amino acids 1-446 of SEQ ID NO: 7, at most 85% amino acid identity with amino acids 1-446 of SEQ ID NO: 7, at most 90% amino acid identity with amino acids 1-446 of SEQ ID NO: 7 or at most 95% amino acid identity with amino acids 1-446 of SEQ ID NO: 7.

In other aspects of this embodiment, a BoNT/G light chain comprises a polypeptide having, e.g., at most one, two, three, four, five, six, seven, eight, nine, 10, 20, 30, 40, 50, 100, or 200 non-contiguous amino acid substitutions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 non-contiguous amino acid substitutions relative to amino acids 1-446 of SEQ ID NO: 7. In yet other aspects of this embodiment, a BoNT/G light chain comprises a polypeptide having, e.g., at most one, two, three, four, five, six, seven, eight, nine, 10, 20, 30, 40, 50, 100 or 200 non-contiguous amino acid deletions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 non-contiguous amino acid deletions relative to amino acids 1-446 of SEQ ID NO: 7. In still other aspects of this embodiment, a BoNT/G light chain comprises a polypeptide having, e.g., at most one, two, three, four, five, six, seven, eight, nine, 10, 20, 30, 40, 50, 100 or 200 non-contiguous amino acid additions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50,100 or 200 non-contiguous amino acid additions relative to amino acids 1-446 of SEQ ID NO: 7.

In other aspects of this embodiment, a BoNT/G light chain comprises a polypeptide having, e.g., at most one, two, three, four, five, six, seven, eight, nine, 10, 20, 30, 40, 50, 100 or 200 contiguous amino acid substitutions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 contiguous amino acid substitutions relative to amino acids 1-446 of SEQ ID NO: 7. In yet other aspects of this embodiment, a BoNT/G light chain comprises a polypeptide having, e.g., at most one, two, three, four, five, six, seven, eight, nine, 10, 20, 30, 40, 50, 100 or 200 contiguous amino acid deletions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 contiguous amino acid deletions relative to amino acids 1-446 of SEQ ID NO: 7. In still other aspects of this embodiment, a BoNT/G light chain comprises a polypeptide having, e.g., at most one, two, three, four, five, six, seven, eight, nine, 10, 20, 30, 40, 50, 100 or 200 contiguous amino acid additions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 contiguous amino acid additions relative to amino acids 1-446 of SEQ ID NO: 7.

In another embodiment, a Clostridial toxin enzymatic domain comprises a TeNT light chain. In an aspect of this embodiment, a TeNT light chain comprises amino acids 1-457 of SEQ ID NO: 8. In another aspect of this embodiment, a TeNT light chain comprises a naturally occurring TeNT light chain variant, such as, e.g., a light chain from a TeNT isoform or a light chain from a TeNT subtype. In another aspect of this embodiment, a TeNT light chain comprises amino acids 1-457 of a naturally occurring TeNT light chain variant of SEQ ID NO: 8, such as, e.g., amino acids 1-457 of a TeNT isoform of SEQ ID NO: 8 or amino acids 1-457 of a TeNT subtype of SEQ ID NO: 8. In still another aspect of this embodiment, a TeNT light chain comprises a non-naturally occurring TeNT light chain variant, such as, e.g., a conservative TeNT light chain variant, a non-conservative TeNT light chain variant, a TeNT chimeric light chain, an active TeNT light chain fragment, or any combination thereof. In still another aspect of this embodiment, a TeNT light chain comprises amino acids 1-457 of a non-naturally occurring TeNT light chain variant of SEQ ID NO: 8, such as, e.g., amino acids 1-457 of a conservative TeNT light chain variant of SEQ ID NO: 8, amino acids 1-457 of a non-conservative TeNT light chain variant of SEQ ID NO: 8, amino acids 1-457 of an active TeNT light chain fragment of SEQ ID NO: 8, or any combination thereof.

In other aspects of this embodiment, a TeNT light chain comprises a polypeptide having, e.g., at least 70% amino acid identity with amino acids 1-457 of SEQ ID NO: 8, at least 75% amino acid identity with amino acids 1-457 of SEQ ID NO: 8, at least 80% amino acid identity with amino acids 1-457 of SEQ ID NO: 8, at least 85% amino acid identity with amino acids 1-457 of SEQ ID NO: 8, at least 90% amino acid identity with amino acids 1-457 of SEQ ID NO: 8 or at least 95% amino acid identity with amino acids 1-457 of SEQ ID NO: 8. In yet other aspects of this embodiment, a TeNT light chain comprises a polypeptide having, e.g., at most 70% amino acid identity with amino acids 1-457 of SEQ ID NO: 8, at most 75% amino acid identity with amino acids 1-457 of SEQ ID NO: 8, at most 80% amino acid identity with amino acids 1-457 of SEQ ID NO: 8, at most 85% amino acid identity with amino acids 1-457 of SEQ ID NO: 8, at most 90% amino acid identity with amino acids 1-457 of SEQ ID NO: 8 or at most 95% amino acid identity with amino acids 1-457 of SEQ ID NO: 8.

In other aspects of this embodiment, a TeNT light chain comprises a polypeptide having, e.g., at most one, two, three, four, five, six, seven, eight, nine, 10, 20, 30, 40, 50, 100, or 200 non-contiguous amino acid substitutions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 non-contiguous amino acid substitutions relative to amino acids 1-457 of SEQ ID NO: 8. In yet other aspects of this embodiment, a TeNT light chain comprises a polypeptide having, e.g., at most one, two, three, four, five, six, seven, eight, nine, 10, 20, 30, 40, 50, 100 or 200 non-contiguous amino acid deletions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 non-contiguous amino acid deletions relative to amino acids 1-457 of SEQ ID NO: 8. In still other aspects of this embodiment, a TeNT light chain comprises a polypeptide having, e.g., at most one, two, three, four, five, six, seven, eight, nine, 10, 20, 30, 40, 50, 100 or 200 non-contiguous amino acid additions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 non-contiguous amino acid additions relative to amino acids 1-457 of SEQ ID NO: 8.

In other aspects of this embodiment, a TeNT light chain comprises a polypeptide having, e.g., at most one, two, three, four, five, six, seven, eight, nine, 10, 20, 30, 40, 50, 100 or 200 contiguous amino acid substitutions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 contiguous amino acid substitutions relative to amino acids 1-457 of SEQ ID NO: 8. In yet other aspects of this embodiment, a TeNT light chain comprises a polypeptide having, e.g., at most one, two, three, four, five, six, seven, eight, nine, 10, 20, 30, 40, 50, 100 or 200 contiguous amino acid deletions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 contiguous amino acid deletions relative to amino acids 1-457 of SEQ ID NO: 8. In still other aspects of this embodiment, a TeNT light chain comprises a polypeptide having, e.g., at most one, two, three, four, five, six, seven, eight, nine, 10, 20, 30, 40, 50, 100 or 200 contiguous amino acid additions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 contiguous amino acid additions relative to amino acids 1-457 of SEQ ID NO: 8.

Aspects of the present invention provide, in part, a Clostridial toxin translocation domain. As used herein, the term "Clostridial toxin translocation domain" means any Clostridial toxin polypeptide that can execute the translocation step of the intoxication process that mediates Clostridial toxin light chain translocation. Thus, a Clostridial toxin translocation domain facilitates the movement of a Clostridial toxin light chain across a membrane and encompasses the movement of a Clostridial toxin light chain through the membrane an intracellular vesicle into the cytoplasm of a cell. Non-limiting examples of a Clostridial toxin translocation domain include, e.g., a Clostridial toxin $H_N$ region such as, e.g., a BoNT/A $H_N$ region, a BoNT/B $H_N$ region, a BoNT/C1 $H_N$ region, a BoNT/D $H_N$ region, a BoNT/E $H_N$ region, a BoNT/F $H_N$ region, a BoNT/G $H_N$ region, and a TeNT $H_N$ region.

A Clostridial toxin translocation domain includes, without limitation, naturally occurring Clostridial toxin $H_N$ region variants, such as, e.g., Clostridial toxin $H_N$ region isoforms and Clostridial toxin $H_N$ region subtypes; non-naturally occurring Clostridial toxin $H_N$ region variants, such as, e.g., conservative Clostridial toxin $H_N$ region variants, non-conservative Clostridial toxin $H_N$ region variants, Clostridial toxin $H_N$ region chimerics, active Clostridial toxin $H_N$ region fragments thereof, or any combination thereof.

As used herein, the term "Clostridial toxin $H_N$ region variant," whether naturally-occurring or non-naturally-occurring, means a Clostridial toxin $H_N$ region that has at least one amino acid change from the corresponding region of the disclosed reference sequences (see Table 1) and can be described in percent identity to the corresponding region of that reference sequence. Unless expressly indicated, all Clostridial toxin $H_N$ region variants disclosed in the present specification are capable of executing the translocation step of the intoxication process that mediates Clostridial toxin light chain translocation. As non-limiting examples, a BoNT/A $H_N$ region variant comprising amino acids 449-871 of SEQ ID NO: 1 will have at least one amino acid difference, such as, e.g., an amino acid substitution, deletion or addition, as compared to the amino acid region 449-871 of SEQ ID NO: 1; a BoNT/B $H_N$ region variant comprising amino acids 442-858 of SEQ ID NO: 2 will have at least one amino acid difference, such as, e.g., an amino acid substitution, deletion or addition, as compared to the amino acid region 442-858 of SEQ ID NO: 2; a BoNT/C1 $H_N$ region variant comprising amino acids 450-866 of SEQ ID NO: 3 will have at least one amino acid difference, such as, e.g., an amino acid substitution, deletion or addition, as compared to the amino acid region 450-866 of SEQ ID NO: 3; a BoNT/D $H_N$ region variant comprising amino acids 446-862 of SEQ ID NO: 4 will have at least one amino acid difference, such as, e.g., an amino acid substitution, deletion or addition, as compared to the amino acid region 446-862 of SEQ ID NO: 4; a BoNT/E $H_N$ region variant comprising amino acids 423-845 of SEQ ID NO: 5 will have at least one amino acid difference, such as, e.g., an amino acid substitution, deletion or addition, as compared to the amino acid region 423-845 of SEQ ID NO: 5; a BoNT/F $H_N$ region variant comprising amino acids 440-864 of SEQ ID NO: 6 will have at least one amino acid difference, such as, e.g., an amino acid substitution, deletion or addition, as compared to the amino acid region 440-864 of SEQ ID NO: 6; a BoNT/G $H_N$ region variant comprising amino acids 447-863 of SEQ ID NO: 7 will have at least one amino acid difference, such as, e.g., an amino acid substitution, deletion or addition, as compared to the amino acid region 447-863 of SEQ ID NO: 7; and a TeNT $H_N$ region variant comprising amino acids 458-879 of SEQ ID NO: 8 will have at least one amino acid difference, such as, e.g., an amino acid substitution, deletion or addition, as compared to the amino acid region 458-879 of SEQ ID NO: 8.

It is recognized by those of skill in the art that within each serotype of Clostridial toxin there can be naturally occurring Clostridial toxin $H_N$ region variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific $H_N$ region subtypes showing approximately 87% amino acid identity when compared to another BoNT/A $H_N$ region subtype. As used herein, the term "naturally occurring Clostridial toxin $H_N$ region variant" means any Clostridial toxin $H_N$ region produced by a naturally-occurring process, including, without limitation, Clostridial toxin $H_N$ region isoforms produced from alternatively-spliced transcripts, Clostridial toxin $H_N$ region isoforms produced by spontaneous mutation and Clostridial toxin $H_N$ region subtypes. A naturally occurring Clostridial toxin $H_N$ region variant can function in substantially the same manner as the reference Clostridial toxin $H_N$ region on which the naturally occurring Clostridial toxin $H_N$ region variant is based, and can be substituted for the reference Clostridial toxin $H_N$ region in any aspect of the present invention. A naturally occurring Clostridial toxin $H_N$ region variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin $H_N$ region on which the naturally occurring Clostridial toxin $H_N$ region variant is based. A naturally occurring Clostridial toxin $H_N$ region variant can also substitute at least 10 contiguous amino acids, at least 15 contiguous amino acids, at least 20 contiguous amino acids, or at least 25 contiguous amino acids from the reference Clostridial toxin $H_N$ region on which the naturally occurring Clostridial toxin $H_N$ region variant is based, that possess at least 50% amino acid identity, 65% amino acid identity, 75% amino acid identity, 85% amino acid identity or 95% amino acid identity to the reference Clostridial toxin $H_N$ region on which the naturally occurring Clostridial toxin $H_N$ region variant is based.

A non-limiting examples of a naturally occurring Clostridial toxin $H_N$ region variant is a Clostridial toxin $H_N$ region isoform such as, e.g., a BoNT/A $H_N$ region isoform, a BoNT/B $H_N$ region isoform, a BoNT/C1 $H_N$ region isoform, a BoNT/D $H_N$ region isoform, a BoNT/E $H_N$ region isoform, a BoNT/F $H_N$ region isoform, a BoNT/G $H_N$ region isoform, and a TeNT $H_N$ region isoform. A Clostridial toxin $H_N$ region isoform can function in substantially the same manner as the reference Clostridial toxin $H_N$ region on which the Clostridial toxin $H_N$ region isoform is based, and can be substituted for the reference Clostridial toxin $H_N$ region in any aspect of the present invention.

Another non-limiting examples of a naturally occurring Clostridial toxin $H_N$ region variant is a Clostridial toxin $H_N$ region subtype such as, e.g., a $H_N$ region from subtype BoNT/A1, BoNT/A2, BoNT/A3 and BoNT/A4; a $H_N$ region from subtype BoNT/B1, BoNT/B2, BoNT/B bivalent and BoNT/B nonproteolytic; a $H_N$ region from subtype BoNT/C1-1 and BoNT/C1-2; a $H_N$ region from subtype BoNT/E1, BoNT/E2 and BoNT/E3; and a $H_N$ region from subtype BoNT/F1, BoNT/F2, BoNT/F3 and BoNT/F4. A Clostridial toxin $H_N$ region subtype can function in substantially the same manner as the reference Clostridial toxin $H_N$ region on which the Clostridial toxin $H_N$ region subtype is based, and can be substituted for the reference Clostridial toxin $H_N$ region in any aspect of the present invention.

As used herein, the term "non-naturally occurring Clostridial toxin $H_N$ region variant" means any Clostridial toxin $H_N$ region produced with the aid of human manipulation, including, without limitation, Clostridial toxin $H_N$ regions produced by genetic engineering using random mutagenesis or rational design and Clostridial toxin $H_N$ regions produced by chemical synthesis. Non-limiting examples of non-naturally occurring Clostridial toxin $H_N$ region variants include, e.g., conservative Clostridial toxin $H_N$ region variants, non-conservative Clostridial toxin $H_N$ region variants, Clostridial toxin $H_N$ region chimeric variants and active Clostridial toxin $H_N$ region fragments.

As used herein, the term "conservative Clostridial toxin $H_N$ region variant" means a Clostridial toxin $H_N$ region that has at least one amino acid substituted by another amino acid or an amino acid analog that has at least one property similar to that of the original amino acid from the reference Clostridial toxin $H_N$ region sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin $H_N$ region variant can function in substantially the same manner as the reference Clostridial toxin $H_N$ region on which the conservative Clostridial toxin $H_N$ region variant is based, and can be substituted for the reference Clostridial toxin $H_N$ region in any aspect of the present invention. A conservative Clostridial toxin $H_N$ region variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin $H_N$ region on which the conservative Clostridial toxin $H_N$ region variant is based. A conservative Clostridial toxin $H_N$ region variant can also substitute at least 10 contiguous amino acids, at least 15 contiguous amino acids, at least 20 contiguous amino acids, or at least 25 contiguous amino acids from the reference Clostridial toxin $H_N$ region on which the conservative Clostridial toxin $H_N$ region variant is based, that possess at least 50% amino acid identity, 65% amino acid identity, 75% amino acid identity, 85% amino acid identity or 95% amino acid identity to the reference Clostridial toxin $H_N$ region on which the conservative Clostridial toxin $H_N$ region variant is based. Non-limiting examples of a conservative Clostridial toxin $H_N$ region variant include, e.g., conservative BoNT/A $H_N$ region variants, conservative BoNT/B $H_N$ region variants, conservative BoNT/C1 $H_N$ region variants, conservative BoNT/D $H_N$ region variants, conservative BoNT/E $H_N$ region variants, conservative BoNT/F $H_N$ region variants, conservative BoNT/G $H_N$ region variants, and conservative TeNT $H_N$ region variants.

As used herein, the term "non-conservative Clostridial toxin $H_N$ region variant" means a Clostridial toxin $H_N$ region in which 1) at least one amino acid is deleted from the reference Clostridial toxin $H_N$ region on which the non-conservative Clostridial toxin $H_N$ region variant is based; 2) at least one amino acid added to the reference Clostridial toxin $H_N$ region on which the non-conservative Clostridial toxin $H_N$ region is based; or 3) at least one amino acid is substituted by another amino acid or an amino acid analog that does not share any property similar to that of the original amino acid from the reference Clostridial toxin $H_N$ region sequence (Table 1). A non-conservative Clostridial toxin $H_N$ region variant can function in substantially the same manner as the reference Clostridial toxin $H_N$ region on which the non-conservative Clostridial toxin $H_N$ region variant is based, and can be substituted for the reference Clostridial toxin $H_N$ region in any aspect of the present invention. A non-conservative Clostridial toxin $H_N$ region variant can delete one or more amino acids, two or more amino acids, three or more amino acids, four or more amino acids, five or more amino acids, and ten or more amino acids from the reference Clostridial toxin $H_N$ region on which the non-conservative Clostridial toxin $H_N$ region variant is based. A non-conservative Clostridial toxin $H_N$ region variant can add one or more amino acids, two or more amino acids, three or more amino acids, four or more amino acids, five or more amino acids, and ten or more amino acids to the reference Clostridial toxin $H_N$ region on which the non-conservative Clostridial toxin $H_N$ region variant is based. A non-conservative Clostridial toxin $H_N$ region variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin $H_N$ region on which the non-conservative Clostridial toxin $H_N$ region variant is based. A non-conservative Clostridial toxin $H_N$ region variant can also substitute at least 10 contiguous amino acids, at least 15 contiguous amino acids, at least 20 contiguous amino acids, or at least 25 contiguous amino acids from the reference Clostridial toxin $H_N$ region on which the non-conservative Clostridial toxin $H_N$ region variant is based, that possess at least 50% amino acid identity, 65% amino acid identity, 75% amino acid identity, 85% amino acid identity or 95% amino acid identity to the reference Clostridial toxin $H_N$ region on which the non-conservative Clostridial toxin $H_N$ region variant is based. Non-limiting examples of a non-conservative Clostridial toxin $H_N$ region variant include, e.g., non-conservative BoNT/A $H_N$ region variants, non-conservative BoNT/B $H_N$ region variants, non-conservative BoNT/C1 $H_N$ region variants, non-conservative BoNT/D $H_N$ region variants, non-conservative BoNT/E $H_N$ region variants, non-conservative BoNT/F $H_N$ region variants, non-conservative BoNT/G $H_N$ region variants, and non-conservative TeNT $H_N$ region variants.

As used herein, the term "Clostridial toxin $H_N$ region chimeric" means a polypeptide comprising at least a portion of a Clostridial toxin $H_N$ region and at least a portion of at least one other polypeptide to form a toxin $H_N$ region with at least one property different from the reference Clostridial toxin $H_N$ regions of Table 1, with the proviso that this Clostridial toxin $H_N$ region chimeric is still capable of specifically targeting the core components of the neurotransmitter release apparatus and thus participate in executing the overall cellular mechanism whereby a Clostridial toxin proteolytically cleaves a substrate.

As used herein, the term "active Clostridial toxin $H_N$ region fragment" means any of a variety of Clostridial toxin fragments comprising the $H_N$ region can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The $H_N$ regions from the heavy chains of Clostridial toxins are approximately 410-430 amino acids in length and comprise a translocation domain (Table 1). Research has shown that the entire length of a $H_N$ region from a Clostridial toxin heavy chain is not necessary for the translocating activity of the translocation domain. Thus, aspects of this embodiment can include Clostridial toxin $H_N$ regions comprising a translocation domain having a length of, e.g., at least 350 amino acids, at least 375 amino acids, at least 400 amino acids and at least 425 amino acids. Other aspects of this embodiment can include Clostridial toxin $H_N$ regions comprising translocation domain having a length of, e.g., at most 350 amino acids, at most 375 amino acids, at most 400 amino acids and at most 425 amino acids.

Any of a variety of sequence alignment methods can be used to determine percent identity of naturally-occurring Clostridial toxin $H_N$ region variants and non-naturally-occurring Clostridial toxin $H_N$ region variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a Clostridial toxin translocation domain. In an aspect of this embodiment, a Clostridial toxin translocation domain comprises a naturally occurring Clostridial toxin $H_N$ region variant, such as, e.g., a Clostridial toxin $H_N$ region isoform or a Clostridial toxin $H_N$ region subtype. In another aspect of this embodiment, a Clostridial toxin translocation domain comprises a non-naturally occurring Clostridial toxin $H_N$ region variant, such as, e.g., a conservative Clostridial toxin $H_N$ region variant, a non-conservative Clostridial toxin $H_N$ region variant, a Clostridial toxin chimeric $H_N$ region, an active Clostridial toxin $H_N$ region fragment, or any combination thereof.

In another embodiment, a Clostridial toxin translocation domain comprises a BoNT/A $H_N$ region. In an aspect of this embodiment, a BoNT/A $H_N$ region comprises amino acids 449-871 of SEQ ID NO: 1. In another aspect of this embodiment, a BoNT/A $H_N$ region comprises a naturally occurring BoNT/A $H_N$ region variant, such as, e.g., a $H_N$ region from a BoNT/A isoform or a $H_N$ region from a BoNT/A subtype. In another aspect of this embodiment, a BoNT/A $H_N$ region comprises amino acids 449-871 of a naturally occurring BoNT/A $H_N$ region variant of SEQ ID NO: 1, such as, e.g., amino acids 449-871 of a BoNT/A isoform of SEQ ID NO: 1 or amino acids 449-871 of a BoNT/A subtype of SEQ ID NO: 1. In still another aspect of this embodiment, a BoNT/A $H_N$ region comprises a non-naturally occurring BoNT/A $H_N$ region variant, such as, e.g., a conservative BoNT/A $H_N$ region variant, a non-conservative BoNT/A $H_N$ region variant, a BoNT/A chimeric $H_N$ region, an active BoNT/A $H_N$ region fragment, or any combination thereof. In still another aspect of this embodiment, a BoNT/A $H_N$ region comprises amino acids 449-871 of a non-naturally occurring BoNT/A $H_N$ region variant of SEQ ID NO: 1, such as, e.g., amino acids 449-871 of a conservative BoNT/A $H_N$ region variant of SEQ ID NO: 1, amino acids 449-871 of a non-conservative BoNT/A $H_N$ region variant of SEQ ID NO: 1, amino acids 449-871 of an active BoNT/A $H_N$ region fragment of SEQ ID NO: 1, or any combination thereof.

In other aspects of this embodiment, a BoNT/A $H_N$ region comprises a polypeptide having, e.g., at least 70% amino acid identity with amino acids 449-871 of SEQ ID NO: 1, at least 75% amino acid identity with amino acids 449-871 of SEQ ID NO: 1, at least 80% amino acid identity with amino acids 449-871 of SEQ ID NO: 1, at least 85% amino acid identity with amino acids 449-871 of SEQ ID NO: 1, at least 90% amino acid identity with amino acids 449-871 of SEQ ID NO: 1 or at least 95% amino acid identity with amino acids 449-871 of SEQ ID NO: 1. In yet other aspects of this embodiment, a BoNT/A $H_N$ region comprises a polypeptide having, e.g., at most 70% amino acid identity with amino acids 449-871 of SEQ ID NO: 1, at most 75% amino acid identity with amino acids 449-871 of SEQ ID NO: 1, at most 80% amino acid identity with amino acids 449-871 of SEQ ID NO: 1, at most 85% amino acid identity with amino acids 449-871 of SEQ ID NO: 1, at most 90% amino acid identity with amino acids 449-871 of SEQ ID NO: 1 or at most 95% amino acid identity with amino acids 449-871 of SEQ ID NO: 1.

In other aspects of this embodiment, a BoNT/A $H_N$ region comprises a polypeptide having, e.g., at most one, two, three, four, five, six, seven, eight, nine, 10, 20, 30, 40, 50, 100, or 200 non-contiguous amino acid substitutions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 non-contiguous amino acid substitutions relative to amino acids 449-871 of SEQ ID NO: 1. In yet other aspects of this embodiment, a BoNT/A $H_N$ region comprises a polypeptide having, e.g., at most one, two, three, four, five, six, seven, eight, nine, 10, 20, 30, 40, 50, 100 or 200 non-contiguous amino acid deletions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 non-contiguous amino acid deletions relative to amino acids 449-871 of SEQ ID NO: 1. In still other aspects of this embodiment, a BoNT/A $H_N$ region comprises a polypeptide having, e.g., at most one, two, three, four, five, six, seven, eight, nine, 10, 20, 30, 40, 50, 100 or 200 non-contiguous amino acid additions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 non-contiguous amino acid additions relative to amino acids 449-871 of SEQ ID NO: 1.

In other aspects of this embodiment, a BoNT/A $H_N$ region comprises a polypeptide having, e.g., at most one, two, three, four, five, six, seven, eight, nine, 10, 20, 30, 40, 50, 100 or 200 contiguous amino acid substitutions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 contiguous amino acid substitutions relative to amino acids 449-871 of SEQ ID NO: 1. In yet other aspects of this embodiment, a BoNT/A $H_N$ region comprises a polypeptide having, e.g., at most one, two, three, four, five, six, seven, eight, nine, 10, 20, 30, 40, 50, 100 or 200 contiguous amino acid deletions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 contiguous amino acid deletions relative to amino acids 449-871 of SEQ ID NO: 1. In still other aspects of this embodiment, a BoNT/A $H_N$ region comprises a polypeptide having, e.g., at most one, two, three, four, five, six, seven, eight, nine, 10, 20, 30, 40, 50, 100 or 200 contiguous amino acid additions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 contiguous amino acid additions relative to amino acids 449-871 of SEQ ID NO: 1.

In another embodiment, a Clostridial toxin translocation domain comprises a BoNT/B $H_N$ region. In an aspect of this embodiment, a BoNT/B $H_N$ region comprises amino acids 442-858 of SEQ ID NO: 2. In another aspect of this embodiment, a BoNT/B $H_N$ region comprises a naturally occurring BoNT/B $H_N$ region variant, such as, e.g., a $H_N$ region from a BoNT/B isoform or a $H_N$ region from a BoNT/B subtype. In another aspect of this embodiment, a BoNT/B $H_N$ region comprises amino acids 442-858 of a naturally occurring BoNT/B $H_N$ region variant of SEQ ID NO: 2, such as, e.g., amino acids 442-858 of a BoNT/B isoform of SEQ ID NO: 2 or amino acids 442-858 of a BoNT/B subtype of SEQ ID NO: 2. In still another aspect of this embodiment, a BoNT/B $H_N$ region comprises a non-naturally occurring BoNT/B $H_N$ region variant, such as, e.g., a conservative BoNT/B $H_N$ region variant, a non-conservative BoNT/B $H_N$ region variant, a BoNT/B chimeric $H_N$ region, an active BoNT/B $H_N$ region fragment, or any combination thereof. In still another aspect of this embodiment, a BoNT/B $H_N$ region comprises amino acids 442-858 of a non-naturally occurring BoNT/B $H_N$ region variant of SEQ ID NO: 2, such as, e.g., amino acids 442-858 of a conservative BoNT/B $H_N$ region variant of SEQ ID NO: 2, amino acids 442-858 of a non-conservative BoNT/B $H_N$ region variant of SEQ ID NO: 2, amino acids 442-858 of an active BoNT/B $H_N$ region fragment of SEQ ID NO: 2, or any combination thereof.

In other aspects of this embodiment, a BoNT/B $H_N$ region comprises a polypeptide having, e.g., at least 70% amino acid identity with amino acids 442-858 of SEQ ID NO: 2, at least 75% amino acid identity with amino acids 442-858 of SEQ ID NO: 2, at least 80% amino acid identity with amino acids 442-858 of SEQ ID NO: 2, at least 85% amino acid identity with amino acids 442-858 of SEQ ID NO: 2, at least 90% amino acid identity with amino acids 442-858 of SEQ ID NO: 2 or at least 95% amino acid identity with amino acids 442-858 of SEQ ID NO: 2. In yet other aspects of this embodiment, a BoNT/B $H_N$ region comprises a polypeptide having, e.g., at most 70% amino acid identity with amino acids 442-858 of SEQ ID NO: 2, at most 75% amino acid identity with amino acids 442-858 of SEQ ID NO: 2, at most 80% amino acid identity with amino acids 442-858 of SEQ ID NO: 2, at most 85% amino acid identity with amino acids 442-858 of SEQ ID NO: 2, at most 90% amino acid identity with amino acids 442-858 of SEQ ID NO: 2 or at most 95% amino acid identity with amino acids 442-858 of SEQ ID NO: 2.

In other aspects of this embodiment, a BoNT/B $H_N$ region comprises a polypeptide having, e.g., at most one, two, three, four, five, six, seven, eight, nine, 10, 20, 30, 40, 50, 100, or 200 non-contiguous amino acid substitutions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 non-contiguous amino acid substitutions relative to amino acids 442-858 of SEQ ID NO: 2. In yet other aspects of this embodiment, a BoNT/B $H_N$ region comprises a polypeptide having, e.g., at most one, two, three, four, five, six, seven, eight, nine, 10, 20, 30, 40, 50, 100 or 200 non-contiguous amino acid deletions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 non-contiguous amino acid deletions relative to amino acids 442-858 of SEQ ID NO: 2. In still other aspects of this embodiment, a BoNT/B $H_N$ region comprises a polypeptide having, e.g., at most one, two, three, four, five, six, seven, eight, nine, 10, 20, 30, 40, 50, 100 or 200 non-contiguous amino acid additions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 non-contiguous amino acid additions relative to amino acids 442-858 of SEQ ID NO: 2.

In other aspects of this embodiment, a BoNT/B $H_N$ region comprises a polypeptide having, e.g., at most one, two, three, four, five, six, seven, eight, nine, 10, 20, 30, 40, 50, 100 or 200 contiguous amino acid substitutions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 contiguous amino acid substitutions relative to amino acids 442-858 of SEQ ID NO: 2. In yet other aspects of this embodiment, a BoNT/B $H_N$ region comprises a polypeptide having, e.g., at most one, two, three, four, five, six, seven, eight, nine, 10, 20, 30, 40, 50, 100 or 200 contiguous amino acid deletions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 contiguous amino acid deletions relative to amino acids 442-858 of SEQ ID NO: 2. In still other aspects of this embodiment, a BoNT/B $H_N$ region comprises a polypeptide having, e.g., at most one, two, three, four, five, six, seven, eight, nine, 10, 20, 30, 40, 50, 100 or 200 contiguous amino acid additions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 contiguous amino acid additions relative to amino acids 442-858 of SEQ ID NO: 2.

In another embodiment, a Clostridial toxin translocation domain comprises a BoNT/C1 $H_N$ region. In an aspect of this embodiment, a BoNT/C1 $H_N$ region comprises amino acids 450-866 of SEQ ID NO: 3. In another aspect of this embodiment, a BoNT/C1 $H_N$ region comprises a naturally occurring BoNT/C1 $H_N$ region variant, such as, e.g., a $H_N$ region from a BoNT/C1 isoform or a $H_N$ region from a BoNT/C1 subtype. In another aspect of this embodiment, a BoNT/C1 $H_N$ region comprises amino acids 450-866 of a naturally occurring BoNT/C1 $H_N$ region variant of SEQ ID NO: 3, such as, e.g., amino acids 450-866 of a BoNT/C1 isoform of SEQ ID NO: 3 or amino acids 450-866 of a BoNT/C1 subtype of SEQ ID NO: 3. In still another aspect of this embodiment, a BoNT/C1 $H_N$ region comprises a non-naturally occurring BoNT/C1 $H_N$ region variant, such as, e.g., a conservative BoNT/C1 $H_N$ region variant, a non-conservative BoNT/C1 $H_N$ region variant, a BoNT/C1 chimeric $H_N$ region, an active BoNT/C1 $H_N$ region fragment, or any combination thereof. In still another aspect of this embodiment, a BoNT/C1 $H_N$ region comprises amino acids 450-866 of a non-naturally occurring BoNT/C1 $H_N$ region variant of SEQ ID NO: 3, such as, e.g., amino acids 450-866 of a conservative BoNT/C1 $H_N$ region variant of SEQ ID NO: 3, amino acids 450-866 of a non-conservative BoNT/C1 $H_N$ region variant of SEQ ID NO: 3, amino acids 450-866 of an active BoNT/C1 $H_N$ region fragment of SEQ ID NO: 3, or any combination thereof.

In other aspects of this embodiment, a BoNT/C1 $H_N$ region comprises a polypeptide having, e.g., at least 70% amino acid identity with amino acids 450-866 of SEQ ID NO: 3, at least 75% amino acid identity with amino acids 450-866 of SEQ ID NO: 3, at least 80% amino acid identity with amino acids 450-866 of SEQ ID NO: 3, at least 85% amino acid identity with amino acids 450-866 of SEQ ID NO: 3, at least 90% amino acid identity with amino acids 450-866 of SEQ ID NO: 3 or at least 95% amino acid identity with amino acids 450-866 of SEQ ID NO: 3. In yet other aspects of this embodiment, a BoNT/C1 $H_N$ region comprises a polypeptide having, e.g., at most 70% amino acid identity with amino acids 450-866 of SEQ ID NO: 3, at most 75% amino acid identity with amino acids 450-866 of SEQ ID NO: 3, at most 80% amino acid identity with amino acids 450-866 of SEQ ID NO: 3, at most 85% amino acid identity with amino acids 450-866 of SEQ ID NO: 3, at most 90% amino acid identity with amino acids 450-866 of SEQ ID NO: 3 or at most 95% amino acid identity with amino acids 450-866 of SEQ ID NO: 3.

In other aspects of this embodiment, a BoNT/C1 $H_N$ region comprises a polypeptide having, e.g., at most one, two, three, four, five, six, seven, eight, nine, 10, 20, 30, 40, 50, 100, or 200 non-contiguous amino acid substitutions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 non-contiguous amino acid substitutions relative to amino acids 450-866 of SEQ ID NO: 3. In yet other aspects of this embodiment, a BoNT/C1 $H_N$ region comprises a polypeptide having, e.g., at most one, two, three, four, five, six, seven, eight, nine, 10, 20, 30, 40, 50, 100 or 200 non-contiguous amino acid deletions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 non-contiguous amino acid deletions relative to amino acids 450-866 of SEQ ID NO: 3. In still other aspects of this embodiment, a BoNT/C1 $H_N$ region comprises a polypeptide having, e.g., at most one, two, three, four, five, six, seven, eight, nine, 10, 20, 30, 40, 50, 100 or 200 non-contiguous amino acid additions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 non-contiguous amino acid additions relative to amino acids 450-866 of SEQ ID NO: 3.

In other aspects of this embodiment, a BoNT/C1 $H_N$ region comprises a polypeptide having, e.g., at most one, two, three, four, five, six, seven, eight, nine, 10, 20, 30, 40, 50, 100 or 200 contiguous amino acid substitutions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 contiguous amino acid substitutions relative to amino acids 450-866 of SEQ ID NO: 3. In yet other aspects of this embodiment, a BoNT/C1 $H_N$ region comprises a polypeptide having, e.g., at most one, two, three, four, five, six, seven, eight, nine, 10, 20, 30, 40, 50, 100 or 200 contiguous amino acid deletions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 contiguous amino acid deletions relative to amino acids 450-866 of SEQ ID NO: 3. In still other aspects of this embodiment, a BoNT/C1 $H_N$ region comprises a polypeptide having, e.g., at most one, two, three, four, five, six, seven, eight, nine, 10, 20, 30, 40, 50, 100 or 200 contiguous amino acid additions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 contiguous amino acid additions relative to amino acids 450-866 of SEQ ID NO: 3.

In another embodiment, a Clostridial toxin translocation domain comprises a BoNT/D $H_N$ region. In an aspect of this embodiment, a BoNT/D $H_N$ region comprises amino acids 446-862 of SEQ ID NO: 4. In another aspect of this embodiment, a BoNT/D $H_N$ region comprises a naturally occurring BoNT/D $H_N$ region variant, such as, e.g., a $H_N$ region from a BoNT/D isoform or a $H_N$ region from a BoNT/D subtype. In another aspect of this embodiment, a BoNT/D $H_N$ region comprises amino acids 446-862 of a naturally occurring BoNT/D $H_N$ region variant of SEQ ID NO: 4, such as, e.g., amino acids 446-862 of a BoNT/D isoform of SEQ ID NO: 4 or amino acids 446-862 of a BoNT/D subtype of SEQ ID NO: 4. In still another aspect of this embodiment, a BoNT/D $H_N$ region comprises a non-naturally occurring BoNT/D $H_N$ region variant, such as, e.g., a conservative BoNT/D $H_N$ region variant, a non-conservative BoNT/D $H_N$ region variant, a BoNT/D chimeric $H_N$ region, an active BoNT/D $H_N$ region fragment, or any combination thereof. In still another aspect of this embodiment, a BoNT/D $H_N$ region comprises amino acids 446-862 of a non-naturally occurring BoNT/D $H_N$ region variant of SEQ ID NO: 4, such as, e.g., amino acids 446-862 of a conservative BoNT/D $H_N$ region variant of SEQ ID NO: 4, amino acids 446-862 of a non-conservative BoNT/D $H_N$ region variant of SEQ ID NO: 4, amino acids 446-862 of an active BoNT/D $H_N$ region fragment of SEQ ID NO: 4, or any combination thereof.

In other aspects of this embodiment, a BoNT/D $H_N$ region comprises a polypeptide having, e.g., at least 70% amino acid identity with amino acids 446-862 of SEQ ID NO: 4, at least 75% amino acid identity with amino acids 446-862 of SEQ ID NO: 4, at least 80% amino acid identity with amino acids 446-862 of SEQ ID NO: 4, at least 85% amino acid identity with amino acids 446-862 of SEQ ID NO: 4, at least 90% amino acid identity with amino acids 446-862 of SEQ ID NO: 4 or at least 95% amino acid identity with amino acids 446-862 of SEQ ID NO: 4. In yet other aspects of this embodiment, a BoNT/D $H_N$ region comprises a polypeptide having, e.g., at most 70% amino acid identity with amino acids 446-862 of SEQ ID NO: 4, at most 75% amino acid identity with amino acids 446-862 of SEQ ID NO: 4, at most 80% amino acid identity with amino acids 446-862 of SEQ ID NO: 4, at most 85% amino acid identity with amino acids 446-862 of SEQ ID NO: 4, at most 90% amino acid identity with amino acids 446-862 of SEQ ID NO: 4 or at most 95% amino acid identity with amino acids 446-862 of SEQ ID NO: 4.

In other aspects of this embodiment, a BoNT/D $H_N$ region comprises a polypeptide having, e.g., at most one, two, three, four, five, six, seven, eight, nine, 10, 20, 30, 40, 50, 100, or 200 non-contiguous amino acid substitutions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 non-contiguous amino acid substitutions relative to amino acids 446-862 of SEQ ID NO: 4. In yet other aspects of this embodiment, a BoNT/D $H_N$ region comprises a polypeptide having, e.g., at most one, two, three, four, five, six, seven, eight, nine, 10, 20, 30, 40, 50, 100 or 200 non-contiguous amino acid deletions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 non-contiguous amino acid deletions relative to amino acids 446-862 of SEQ ID NO: 4. In still other aspects of this embodiment, a BoNT/D $H_N$ region comprises a polypeptide having, e.g., at most one, two, three, four, five, six, seven, eight, nine, 10, 20, 30, 40, 50, 100 or 200 non-contiguous amino acid additions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 non-contiguous amino acid additions relative to amino acids 446-862 of SEQ ID NO: 4.

In other aspects of this embodiment, a BoNT/D $H_N$ region comprises a polypeptide having, e.g., at most one, two, three, four, five, six, seven, eight, nine, 10, 20, 30, 40, 50, 100 or 200 contiguous amino acid substitutions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 contiguous amino acid substitutions relative to amino acids 446-862 of SEQ ID NO: 4. In yet other aspects of this embodiment, a BoNT/D $H_N$ region comprises a polypeptide having, e.g., at most one, two, three, four, five, six, seven, eight, nine, 10, 20, 30, 40, 50, 100 or 200 contiguous amino acid deletions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 contiguous amino acid deletions relative to amino acids 446-862 of SEQ ID NO: 4. In still other aspects of this embodiment, a BoNT/D $H_N$ region comprises a polypeptide having, e.g., at most one, two, three, four, five, six, seven, eight, nine, 10, 20, 30, 40, 50, 100 or 200 contiguous amino acid additions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 contiguous amino acid additions relative to amino acids 446-862 of SEQ ID NO: 4.

In another embodiment, a Clostridial toxin translocation domain comprises a BoNT/E $H_N$ region. In an aspect of this embodiment, a BoNT/E $H_N$ region comprises amino acids 423-845 of SEQ ID NO: 5. In another aspect of this embodiment, a BoNT/E $H_N$ region comprises a naturally occurring BoNT/E $H_N$ region variant, such as, e.g., a $H_N$ region from a BoNT/E isoform or a $H_N$ region from a BoNT/E subtype. In another aspect of this embodiment, a BoNT/E $H_N$ region comprises amino acids 423-845 of a naturally occurring BoNT/E $H_N$ region variant of SEQ ID NO: 5, such as, e.g., amino acids 423-845 of a BoNT/E isoform of SEQ ID NO: 5 or amino acids 423-845 of a BoNT/E subtype of SEQ ID NO: 5. In still another aspect of this embodiment, a BoNT/E $H_N$ region comprises a non-naturally occurring BoNT/E $H_N$ region variant, such as, e.g., a conservative BoNT/E $H_N$ region variant, a non-conservative BoNT/E $H_N$ region variant, a BoNT/E chimeric $H_N$ region, an active BoNT/E $H_N$ region fragment, or any combination thereof. In still another aspect of this embodiment, a BoNT/E $H_N$ region comprises amino acids 423-845 of a non-naturally occurring BoNT/E $H_N$ region variant of SEQ ID NO: 5, such as, e.g., amino acids 423-845 of a conservative BoNT/E $H_N$ region variant of SEQ ID NO: 5, amino acids 423-845 of a non-conservative BoNT/E $H_N$ region variant of SEQ ID NO: 5, amino acids 423-845 of an active BoNT/E $H_N$ region fragment of SEQ ID NO: 5, or any combination thereof.

In other aspects of this embodiment, a BoNT/E $H_N$ region comprises a polypeptide having, e.g., at least 70% amino acid identity with amino acids 423-845 of SEQ ID NO: 5, at least 75% amino acid identity with amino acids 423-845 of SEQ ID NO: 5, at least 80% amino acid identity with amino acids 423-845 of SEQ ID NO: 5, at least 85% amino acid identity with amino acids 423-845 of SEQ ID NO: 5, at least 90% amino acid identity with amino acids 423-845 of SEQ ID NO: 5 or at least 95% amino acid identity with amino acids 423-845 of SEQ ID NO: 5. In yet other aspects of this embodiment, a BoNT/E $H_N$ region comprises a polypeptide having, e.g., at most 70% amino acid identity with amino acids 423-845 of SEQ ID NO: 5, at most 75% amino acid identity with amino acids 423-845 of SEQ ID NO: 5, at most 80% amino acid identity with amino acids 423-845 of SEQ ID NO: 5, at most 85% amino acid identity with amino acids 423-845 of SEQ ID NO: 5, at most 90% amino acid identity with amino acids 423-845 of SEQ ID NO: 5 or at most 95% amino acid identity with amino acids 423-845 of SEQ ID NO: 5.

In other aspects of this embodiment, a BoNT/E $H_N$ region comprises a polypeptide having, e.g., at most one, two, three, four, five, six, seven, eight, nine, 10, 20, 30, 40, 50, 100, or 200 non-contiguous amino acid substitutions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 non-contiguous amino acid substitutions relative to amino acids 423-845 of SEQ ID NO: 5. In yet other aspects of this embodiment, a BoNT/E $H_N$ region comprises a polypeptide having, e.g., at most one, two, three, four, five, six, seven, eight, nine, 10, 20, 30, 40, 50, 100 or 200 non-contiguous amino acid deletions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 non-contiguous amino acid deletions relative to amino acids 423-845 of SEQ ID NO: 5. In still other aspects of this embodiment, a BoNT/E $H_N$ region comprises a polypeptide having, e.g., at most one, two, three, four, five, six, seven, eight, nine, 10, 20, 30, 40, 50, 100 or 200 non-contiguous amino acid additions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 non-contiguous amino acid additions relative to amino acids 423-845 of SEQ ID NO: 5.

In other aspects of this embodiment, a BoNT/E $H_N$ region comprises a polypeptide having, e.g., at most one, two, three, four, five, six, seven, eight, nine, 10, 20, 30, 40, 50, 100 or 200 contiguous amino acid substitutions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 contiguous amino acid substitutions relative to amino acids 423-845 of SEQ ID NO: 5. In yet other aspects of this embodiment, a BoNT/E $H_N$ region comprises a polypeptide having, e.g., at most one, two, three, four, five, six, seven, eight, nine, 10, 20, 30, 40, 50, 100 or 200 contiguous amino acid deletions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 contiguous amino acid deletions relative to amino acids 423-845 of SEQ ID NO: 5. In still other aspects of this embodiment, a BoNT/E $H_N$ region comprises a polypeptide having, e.g., at most one, two, three, four, five, six, seven, eight, nine, 10, 20, 30, 40, 50, 100 or 200 contiguous amino acid additions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 contiguous amino acid additions relative to amino acids 423-845 of SEQ ID NO: 5.

In another embodiment, a Clostridial toxin translocation domain comprises a BoNT/F $H_N$ region. In an aspect of this embodiment, a BoNT/F $H_N$ region comprises amino acids 440-864 of SEQ ID NO: 6. In another aspect of this embodiment, a BoNT/F $H_N$ region comprises a naturally occurring BoNT/F $H_N$ region variant, such as, e.g., a $H_N$ region from a BoNT/F isoform or a $H_N$ region from a BoNT/F subtype. In another aspect of this embodiment, a BoNT/F $H_N$ region comprises amino acids 440-864 of a naturally occurring BoNT/F $H_N$ region variant of SEQ ID NO: 6, such as, e.g., amino acids 440-864 of a BoNT/F isoform of SEQ ID NO: 6 or amino acids 440-864 of a BoNT/F subtype of SEQ ID NO: 6. In still another aspect of this embodiment, a BoNT/F $H_N$ region comprises a non-naturally occurring BoNT/F $H_N$ region variant, such as, e.g., a conservative BoNT/F $H_N$ region variant, a non-conservative BoNT/F $H_N$ region variant, a BoNT/F chimeric $H_N$ region, an active BoNT/F $H_N$ region fragment, or any combination thereof. In still another aspect of this embodiment, a BoNT/F $H_N$ region comprises amino acids 440-864 of a non-naturally occurring BoNT/F $H_N$ region variant of SEQ ID NO: 6, such as, e.g., amino acids 440-864 of a conservative BoNT/F $H_N$ region variant of SEQ ID NO: 6, amino acids 440-864 of a non-conservative BoNT/F $H_N$ region variant of SEQ ID NO: 6, amino acids 440-864 of an active BoNT/F $H_N$ region fragment of SEQ ID NO: 6, or any combination thereof.

In other aspects of this embodiment, a BoNT/F $H_N$ region comprises a polypeptide having, e.g., at least 70% amino acid identity with amino acids 440-864 of SEQ ID NO: 6, at least 75% amino acid identity with amino acids 440-864 of SEQ ID NO: 6, at least 80% amino acid identity with amino acids 440-864 of SEQ ID NO: 6, at least 85% amino acid identity with amino acids 440-864 of SEQ ID NO: 6, at least 90% amino acid identity with amino acids 440-864 of SEQ ID NO: 6 or at least 95% amino acid identity with amino acids 440-864 of SEQ ID NO: 6. In yet other aspects of this embodiment, a BoNT/F $H_N$ region comprises a polypeptide having, e.g., at most 70% amino acid identity with amino acids 440-864 of SEQ ID NO: 6, at most 75% amino acid identity with amino acids 440-864 of SEQ ID NO: 6, at most 80% amino acid identity with amino acids 440-864 of SEQ ID NO: 6, at most 85% amino acid identity with amino acids 440-864 of SEQ ID NO: 6, at most 90% amino acid identity with amino acids 440-864 of SEQ ID NO: 6 or at most 95% amino acid identity with amino acids 440-864 of SEQ ID NO: 6.

In other aspects of this embodiment, a BoNT/F $H_N$ region comprises a polypeptide having, e.g., at most one, two, three, four, five, six, seven, eight, nine, 10, 20, 30, 40, 50, 100, or 200 non-contiguous amino acid substitutions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 non-contiguous amino acid substitutions relative to amino acids 440-864 of SEQ ID NO: 6. In yet other aspects of this embodiment, a BoNT/F $H_N$ region comprises a polypeptide having, e.g., at most one, two, three, four, five, six, seven, eight, nine, 10, 20, 30, 40, 50, 100 or 200 non-contiguous amino acid deletions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 non-contiguous amino acid deletions relative to amino acids 440-864 of SEQ ID NO: 6. In still other aspects of this embodiment, a BoNT/F $H_N$ region comprises a polypeptide having, e.g., at most one, two, three, four, five, six, seven, eight, nine, 10, 20, 30, 40, 50, 100 or 200 non-contiguous amino acid additions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 non-contiguous amino acid additions relative to amino acids 440-864 of SEQ ID NO: 6.

In other aspects of this embodiment, a BoNT/F $H_N$ region comprises a polypeptide having, e.g., at most one, two, three, four, five, six, seven, eight, nine, 10, 20, 30, 40, 50, 100 or 200 contiguous amino acid substitutions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 contiguous amino acid substitutions relative to amino acids 440-864 of SEQ ID NO: 6. In yet other aspects of this embodiment, a BoNT/F $H_N$ region comprises a polypeptide having, e.g., at most one, two, three, four, five, six, seven, eight, nine, 10, 20, 30, 40, 50, 100 or 200 contiguous amino acid deletions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 contiguous amino acid deletions relative to amino acids 440-864 of SEQ ID NO: 6. In still other aspects of this embodiment, a BoNT/F $H_N$ region comprises a polypeptide having, e.g., at most one, two, three, four, five, six, seven, eight, nine, 10, 20, 30, 40, 50, 100 or 200 contiguous amino acid additions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 contiguous amino acid additions relative to amino acids 440-864 of SEQ ID NO: 6.

In another embodiment, a Clostridial toxin translocation domain comprises a BoNT/G $H_N$ region. In an aspect of this embodiment, a BoNT/G $H_N$ region comprises amino acids 447-863 of SEQ ID NO: 7. In another aspect of this embodiment, a BoNT/G $H_N$ region comprises a naturally occurring BoNT/G $H_N$ region variant, such as, e.g., a $H_N$ region from a BoNT/G isoform or a $H_N$ region from a BoNT/G subtype. In another aspect of this embodiment, a BoNT/G $H_N$ region comprises amino acids 447-863 of a naturally occurring BoNT/G $H_N$ region variant of SEQ ID NO: 7, such as, e.g., amino acids 447-863 of a BoNT/G isoform of SEQ ID NO: 7 or amino acids 447-863 of a BoNT/G subtype of SEQ ID NO: 7. In still another aspect of this embodiment, a BoNT/G $H_N$ region comprises a non-naturally occurring BoNT/G $H_N$ region variant, such as, e.g., a conservative BoNT/G $H_N$ region variant, a non-conservative BoNT/G $H_N$ region variant, a BoNT/G chimeric $H_N$ region, an active BoNT/G $H_N$ region fragment, or any combination thereof. In still another aspect of this embodiment, a BoNT/G $H_N$ region comprises amino acids 447-863 of a non-naturally occurring BoNT/G $H_N$ region variant of SEQ ID NO: 7, such as, e.g., amino acids 447-863 of a conservative BoNT/G $H_N$ region variant of SEQ ID NO: 7, amino acids 447-863 of a non-conservative BoNT/G $H_N$ region variant of SEQ ID NO: 7, amino acids 447-863 of an active BoNT/G $H_N$ region fragment of SEQ ID NO: 7, or any combination thereof.

In other aspects of this embodiment, a BoNT/G $H_N$ region comprises a polypeptide having, e.g., at least 70% amino acid identity with amino acids 447-863 of SEQ ID NO: 7, at least 75% amino acid identity with amino acids 447-863 of SEQ ID NO: 7, at least 80% amino acid identity with amino acids 447-863 of SEQ ID NO: 7, at least 85% amino acid identity with amino acids 447-863 of SEQ ID NO: 7, at least 90% amino acid identity with amino acids 447-863 of SEQ ID NO: 7 or at least 95% amino acid identity with amino acids 447-863 of SEQ ID NO: 7. In yet other aspects of this embodiment, a BoNT/G $H_N$ region comprises a polypeptide having, e.g., at most 70% amino acid identity with amino acids 447-863 of SEQ ID NO: 7, at most 75% amino acid identity with amino acids 447-863 of SEQ ID NO: 7, at most 80% amino acid identity with amino acids 447-863 of SEQ ID NO: 7, at most 85% amino acid identity with amino acids 447-863 of SEQ ID NO: 7, at most 90% amino acid identity with amino acids 447-863 of SEQ ID NO: 7 or at most 95% amino acid identity with amino acids 447-863 of SEQ ID NO: 7.

In other aspects of this embodiment, a BoNT/G $H_N$ region comprises a polypeptide having, e.g., at most one, two, three, four, five, six, seven, eight, nine, 10, 20, 30, 40, 50, 100, or 200 non-contiguous amino acid substitutions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 non-contiguous amino acid substitutions relative to amino acids 447-863 of SEQ ID NO: 7. In yet other aspects of this embodiment, a BoNT/G $H_N$ region comprises a polypeptide having, e.g., at most one, two, three, four, five, six, seven, eight, nine, 10, 20, 30, 40, 50, 100 or 200 non-contiguous amino acid deletions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 non-contiguous amino acid deletions relative to amino acids 447-863 of SEQ ID NO: 7. In still other aspects of this embodiment, a BoNT/G $H_N$ region comprises a polypeptide having, e.g., at most one, two, three, four, five, six, seven, eight, nine, 10, 20, 30, 40, 50, 100 or 200 non-contiguous amino acid additions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 non-contiguous amino acid additions relative to amino acids 447-863 of SEQ ID NO: 7.

In other aspects of this embodiment, a BoNT/G $H_N$ region comprises a polypeptide having, e.g., at most one, two, three, four, five, six, seven, eight, nine, 10, 20, 30, 40, 50, 100 or 200 contiguous amino acid substitutions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 contiguous amino acid substitutions relative to amino acids 447-863 of SEQ ID NO: 7. In yet other aspects of this embodiment, a BoNT/G $H_N$ region comprises a polypeptide having, e.g., at most one, two, three, four, five, six, seven, eight, nine, 10, 20, 30, 40, 50, 100 or 200 contiguous amino acid deletions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 contiguous amino acid deletions relative to amino acids 447-863 of SEQ ID NO: 7. In still other aspects of this embodiment, a BoNT/G $H_N$ region comprises a polypeptide having, e.g., at most one, two, three, four, five, six, seven, eight, nine, 10, 20, 30, 40, 50, 100 or 200 contiguous amino acid additions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 contiguous amino acid additions relative to amino acids 447-863 of SEQ ID NO: 7.

In another embodiment, a Clostridial toxin translocation domain comprises a TeNT $H_N$ region. In an aspect of this embodiment, a TeNT $H_N$ region comprises amino acids 458-879 of SEQ ID NO: 8. In another aspect of this embodiment, a TeNT $H_N$ region comprises a naturally occurring TeNT $H_N$ region variant, such as, e.g., a $H_N$ region from a TeNT isoform or a $H_N$ region from a TeNT subtype. In another aspect of this embodiment, a TeNT $H_N$ region comprises amino acids 458-879 of a naturally occurring TeNT $H_N$ region variant of SEQ ID NO: 8, such as, e.g., amino acids 458-879 of a TeNT isoform of SEQ ID NO: 8 or amino acids 458-879 of a TeNT subtype of SEQ ID NO: 8. In still another aspect of this embodiment, a TeNT $H_N$ region comprises a non-naturally occurring TeNT $H_N$ region variant, such as, e.g., a conservative TeNT $H_N$ region variant, a non-conservative TeNT $H_N$ region variant, a TeNT chimeric $H_N$ region, an active TeNT $H_N$ region fragment, or any combination thereof. In still another aspect of this embodiment, a TeNT $H_N$ region comprises amino acids 458-879 of a non-naturally occurring TeNT $H_N$ region variant of SEQ ID NO: 8, such as, e.g., amino acids 458-879 of a conservative TeNT $H_N$ region variant of SEQ ID NO: 8, amino acids 458-879 of a non-conservative TeNT $H_N$ region variant of SEQ ID NO: 8, amino acids 458-879 of an active TeNT $H_N$ region fragment of SEQ ID NO: 8, or any combination thereof.

In other aspects of this embodiment, a TeNT $H_N$ region comprises a polypeptide having, e.g., at least 70% amino acid identity with amino acids 458-879 of SEQ ID NO: 8, at least 75% amino acid identity with amino acids 458-879 of SEQ ID NO: 8, at least 80% amino acid identity with amino acids 458-879 of SEQ ID NO: 8, at least 85% amino acid identity with amino acids 458-879 of SEQ ID NO: 8, at least 90% amino acid identity with amino acids 458-879 of SEQ ID NO: 8 or at least 95% amino acid identity with amino acids 458-879 of SEQ ID NO: 8. In yet other aspects of this embodiment, a TeNT $H_N$ region comprises a polypeptide having, e.g., at most 70% amino acid identity with amino acids 458-879 of SEQ ID NO: 8, at most 75% amino acid identity with amino acids 458-879 of SEQ ID NO: 8, at most 80% amino acid identity with amino acids 458-879 of SEQ ID NO: 8, at most 85% amino acid identity with amino acids 458-879 of SEQ ID NO: 8, at most 90% amino acid identity with amino acids 458-879 of SEQ ID NO: 8 or at most 95% amino acid identity with amino acids 458-879 of SEQ ID NO: 8.

In other aspects of this embodiment, a TeNT $H_N$ region comprises a polypeptide having, e.g., at most one, two, three, four, five, six, seven, eight, nine, 10, 20, 30, 40, 50, 100, or 200 non-contiguous amino acid substitutions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 non-contiguous amino acid substitutions relative to amino acids 458-879 of SEQ ID NO: 8. In yet other aspects of this embodiment, a TeNT $H_N$ region comprises a polypeptide having, e.g., at most one, two, three, four, five, six, seven, eight, nine, 10, 20, 30, 40, 50, 100 or 200 non-contiguous amino acid deletions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 non-contiguous amino acid deletions relative to amino acids 458-879 of SEQ ID NO: 8. In still other aspects of this embodiment, a TeNT $H_N$ region comprises a polypeptide having, e.g., at most one, two, three, four, five, six, seven, eight, nine, 10, 20, 30, 40, 50, 100 or 200 non-contiguous amino acid additions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 non-contiguous amino acid additions relative to amino acids 458-879 of SEQ ID NO: 8.

In other aspects of this embodiment, a TeNT $H_N$ region comprises a polypeptide having, e.g., at most one, two, three, four, five, six, seven, eight, nine, 10, 20, 30, 40, 50, 100 or 200 contiguous amino acid substitutions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 contiguous amino acid substitutions relative to amino acids 458-879 of SEQ ID NO: 8. In yet other aspects of this embodiment, a TeNT $H_N$ region comprises a polypeptide having, e.g., at most one, two, three, four, five, six, seven, eight, nine, 10, 20, 30, 40, 50, 100 or 200 contiguous amino acid deletions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 contiguous amino acid deletions relative to amino acids 458-879 of SEQ ID NO: 8. In still other aspects of this embodiment, a TeNT $H_N$ region comprises a polypeptide having, e.g., at most one, two, three, four, five, six, seven, eight, nine, 10, 20, 30, 40, 50, 100 or 200 contiguous amino acid additions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 contiguous amino acid additions relative to amino acids 458-879 of SEQ ID NO: 8.

Aspects of the present invention provide, in part, an enhanced targeting domain. As used herein, the term "enhanced targeting domain" means any polypeptide that can selectively bind to a non-Clostridial toxin receptor system present on a Clostridial toxin target cell and initiate the overall internalization mechanism whereby a Clostridial toxin intoxicates a target cell. As used herein, the term "selectively" means having a highly preferred activity or effect. As used herein, the term "selectively bind" means a molecule is able to bind its target receptor system under physiological conditions, or in vitro conditions substantially approximating physiological conditions, to a statistically significantly greater degree relative to other, non-target receptor systems. Thus, with reference to an enhanced targeting domain of the present specification, there is a discriminatory binding of the enhanced targeting domain to an non-Clostridial toxin receptor system.

An enhanced targeting domain disclosed in the present specification facilitates the binding activity of the modified Clostridial toxins disclosed in the present specification to a non-Clostridial toxin receptor system located at the surface of a Clostridial toxin target cell. As used herein, the term "binding activity" means that one molecule is directly or indirectly contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. "Bound" and "bind" are considered terms for binding.

As used herein, the term "binding affinity" means how strong a molecule's binding activity is for a particular receptor system. In general, high binding affinity results from greater intermolecular force between a binding domain and its receptor system while low binding affinity involves less intermolecular force between the ligand and its receptor. High binding affinity involves a longer residence time for the binding domain at its receptor binding site than is the case for low binding affinity. As such, a molecule with a high binding affinity means a lower concentration of that molecule is required to maximally occupy the binding sites of a receptor system and trigger a physiological response. Conversely, low binding affinity means a relatively high concentration of a molecule is required before the receptor binding sites of a receptor system is maximally occupied and the maximum physiological response is achieved. Thus, modified Clostridial toxins with increased binding activity due to high binding affinity will allow administration of reduced doses of the toxin, thereby reducing or preventing unwanted side-effects associated with toxin dispersal into non-targeted areas.

As used herein, the term "binding specificity" means how specific a molecule's binding activity is one particular receptor system. In general, high binding specificity results in a more exclusive interaction with one particular receptor system or subgroup of receptor systems while low binding specificity results in a more promiscuous interaction with a larger group of receptor systems. As such, a molecule with a high binding specificity means that molecule will occupy the binding sites of a particular receptor system and trigger a physiological response. Conversely, low binding specificity means a molecule will occupy the binding sites of a many receptor systems and trigger a multitude of physiological responses. Thus, modified Clostridial toxins with increased binding activity due to high binding specificity will only target non-Clostridial toxin receptors present on a subgroup of Clostridial toxin target cells, thereby reducing the side effects associated with the targeting of all Clostridial toxin target cells.

As used herein, the term "Clostridial toxin target cell" means a cell that is a naturally occurring cell that a naturally occurring Clostridial toxin is capable of intoxicating, including, without limitation, motor neurons; sensory neurons; autonomic neurons; such as, e.g., sympathetic neurons and parasympathetic neurons; non-petidergic neurons, such as, e.g., cholinergic neurons, adrenergic neurons, noradrenergic neurons, serotonergic neurons, GABAergic neurons; and peptidergic neurons, such as, e.g., Substance P neurons, Calcitonin Gene Related Peptide neurons, vasoactive intestinal peptide neurons, Neuropeptide Y neurons, cholecystokinin neurons.

It is envisioned that any and all enhanced targeting domains that exhibits a binding activity for a non-Clostridial toxin receptor system present on a naturally-occurring Clostridial toxin target cell can be used to practice aspects of the present invention, including, without limitation, polypeptides that selectively bind to a receptor system present on a presynaptic membrane and polypeptides that selectively bind to a receptor system present on a postsynaptic membrane. Polypeptides that appear to bind to a receptor system present on a presynaptic membrane, include, without limitation, Glucagon like hormones, such as, e.g., secretin, glucagon-like peptides, pituitary adenylate cyclase activating peptide (PACAP), glicentin, glicentin-related polypeptide (GRPP), oxyntomodulin (OXY), vasoactive intestinal peptides (VIPs), gastric inhibitory polypeptide (GIP), and calcitonin-related peptidesvisceral gut peptides; neurohormones, such as, e.g., corticotropin-releasing hormone (CCRH) and parathyroid hormone (PTH); neuroregulatory cytokines, such as, e.g., ciliary neurotrophic factor (CNTF), glycophorin-A (GPA), leukemia inhibitory factor (LIF), interleukins (ILs), onostatin M, cardiotrophin-1 (CT-1), cardiotrophin-like cytokine (CLC), neuroleukins, VEGF, insulin-like growth factors (IGFs), epidermal growth factor (EGF); neurotrophins, such as, e.g., nerve growth factors (NGFs), brain-derived growth factors (BDNFs), neurotrophin-3s (NT-3s) and neurotrophin-4/5s (NT-4/5s); growth factors, such as, e.g., glial cell derived neurotrophic factor (GDNF), neurturin, persephrin, artemin, transformation growth factor betas (TGFβs), bone morphogenetic proteins (BMPs), growth and differentiation factors (GDFs), activins; axon guidance signaling molecules, such as, e.g., netrins, semaphrorings and ephrins; sugar binding proteins, such as, e.g., serum amyloid P, β-glucanase, sialidase, lectin, cryia, insecticidal delta-endotoxin, agglutinin, abrin and ricin; ligands that selectively bind neurexins, such as, e.g., ligands for neurexin-1α and neurexin-1β; ligands for neurexin-2α and neurexin-2β; and ligands for neurexin-3α and neurexin-3β; and WNTs. Ligands that appear to bind to a receptor system present on a postsynaptic membrane, include, without limitation, Ng-CAM(L1), NCAM, N-cadherin, Agrin-MUSK, basement membrane polypeptides, such as, e.g., laminin β-2.

An enhanced targeting domain includes, without limitation, naturally occurring enhanced targeting domain variants, such as, e.g., enhanced targeting domain isoforms; non-naturally occurring enhanced targeting domain variants, such as, e.g., conservative enhanced targeting domain variants, non-conservative enhanced targeting domain variants, enhanced targeting domain chimerics, active enhanced targeting domain fragments thereof, or any combination thereof.

As used herein, the term "variant," when used to describe an enhanced targeting domain variant, whether naturally-occurring or non-naturally-occurring, means an enhanced targeting domain that has at least one amino acid change from the corresponding region of the disclosed reference sequences and can be described in percent identity to the corresponding region of that reference sequence. Unless expressly indicated, all enhanced targeting domain variants disclosed in the present specification are capable of selectively binding to an non-Clostridial toxin receptor system present on a Clostridial toxin target cell and initiate the overall internalization mechanism whereby a Clostridial toxin intoxicates a target cell. As non-limiting examples, a glycogen-like peptide variant derived from amino acids 21-50 of SEQ ID NO: 9 will have at least one amino acid difference, such as, e.g., an amino acid substitution, deletion or addition, as compared to the amino acid region 21-50 of SEQ ID NO: 9; a PACAP variant derived from amino acids 132-158 of SEQ ID NO: 10 will have at least one amino acid difference, such as, e.g., an amino acid substitution, deletion or addition, as compared to the amino acid region 132-158 of SEQ ID NO: 10; a CCRH variant derived from amino acids 159-193 of SEQ ID NO: 19 will have at least one amino acid difference, such as, e.g., an amino acid substitution, deletion or addition, as compared to the amino acid region 159-193 of SEQ ID NO: 19; a PTH variant derived from amino acids 35-70 of SEQ ID NO: 20 will have at least one amino acid difference, such as, e.g., an amino acid substitution, deletion or addition, as compared to the amino acid region 35-70 of SEQ ID NO: 20; an IL-6 variant derived from amino acids 57-210 of SEQ ID NO: 28 will have at least one amino acid difference, such as, e.g., an amino acid substitution, deletion or addition, as compared to the amino acid region 57-210 of SEQ ID NO: 28; a neuroleukin variant derived from amino acids 54-546 of SEQ ID NO: 31 will have at least one amino acid difference, such as, e.g., an amino acid substitution, deletion or addition, as compared to the amino acid region 54-546 of SEQ ID NO: 31; an IGF-1 variant derived from amino acids 52-109 of SEQ ID NO: 33 will have at least one amino acid difference, such as, e.g., an amino acid substitution, deletion or addition, as compared to the amino acid region 52-109 of SEQ ID NO: 33; and a NT-3 variant derived from amino acids 144-249 of SEQ ID NO: 38 will have at least one amino acid difference, such as, e.g., an amino acid substitution, deletion or addition, as compared to the amino acid region 144-249 of SEQ ID NO: 38.

It is recognized by those of skill in the art that there can be naturally occurring enhanced targeting domain variants that differ somewhat in their amino acid sequence, and also in the nucleic acids encoding these proteins. As used herein, the term "naturally occurring enhanced targeting domain variant" means any enhanced targeting domain produced by a naturally-occurring process, including, without limitation, enhanced targeting domain isoforms produced from alternatively-spliced transcripts, enhanced targeting domain isoforms produced by spontaneous mutation and enhanced targeting domain subtypes. A naturally occurring enhanced targeting domain variant can function in substantially the same manner as the reference enhanced targeting domain on which the naturally occurring enhanced targeting domain variant is based, and can be substituted for the reference enhanced targeting domain in any aspect of the present invention. A naturally occurring enhanced targeting domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference enhanced targeting domain on which the naturally occurring enhanced targeting domain variant is based. A naturally occurring enhanced targeting domain variant can also substitute at least 10 contiguous amino acids, at least 15 contiguous amino acids, at least 20 contiguous amino acids, or at least 25 contiguous amino acids from the reference enhanced targeting domain on which the naturally occurring enhanced targeting domain variant is based, that possess at least 50% amino acid identity, 65% amino acid identity, 75% amino acid identity, 85% amino acid identity or 95% amino acid identity to the reference enhanced targeting domain on which the naturally occurring enhanced targeting domain variant is based.

A non-limiting examples of a naturally occurring enhanced targeting domain variant is an enhanced targeting domain isoform such as, e.g., a glucogen-like peptide isoform, a PACAP isoform, a CCRH isoform, a PTH isoform, an IL-6 isoform, a neuroleukin isoform, an IGF-1 isoform, and a NT-3 isoform. An enhanced targeting domain isoform can function in substantially the same manner as the reference enhanced targeting domain on which the enhanced targeting domain isoform is based, and can be substituted for the reference enhanced targeting domain in any aspect of the present invention.

As used herein, the term "non-naturally occurring enhanced targeting domain variant" means any enhanced targeting domain produced with the aid of human manipulation, including, without limitation, enhanced targeting domains produced by genetic engineering using random mutagenesis or rational design and enhanced targeting domains produced by chemical synthesis. Non-limiting examples of non-naturally occurring enhanced targeting domain variants include, e.g., conservative enhanced targeting domain variants, non-conservative enhanced targeting domain variants, enhanced targeting domain chimeric variants and active enhanced targeting domain fragments.

As used herein, the term "conservative enhanced targeting domain variant" means an enhanced targeting domain that has at least one amino acid substituted by another amino acid or an amino acid analog that has at least one property similar to that of the original amino acid from the reference enhanced targeting domain sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative enhanced targeting domain variant can function in substantially the same manner as the reference enhanced targeting domain on which the conservative enhanced targeting domain variant is based, and can be substituted for the reference enhanced targeting domain in any aspect of the present invention. A conservative enhanced targeting domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference enhanced targeting domain on which the conservative enhanced targeting domain variant is based. A conservative enhanced targeting domain variant can also substitute at least 10 contiguous amino acids, at least 15 contiguous amino acids, at least 20 contiguous amino acids, or at least 25 contiguous amino acids from the reference enhanced targeting domain on which the conservative enhanced targeting domain variant is based, that possess at least 50% amino acid identity, 65% amino acid identity, 75% amino acid identity, 85% amino acid identity or 95% amino acid identity to the reference enhanced targeting domain on which the conservative enhanced targeting domain variant is based. Non-limiting examples of a conservative enhanced targeting domain variant include, e.g., conservative glucogen-like peptide variants, conservative PACAP region variants, conservative CCRH region variants, conservative PTH variants, conservative IL-6 variants, conservative neuroleukin variants, conservative IGF-1 variants, and conservative NT-3 region variants.

As used herein, the term "non-conservative enhanced targeting domain variant" means an enhanced targeting domain in which 1) at least one amino acid is deleted from the reference enhanced targeting domain on which the non-conservative enhanced targeting domain variant is based; 2) at least one amino acid added to the reference enhanced targeting domain on which the non-conservative enhanced targeting domain is based; or 3) at least one amino acid is substituted by another amino acid or an amino acid analog that does not share any property similar to that of the original amino acid from the reference enhanced targeting domain sequence. A non-conservative enhanced targeting domain variant can function in substantially the same manner as the reference enhanced targeting domain on which the non-conservative enhanced targeting domain variant is based, and can be substituted for the reference enhanced targeting domain in any aspect of the present invention. A non-conservative enhanced targeting domain variant can delete one or more amino acids, two or more amino acids, three or more amino acids, four or more amino acids, five or more amino acids, and ten or more amino acids from the reference enhanced targeting domain on which the non-conservative enhanced targeting domain variant is based. A non-conservative enhanced targeting domain variant can add one or more amino acids, two or more amino acids, three or more amino acids, four or more amino acids, five or more amino acids, and ten or more amino acids to the reference enhanced targeting domain on which the non-conservative enhanced targeting domain variant is based. A non-conservative enhanced targeting domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference enhanced targeting domain on which the non-conservative enhanced targeting domain variant is based. A non-conservative enhanced targeting domain variant can also substitute at least 10 contiguous amino acids, at least 15 contiguous amino acids, at least 20 contiguous amino acids, or at least 25 contiguous amino acids from the reference enhanced targeting domain on which the non-conservative enhanced targeting domain variant is based, that possess at least 50% amino acid identity, 65% amino acid identity, 75% amino acid identity, 85% amino acid identity or 95% amino acid identity to the reference enhanced targeting domain on which the non-conservative enhanced targeting domain variant is based. Non-limiting examples of a non-conservative enhanced targeting domain variant include, e.g., non-conservative glucogen-like peptide variants, non-conservative PACAP region variants, non-conservative CCRH region variants, non-conservative PTH variants, non-conservative IL-6 variants, non-conservative neuroleukin variants, non-conservative IGF-1 variants, and non-conservative NT-3 region variants.

As used herein, the term "enhanced targeting domain chimeric" means a polypeptide comprising at least a portion of an enhanced targeting domain and at least a portion of at least one other polypeptide to form an enhanced targeting domain with at least one property different from the reference enhanced targeting domain, with the proviso that this enhanced targeting domain chimeric is still capable of selectively binding to an non-Clostridial toxin receptor system present on a Clostridial toxin target cell and initiate the overall internalization mechanism whereby a Clostridial toxin intoxicates a target cell.

As used herein, the term "active enhanced targeting domain fragment" means any of a variety of enhanced targeting domain fragments can be useful in aspects of the present invention with the proviso that these active fragments are still capable of selectively binding to an non-Clostridial toxin receptor system present on a Clostridial toxin target cell and initiate the overall internalization mechanism whereby a Clostridial toxin intoxicates a target cell. Thus, aspects of this embodiment can include enhanced targeting domains comprising a length of, e.g., at least 50 amino acids, at least 100 amino acids, at least 150 amino acids, at least 200 amino acids, at least 250 amino acids, at least 300 amino acids, at least 350 amino acids, at least 400 amino acids and at least 450 amino acids. Other aspects of this embodiment can include enhanced targeting domains comprising translocation domain having a length of, e.g., at most 50 amino acids, at most 100 amino acids, at most 150 amino acids, at most 200 amino acids, at most 250 amino acids, at most 300 amino acids, at most 350 amino acids, at most 400 amino acids and at most 450 amino acids.

Any of a variety of sequence alignment methods can be used to determine percent identity of naturally-occurring enhanced targeting domain variants and non-naturally-occurring enhanced targeting domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises an enhanced targeting domain. In an aspect of this embodiment, an enhanced targeting domain comprises a naturally occurring enhanced targeting domain variant, such as, e.g., an enhanced targeting domain isoform or an enhanced targeting domain subtype. In another aspect of this embodiment, a Clostridial toxin translocation domain comprises a non-naturally occurring enhanced targeting domain variant, such as, e.g., a conservative enhanced targeting domain variant, a non-conservative enhanced targeting domain variant, a enhanced targeting domain chimeric, an active enhanced targeting domain fragment, or any combination thereof.

An example of an enhanced targeting domain disclosed in the present specification is, e.g., Glucagon like hormones, such as, e.g., secretin, glucagon-like peptides, like GLP-1 and GLP-2, pituitary adenylate cyclase activating peptide (PACAP), glicentin, glicentin-related polypeptide (GRPP), oxyntomodulin (OXY), growth hormone-releasing hormone (GHRH), vasoactive intestinal peptides (VIPs), gastric inhibitory polypeptide (GIP), and calcitonin-related peptidesvisceral gut peptides, such as, e.g., gastrin, gastrin-releasing peptide (GRP, bombesin) or cholecystokinin (CCK).

Thus, in an embodiment, an enhanced binding domain is derived from a glycogen-like peptide. In another embodiment, an enhanced binding domain is derived from a glycogen-like peptide of SEQ ID NO: 9. In aspects of this embodiment, an enhanced binding domain is derived from a glycogen-like peptide comprises a GRPP, a GLP-1, a GLP-2, a glucagon or an oxyntomodulin. In aspects of this embodiment, an enhanced binding domain is derived from a glycogen-like peptide comprises amino acids 21-50, amino acids 53-81, amino acids 53-89, amino acids 98-124, or amino acids 146-178 of SEQ ID NO: 9.

In other aspects of this embodiment, a glycogen-like peptide comprises a polypeptide having, e.g., at least 70% amino acid identity with amino acids 21-50, amino acids 53-81, amino acids 53-89, amino acids 98-124, or amino acids 146-178 of SEQ ID NO: 9, at least 75% amino acid identity with amino acids 21-50, amino acids 53-81, amino acids 53-89, amino acids 98-124, or amino acids 146-178 of SEQ ID NO: 9, at least 80% amino acid identity with amino acids 21-50, amino acids 53-81, amino acids 53-89, amino acids 98-124, or amino acids 146-178 of SEQ ID NO: 9, at least 85% amino acid identity with amino acids 21-50, amino acids 53-81, amino acids 53-89, amino acids 98-124, or amino acids 146-178 of SEQ ID NO: 9, at least 90% amino acid identity with amino acids 21-50, amino acids 53-81, amino acids 53-89, amino acids 98-124, or amino acids 146-178 of SEQ ID NO: 9 or at least 95% amino acid identity with amino acids 21-50, amino acids 53-81, amino acids 53-89, amino acids 98-124, or amino acids 146-178 of SEQ ID NO: 9. In yet other aspects of this embodiment, a glycogen-like peptide comprises a polypeptide having, e.g., at most 70% amino acid identity with amino acids 21-50, amino acids 53-81, amino acids 53-89, amino acids 98-124, or amino acids 146-178 of SEQ ID NO: 9, at most 75% amino acid identity with amino acids 21-50, amino acids 53-81, amino acids 53-89, amino acids 98-124, or amino acids 146-178 of SEQ ID NO: 9, at most 80% amino acid identity with amino acids 21-50, amino acids 53-81, amino acids 53-89, amino acids 98-124, or amino acids 146-178 of SEQ ID NO: 9, at most 85% amino acid identity with amino acids 21-50, amino acids 53-81, amino acids 53-89, amino acids 98-124, or amino acids 146-178 of SEQ ID NO: 9, at most 90% amino acid identity with amino acids 21-50, amino acids 53-81, amino acids 53-89, amino acids 98-124, or amino acids 146-178 of SEQ ID NO: 9 or at most 95% amino acid identity with amino acids 21-50, amino acids 53-81, amino acids 53-89, amino acids 98-124, or amino acids 146-178 of SEQ ID NO: 9.

In other aspects of this embodiment, a glycogen-like peptide comprises a polypeptide having, e.g., at most one, two, three, four, five, six, seven, eight, nine, 10 or 20 non-contiguous amino acid substitutions relative to amino acids 21-50, amino acids 53-81, amino acids 53-89, amino acids 98-124, or amino acids 146-178 of SEQ ID NO: 9. In other aspects of this embodiment, a glycogen-like peptide comprises a polypeptide having, e.g., at least one, two, three, four, five, six, seven, eight, nine, 10 or 20 non-contiguous amino acid substitutions relative to amino acids 21-50, amino acids 53-81, amino acids 53-89, amino acids 98-124, or amino acids 146-178 of SEQ ID NO: 9. In yet other aspects of this embodiment, a glycogen-like peptide comprises a polypeptide having, e.g., at most one, two, three, four, five, six, seven, eight, nine, 10 or 20 non-contiguous amino acid deletions relative to amino acids 21-50, amino acids 53-81, amino acids 53-89, amino acids 98-124, or amino acids 146-178 of SEQ ID NO: 9. In other aspects of this embodiment, a glycogen-like peptide comprises a polypeptide having, e.g., at least one, two, three, four, five, six, seven, eight, nine, 10 or 20 non-contiguous amino acid deletions relative to amino acids 21-50, amino acids 53-81, amino acids 53-89, amino acids 98-124, or amino acids 146-178 of SEQ ID NO: 9. In still other aspects of this embodiment, a glycogen-like peptide comprises a polypeptide having, e.g., at most one, two, three, four, five, six, seven, eight, nine, 10 or 20 non-contiguous amino acid additions relative to amino acids 21-50, amino acids 53-81, amino acids 53-89, amino acids 98-124, or amino acids 146-178 of SEQ ID NO: 9. In other aspects of this embodiment, a glycogen-like peptide comprises a polypeptide having, e.g., at least one, two, three, four, five, six, seven, eight, nine, 10 or 20 non-contiguous amino acid additions relative to amino acids 21-50, amino acids 53-81, amino acids 53-89, amino acids 98-124, or amino acids 146-178 of SEQ ID NO: 9.

In other aspects of this embodiment, a glycogen-like peptide comprises a polypeptide having, e.g., at most one, two, three, four, five, six, seven, eight, nine, 10 or 20 contiguous amino acid substitutions relative to amino acids 21-50, amino acids 53-81, amino acids 53-89, amino acids 98-124, or amino acids 146-178 of SEQ ID NO: 9. In other aspects of this embodiment, a glycogen-like peptide comprises a polypeptide having, e.g., at least one, two, three, four, five, six, seven, eight, nine, 10 or 20 contiguous amino acid substitutions relative to amino acids 21-50, amino acids 53-81, amino acids 53-89, amino acids 98-124, or amino acids 146-178 of SEQ ID NO: 9. In yet other aspects of this embodiment, a glycogen-like peptide comprises a polypeptide having, e.g., at most one, two, three, four, five, six, seven, eight, nine, 10 or 20 contiguous amino acid deletions relative to amino acids 21-50, amino acids 53-81, amino acids 53-89, amino acids 98-124, or amino acids 146-178 of SEQ ID NO: 9. In other aspects of this embodiment, a glycogen-like peptide comprises a polypeptide having, e.g., at least one, two, three, four, five, six, seven, eight, nine, 10 or 20 contiguous amino acid deletions relative to amino acids 21-50, amino acids 53-81, amino acids 53-89, amino acids 98-124, or amino acids 146-178 of SEQ ID NO: 9. In still other aspects of this embodiment, a glycogen-like peptide comprises a polypeptide having, e.g., at most one, two, three, four, five, six, seven, eight, nine, 10 or 20 contiguous amino acid additions relative to amino acids 21-50, amino acids 53-81, amino acids 53-89, amino acids 98-124, or amino acids 146-178 of SEQ ID NO: 9. In other aspects of this embodiment, a glycogen-like peptide comprises a polypeptide having, e.g., at least one, two, three, four, five, six, seven, eight, nine, 10 or 20 contiguous amino acid additions relative to amino acids 21-50, amino acids 53-81, amino acids 53-89, amino acids 98-124, or amino acids 146-178 of SEQ ID NO: 9.

In another embodiment, an enhanced binding domain is derived from a PACAP. In another embodiment, an enhanced binding domain is derived from a PACAP of SEQ ID NO: 10. In an aspect of this embodiment, an enhanced binding domain is derived from a PACAP comprises amino acids 132-158 of SEQ ID NO: 10.

In other aspects of this embodiment, a PACAP comprises a polypeptide having, e.g., at least 70% amino acid identity with amino acids 132-158 of SEQ ID NO: 10, at least 75% amino acid identity with amino acids 132-158 of SEQ ID NO: 10, at least 80% amino acid identity with amino acids 132-158 of SEQ ID NO: 10, at least 85% amino acid identity with amino acids 132-158 of SEQ ID NO: 10, at least 90% amino acid identity with amino acids 132-158 of SEQ ID NO: 10 or at least 95% amino acid identity with amino acids 132-158 of SEQ ID NO: 10. In yet other aspects of this embodiment, a PACAP comprises a polypeptide having, e.g., at most 70% amino acid identity with amino acids 132-158 of SEQ ID NO: 10, at most 75% amino acid identity with amino acids 132-158 of SEQ ID NO: 10, at most 80% amino acid identity with amino acids 132-158 of SEQ ID NO: 10, at most 85% amino acid identity with amino acids 132-158 of SEQ ID NO: 10, at most 90% amino acid identity with amino acids 132-158 of SEQ ID NO: 10 or at most 95% amino acid identity with amino acids 132-158 of SEQ ID NO: 10.

In other aspects of this embodiment, a PACAP comprises a polypeptide having, e.g., at most one, two, three, four, five, six, seven, eight, nine, 10 or 20 non-contiguous amino acid substitutions relative to amino acids 132-158 of SEQ ID NO: 10. In other aspects of this embodiment, a PACAP comprises a polypeptide having, e.g., at least one, two, three, four, five, six, seven, eight, nine, 10 or 20 non-contiguous amino acid substitutions relative to amino acids 132-158 of SEQ ID NO: 10. In yet other aspects of this embodiment, a PACAP comprises a polypeptide having, e.g., at most one, two, three, four, five, six, seven, eight, nine, 10 or 20 non-contiguous amino acid deletions relative to amino acids 132-158 of SEQ ID NO: 10. In other aspects of this embodiment, a PACAP comprises a polypeptide having, e.g., at least one, two, three, four, five, six, seven, eight, nine, 10 or 20 non-contiguous amino acid deletions relative to amino acids 132-158 of SEQ ID NO: 10. In still other aspects of this embodiment, a PACAP comprises a polypeptide having, e.g., at most one, two, three, four, five, six, seven, eight, nine, 10 or 20 non-contiguous amino acid additions relative to amino acids 132-158 of SEQ ID NO: 10. In other aspects of this embodiment, a PACAP comprises a polypeptide having, e.g., at least one, two, three, four, five, six, seven, eight, nine, 10 or 20 non-contiguous amino acid additions relative to amino acids 132-158 of SEQ ID NO: 10.

In other aspects of this embodiment, a PACAP comprises a polypeptide having, e.g., at most one, two, three, four, five, six, seven, eight, nine, 10 or 20 contiguous amino acid substitutions relative to amino acids 132-158 of SEQ ID NO: 10. In other aspects of this embodiment, a PACAP comprises a polypeptide having, e.g., at least one, two, three, four, five, six, seven, eight, nine, 10 or 20 contiguous amino acid substitutions relative to amino acids 132-158 of SEQ ID NO: 10. In yet other aspects of this embodiment, a PACAP comprises a polypeptide having, e.g., at most one, two, three, four, five, six, seven, eight, nine, 10 or 20 contiguous amino acid deletions relative to amino acids 132-158 of SEQ ID NO: 10. In other aspects of this embodiment, a PACAP comprises a polypeptide having, e.g., at least one, two, three, four, five, six, seven, eight, nine, 10 or 20 contiguous amino acid deletions relative to amino acids 132-158 of SEQ ID NO: 10. In still other aspects of this embodiment, a PACAP comprises a polypeptide having, e.g., at most one, two, three, four, five, six, seven, eight, nine, 10 or 20 contiguous amino acid additions relative to amino acids 132-158 of SEQ ID NO: 10. In other aspects of this embodiment, a PACAP comprises a polypeptide having, e.g., at least one, two, three, four, five, six, seven, eight, nine, 10 or 20 contiguous amino acid additions relative to amino acids 132-158 of SEQ ID NO: 10.

In another embodiment, an enhanced binding domain is derived from a GHRH. In another embodiment, an enhanced binding domain is derived from a GHRH of SEQ ID NO: 11. In aspects of this embodiment, an enhanced binding domain is derived from a GHRH comprises amino acids 32-58 or amino acids 32-75 of SEQ ID NO: 11.

In other aspects of this embodiment, a GHRH comprises a polypeptide having, e.g., at least 70% amino acid identity with amino acids 32-58 or amino acids 32-75 of SEQ ID NO: 11, at least 75% amino acid identity with amino acids 32-58 or amino acids 32-75 of SEQ ID NO: 11, at least 80% amino acid identity with amino acids 32-58 or amino acids 32-75 of SEQ ID NO: 11, at least 85% amino acid identity with amino acids 32-58 or amino acids 32-75 of SEQ ID NO: 11, at least 90% amino acid identity with amino acids 32-58 or amino acids 32-75 of SEQ ID NO: 11 or at least 95% amino acid identity with amino acids 32-58 or amino acids 32-75 of SEQ ID NO: 11. In yet other aspects of this embodiment, a GHRH comprises a polypeptide having, e.g., at most 70% amino acid identity with amino acids 32-58 or amino acids 32-75 of SEQ ID NO: 11, at most 75% amino acid identity with amino acids 32-58 or amino acids 32-75 of SEQ ID NO: 11, at most 80% amino acid identity with amino acids 32-58 or amino acids 32-75 of SEQ ID NO: 11, at most 85% amino acid identity with amino acids 32-58 or amino acids 32-75 of SEQ ID NO: 11, at most 90% amino acid identity with amino acids 32-58 or amino acids 32-75 of SEQ ID NO: 11 or at most 95% amino acid identity with amino acids 32-58 or amino acids 32-75 of SEQ ID NO: 11.

In other aspects of this embodiment, a GHRH comprises a polypeptide having, e.g., at most one, two, three, four, five, six, seven, eight, nine, 10 or 20 non-contiguous amino acid substitutions relative to amino acids 32-58 or amino acids 32-75 of SEQ ID NO: 11. In other aspects of this embodiment, a GHRH comprises a polypeptide having, e.g., at least one, two, three, four, five, six, seven, eight, nine, 10 or 20 non-contiguous amino acid substitutions relative to amino acids 32-58 or amino acids 32-75 of SEQ ID NO: 11. In yet other aspects of this embodiment, a GHRH comprises a polypeptide having, e.g., at most one, two, three, four, five, six, seven, eight, nine, 10 or 20 non-contiguous amino acid deletions relative to amino acids 32-58 or amino acids 32-75 of SEQ ID NO: 11. In other aspects of this embodiment, a GHRH comprises a polypeptide having, e.g., at least one, two, three, four, five, six, seven, eight, nine, 10 or 20 non-contiguous amino acid deletions relative to amino acids 32-58 or amino acids 32-75 of SEQ ID NO: 11. In still other aspects of this embodiment, a GHRH comprises a polypeptide having, e.g., at most one, two, three, four, five, six, seven, eight, nine, 10 or 20 non-contiguous amino acid additions relative to amino acids 32-58 or amino acids 32-75 of SEQ ID NO: 11. In other aspects of this embodiment, a GHRH comprises a polypeptide having, e.g., at least one, two, three, four, five, six, seven, eight, nine, 10 or 20 non-contiguous amino acid additions relative to amino acids 32-58 or amino acids 32-75 of SEQ ID NO: 11.

In other aspects of this embodiment, a GHRH comprises a polypeptide having, e.g., at most one, two, three, four, five, six, seven, eight, nine, 10 or 20 contiguous amino acid substitutions relative to amino acids 32-58 or amino acids 32-75 of SEQ ID NO: 11. In other aspects of this embodiment, a GHRH comprises a polypeptide having, e.g., at least one, two, three, four, five, six, seven, eight, nine, 10 or 20 contiguous amino acid substitutions relative to amino acids 32-58 or amino acids 32-75 of SEQ ID NO: 11. In yet other aspects of this embodiment, a GHRH comprises a polypeptide having, e.g., at most one, two, three, four, five, six, seven, eight, nine, 10 or 20 contiguous amino acid deletions relative to amino acids 32-58 or amino acids 32-75 of SEQ ID NO: 11. In other aspects of this embodiment, a GHRH comprises a polypeptide having, e.g., at least one, two, three, four, five, six, seven, eight, nine, 10 or 20 contiguous amino acid deletions relative to amino acids 32-58 or amino acids 32-75 of SEQ ID NO: 11. In still other aspects of this embodiment, a GHRH comprises a polypeptide having, e.g., at most one, two, three, four, five, six, seven, eight, nine, 10 or 20 contiguous amino acid additions relative to amino acids 32-58 or amino acids 32-75 of SEQ ID NO: 11. In other aspects of this embodiment, a GHRH comprises a polypeptide having, e.g., at least one, two, three, four, five, six, seven, eight, nine, 10 or 20 contiguous amino acid additions relative to amino acids 32-58 or amino acids 32-75 of SEQ ID NO: 11.

In another embodiment, an enhanced binding domain is derived from a VIP1. In another embodiment, an enhanced binding domain is derived from a VIP1 of SEQ ID NO: 12. In aspects of this embodiment, an enhanced binding domain is derived from a VIP1 comprises amino acids 81-107 or amino acids 125-151 of SEQ ID NO: 12.

In other aspects of this embodiment, a VIP1 comprises a polypeptide having, e.g., at least 70% amino acid identity with amino acids 81-107 or amino acids 125-151 of SEQ ID NO: 12, at least 75% amino acid identity with amino acids 81-107 or amino acids 125-151 of SEQ ID NO: 12, at least 80% amino acid identity with amino acids 81-107 or amino acids 125-151 of SEQ ID NO: 12, at least 85% amino acid identity with amino acids 81-107 or amino acids 125-151 of SEQ ID NO: 12, at least 90% amino acid identity with amino acids 81-107 or amino acids 125-151 of SEQ ID NO: 12 or at least 95% amino acid identity with amino acids 81-107 or amino acids 125-151 of SEQ ID NO: 12. In yet other aspects of this embodiment, a VIP1 comprises a polypeptide having, e.g., at most 70% amino acid identity with amino acids 81-107 or amino acids 125-151 of SEQ ID NO: 12, at most 75% amino acid identity with amino acids 81-107 or amino acids 125-151 of SEQ ID NO: 12, at most 80% amino acid identity with amino acids 81-107 or amino acids 125-151 of SEQ ID NO: 12, at most 85% amino acid identity with amino acids 81-107 or amino acids 125-151 of SEQ ID NO: 12, at most 90% amino acid identity with amino acids 81-107 or amino acids 125-151 of SEQ ID NO: 12 or at most 95% amino acid identity with amino acids 81-107 or amino acids 125-151 of SEQ ID NO: 12.

In other aspects of this embodiment, a VIP1 comprises a polypeptide having, e.g., at most one, two, three, four, five, six, seven, eight, nine, 10 or 20 non-contiguous amino acid substitutions relative to amino acids 81-107 or amino acids 125-151 of SEQ ID NO: 12. In other aspects of this embodiment, a VIP1 comprises a polypeptide having, e.g., at least one, two, three, four, five, six, seven, eight, nine, 10 or 20 non-contiguous amino acid substitutions relative to amino acids 81-107 or amino acids 125-151 of SEQ ID NO: 12. In yet other aspects of this embodiment, a VIP1 comprises a polypeptide having, e.g., at most one, two, three, four, five, six, seven, eight, nine, 10 or 20 non-contiguous amino acid deletions relative to amino acids 81-107 or amino acids 125-151 of SEQ ID NO: 12. In other aspects of this embodiment, a VIP1 comprises a polypeptide having, e.g., at least one, two, three, four, five, six, seven, eight, nine, 10 or 20 non-contiguous amino acid deletions relative to amino acids 81-107 or amino acids 125-151 of SEQ ID NO: 12. In still other aspects of this embodiment, a VIP1 comprises a polypeptide having, e.g., at most one, two, three, four, five, six, seven, eight, nine, 10 or 20 non-contiguous amino acid additions relative to amino acids 81-107 or amino acids 125-151 of SEQ ID NO: 12. In other aspects of this embodiment, a VIP1 comprises a polypeptide having, e.g., at least one, two, three, four, five, six, seven, eight, nine, 10 or 20 non-contiguous amino acid additions relative to amino acids 81-107 or amino acids 125-151 of SEQ ID NO: 12.

In other aspects of this embodiment, a VIP1 comprises a polypeptide having, e.g., at most one, two, three, four, five, six, seven, eight, nine, 10 or 20 contiguous amino acid substitutions relative to amino acids 81-107 or amino acids 125-151 of SEQ ID NO: 12. In other aspects of this embodiment, a VIP1 comprises a polypeptide having, e.g., at least one, two, three, four, five, six, seven, eight, nine, 10 or 20 contiguous amino acid substitutions relative to amino acids 81-107 or amino acids 125-151 of SEQ ID NO: 12. In yet other aspects of this embodiment, a VIP1 comprises a polypeptide having, e.g., at most one, two, three, four, five, six, seven, eight, nine, 10 or 20 contiguous amino acid deletions relative to amino acids 81-107 or amino acids 125-151 of SEQ ID NO: 12. In other aspects of this embodiment, a VIP1 comprises a polypeptide having, e.g., at least one, two, three, four, five, six, seven, eight, nine, 10 or 20 contiguous amino acid deletions relative to amino acids 81-107 or amino acids 125-151 of SEQ ID NO: 12. In still other aspects of this embodiment, a VIP1 comprises a polypeptide having, e.g., at most one, two, three, four, five, six, seven, eight, nine, 10 or 20 contiguous amino acid additions relative to amino acids 81-107 or amino acids 125-151 of SEQ ID NO: 12. In other aspects of this embodiment, a VIP1 comprises a polypeptide having, e.g., at least one, two, three, four, five, six, seven, eight, nine, 10 or 20 contiguous amino acid additions relative to amino acids 81-107 or amino acids 125-151 of SEQ ID NO: 12.

In another embodiment, an enhanced binding domain is derived from a VIP2. In another embodiment, an enhanced binding domain is derived from a VIP2 of SEQ ID NO: 13. In aspects of this embodiment, an enhanced binding domain is derived from a VIP2 comprises amino acids 81-107 or amino acids 124-150 of SEQ ID NO: 13.

In other aspects of this embodiment, a VIP2 comprises a polypeptide having, e.g., at least 70% amino acid identity with amino acids 81-107 or amino acids 124-150 of SEQ ID NO: 13, at least 75% amino acid identity with amino acids 81-107 or amino acids 124-150 of SEQ ID NO: 13, at least 80% amino acid identity with amino acids 81-107 or amino acids 124-150 of SEQ ID NO: 13, at least 85% amino acid identity with amino acids 81-107 or amino acids 124-150 of SEQ ID NO: 13, at least 90% amino acid identity with amino acids 81-107 or amino acids 124-150 of SEQ ID NO: 13 or at least 95% amino acid identity with amino acids 81-107 or amino acids 124-150 of SEQ ID NO: 13. In yet other aspects of this embodiment, a VIP2 comprises a polypeptide having, e.g., at most 70% amino acid identity with amino acids 81-107 or amino acids 124-150 of SEQ ID NO: 13, at most 75% amino acid identity with amino acids 81-107 or amino acids 124-150 of SEQ ID NO: 13, at most 80% amino acid identity with amino acids 81-107 or amino acids 124-150 of SEQ ID NO: 13, at most 85% amino acid identity with amino acids 81-107 or amino acids 124-150 of SEQ ID NO: 13, at most 90% amino acid identity with amino acids 81-107 or amino acids 124-150 of SEQ ID NO: 13 or at most 95% amino acid identity with amino acids 81-107 or amino acids 124-150 of SEQ ID NO: 13.

In other aspects of this embodiment, a VIP2 comprises a polypeptide having, e.g., at most one, two, three, four, five, six, seven, eight, nine, 10 or 20 non-contiguous amino acid substitutions relative to amino acids 81-107 or amino acids 124-150 of SEQ ID NO: 13. In other aspects of this embodiment, a VIP2 comprises a polypeptide having, e.g., at least one, two, three, four, five, six, seven, eight, nine, 10 or 20 non-contiguous amino acid substitutions relative to amino acids 81-107 or amino acids 124-150 of SEQ ID NO: 13. In yet other aspects of this embodiment, a VIP2 comprises a polypeptide having, e.g., at most one, two, three, four, five, six, seven, eight, nine, 10 or 20 non-contiguous amino acid deletions relative to amino acids 81-107 or amino acids 124-150 of SEQ ID NO: 13. In other aspects of this embodiment, a VIP2 comprises a polypeptide having, e.g., at least one, two, three, four, five, six, seven, eight, nine, 10 or 20 non-contiguous amino acid deletions relative to amino acids 81-107 or amino acids 124-150 of SEQ ID NO: 13. In still other aspects of this embodiment, a VIP2 comprises a polypeptide having, e.g., at most one, two, three, four, five, six, seven, eight, nine, 10 or 20 non-contiguous amino acid additions relative to amino acids 81-107 or amino acids 124-150 of SEQ ID NO: 13. In other aspects of this embodiment, a VIP2 comprises a polypeptide having, e.g., at least one, two, three, four, five, six, seven, eight, nine, 10 or 20 non-contiguous amino acid additions relative to amino acids 81-107 or amino acids 124-150 of SEQ ID NO: 13.

In other aspects of this embodiment, a VIP2 comprises a polypeptide having, e.g., at most one, two, three, four, five, six, seven, eight, nine, 10 or 20 contiguous amino acid substitutions relative to amino acids 81-107 or amino acids 124-150 of SEQ ID NO: 13. In other aspects of this embodiment, a VIP2 comprises a polypeptide having, e.g., at least one, two, three, four, five, six, seven, eight, nine, 10 or 20 contiguous amino acid substitutions relative to amino acids 81-107 or amino acids 124-150 of SEQ ID NO: 13. In yet other aspects of this embodiment, a VIP2 comprises a polypeptide having, e.g., at most one, two, three, four, five, six, seven, eight, nine, 10 or 20 contiguous amino acid deletions relative to amino acids 81-107 or amino acids 124-150 of SEQ ID NO: 13. In other aspects of this embodiment, a VIP2 comprises a polypeptide having, e.g., at least one, two, three, four, five, six, seven, eight, nine, 10 or 20 contiguous amino acid deletions relative to amino acids 81-107 or amino acids 124-150 of SEQ ID NO: 13. In still other aspects of this embodiment, a VIP2 comprises a polypeptide having, e.g., at most one, two, three, four, five, six, seven, eight, nine, 10 or 20 contiguous amino acid additions relative to amino acids 81-107 or amino acids 124-150 of SEQ ID NO: 13. In other aspects of this embodiment, a VIP2 comprises a polypeptide having, e.g., at least one, two, three, four, five, six, seven, eight, nine, 10 or 20 contiguous amino acid additions relative to amino acids 81-107 or amino acids 124-150 of SEQ ID NO: 13.

In another embodiment, an enhanced binding domain is derived from a GIP. In another embodiment, an enhanced binding domain is derived from a GIP of SEQ ID NO: 14. In aspects of this embodiment, an enhanced binding domain is derived from a GIP comprises amino acids 52-78 or amino acids 52-93 of SEQ ID NO: 14.

In other aspects of this embodiment, a GIP comprises a polypeptide having, e.g., at least 70% amino acid identity with amino acids 52-78 or amino acids 52-93 of SEQ ID NO: 14, at least 75% amino acid identity with amino acids 52-78 or amino acids 52-93 of SEQ ID NO: 14, at least 80% amino acid identity with amino acids 52-78 or amino acids 52-93 of SEQ ID NO: 14, at least 85% amino acid identity with amino acids 52-78 or amino acids 52-93 of SEQ ID NO: 14, at least 90% amino acid identity with amino acids 52-78 or amino acids 52-93 of SEQ ID NO: 14 or at least 95% amino acid identity with amino acids 52-78 or amino acids 52-93 of SEQ ID NO: 14. In yet other aspects of this embodiment, a GIP comprises a polypeptide having, e.g., at most 70% amino acid identity with amino acids 52-78 or amino acids 52-93 of SEQ ID NO: 14, at most 75% amino acid identity with amino acids 52-78 or amino acids 52-93 of SEQ ID NO: 14, at most 80% amino acid identity with amino acids 52-78 or amino acids 52-93 of SEQ ID NO: 14, at most 85% amino acid identity with amino acids 52-78 or amino acids 52-93 of SEQ ID NO: 14, at most 90% amino acid identity with amino acids 52-78 or amino acids 52-93 of SEQ ID NO: 14 or at most 95% amino acid identity with amino acids 52-78 or amino acids 52-93 of SEQ ID NO: 14.

In other aspects of this embodiment, a GIP comprises a polypeptide having, e.g., at most one, two, three, four, five, six, seven, eight, nine, 10 or 20 non-contiguous amino acid substitutions relative to amino acids 52-78 or amino acids 52-93 of SEQ ID NO: 14. In other aspects of this embodiment, a GIP comprises a polypeptide having, e.g., at least one, two, three, four, five, six, seven, eight, nine, 10 or 20 non-contiguous amino acid substitutions relative to amino acids 52-78 or amino acids 52-93 of SEQ ID NO: 14. In yet other aspects of this embodiment, a GIP comprises a polypeptide having, e.g., at most one, two, three, four, five, six, seven, eight, nine, 10 or 20 non-contiguous amino acid deletions relative to amino acids 52-78 or amino acids 52-93 of SEQ ID NO: 14. In other aspects of this embodiment, a GIP comprises a polypeptide having, e.g., at least one, two, three, four, five, six, seven, eight, nine, 10 or 20 non-contiguous amino acid deletions relative to amino acids 52-78 or amino acids 52-93 of SEQ ID NO: 14. In still other aspects of this embodiment, a GIP comprises a polypeptide having, e.g., at most one, two, three, four, five, six, seven, eight, nine, 10 or 20 non-contiguous amino acid additions relative to amino acids 52-78 or amino acids 52-93 of SEQ ID NO: 14. In other aspects of this embodiment, a GIP comprises a polypeptide having, e.g., at least one, two, three, four, five, six, seven, eight, nine, 10 or 20 non-contiguous amino acid additions relative to amino acids 52-78 or amino acids 52-93 of SEQ ID NO: 14.

In other aspects of this embodiment, a GIP comprises a polypeptide having, e.g., at most one, two, three, four, five, six, seven, eight, nine, 10 or 20 contiguous amino acid substitutions relative to amino acids 52-78 or amino acids 52-93 of SEQ ID NO: 14. In other aspects of this embodiment, a GIP comprises a polypeptide having, e.g., at least one, two, three, four, five, six, seven, eight, nine, 10 or 20 contiguous amino acid substitutions relative to amino acids 52-78 or amino acids 52-93 of SEQ ID NO: 14. In yet other aspects of this embodiment, a GIP comprises a polypeptide having, e.g., at most one, two, three, four, five, six, seven, eight, nine, 10 or 20 contiguous amino acid deletions relative to amino acids 52-78 or amino acids 52-93 of SEQ ID NO: 14. In other aspects of this embodiment, a GIP comprises a polypeptide having, e.g., at least one, two, three, four, five, six, seven, eight, nine, 10 or 20 contiguous amino acid deletions relative to amino acids 52-78 or amino acids 52-93 of SEQ ID NO: 14. In still other aspects of this embodiment, a GIP comprises a polypeptide having, e.g., at most one, two, three, four, five, six, seven, eight, nine, 10 or 20 contiguous amino acid additions relative to amino acids 52-78 or amino acids 52-93 of SEQ ID NO: 14. In other aspects of this embodiment, a GIP comprises a polypeptide having, e.g., at least one, two, three, four, five, six, seven, eight, nine, 10 or 20 contiguous amino acid additions relative to amino acids 52-78 or amino acids 52-93 of SEQ ID NO: 14.

In another embodiment, an enhanced binding domain is derived from a Secretin. In another embodiment, an enhanced binding domain is derived from a Secretin of SEQ ID NO: 15. In an aspect of this embodiment, an enhanced binding domain is derived from a Secretin comprises amino acids 28-54 of SEQ ID NO: 15.

In other aspects of this embodiment, a Secretin comprises a polypeptide having, e.g., at least 70% amino acid identity with amino acids 28-54 of SEQ ID NO: 15, at least 75% amino acid identity with amino acids 28-54 of SEQ ID NO: 15, at least 80% amino acid identity with amino acids 28-54 of SEQ ID NO: 15, at least 85% amino acid identity with amino acids 28-54 of SEQ ID NO: 15, at least 90% amino acid identity with amino acids 28-54 of SEQ ID NO: 15 or at least 95% amino acid identity with amino acids 28-54 of SEQ ID NO: 15. In yet other aspects of this embodiment, a Secretin comprises a polypeptide having, e.g., at most 70% amino acid identity with amino acids 28-54 of SEQ ID NO: 15, at most 75% amino acid identity with amino acids 28-54 of SEQ ID NO: 15, at most 80% amino acid identity with amino acids 28-54 of SEQ ID NO: 15, at most 85% amino acid identity with amino acids 28-54 of SEQ ID NO: 15, at most 90% amino acid identity with amino acids 28-54 of SEQ ID NO: 15 or at most 95% amino acid identity with amino acids 28-54 of SEQ ID NO: 15.

In other aspects of this embodiment, a Secretin comprises a polypeptide having, e.g., at most one, two, three, four, five, six, seven, eight, nine, 10 or 20 non-contiguous amino acid substitutions relative to amino acids 28-54 of SEQ ID NO: 15. In other aspects of this embodiment, a Secretin comprises a polypeptide having, e.g., at least one, two, three, four, five, six, seven, eight, nine, 10 or 20 non-contiguous amino acid substitutions relative to amino acids 28-54 of SEQ ID NO: 15. In yet other aspects of this embodiment, a Secretin comprises a polypeptide having, e.g., at most one, two, three, four, five, six, seven, eight, nine, 10 or 20 non-contiguous amino acid deletions relative to amino acids 28-54 of SEQ ID NO: 15. In other aspects of this embodiment, a Secretin comprises a polypeptide having, e.g., at least one, two, three, four, five, six, seven, eight, nine, 10 or 20 non-contiguous amino acid deletions relative to amino acids 28-54 of SEQ ID NO: 15. In still other aspects of this embodiment, a Secretin comprises a polypeptide having, e.g., at most one, two, three, four, five, six, seven, eight, nine, 10 or 20 non-contiguous amino acid additions relative to amino acids 28-54 of SEQ ID NO: 15. In other aspects of this embodiment, a Secretin comprises a polypeptide having, e.g., at least one, two, three, four, five, six, seven, eight, nine, 10 or 20 non-contiguous amino acid additions relative to amino acids 28-54 of SEQ ID NO: 15.

In other aspects of this embodiment, a Secretin comprises a polypeptide having, e.g., at most one, two, three, four, five, six, seven, eight, nine, 10 or 20 contiguous amino acid substitutions relative to amino acids 28-54 of SEQ ID NO: 15. In other aspects of this embodiment, a Secretin comprises a polypeptide having, e.g., at least one, two, three, four, five, six, seven, eight, nine, 10 or 20 contiguous amino acid substitutions relative to amino acids 28-54 of SEQ ID NO: 15. In yet other aspects of this embodiment, a Secretin comprises a polypeptide having, e.g., at most one, two, three, four, five, six, seven, eight, nine, 10 or 20 contiguous amino acid deletions relative to amino acids 28-54 of SEQ ID NO: 15. In other aspects of this embodiment, a Secretin comprises a polypeptide having, e.g., at least one, two, three, four, five, six, seven, eight, nine, 10 or 20 contiguous amino acid deletions relative to amino acids 28-54 of SEQ ID NO: 15. In still other aspects of this embodiment, a Secretin comprises a polypeptide having, e.g., at most one, two, three, four, five, six, seven, eight, nine, 10 or 20 contiguous amino acid additions relative to amino acids 28-54 of SEQ ID NO: 15. In other aspects of this embodiment, a Secretin comprises a polypeptide having, e.g., at least one, two, three, four, five, six, seven, eight, nine, 10 or 20 contiguous amino acid additions relative to amino acids 28-54 of SEQ ID NO: 15.

In another embodiment, an enhanced binding domain is derived from a Gastrin. In another embodiment, an enhanced binding domain is derived from a Gastrin of SEQ ID NO: 16. In aspects of this embodiment, an enhanced binding domain is derived from a Gastrin comprises amino acids 76-92 or amino acids 59-92 of SEQ ID NO: 16.

In other aspects of this embodiment, a Gastrin comprises a polypeptide having, e.g., at least 70% amino acid identity with amino acids 76-92 or amino acids 59-92 of SEQ ID NO: 16, at least 75% amino acid identity with amino acids 76-92 or amino acids 59-92 of SEQ ID NO: 16, at least 80% amino acid identity with amino acids 76-92 or amino acids 59-92 of SEQ ID NO: 16, at least 85% amino acid identity with amino acids 76-92 or amino acids 59-92 of SEQ ID NO: 16, at least 90% amino acid identity with amino acids 76-92 or amino acids 59-92 of SEQ ID NO: 16 or at least 95% amino acid identity with amino acids 76-92 or amino acids 59-92 of SEQ ID NO: 16. In yet other aspects of this embodiment, a Gastrin comprises a polypeptide having, e.g., at most 70% amino acid identity with amino acids 76-92 or amino acids 59-92 of SEQ ID NO: 16, at most 75% amino acid identity with amino acids 76-92 or amino acids 59-92 of SEQ ID NO: 16, at most 80% amino acid identity with amino acids 76-92 or amino acids 59-92 of SEQ ID NO: 16, at most 85% amino acid identity with amino acids 76-92 or amino acids 59-92 of SEQ ID NO: 16, at most 90% amino acid identity with amino acids 76-92 or amino acids 59-92 of SEQ ID NO: 16 or at most 95% amino acid identity with amino acids 76-92 or amino acids 59-92 of SEQ ID NO: 16.

In other aspects of this embodiment, a Gastrin comprises a polypeptide having, e.g., at most one, two, three, four, five, six, seven, eight, nine, 10 or 20 non-contiguous amino acid substitutions relative to amino acids 76-92 or amino acids 59-92 of SEQ ID NO: 16. In other aspects of this embodiment, a Gastrin comprises a polypeptide having, e.g., at least one, two, three, four, five, six, seven, eight, nine, 10 or 20 non-contiguous amino acid substitutions relative to amino acids 76-92 or amino acids 59-92 of SEQ ID NO: 16. In yet other aspects of this embodiment, a Gastrin comprises a polypeptide having, e.g., at most one, two, three, four, five, six, seven, eight, nine, 10 or 20 non-contiguous amino acid deletions relative to amino acids 76-92 or amino acids 59-92 of SEQ ID NO: 16. In other aspects of this embodiment, a Gastrin comprises a polypeptide having, e.g., at least one, two, three, four, five, six, seven, eight, nine, 10 or 20 non-contiguous amino acid deletions relative to amino acids 76-92 or amino acids 59-92 of SEQ ID NO: 16. In still other aspects of this embodiment, a Gastrin comprises a polypeptide having, e.g., at most one, two, three, four, five, six, seven, eight, nine, 10 or 20 non-contiguous amino acid additions relative to amino acids 76-92 or amino acids 59-92 of SEQ ID NO: 16. In other aspects of this embodiment, a Gastrin comprises a polypeptide having, e.g., at least one, two, three, four, five, six, seven, eight, nine, 10 or 20 non-contiguous amino acid additions relative to amino acids 76-92 or amino acids 59-92 of SEQ ID NO: 16.

In other aspects of this embodiment, a Gastrin comprises a polypeptide having, e.g., at most one, two, three, four, five, six, seven, eight, nine, 10 or 20 contiguous amino acid substitutions relative to amino acids 76-92 or amino acids 59-92 of SEQ ID NO: 16. In other aspects of this embodiment, a Gastrin comprises a polypeptide having, e.g., at least one, two, three, four, five, six, seven, eight, nine, 10 or 20 contiguous amino acid substitutions relative to amino acids 76-92 or amino acids 59-92 of SEQ ID NO: 16. In yet other aspects of this embodiment, a Gastrin comprises a polypeptide having, e.g., at most one, two, three, four, five, six, seven, eight, nine, 10 or 20 contiguous amino acid deletions relative to amino acids 76-92 or amino acids 59-92 of SEQ ID NO: 16. In other aspects of this embodiment, a Gastrin comprises a polypeptide having, e.g., at least one, two, three, four, five, six, seven, eight, nine, 10 or 20 contiguous amino acid deletions relative to amino acids 76-92 or amino acids 59-92 of SEQ ID NO: 16. In still other aspects of this embodiment, a Gastrin comprises a polypeptide having, e.g., at most one, two, three, four, five, six, seven, eight, nine, 10 or 20 contiguous amino acid additions relative to amino acids 76-92 or amino acids 59-92 of SEQ ID NO: 16. In other aspects of this embodiment, a Gastrin comprises a polypeptide having, e.g., at least one, two, three, four, five, six, seven, eight, nine, 10 or 20 contiguous amino acid additions relative to amino acids 76-92 or amino acids 59-92 of SEQ ID NO: 16.

In another embodiment, an enhanced binding domain is derived from a GRP. In another embodiment, an enhanced binding domain is derived from a GRP of SEQ ID NO: 17. In aspects of this embodiment, an enhanced binding domain is derived from a GRP comprises amino acids 41-50 or amino acids 24-50 of SEQ ID NO: 17.

In other aspects of this embodiment, a GRP comprises a polypeptide having, e.g., at least 70% amino acid identity with amino acids 41-50 or amino acids 24-50 of SEQ ID NO: 17, at least 75% amino acid identity with amino acids 41-50 or amino acids 24-50 of SEQ ID NO: 17, at least 80% amino acid identity with amino acids 41-50 or amino acids 24-50 of SEQ ID NO: 17, at least 85% amino acid identity with amino acids 41-50 or amino acids 24-50 of SEQ ID NO: 17, at least 90% amino acid identity with amino acids 41-50 or amino acids 24-50 of SEQ ID NO: 17 or at least 95% amino acid identity with amino acids 41-50 or amino acids 24-50 of SEQ ID NO: 17. In yet other aspects of this embodiment, a GRP comprises a polypeptide having, e.g., at most 70% amino acid identity with amino acids 41-50 or amino acids 24-50 of SEQ ID NO: 17, at most 75% amino acid identity with amino acids 41-50 or amino acids 24-50 of SEQ ID NO: 17, at most 80% amino acid identity with amino acids 41-50 or amino acids 24-50 of SEQ ID NO: 17, at most 85% amino acid identity with amino acids 41-50 or amino acids 24-50 of SEQ ID NO: 17, at most 90% amino acid identity with amino acids 41-50 or amino acids 24-50 of SEQ ID NO: 17 or at most 95% amino acid identity with amino acids 41-50 or amino acids 24-50 of SEQ ID NO: 17.

In other aspects of this embodiment, a GRP comprises a polypeptide having, e.g., at most one, two, three, four, five, six, seven, eight, nine, 10 or 20 non-contiguous amino acid substitutions relative to amino acids 41-50 or amino acids 24-50 of SEQ ID NO: 17. In other aspects of this embodiment, a GRP comprises a polypeptide having, e.g., at least one, two, three, four, five, six, seven, eight, nine, 10 or 20 non-contiguous amino acid substitutions relative to amino acids 41-50 or amino acids 24-50 of SEQ ID NO: 17. In yet other aspects of this embodiment, a GRP comprises a polypeptide having, e.g., at most one, two, three, four, five, six, seven, eight, nine, 10 or 20 non-contiguous amino acid deletions relative to amino acids 41-50 or amino acids 24-50 of SEQ ID NO: 17. In other aspects of this embodiment, a GRP comprises a polypeptide having, e.g., at least one, two, three, four, five, six, seven, eight, nine, 10 or 20 non-contiguous amino acid deletions relative to amino acids 41-50 or amino acids 24-50 of SEQ ID NO: 17. In still other aspects of this embodiment, a GRP comprises a polypeptide having, e.g., at most one, two, three, four, five, six, seven, eight, nine, 10 or 20 non-contiguous amino acid additions relative to amino acids 41-50 or amino acids 24-50 of SEQ ID NO: 17. In other aspects of this embodiment, a GRP comprises a polypeptide having, e.g., at least one, two, three, four, five, six, seven, eight, nine, 10 or 20 non-contiguous amino acid additions relative to amino acids 41-50 or amino acids 24-50 of SEQ ID NO: 17.

In other aspects of this embodiment, a GRP comprises a polypeptide having, e.g., at most one, two, three, four, five, six, seven, eight, nine, 10 or 20 contiguous amino acid substitutions relative to amino acids 41-50 or amino acids 24-50 of SEQ ID NO: 17. In other aspects of this embodiment, a GRP comprises a polypeptide having, e.g., at least one, two, three, four, five, six, seven, eight, nine, 10 or 20 contiguous amino acid substitutions relative to amino acids 41-50 or amino acids 24-50 of SEQ ID NO: 17. In yet other aspects of this embodiment, a GRP comprises a polypeptide having, e.g., at most one, two, three, four, five, six, seven, eight, nine, 10 or 20 contiguous amino acid deletions relative to amino acids 41-50 or amino acids 24-50 of SEQ ID NO: 17. In other aspects of this embodiment, a GRP comprises a polypeptide having, e.g., at least one, two, three, four, five, six, seven, eight, nine, 10 or 20 contiguous amino acid deletions relative to amino acids 41-50 or amino acids 24-50 of SEQ ID NO: 17. In still other aspects of this embodiment, a GRP comprises a polypeptide having, e.g., at most one, two, three, four, five, six, seven, eight, nine, 10 or 20 contiguous amino acid additions relative to amino acids 41-50 or amino acids 24-50 of SEQ ID NO: 17. In other aspects of this embodiment, a GRP comprises a polypeptide having, e.g., at least one, two, three, four, five, six, seven, eight, nine, 10 or 20 contiguous amino acid additions relative to amino acids 41-50 or amino acids 24-50 of SEQ ID NO: 17.

In another embodiment, an enhanced binding domain is derived from a CCK. In another embodiment, an enhanced binding domain is derived from a CCK of SEQ ID NO: 18. In an aspect of this embodiment, an enhanced binding domain is derived from a CCK comprises amino acids 99-112 of SEQ ID NO: 18.

In other aspects of this embodiment, a CCK comprises a polypeptide having, e.g., at least 70% amino acid identity with amino acids 99-112 of SEQ ID NO: 18, at least 75% amino acid identity with amino acids 99-112 of SEQ ID NO: 18, at least 80% amino acid identity with amino acids 99-112 of SEQ ID NO: 18, at least 85% amino acid identity with amino acids 99-112 of SEQ ID NO: 18, at least 90% amino acid identity with amino acids 99-112 of SEQ ID NO: 18 or at least 95% amino acid identity with amino acids 99-112 of SEQ ID NO: 18. In yet other aspects of this embodiment, a CCK comprises a polypeptide having, e.g., at most 70% amino acid identity with amino acids 99-112 of SEQ ID NO: 18, at most 75% amino acid identity with amino acids 99-112 of SEQ ID NO: 18, at most 80% amino acid identity with amino acids 99-112 of SEQ ID NO: 18, at most 85% amino acid identity with amino acids 99-112 of SEQ ID NO: 18, at most 90% amino acid identity with amino acids 99-112 of SEQ ID NO: 18 or at most 95% amino acid identity with amino acids 99-112 of SEQ ID NO: 18.

In other aspects of this embodiment, a CCK comprises a polypeptide having, e.g., at most one, two, three, four, five, six, seven, eight, nine, 10 or 20 non-contiguous amino acid substitutions relative to amino acids 99-112 of SEQ ID NO: 18. In other aspects of this embodiment, a CCK comprises a polypeptide having, e.g., at least one, two, three, four, five, six, seven, eight, nine, 10 or 20 non-contiguous amino acid substitutions relative to amino acids 99-112 of SEQ ID NO: 18. In yet other aspects of this embodiment, a CCK comprises a polypeptide having, e.g., at most one, two, three, four, five, six, seven, eight, nine, 10 or 20 non-contiguous amino acid deletions relative to amino acids 99-112 of SEQ ID NO: 18. In other aspects of this embodiment, a CCK comprises a polypeptide having, e.g., at least one, two, three, four, five, six, seven, eight, nine, 10 or 20 non-contiguous amino acid deletions relative to amino acids 99-112 of SEQ ID NO: 18. In still other aspects of this embodiment, a CCK comprises a polypeptide having, e.g., at most one, two, three, four, five, six, seven, eight, nine, 10 or 20 non-contiguous amino acid additions relative to amino acids 99-112 of SEQ ID NO: 18. In other aspects of this embodiment, a CCK comprises a polypeptide having, e.g., at least one, two, three, four, five, six, seven, eight, nine, 10 or 20 non-contiguous amino acid additions relative to amino acids 99-112 of SEQ ID NO: 18.

In other aspects of this embodiment, a CCK comprises a polypeptide having, e.g., at most one, two, three, four, five, six, seven, eight, nine, 10 or 20 contiguous amino acid substitutions relative to amino acids 99-112 of SEQ ID NO: 18. In other aspects of this embodiment, a CCK comprises a polypeptide having, e.g., at least one, two, three, four, five, six, seven, eight, nine, 10 or 20 contiguous amino acid substitutions relative to amino acids 99-112 of SEQ ID NO: 18. In yet other aspects of this embodiment, a CCK comprises a polypeptide having, e.g., at most one, two, three, four, five, six, seven, eight, nine, 10 or 20 contiguous amino acid deletions relative to amino acids 99-112 of SEQ ID NO: 18. In other aspects of this embodiment, a CCK comprises a polypeptide having, e.g., at least one, two, three, four, five, six, seven, eight, nine, 10 or 20 contiguous amino acid deletions relative to amino acids 99-112 of SEQ ID NO: 18. In still other aspects of this embodiment, a CCK comprises a polypeptide having, e.g., at most one, two, three, four, five, six, seven, eight, nine, 10 or 20 contiguous amino acid additions relative to amino acids 99-112 of SEQ ID NO: 18. In other aspects of this embodiment, a CCK comprises a polypeptide having, e.g., at least one, two, three, four, five, six, seven, eight, nine, 10 or 20 contiguous amino acid additions relative to amino acids 99-112 of SEQ ID NO: 18.

Another example of an enhanced targeting domain disclosed in the present specification is, e.g., neurohormones, such as, e.g., corticotropin-releasing hormone (CCRH) or parathyroid hormone (PTH).

Thus, in an embodiment, an enhanced binding domain is derived from a CCRH. In another embodiment, an enhanced binding domain is derived from a CCRH of SEQ ID NO: 19. In aspects of this embodiment, an enhanced binding domain is derived from a CCRH comprises amino acids 159-193 or amino acids 154-194 of SEQ ID NO: 19.

In other aspects of this embodiment, a CCRH comprises a polypeptide having, e.g., at least 70% amino acid identity with amino acids 159-193 or amino acids 154-194 of SEQ ID NO: 19, at least 75% amino acid identity with amino acids 159-193 or amino acids 154-194 of SEQ ID NO: 19, at least 80% amino acid identity with amino acids 159-193 or amino acids 154-194 of SEQ ID NO: 19, at least 85% amino acid identity with amino acids 159-193 or amino acids 154-194 of SEQ ID NO: 19, at least 90% amino acid identity with amino acids 159-193 or amino acids 154-194 of SEQ ID NO: 19 or at least 95% amino acid identity with amino acids 159-193 or amino acids 154-194 of SEQ ID NO: 19. In yet other aspects of this embodiment, a CCRH comprises a polypeptide having, e.g., at most 70% amino acid identity with amino acids 159-193 or amino acids 154-194 of SEQ ID NO: 19, at most 75% amino acid identity with amino acids 159-193 or amino acids 154-194 of SEQ ID NO: 19, at most 80% amino acid identity with amino acids 159-193 or amino acids 154-194 of SEQ ID NO: 19, at most 85% amino acid identity with amino acids 159-193 or amino acids 154-194 of SEQ ID NO: 19, at most 90% amino acid identity with amino acids 159-193 or amino acids 154-194 of SEQ ID NO: 19 or at most 95% amino acid identity with amino acids 159-193 or amino acids 154-194 of SEQ ID NO: 19.

In other aspects of this embodiment, a CCRH comprises a polypeptide having, e.g., at most one, two, three, four, five, six, seven, eight, nine, 10 or 20 non-contiguous amino acid substitutions relative to amino acids 159-193 or amino acids 154-194 of SEQ ID NO: 19. In other aspects of this embodiment, a CCRH comprises a polypeptide having, e.g., at least one, two, three, four, five, six, seven, eight, nine, 10 or 20 non-contiguous amino acid substitutions relative to amino acids 159-193 or amino acids 154-194 of SEQ ID NO: 19. In yet other aspects of this embodiment, a CCRH comprises a polypeptide having, e.g., at most one, two, three, four, five, six, seven, eight, nine, 10 or 20 non-contiguous amino acid deletions relative to amino acids 159-193 or amino acids 154-194 of SEQ ID NO: 19. In other aspects of this embodiment, a CCRH comprises a polypeptide having, e.g., at least one, two, three, four, five, six, seven, eight, nine, 10 or 20 non-contiguous amino acid deletions relative to amino acids 159-193 or amino acids 154-194 of SEQ ID NO: 19. In still other aspects of this embodiment, a CCRH comprises a polypeptide having, e.g., at most one, two, three, four, five, six, seven, eight, nine, 10 or 20 non-contiguous amino acid additions relative to amino acids 159-193 or amino acids 154-194 of SEQ ID NO: 19. In other aspects of this embodiment, a CCRH comprises a polypeptide having, e.g., at least one, two, three, four, five, six, seven, eight, nine, 10 or 20 non-contiguous amino acid additions relative to amino acids 159-193 or amino acids 154-194 of SEQ ID NO: 19.

In other aspects of this embodiment, a CCRH comprises a polypeptide having, e.g., at most one, two, three, four, five, six, seven, eight, nine, 10 or 20 contiguous amino acid substitutions relative to amino acids 159-193 or amino acids 154-194 of SEQ ID NO: 19. In other aspects of this embodiment, a CCRH comprises a polypeptide having, e.g., at least one, two, three, four, five, six, seven, eight, nine, 10 or 20 contiguous amino acid substitutions relative to amino acids 159-193 or amino acids 154-194 of SEQ ID NO: 19. In yet other aspects of this embodiment, a CCRH comprises a polypeptide having, e.g., at most one, two, three, four, five, six, seven, eight, nine, 10 or 20 contiguous amino acid deletions relative to amino acids 159-193 or amino acids 154-194 of SEQ ID NO: 19. In other aspects of this embodiment, a CCRH comprises a polypeptide having, e.g., at least one, two, three, four, five, six, seven, eight, nine, 10 or 20 contiguous amino acid deletions relative to amino acids 159-193 or amino acids 154-194 of SEQ ID NO: 19. In still other aspects of this embodiment, a CCRH comprises a polypeptide having, e.g., at most one, two, three, four, five, six, seven, eight, nine, 10 or 20 contiguous amino acid additions relative to amino acids 159-193 or amino acids 154-194 of SEQ ID NO: 19. In other aspects of this embodiment, a CCRH comprises a polypeptide having, e.g., at least one, two, three, four, five, six, seven, eight, nine, 10 or 20 contiguous amino acid additions relative to amino acids 159-193 or amino acids 154-194 of SEQ ID NO: 19.

In another embodiment, an enhanced binding domain is derived from a PTH. In another embodiment, an enhanced binding domain is derived from a PTH of SEQ ID NO: 20. In aspects of this embodiment, an enhanced binding domain is derived from a PTH comprises amino acids 35-70 or amino acids 145-177 of SEQ ID NO: 20.

In other aspects of this embodiment, a PTH comprises a polypeptide having, e.g., at least 70% amino acid identity with amino acids 35-70 or amino acids 145-177 of SEQ ID NO: 20, at least 75% amino acid identity with amino acids 35-70 or amino acids 145-177 of SEQ ID NO: 20, at least 80% amino acid identity with amino acids 35-70 or amino acids 145-177 of SEQ ID NO: 20, at least 85% amino acid identity with amino acids 35-70 or amino acids 145-177 of SEQ ID NO: 20, at least 90% amino acid identity with amino acids 35-70 or amino acids 145-177 of SEQ ID NO: 20 or at least 95% amino acid identity with amino acids 35-70 or amino acids 145-177 of SEQ ID NO: 20. In yet other aspects of this embodiment, a PTH comprises a polypeptide having, e.g., at most 70% amino acid identity with amino acids 35-70 or amino acids 145-177 of SEQ ID NO: 20, at most 75% amino acid identity with amino acids 35-70 or amino acids 145-177 of SEQ ID NO: 20, at most 80% amino acid identity with amino acids 35-70 or amino acids 145-177 of SEQ ID NO: 20, at most 85% amino acid identity with amino acids 35-70 or amino acids 145-177 of SEQ ID NO: 20, at most 90% amino acid identity with amino acids 35-70 or amino acids 145-177 of SEQ ID NO: 20 or at most 95% amino acid identity with amino acids 35-70 or amino acids 145-177 of SEQ ID NO: 20.

In other aspects of this embodiment, a PTH comprises a polypeptide having, e.g., at most one, two, three, four, five, six, seven, eight, nine, 10 or 20 non-contiguous amino acid substitutions relative to amino acids 35-70 or amino acids 145-177 of SEQ ID NO: 20. In other aspects of this embodiment, a PTH comprises a polypeptide having, e.g., at least one, two, three, four, five, six, seven, eight, nine, 10 or 20 non-contiguous amino acid substitutions relative to amino acids 35-70 or amino acids 145-177 of SEQ ID NO: 20. In yet other aspects of this embodiment, a PTH comprises a polypeptide having, e.g., at most one, two, three, four, five, six, seven, eight, nine, 10 or 20 non-contiguous amino acid deletions relative to amino acids 35-70 or amino acids 145-

177 of SEQ ID NO: 20. In other aspects of this embodiment, a PTH comprises a polypeptide having, e.g., at least one, two, three, four, five, six, seven, eight, nine, 10 or 20 non-contiguous amino acid deletions relative to amino acids 35-70 or amino acids 145-177 of SEQ ID NO: 20. In still other aspects of this embodiment, a PTH comprises a polypeptide having, e.g., at most one, two, three, four, five, six, seven, eight, nine, 10 or 20 non-contiguous amino acid additions relative to amino acids 35-70 or amino acids 145-177 of SEQ ID NO: 20. In other aspects of this embodiment, a PTH comprises a polypeptide having, e.g., at least one, two, three, four, five, six, seven, eight, nine, 10 or 20 non-contiguous amino acid additions relative to amino acids 35-70 or amino acids 145-177 of SEQ ID NO: 20.

In other aspects of this embodiment, a PTH comprises a polypeptide having, e.g., at most one, two, three, four, five, six, seven, eight, nine, 10 or 20 contiguous amino acid substitutions relative to amino acids 35-70 or amino acids 145-177 of SEQ ID NO: 20. In other aspects of this embodiment, a PTH comprises a polypeptide having, e.g., at least one, two, three, four, five, six, seven, eight, nine, 10 or 20 contiguous amino acid substitutions relative to amino acids 35-70 or amino acids 145-177 of SEQ ID NO: 20. In yet other aspects of this embodiment, a PTH comprises a polypeptide having, e.g., at most one, two, three, four, five, six, seven, eight, nine, 10 or 20 contiguous amino acid deletions relative to amino acids 35-70 or amino acids 145-177 of SEQ ID NO: 20. In other aspects of this embodiment, a PTH comprises a polypeptide having, e.g., at least one, two, three, four, five, six, seven, eight, nine, 10 or 20 contiguous amino acid deletions relative to amino acids 35-70 or amino acids 145-177 of SEQ ID NO: 20. In still other aspects of this embodiment, a PTH comprises a polypeptide having, e.g., at most one, two, three, four, five, six, seven, eight, nine, 10 or 20 contiguous amino acid additions relative to amino acids 35-70 or amino acids 145-177 of SEQ ID NO: 20. In other aspects of this embodiment, a PTH comprises a polypeptide having, e.g., at least one, two, three, four, five, six, seven, eight, nine, 10 or 20 contiguous amino acid additions relative to amino acids 35-70 or amino acids 145-177 of SEQ ID NO: 20.

Another example of an enhanced targeting domain disclosed in the present specification is, e.g., neuroregulatory cytokines, such as, e.g., ciliary neurotrophic factor (CNTF), glycophorin-A (GPA), leukemia inhibitory factor (LIF), also known as cholinergic differentiation factor (CDF), interleukins (ILs), like IL1, IL2, IL6, IL8 and IL10, onostatin M, cardiotrophin-1 (CT-1), cardiotrophin-like cytokine (CLC), or neuroleukin, also known as glucose phosphate isomerase (GPI), autocrine motility factor (AMF), maturation and differentiation factor (MF).

Thus, in an embodiment, an enhanced binding domain is derived from a CNTF. In another embodiment, an enhanced binding domain is derived from a CNTF of SEQ ID NO: 21. In aspects of this embodiment, a CNTF comprises a polypeptide having, e.g., at least 70% amino acid identity with the amino acid sequence of SEQ ID NO: 21, at least 75% amino acid identity with the amino acid sequence of SEQ ID NO: 21, at least 80% amino acid identity with the amino acid sequence of SEQ ID NO: 21, at least 85% amino acid identity with the amino acid sequence of SEQ ID NO: 21, at least 90% amino acid identity with the amino acid sequence of SEQ ID NO: 21 or at least 95% amino acid identity with the amino acid sequence of SEQ ID NO: 21. In yet other aspects of this embodiment, a CNTF comprises a polypeptide having, e.g., at most 70% amino acid identity with the amino acid sequence of SEQ ID NO: 21, at most 75% amino acid identity with the amino acid sequence of SEQ ID NO: 21, at most 80% amino acid identity with the amino acid sequence of SEQ ID NO: 21, at most 85% amino acid identity with the amino acid sequence of SEQ ID NO: 21, at most 90% amino acid identity with the amino acid sequence of SEQ ID NO: 21 or at most 95% amino acid identity with the amino acid sequence of SEQ ID NO: 21.

In other aspects of this embodiment, a CNTF comprises a polypeptide having, e.g., at most one, two, three, four, five, six, seven, eight, nine, 10 or 20 non-contiguous amino acid substitutions relative to the amino acid sequence of SEQ ID NO: 21. In other aspects of this embodiment, a CNTF comprises a polypeptide having, e.g., at least one, two, three, four, five, six, seven, eight, nine, 10 or 20 non-contiguous amino acid substitutions relative to the amino acid sequence of SEQ ID NO: 21. In yet other aspects of this embodiment, a CNTF comprises a polypeptide having, e.g., at most one, two, three, four, five, six, seven, eight, nine, 10 or 20 non-contiguous amino acid deletions relative to the amino acid sequence of SEQ ID NO: 21. In other aspects of this embodiment, a CNTF comprises a polypeptide having, e.g., at least one, two, three, four, five, six, seven, eight, nine, 10 or 20 non-contiguous amino acid deletions relative to the amino acid sequence of SEQ ID NO: 21. In still other aspects of this embodiment, a CNTF comprises a polypeptide having, e.g., at most one, two, three, four, five, six, seven, eight, nine, 10 or 20 non-contiguous amino acid additions relative to the amino acid sequence of SEQ ID NO: 21. In other aspects of this embodiment, a CNTF comprises a polypeptide having, e.g., at least one, two, three, four, five, six, seven, eight, nine, 10 or 20 non-contiguous amino acid additions relative to the amino acid sequence of SEQ ID NO: 21.

In other aspects of this embodiment, a CNTF comprises a polypeptide having, e.g., at most one, two, three, four, five, six, seven, eight, nine, 10 or 20 contiguous amino acid substitutions relative to the amino acid sequence of SEQ ID NO: 21. In other aspects of this embodiment, a CNTF comprises a polypeptide having, e.g., at least one, two, three, four, five, six, seven, eight, nine, 10 or 20 contiguous amino acid substitutions relative to the amino acid sequence of SEQ ID NO: 21. In yet other aspects of this embodiment, a CNTF comprises a polypeptide having, e.g., at most one, two, three, four, five, six, seven, eight, nine, 10 or 20 contiguous amino acid deletions relative to the amino acid sequence of SEQ ID NO: 21. In other aspects of this embodiment, a CNTF comprises a polypeptide having, e.g., at least one, two, three, four, five, six, seven, eight, nine, 10 or 20 contiguous amino acid deletions relative to the amino acid sequence of SEQ ID NO: 21. In still other aspects of this embodiment, a CNTF comprises a polypeptide having, e.g., at most one, two, three, four, five, six, seven, eight, nine, 10 or 20 contiguous amino acid additions relative to the amino acid sequence of SEQ ID NO: 21. In other aspects of this embodiment, a CNTF comprises a polypeptide having, e.g., at least one, two, three, four, five, six, seven, eight, nine, 10 or 20 contiguous amino acid additions relative to the amino acid sequence of SEQ ID NO: 21.

In another embodiment, an enhanced binding domain is derived from a GPA. In another embodiment, an enhanced binding domain is derived from a GPA of SEQ ID NO: 22. In aspects of this embodiment, a GPA comprises a polypeptide having, e.g., at least 70% amino acid identity with the amino acid sequence of SEQ ID NO: 22, at least 75% amino acid identity with the amino acid sequence of SEQ ID NO: 22, at least 80% amino acid identity with the amino acid sequence of SEQ ID NO: 22, at least 85% amino acid identity with the amino acid sequence of SEQ ID NO: 22, at least 90% amino acid identity with the amino acid sequence of SEQ ID NO: 22 or at least 95% amino acid identity with the amino acid sequence of SEQ ID NO: 22. In yet other aspects of this embodiment, a GPA comprises a polypeptide having, e.g., at most 70% amino acid identity with the amino acid sequence of SEQ ID NO: 22, at most 75% amino acid identity with the amino acid sequence of SEQ ID NO: 22, at most 80% amino acid identity with the amino acid sequence of SEQ ID NO: 22, at most 85% amino acid identity with the amino acid sequence of SEQ ID NO: 22, at most 90% amino acid identity with the amino acid sequence of SEQ ID NO: 22 or at most 95% amino acid identity with the amino acid sequence of SEQ ID NO: 22.

In other aspects of this embodiment, a GPA comprises a polypeptide having, e.g., at most one, two, three, four, five, six, seven, eight, nine, 10 or 20 non-contiguous amino acid substitutions relative to the amino acid sequence of SEQ ID NO: 22. In other aspects of this embodiment, a GPA comprises a polypeptide having, e.g., at least one, two, three, four, five, six, seven, eight, nine, 10 or 20 non-contiguous amino acid substitutions relative to the amino acid sequence of SEQ ID NO: 22. In yet other aspects of this embodiment, a GPA comprises a polypeptide having, e.g., at most one, two, three, four, five, six, seven, eight, nine, 10 or 20 non-contiguous amino acid deletions relative to the amino acid sequence of SEQ ID NO: 22. In other aspects of this embodiment, a GPA comprises a polypeptide having, e.g., at least one, two, three, four, five, six, seven, eight, nine, 10 or 20 non-contiguous amino acid deletions relative to the amino acid sequence of SEQ ID NO: 22. In still other aspects of this embodiment, a GPA comprises a polypeptide having, e.g., at most one, two, three, four, five, six, seven, eight, nine, 10 or 20 non-contiguous amino acid additions relative to the amino acid sequence of SEQ ID NO: 22. In other aspects of this embodiment, a GPA comprises a polypeptide having, e.g., at least one, two, three, four, five, six, seven, eight, nine, 10 or 20 non-contiguous amino acid additions relative to the amino acid sequence of SEQ ID NO: 22.

In other aspects of this embodiment, a GPA comprises a polypeptide having, e.g., at most one, two, three, four, five, six, seven, eight, nine, 10 or 20 contiguous amino acid substitutions relative to the amino acid sequence of SEQ ID NO: 22. In other aspects of this embodiment, a GPA comprises a polypeptide having, e.g., at least one, two, three, four, five, six, seven, eight, nine, 10 or 20 contiguous amino acid substitutions relative to the amino acid sequence of SEQ ID NO: 22. In yet other aspects of this embodiment, a GPA comprises a polypeptide having, e.g., at most one, two, three, four, five, six, seven, eight, nine, 10 or 20 contiguous amino acid deletions relative to the amino acid sequence of SEQ ID NO: 22. In other aspects of this embodiment, a GPA comprises a polypeptide having, e.g., at least one, two, three, four, five, six, seven, eight, nine, 10 or 20 contiguous amino acid deletions relative to the amino acid sequence of SEQ ID NO: 22. In still other aspects of this embodiment, a GPA comprises a polypeptide having, e.g., at most one, two, three, four, five, six, seven, eight, nine, 10 or 20 contiguous amino acid additions relative to the amino acid sequence of SEQ ID NO: 22. In other aspects of this embodiment, a GPA comprises a polypeptide having, e.g., at least one, two, three, four, five, six, seven, eight, nine, 10 or 20 contiguous amino acid additions relative to the amino acid sequence of SEQ ID NO: 22.

In another embodiment, an enhanced binding domain is derived from a LIF. In another embodiment, an enhanced binding domain is derived from a LIF of SEQ ID NO: 23. In aspects of this embodiment, a LIF comprises a polypeptide having, e.g., at least 70% amino acid identity with the amino acid sequence of SEQ ID NO: 23, at least 75% amino acid identity with the amino acid sequence of SEQ ID NO: 23, at least 80% amino acid identity with the amino acid sequence of SEQ ID NO: 23, at least 85% amino acid identity with the amino acid sequence of SEQ ID NO: 23, at least 90% amino acid identity with the amino acid sequence of SEQ ID NO: 23 or at least 95% amino acid identity with the amino acid sequence of SEQ ID NO: 23. In yet other aspects of this embodiment, a LIF comprises a polypeptide having, e.g., at most 70% amino acid identity with the amino acid sequence of SEQ ID NO: 23, at most 75% amino acid identity with the amino acid sequence of SEQ ID NO: 23, at most 80% amino acid identity with the amino acid sequence of SEQ ID NO: 23, at most 85% amino acid identity with the amino acid sequence of SEQ ID NO: 23, at most 90% amino acid identity with the amino acid sequence of SEQ ID NO: 23 or at most 95% amino acid identity with the amino acid sequence of SEQ ID NO: 23.

In other aspects of this embodiment, a LIF comprises a polypeptide having, e.g., at most one, two, three, four, five, six, seven, eight, nine, 10 or 20 non-contiguous amino acid substitutions relative to the amino acid sequence of SEQ ID NO: 23. In other aspects of this embodiment, a LIF comprises a polypeptide having, e.g., at least one, two, three, four, five, six, seven, eight, nine, 10 or 20 non-contiguous amino acid substitutions relative to the amino acid sequence of SEQ ID NO: 23. In yet other aspects of this embodiment, a LIF comprises a polypeptide having, e.g., at most one, two, three, four, five, six, seven, eight, nine, 10 or 20 non-contiguous amino acid deletions relative to the amino acid sequence of SEQ ID NO: 23. In other aspects of this embodiment, a LIF comprises a polypeptide having, e.g., at least one, two, three, four, five, six, seven, eight, nine, 10 or 20 non-contiguous amino acid deletions relative to the amino acid sequence of SEQ ID NO: 23. In still other aspects of this embodiment, a LIF comprises a polypeptide having, e.g., at most one, two, three, four, five, six, seven, eight, nine, 10 or 20 non-contiguous amino acid additions relative to the amino acid sequence of SEQ ID NO: 23. In other aspects of this embodiment, a LIF comprises a polypeptide having, e.g., at least one, two, three, four, five, six, seven, eight, nine, 10 or 20 non-contiguous amino acid additions relative to the amino acid sequence of SEQ ID NO: 23.

In other aspects of this embodiment, a LIF comprises a polypeptide having, e.g., at most one, two, three, four, five, six, seven, eight, nine, 10 or 20 contiguous amino acid substitutions relative to the amino acid sequence of SEQ ID NO: 23. In other aspects of this embodiment, a LIF comprises a polypeptide having, e.g., at least one, two, three, four, five, six, seven, eight, nine, 10 or 20 contiguous amino acid substitutions relative to the amino acid sequence of SEQ ID NO: 23. In yet other aspects of this embodiment, a LIF comprises a polypeptide having, e.g., at most one, two, three, four, five, six, seven, eight, nine, 10 or 20 contiguous amino acid deletions relative to the amino acid sequence of SEQ ID NO: 23. In other aspects of this embodiment, a LIF comprises a polypeptide having, e.g., at least one, two, three, four, five, six, seven, eight, nine, 10 or 20 contiguous amino acid deletions relative to the amino acid sequence of SEQ ID NO: 23. In still other aspects of this embodiment, a LIF comprises a polypeptide having, e.g., at most one, two, three, four, five, six, seven, eight, nine, 10 or 20 contiguous amino acid additions relative to the amino acid sequence of SEQ ID NO: 23. In other aspects of this embodiment, a LIF comprises a polypeptide having, e.g., at least one, two, three, four, five, six, seven, eight, nine, 10 or 20 contiguous amino acid additions relative to the amino acid sequence of SEQ ID NO: 23.

In another embodiment, an enhanced binding domain is derived from a CT-1. In another embodiment, an enhanced binding domain is derived from a CT-1 of SEQ ID NO: 24. In aspects of this embodiment, a CT-1 comprises a polypeptide having, e.g., at least 70% amino acid identity with the amino acid sequence of SEQ ID NO: 24, at least 75% amino acid identity with the amino acid sequence of SEQ ID NO: 24, at least 80% amino acid identity with the amino acid sequence of SEQ ID NO: 24, at least 85% amino acid identity with the amino acid sequence of SEQ ID NO: 24, at least 90% amino acid identity with the amino acid sequence of SEQ ID NO: 24 or at least 95% amino acid identity with the amino acid sequence of SEQ ID NO: 24. In yet other aspects of this embodiment, a CT-1 comprises a polypeptide having, e.g., at most 70% amino acid identity with the amino acid sequence of SEQ ID NO: 24, at most 75% amino acid identity with the amino acid sequence of SEQ ID NO: 24, at most 80% amino acid identity with the amino acid sequence of SEQ ID NO: 24, at most 85% amino acid identity with the amino acid sequence of SEQ ID NO: 24, at most 90% amino acid identity with the amino acid sequence of SEQ ID NO: 24 or at most 95% amino acid identity with the amino acid sequence of SEQ ID NO: 24.

In other aspects of this embodiment, a CT-1 comprises a polypeptide having, e.g., at most one, two, three, four, five, six, seven, eight, nine, 10 or 20 non-contiguous amino acid substitutions relative to the amino acid sequence of SEQ ID NO: 24. In other aspects of this embodiment, a CT-1 comprises a polypeptide having, e.g., at least one, two, three, four, five, six, seven, eight, nine, 10 or 20 non-contiguous amino acid substitutions relative to the amino acid sequence of SEQ ID NO: 24. In yet other aspects of this embodiment, a CT-1 comprises a polypeptide having, e.g., at most one, two, three, four, five, six, seven, eight, nine, 10 or 20 non-contiguous amino acid deletions relative to the amino acid sequence of SEQ ID NO: 24. In other aspects of this embodiment, a CT-1 comprises a polypeptide having, e.g., at least one, two, three, four, five, six, seven, eight, nine, 10 or 20 non-contiguous amino acid deletions relative to the amino acid sequence of SEQ ID NO: 24. In still other aspects of this embodiment, a CT-1 comprises a polypeptide having, e.g., at most one, two, three, four, five, six, seven, eight, nine, 10 or 20 non-contiguous amino acid additions relative to the amino acid sequence of SEQ ID NO: 24. In other aspects of this embodiment, a CT-1 comprises a polypeptide having, e.g., at least one, two, three, four, five, six, seven, eight, nine, 10 or 20 non-contiguous amino acid additions relative to the amino acid sequence of SEQ ID NO: 24.

In other aspects of this embodiment, a CT-1 comprises a polypeptide having, e.g., at most one, two, three, four, five, six, seven, eight, nine, 10 or 20 contiguous amino acid substitutions relative to the amino acid sequence of SEQ ID NO: 24. In other aspects of this embodiment, a CT-1 comprises a polypeptide having, e.g., at least one, two, three, four, five, six, seven, eight, nine, 10 or 20 contiguous amino acid substitutions relative to the amino acid sequence of SEQ ID NO: 24. In yet other aspects of this embodiment, a CT-1 comprises a polypeptide having, e.g., at most one, two, three, four, five, six, seven, eight, nine, 10 or 20 contiguous amino acid deletions relative to the amino acid sequence of SEQ ID NO: 24. In other aspects of this embodiment, a CT-1 comprises a polypeptide having, e.g., at least one, two, three, four, five, six, seven, eight, nine, 10 or 20 contiguous amino acid deletions relative to the amino acid sequence of SEQ ID NO: 24. In still other aspects of this embodiment, a CT-1 comprises a polypeptide having, e.g., at most one, two, three, four, five, six, seven, eight, nine, 10 or 20 contiguous amino acid additions relative to the amino acid sequence of SEQ ID NO: 24. In other aspects of this embodiment, a CT-1 comprises a polypeptide having, e.g., at least one, two, three, four, five, six, seven, eight, nine, 10 or 20 contiguous amino acid additions relative to the amino acid sequence of SEQ ID NO: 24.

In another embodiment, an enhanced binding domain is derived from a CLC. In another embodiment, an enhanced binding domain is derived from a CLC of SEQ ID NO: 25. In aspects of this embodiment, a CLC comprises a polypeptide having, e.g., at least 70% amino acid identity with the amino acid sequence of SEQ ID NO: 25, at least 75% amino acid identity with the amino acid sequence of SEQ ID NO: 25, at least 80% amino acid identity with the amino acid sequence of SEQ ID NO: 25, at least 85% amino acid identity with the amino acid sequence of SEQ ID NO: 25, at least 90% amino acid identity with the amino acid sequence of SEQ ID NO: 25 or at least 95% amino acid identity with the amino acid sequence of SEQ ID NO: 25. In yet other aspects of this embodiment, a CLC comprises a polypeptide having, e.g., at most 70% amino acid identity with the amino acid sequence of SEQ ID NO: 25, at most 75% amino acid identity with the amino acid sequence of SEQ ID NO: 25, at most 80% amino acid identity with the amino acid sequence of SEQ ID NO: 25, at most 85% amino acid identity with the amino acid sequence of SEQ ID NO: 25, at most 90% amino acid identity with the amino acid sequence of SEQ ID NO: 25 or at most 95% amino acid identity with the amino acid sequence of SEQ ID NO: 25.

In other aspects of this embodiment, a CLC comprises a polypeptide having, e.g., at most one, two, three, four, five, six, seven, eight, nine, 10 or 20 non-contiguous amino acid substitutions relative to the amino acid sequence of SEQ ID NO: 25. In other aspects of this embodiment, a CLC comprises a polypeptide having, e.g., at least one, two, three, four, five, six, seven, eight, nine, 10 or 20 non-contiguous amino acid substitutions relative to the amino acid sequence of SEQ ID NO: 25. In yet other aspects of this embodiment, a CLC comprises a polypeptide having, e.g., at most one, two, three, four, five, six, seven, eight, nine, 10 or 20 non-contiguous amino acid deletions relative to the amino acid sequence of SEQ ID NO: 25. In other aspects of this embodiment, a CLC comprises a polypeptide having, e.g., at least one, two, three, four, five, six, seven, eight, nine, 10 or 20 non-contiguous amino acid deletions relative to the amino acid sequence of SEQ ID NO: 25. In still other aspects of this embodiment, a CLC comprises a polypeptide having, e.g., at most one, two, three, four, five, six, seven, eight, nine, 10 or 20 non-contiguous amino acid additions relative to the amino acid sequence of SEQ ID NO: 25. In other aspects of this embodiment, a CLC comprises a polypeptide having, e.g., at least one, two, three, four, five, six, seven, eight, nine, 10 or 20 non-contiguous amino acid additions relative to the amino acid sequence of SEQ ID NO: 25.

In other aspects of this embodiment, a CLC comprises a polypeptide having, e.g., at most one, two, three, four, five, six, seven, eight, nine, 10 or 20 contiguous amino acid substitutions relative to the amino acid sequence of SEQ ID NO: 25. In other aspects of this embodiment, a CLC comprises a polypeptide having, e.g., at least one, two, three, four, five, six, seven, eight, nine, 10 or 20 contiguous amino acid substitutions relative to the amino acid sequence of SEQ ID NO: 25. In yet other aspects of this embodiment, a CLC comprises a polypeptide having, e.g., at most one, two, three, four, five, six, seven, eight, nine, 10 or 20 contiguous amino acid deletions relative to the amino acid sequence of SEQ ID NO: 25. In other aspects of this embodiment, a CLC comprises a polypeptide having, e.g., at least one, two, three, four, five, six, seven, eight, nine, 10 or 20 contiguous amino acid deletions relative to the amino acid sequence of SEQ ID NO: 25.

In still other aspects of this embodiment, a CLC comprises a polypeptide having, e.g., at most one, two, three, four, five, six, seven, eight, nine, 10 or 20 contiguous amino acid additions relative to the amino acid sequence of SEQ ID NO: 25. In other aspects of this embodiment, a CLC comprises a polypeptide having, e.g., at least one, two, three, four, five, six, seven, eight, nine, 10 or 20 contiguous amino acid additions relative to the amino acid sequence of SEQ ID NO: 25.

In another embodiment, an enhanced binding domain is derived from an IL-1. In another embodiment, an enhanced binding domain is derived from an IL-1 of SEQ ID NO: 26. In an aspect of this embodiment, an enhanced binding domain is derived from an IL-1 comprises amino acids 123-265 of SEQ ID NO: 26.

In other aspects of this embodiment, an IL-1 comprises a polypeptide having, e.g., at least 70% amino acid identity with amino acids 123-265 of SEQ ID NO: 26, at least 75% amino acid identity with amino acids 123-265 of SEQ ID NO: 26, at least 80% amino acid identity with amino acids 123-265 of SEQ ID NO: 26, at least 85% amino acid identity with amino acids 123-265 of SEQ ID NO: 26, at least 90% amino acid identity with amino acids 123-265 of SEQ ID NO: 26 or at least 95% amino acid identity with amino acids 123-265 of SEQ ID NO: 26. In yet other aspects of this embodiment, an IL-1 comprises a polypeptide having, e.g., at most 70% amino acid identity with amino acids 123-265 of SEQ ID NO: 26, at most 75% amino acid identity with amino acids 123-265 of SEQ ID NO: 26, at most 80% amino acid identity with amino acids 123-265 of SEQ ID NO: 26, at most 85% amino acid identity with amino acids 123-265 of SEQ ID NO: 26, at most 90% amino acid identity with amino acids 123-265 of SEQ ID NO: 26 or at most 95% amino acid identity with amino acids 123-265 of SEQ ID NO: 26.

In other aspects of this embodiment, an IL-1 comprises a polypeptide having, e.g., at most one, two, three, four, five, six, seven, eight, nine, 10 or 20 non-contiguous amino acid substitutions relative to amino acids 123-265 of SEQ ID NO: 26. In other aspects of this embodiment, an IL-1 comprises a polypeptide having, e.g., at least one, two, three, four, five, six, seven, eight, nine, 10 or 20 non-contiguous amino acid substitutions relative to amino acids 123-265 of SEQ ID NO: 26. In yet other aspects of this embodiment, an IL-1 comprises a polypeptide having, e.g., at most one, two, three, four, five, six, seven, eight, nine, 10 or 20 non-contiguous amino acid deletions relative to amino acids 123-265 of SEQ ID NO: 26. In other aspects of this embodiment, an IL-1 comprises a polypeptide having, e.g., at least one, two, three, four, five, six, seven, eight, nine, 10 or 20 non-contiguous amino acid deletions relative to amino acids 123-265 of SEQ ID NO: 26. In still other aspects of this embodiment, an IL-1 comprises a polypeptide having, e.g., at most one, two, three, four, five, six, seven, eight, nine, 10 or 20 non-contiguous amino acid additions relative to amino acids 123-265 of SEQ ID NO: 26. In other aspects of this embodiment, an IL-1 comprises a polypeptide having, e.g., at least one, two, three, four, five, six, seven, eight, nine, 10 or 20 non-contiguous amino acid additions relative to amino acids 123-265 of SEQ ID NO: 26.

In other aspects of this embodiment, an IL-1 comprises a polypeptide having, e.g., at most one, two, three, four, five, six, seven, eight, nine, 10 or 20 contiguous amino acid substitutions relative to amino acids 123-265 of SEQ ID NO: 26. In other aspects of this embodiment, an IL-1 comprises a polypeptide having, e.g., at least one, two, three, four, five, six, seven, eight, nine, 10 or 20 contiguous amino acid substitutions relative to amino acids 123-265 of SEQ ID NO: 26. In yet other aspects of this embodiment, an IL-1 comprises a polypeptide having, e.g., at most one, two, three, four, five, six, seven, eight, nine, 10 or 20 contiguous amino acid deletions relative to amino acids 123-265 of SEQ ID NO: 26. In other aspects of this embodiment, an IL-1 comprises a polypeptide having, e.g., at least one, two, three, four, five, six, seven, eight, nine, 10 or 20 contiguous amino acid deletions relative to amino acids 123-265 of SEQ ID NO: 26. In still other aspects of this embodiment, an IL-1 comprises a polypeptide having, e.g., at most one, two, three, four, five, six, seven, eight, nine, 10 or 20 contiguous amino acid additions relative to amino acids 123-265 of SEQ ID NO: 26. In other aspects of this embodiment, an IL-1 comprises a polypeptide having, e.g., at least one, two, three, four, five, six, seven, eight, nine, 10 or 20 contiguous amino acid additions relative to amino acids 123-265 of SEQ ID NO: 26.

In another embodiment, an enhanced binding domain is derived from an IL-2. In another embodiment, an enhanced binding domain is derived from an IL-2 of SEQ ID NO: 27. In an aspect of this embodiment, an enhanced binding domain is derived from an IL-2 comprises amino acids 21-153 of SEQ ID NO: 27.

In other aspects of this embodiment, an IL-2 comprises a polypeptide having, e.g., at least 70% amino acid identity with amino acids 21-153 of SEQ ID NO: 27, at least 75% amino acid identity with amino acids 21-153 of SEQ ID NO: 27, at least 80% amino acid identity with amino acids 21-153 of SEQ ID NO: 27, at least 85% amino acid identity with amino acids 21-153 of SEQ ID NO: 27, at least 90% amino acid identity with amino acids 21-153 of SEQ ID NO: 27 or at least 95% amino acid identity with amino acids 21-153 of SEQ ID NO: 27. In yet other aspects of this embodiment, an IL-2 comprises a polypeptide having, e.g., at most 70% amino acid identity with amino acids 21-153 of SEQ ID NO: 27, at most 75% amino acid identity with amino acids 21-153 of SEQ ID NO: 27, at most 80% amino acid identity with amino acids 21-153 of SEQ ID NO: 27, at most 85% amino acid identity with amino acids 21-153 of SEQ ID NO: 27, at most 90% amino acid identity with amino acids 21-153 of SEQ ID NO: 27 or at most 95% amino acid identity with amino acids 21-153 of SEQ ID NO: 27.

In other aspects of this embodiment, an IL-2 comprises a polypeptide having, e.g., at most one, two, three, four, five, six, seven, eight, nine, 10 or 20 non-contiguous amino acid substitutions relative to amino acids 21-153 of SEQ ID NO: 27. In other aspects of this embodiment, an IL-2 comprises a polypeptide having, e.g., at least one, two, three, four, five, six, seven, eight, nine, 10 or 20 non-contiguous amino acid substitutions relative to amino acids 21-153 of SEQ ID NO: 27. In yet other aspects of this embodiment, an IL-2 comprises a polypeptide having, e.g., at most one, two, three, four, five, six, seven, eight, nine, 10 or 20 non-contiguous amino acid deletions relative to amino acids 21-153 of SEQ ID NO: 27. In other aspects of this embodiment, an IL-2 comprises a polypeptide having, e.g., at least one, two, three, four, five, six, seven, eight, nine, 10 or 20 non-contiguous amino acid deletions relative to amino acids 21-153 of SEQ ID NO: 27. In still other aspects of this embodiment, an IL-2 comprises a polypeptide having, e.g., at most one, two, three, four, five, six, seven, eight, nine, 10 or 20 non-contiguous amino acid additions relative to amino acids 21-153 of SEQ ID NO: 27. In other aspects of this embodiment, an IL-2 comprises a polypeptide having, e.g., at least one, two, three, four, five, six, seven, eight, nine, 10 or 20 non-contiguous amino acid additions relative to amino acids 21-153 of SEQ ID NO: 27.

In other aspects of this embodiment, an IL-2 comprises a polypeptide having, e.g., at most one, two, three, four, five, six, seven, eight, nine, 10 or 20 contiguous amino acid substitutions relative to amino acids 21-153 of SEQ ID NO: 27.

In other aspects of this embodiment, an IL-2 comprises a polypeptide having, e.g., at least one, two, three, four, five, six, seven, eight, nine, 10 or 20 contiguous amino acid substitutions relative to amino acids 21-153 of SEQ ID NO: 27. In yet other aspects of this embodiment, an IL-2 comprises a polypeptide having, e.g., at most one, two, three, four, five, six, seven, eight, nine, 10 or 20 contiguous amino acid deletions relative to amino acids 21-153 of SEQ ID NO: 27. In other aspects of this embodiment, an IL-2 comprises a polypeptide having, e.g., at least one, two, three, four, five, six, seven, eight, nine, 10 or 20 contiguous amino acid deletions relative to amino acids 21-153 of SEQ ID NO: 27. In still other aspects of this embodiment, an IL-2 comprises a polypeptide having, e.g., at most one, two, three, four, five, six, seven, eight, nine, 10 or 20 contiguous amino acid additions relative to amino acids 21-153 of SEQ ID NO: 27. In other aspects of this embodiment, an IL-2 comprises a polypeptide having, e.g., at least one, two, three, four, five, six, seven, eight, nine, 10 or 20 contiguous amino acid additions relative to amino acids 21-153 of SEQ ID NO: 27.

In another embodiment, an enhanced binding domain is derived from an IL-6. In another embodiment, an enhanced binding domain is derived from an IL-6 of SEQ ID NO: 28. In an aspect of this embodiment, an enhanced binding domain is derived from an IL-6 comprises amino acids 57-210 of SEQ ID NO: 28.

In other aspects of this embodiment, an IL-6 comprises a polypeptide having, e.g., at least 70% amino acid identity with amino acids 57-210 of SEQ ID NO: 28, at least 75% amino acid identity with amino acids 57-210 of SEQ ID NO: 28, at least 80% amino acid identity with amino acids 57-210 of SEQ ID NO: 28, at least 85% amino acid identity with amino acids 57-210 of SEQ ID NO: 28, at least 90% amino acid identity with amino acids 57-210 of SEQ ID NO: 28 or at least 95% amino acid identity with amino acids 57-210 of SEQ ID NO: 28. In yet other aspects of this embodiment, an IL-6 comprises a polypeptide having, e.g., at most 70% amino acid identity with amino acids 57-210 of SEQ ID NO: 28, at most 75% amino acid identity with amino acids 57-210 of SEQ ID NO: 28, at most 80% amino acid identity with amino acids 57-210 of SEQ ID NO: 28, at most 85% amino acid identity with amino acids 57-210 of SEQ ID NO: 28, at most 90% amino acid identity with amino acids 57-210 of SEQ ID NO: 28 or at most 95% amino acid identity with amino acids 57-210 of SEQ ID NO: 28.

In other aspects of this embodiment, an IL-6 comprises a polypeptide having, e.g., at most one, two, three, four, five, six, seven, eight, nine, 10 or 20 non-contiguous amino acid substitutions relative to amino acids 57-210 of SEQ ID NO: 28. In other aspects of this embodiment, an IL-6 comprises a polypeptide having, e.g., at least one, two, three, four, five, six, seven, eight, nine, 10 or 20 non-contiguous amino acid substitutions relative to amino acids 57-210 of SEQ ID NO: 28. In yet other aspects of this embodiment, an IL-6 comprises a polypeptide having, e.g., at most one, two, three, four, five, six, seven, eight, nine, 10 or 20 non-contiguous amino acid deletions relative to amino acids 57-210 of SEQ ID NO: 28. In other aspects of this embodiment, an IL-6 comprises a polypeptide having, e.g., at least one, two, three, four, five, six, seven, eight, nine, 10 or 20 non-contiguous amino acid deletions relative to amino acids 57-210 of SEQ ID NO: 28. In still other aspects of this embodiment, an IL-6 comprises a polypeptide having, e.g., at most one, two, three, four, five, six, seven, eight, nine, 10 or 20 non-contiguous amino acid additions relative to amino acids 57-210 of SEQ ID NO: 28. In other aspects of this embodiment, an IL-6 comprises a polypeptide having, e.g., at least one, two, three, four, five, six, seven, eight, nine, 10 or 20 non-contiguous amino acid additions relative to amino acids 57-210 of SEQ ID NO: 28.

In other aspects of this embodiment, an IL-6 comprises a polypeptide having, e.g., at most one, two, three, four, five, six, seven, eight, nine, 10 or 20 contiguous amino acid substitutions relative to amino acids 57-210 of SEQ ID NO: 28. In other aspects of this embodiment, an IL-6 comprises a polypeptide having, e.g., at least one, two, three, four, five, six, seven, eight, nine, 10 or 20 contiguous amino acid substitutions relative to amino acids 57-210 of SEQ ID NO: 28. In yet other aspects of this embodiment, an IL-6 comprises a polypeptide having, e.g., at most one, two, three, four, five, six, seven, eight, nine, 10 or 20 contiguous amino acid deletions relative to amino acids 57-210 of SEQ ID NO: 28. In other aspects of this embodiment, an IL-6 comprises a polypeptide having, e.g., at least one, two, three, four, five, six, seven, eight, nine, 10 or 20 contiguous amino acid deletions relative to amino acids 57-210 of SEQ ID NO: 28. In still other aspects of this embodiment, an IL-6 comprises a polypeptide having, e.g., at most one, two, three, four, five, six, seven, eight, nine, 10 or 20 contiguous amino acid additions relative to amino acids 57-210 of SEQ ID NO: 28. In other aspects of this embodiment, an IL-6 comprises a polypeptide having, e.g., at least one, two, three, four, five, six, seven, eight, nine, 10 or 20 contiguous amino acid additions relative to amino acids 57-210 of SEQ ID NO: 28.

In another embodiment, an enhanced binding domain is derived from an IL-8. In another embodiment, an enhanced binding domain is derived from an IL-8 of SEQ ID NO: 29. In an aspect of this embodiment, an enhanced binding domain is derived from an IL-8 comprises amino acids 21-99 or amino acids 31-94 of SEQ ID NO: 29.

In other aspects of this embodiment, an IL-8 comprises a polypeptide having, e.g., at least 70% amino acid identity with amino acids 21-99 or amino acids 31-94 of SEQ ID NO: 29, at least 75% amino acid identity with amino acids 21-99 or amino acids 31-94 of SEQ ID NO: 29, at least 80% amino acid identity with amino acids 21-99 or amino acids 31-94 of SEQ ID NO: 29, at least 85% amino acid identity with amino acids 21-99 or amino acids 31-94 of SEQ ID NO: 29, at least 90% amino acid identity with amino acids 21-99 or amino acids 31-94 of SEQ ID NO: 29 or at least 95% amino acid identity with amino acids 21-99 or amino acids 31-94 of SEQ ID NO: 29. In yet other aspects of this embodiment, an IL-8 comprises a polypeptide having, e.g., at most 70% amino acid identity with amino acids 21-99 or amino acids 31-94 of SEQ ID NO: 29, at most 75% amino acid identity with amino acids 21-99 or amino acids 31-94 of SEQ ID NO: 29, at most 80% amino acid identity with amino acids 21-99 or amino acids 31-94 of SEQ ID NO: 29, at most 85% amino acid identity with amino acids 21-99 or amino acids 31-94 of SEQ ID NO: 29, at most 90% amino acid identity with amino acids 21-99 or amino acids 31-94 of SEQ ID NO: 29 or at most 95% amino acid identity with amino acids 21-99 or amino acids 31-94 of SEQ ID NO: 29.

In other aspects of this embodiment, an IL-8 comprises a polypeptide having, e.g., at most one, two, three, four, five, six, seven, eight, nine, 10 or 20 non-contiguous amino acid substitutions relative to amino acids 21-99 or amino acids 31-94 of SEQ ID NO: 29. In other aspects of this embodiment, an IL-8 comprises a polypeptide having, e.g., at least one, two, three, four, five, six, seven, eight, nine, 10 or 20 non-contiguous amino acid substitutions relative to amino acids 21-99 or amino acids 31-94 of SEQ ID NO: 29. In yet other aspects of this embodiment, an IL-8 comprises a polypeptide having, e.g., at most one, two, three, four, five, six, seven, eight, nine, 10 or 20 non-contiguous amino acid deletions relative to amino acids 21-99 or amino acids 31-94 of SEQ ID NO: 29. In other aspects of this embodiment, an IL-8 comprises a polypeptide having, e.g., at least one, two, three, four, five, six, seven, eight, nine, 10 or 20 non-contiguous amino acid deletions relative to amino acids 21-99 or amino acids 31-94 of SEQ ID NO: 29. In still other aspects of this embodiment, an IL-8 comprises a polypeptide having, e.g., at most one, two, three, four, five, six, seven, eight, nine, 10 or 20 non-contiguous amino acid additions relative to amino acids 21-99 or amino acids 31-94 of SEQ ID NO: 29. In other aspects of this embodiment, an IL-8 comprises a polypeptide having, e.g., at least one, two, three, four, five, six, seven, eight, nine, 10 or 20 non-contiguous amino acid additions relative to amino acids 21-99 or amino acids 31-94 of SEQ ID NO: 29.

In other aspects of this embodiment, an IL-8 comprises a polypeptide having, e.g., at most one, two, three, four, five, six, seven, eight, nine, 10 or 20 contiguous amino acid substitutions relative to amino acids 21-99 or amino acids 31-94 of SEQ ID NO: 29. In other aspects of this embodiment, an IL-8 comprises a polypeptide having, e.g., at least one, two, three, four, five, six, seven, eight, nine, 10 or 20 contiguous amino acid substitutions relative to amino acids 21-99 or amino acids 31-94 of SEQ ID NO: 29. In yet other aspects of this embodiment, an IL-8 comprises a polypeptide having, e.g., at most one, two, three, four, five, six, seven, eight, nine, 10 or 20 contiguous amino acid deletions relative to amino acids 21-99 or amino acids 31-94 of SEQ ID NO: 29. In other aspects of this embodiment, an IL-8 comprises a polypeptide having, e.g., at least one, two, three, four, five, six, seven, eight, nine, 10 or 20 contiguous amino acid deletions relative to amino acids 21-99 or amino acids 31-94 of SEQ ID NO: 29. In still other aspects of this embodiment, an IL-8 comprises a polypeptide having, e.g., at most one, two, three, four, five, six, seven, eight, nine, 10 or 20 contiguous amino acid additions relative to amino acids 21-99 or amino acids 31-94 of SEQ ID NO: 29. In other aspects of this embodiment, an IL-8 comprises a polypeptide having, e.g., at least one, two, three, four, five, six, seven, eight, nine, 10 or 20 contiguous amino acid additions relative to amino acids 21-99 or amino acids 31-94 of SEQ ID NO: 29.

In another embodiment, an enhanced binding domain is derived from an IL-10. In another embodiment, an enhanced binding domain is derived from an IL-10 of SEQ ID NO: 30. In an aspect of this embodiment, an enhanced binding domain is derived from an IL-10 comprises amino acids 37-173 or amino acids 19-178 of SEQ ID NO: 30.

In other aspects of this embodiment, an IL-10 comprises a polypeptide having, e.g., at least 70% amino acid identity with amino acids 37-173 or amino acids 19-178 of SEQ ID NO: 30, at least 75% amino acid identity with amino acids 37-173 or amino acids 19-178 of SEQ ID NO: 30, at least 80% amino acid identity with amino acids 37-173 or amino acids 19-178 of SEQ ID NO: 30, at least 85% amino acid identity with amino acids 37-173 or amino acids 19-178 of SEQ ID NO: 30, at least 90% amino acid identity with amino acids 37-173 or amino acids 19-178 of SEQ ID NO: 30 or at least 95% amino acid identity with amino acids 37-173 or amino acids 19-178 of SEQ ID NO: 30. In yet other aspects of this embodiment, an IL-10 comprises a polypeptide having, e.g., at most 70% amino acid identity with amino acids 37-173 or amino acids 19-178 of SEQ ID NO: 30, at most 75% amino acid identity with amino acids 37-173 or amino acids 19-178 of SEQ ID NO: 30, at most 80% amino acid identity with amino acids 37-173 or amino acids 19-178 of SEQ ID NO: 30, at most 85% amino acid identity with amino acids 37-173 or amino acids 19-178 of SEQ ID NO: 30, at most 90% amino acid identity with amino acids 37-173 or amino acids 19-178 of SEQ ID NO: 30 or at most 95% amino acid identity with amino acids 37-173 or amino acids 19-178 of SEQ ID NO: 30.

In other aspects of this embodiment, an IL-10 comprises a polypeptide having, e.g., at most one, two, three, four, five, six, seven, eight, nine, 10 or 20 non-contiguous amino acid substitutions relative to amino acids 37-173 or amino acids 19-178 of SEQ ID NO: 30. In other aspects of this embodiment, an IL-10 comprises a polypeptide having, e.g., at least one, two, three, four, five, six, seven, eight, nine, 10 or 20 non-contiguous amino acid substitutions relative to amino acids 37-173 or amino acids 19-178 of SEQ ID NO: 30. In yet other aspects of this embodiment, an IL-10 comprises a polypeptide having, e.g., at most one, two, three, four, five, six, seven, eight, nine, 10 or 20 non-contiguous amino acid deletions relative to amino acids 37-173 or amino acids 19-178 of SEQ ID NO: 30. In other aspects of this embodiment, an IL-10 comprises a polypeptide having, e.g., at least one, two, three, four, five, six, seven, eight, nine, 10 or 20 non-contiguous amino acid deletions relative to amino acids 37-173 or amino acids 19-178 of SEQ ID NO: 30. In still other aspects of this embodiment, an IL-10 comprises a polypeptide having, e.g., at most one, two, three, four, five, six, seven, eight, nine, 10 or 20 non-contiguous amino acid additions relative to amino acids 37-173 or amino acids 19-178 of SEQ ID NO: 30. In other aspects of this embodiment, an IL-10 comprises a polypeptide having, e.g., at least one, two, three, four, five, six, seven, eight, nine, 10 or 20 non-contiguous amino acid additions relative to amino acids 37-173 or amino acids 19-178 of SEQ ID NO: 30.

In other aspects of this embodiment, an IL-10 comprises a polypeptide having, e.g., at most one, two, three, four, five, six, seven, eight, nine, 10 or 20 contiguous amino acid substitutions relative to amino acids 37-173 or amino acids 19-178 of SEQ ID NO: 30. In other aspects of this embodiment, an IL-10 comprises a polypeptide having, e.g., at least one, two, three, four, five, six, seven, eight, nine, 10 or 20 contiguous amino acid substitutions relative to amino acids 37-173 or amino acids 19-178 of SEQ ID NO: 30. In yet other aspects of this embodiment, an IL-10 comprises a polypeptide having, e.g., at most one, two, three, four, five, six, seven, eight, nine, 10 or 20 contiguous amino acid deletions relative to amino acids 37-173 or amino acids 19-178 of SEQ ID NO: 30. In other aspects of this embodiment, an IL-10 comprises a polypeptide having, e.g., at least one, two, three, four, five, six, seven, eight, nine, 10 or 20 contiguous amino acid deletions relative to amino acids 37-173 or amino acids 19-178 of SEQ ID NO: 30. In still other aspects of this embodiment, an IL-10 comprises a polypeptide having, e.g., at most one, two, three, four, five, six, seven, eight, nine, 10 or 20 contiguous amino acid additions relative to amino acids 37-173 or amino acids 19-178 of SEQ ID NO: 30. In other aspects of this embodiment, an IL-10 comprises a polypeptide having, e.g., at least one, two, three, four, five, six, seven, eight, nine, 10 or 20 contiguous amino acid additions relative to amino acids 37-173 or amino acids 19-178 of SEQ ID NO: 30.

In another embodiment, an enhanced binding domain is derived from a neuroleukin. In another embodiment, an enhanced binding domain is derived from a neuroleukin of SEQ ID NO: 31. In aspects of this embodiment, a neuroleukin comprises a polypeptide having, e.g., at least 70% amino acid identity with the amino acid sequence of SEQ ID NO: 31, at least 75% amino acid identity with the amino acid sequence of SEQ ID NO: 31, at least 80% amino acid identity with the amino acid sequence of SEQ ID NO: 31, at least 85% amino acid identity with the amino acid sequence of SEQ ID NO: 31, at least 90% amino acid identity with the amino acid sequence of SEQ ID NO: 31 or at least 95% amino acid identity with the amino acid sequence of SEQ ID NO: 31. In yet other aspects of this embodiment, a neuroleukin comprises a polypeptide having, e.g., at most 70% amino acid identity with the amino acid sequence of SEQ ID NO: 31, at most 75% amino acid identity with the amino acid sequence of SEQ ID NO: 31, at most 80% amino acid identity with the amino acid sequence of SEQ ID NO: 31, at most 85% amino acid identity with the amino acid sequence of SEQ ID NO: 31, at most 90% amino acid identity with the amino acid sequence of SEQ ID NO: 31 or at most 95% amino acid identity with the amino acid sequence of SEQ ID NO: 31.

In other aspects of this embodiment, a neuroleukin comprises a polypeptide having, e.g., at most one, two, three, four, five, six, seven, eight, nine, 10 or 20 non-contiguous amino acid substitutions relative to the amino acid sequence of SEQ ID NO: 31. In other aspects of this embodiment, a neuroleukin comprises a polypeptide having, e.g., at least one, two, three, four, five, six, seven, eight, nine, 10 or 20 non-contiguous amino acid substitutions relative to the amino acid sequence of SEQ ID NO: 31. In yet other aspects of this embodiment, a neuroleukin comprises a polypeptide having, e.g., at most one, two, three, four, five, six, seven, eight, nine, 10 or 20 non-contiguous amino acid deletions relative to the amino acid sequence of SEQ ID NO: 31. In other aspects of this embodiment, a neuroleukin comprises a polypeptide having, e.g., at least one, two, three, four, five, six, seven, eight, nine, 10 or 20 non-contiguous amino acid deletions relative to the amino acid sequence of SEQ ID NO: 31. In still other aspects of this embodiment, a neuroleukin comprises a polypeptide having, e.g., at most one, two, three, four, five, six, seven, eight, nine, 10 or 20 non-contiguous amino acid additions relative to the amino acid sequence of SEQ ID NO: 31. In other aspects of this embodiment, a neuroleukin comprises a polypeptide having, e.g., at least one, two, three, four, five, six, seven, eight, nine, 10 or 20 non-contiguous amino acid additions relative to the amino acid sequence of SEQ ID NO: 31.

In other aspects of this embodiment, a neuroleukin comprises a polypeptide having, e.g., at most one, two, three, four, five, six, seven, eight, nine, 10 or 20 contiguous amino acid substitutions relative to the amino acid sequence of SEQ ID NO: 31. In other aspects of this embodiment, a neuroleukin comprises a polypeptide having, e.g., at least one, two, three, four, five, six, seven, eight, nine, 10 or 20 contiguous amino acid substitutions relative to the amino acid sequence of SEQ ID NO: 31. In yet other aspects of this embodiment, a neuroleukin comprises a polypeptide having, e.g., at most one, two, three, four, five, six, seven, eight, nine, 10 or 20 contiguous amino acid deletions relative to the amino acid sequence of SEQ ID NO: 31. In other aspects of this embodiment, a neuroleukin comprises a polypeptide having, e.g., at least one, two, three, four, five, six, seven, eight, nine, 10 or 20 contiguous amino acid deletions relative to the amino acid sequence of SEQ ID NO: 31. In still other aspects of this embodiment, a neuroleukin comprises a polypeptide having, e.g., at most one, two, three, four, five, six, seven, eight, nine, 10 or 20 contiguous amino acid additions relative to the amino acid sequence of SEQ ID NO: 31. In other aspects of this embodiment, a neuroleukin comprises a polypeptide having, e.g., at least one, two, three, four, five, six, seven, eight, nine, 10 or 20 contiguous amino acid additions relative to the amino acid sequence of SEQ ID NO: 31.

In another embodiment, an enhanced binding domain is derived from a VEGF. In another embodiment, an enhanced binding domain is derived from a VEGF of SEQ ID NO: 32.

In aspects of this embodiment, a VEGF comprises a polypeptide having, e.g., at least 70% amino acid identity with the amino acid sequence of SEQ ID NO: 32, at least 75% amino acid identity with the amino acid sequence of SEQ ID NO: 32, at least 80% amino acid identity with the amino acid sequence of SEQ ID NO: 32, at least 85% amino acid identity with the amino acid sequence of SEQ ID NO: 32, at least 90% amino acid identity with the amino acid sequence of SEQ ID NO: 32 or at least 95% amino acid identity with the amino acid sequence of SEQ ID NO: 32. In yet other aspects of this embodiment, a VEGF comprises a polypeptide having, e.g., at most 70% amino acid identity with the amino acid sequence of SEQ ID NO: 32, at most 75% amino acid identity with the amino acid sequence of SEQ ID NO: 32, at most 80% amino acid identity with the amino acid sequence of SEQ ID NO: 32, at most 85% amino acid identity with the amino acid sequence of SEQ ID NO: 32, at most 90% amino acid identity with the amino acid sequence of SEQ ID NO: 32 or at most 95% amino acid identity with the amino acid sequence of SEQ ID NO: 32.

In other aspects of this embodiment, a VEGF comprises a polypeptide having, e.g., at most one, two, three, four, five, six, seven, eight, nine, 10 or 20 non-contiguous amino acid substitutions relative to the amino acid sequence of SEQ ID NO: 32. In other aspects of this embodiment, a VEGF comprises a polypeptide having, e.g., at least one, two, three, four, five, six, seven, eight, nine, 10 or 20 non-contiguous amino acid substitutions relative to the amino acid sequence of SEQ ID NO: 32. In yet other aspects of this embodiment, a VEGF comprises a polypeptide having, e.g., at most one, two, three, four, five, six, seven, eight, nine, 10 or 20 non-contiguous amino acid deletions relative to the amino acid sequence of SEQ ID NO: 32. In other aspects of this embodiment, a VEGF comprises a polypeptide having, e.g., at least one, two, three, four, five, six, seven, eight, nine, 10 or 20 non-contiguous amino acid deletions relative to the amino acid sequence of SEQ ID NO: 32. In still other aspects of this embodiment, a VEGF comprises a polypeptide having, e.g., at most one, two, three, four, five, six, seven, eight, nine, 10 or 20 non-contiguous amino acid additions relative to the amino acid sequence of SEQ ID NO: 32. In other aspects of this embodiment, a VEGF comprises a polypeptide having, e.g., at least one, two, three, four, five, six, seven, eight, nine, 10 or 20 non-contiguous amino acid additions relative to the amino acid sequence of SEQ ID NO: 32.

In other aspects of this embodiment, a VEGF comprises a polypeptide having, e.g., at most one, two, three, four, five, six, seven, eight, nine, 10 or 20 contiguous amino acid substitutions relative to the amino acid sequence of SEQ ID NO: 32. In other aspects of this embodiment, a VEGF comprises a polypeptide having, e.g., at least one, two, three, four, five, six, seven, eight, nine, 10 or 20 contiguous amino acid substitutions relative to the amino acid sequence of SEQ ID NO: 32. In yet other aspects of this embodiment, a VEGF comprises a polypeptide having, e.g., at most one, two, three, four, five, six, seven, eight, nine, 10 or 20 contiguous amino acid deletions relative to the amino acid sequence of SEQ ID NO: 32. In other aspects of this embodiment, a VEGF comprises a polypeptide having, e.g., at least one, two, three, four, five, six, seven, eight, nine, 10 or 20 contiguous amino acid deletions relative to the amino acid sequence of SEQ ID NO: 32. In still other aspects of this embodiment, a VEGF comprises a polypeptide having, e.g., at most one, two, three, four, five, six, seven, eight, nine, 10 or 20 contiguous amino acid additions relative to the amino acid sequence of SEQ ID NO: 32. In other aspects of this embodiment, a VEGF comprises a polypeptide having, e.g., at least one, two, three, four, five, six, seven, eight, nine, 10 or 20 contiguous amino acid additions relative to the amino acid sequence of SEQ ID NO: 32.

In another embodiment, an enhanced binding domain is derived from an IGF-1. In another embodiment, an enhanced binding domain is derived from an IGF-1 of SEQ ID NO: 33. In an aspect of this embodiment, an enhanced binding domain is derived from an IGF-1 comprises amino acids 52-109 or amino acids 49-118 of SEQ ID NO: 33.

In other aspects of this embodiment, an IGF-1 comprises a polypeptide having, e.g., at least 70% amino acid identity with amino acids 52-109 or amino acids 49-118 of SEQ ID NO: 33, at least 75% amino acid identity with amino acids 52-109 or amino acids 49-118 of SEQ ID NO: 33, at least 80% amino acid identity with amino acids 52-109 or amino acids 49-118 of SEQ ID NO: 33, at least 85% amino acid identity with amino acids 52-109 or amino acids 49-118 of SEQ ID NO: 33, at least 90% amino acid identity with amino acids 52-109 or amino acids 49-118 of SEQ ID NO: 33 or at least 95% amino acid identity with amino acids 52-109 or amino acids 49-118 of SEQ ID NO: 33. In yet other aspects of this embodiment, an IGF-1 comprises a polypeptide having, e.g., at most 70% amino acid identity with amino acids 52-109 or amino acids 49-118 of SEQ ID NO: 33, at most 75% amino acid identity with amino acids 52-109 or amino acids 49-118 of SEQ ID NO: 33, at most 80% amino acid identity with amino acids 52-109 or amino acids 49-118 of SEQ ID NO: 33, at most 85% amino acid identity with amino acids 52-109 or amino acids 49-118 of SEQ ID NO: 33, at most 90% amino acid identity with amino acids 52-109 or amino acids 49-118 of SEQ ID NO: 33 or at most 95% amino acid identity with amino acids 52-109 or amino acids 49-118 of SEQ ID NO: 33.

In other aspects of this embodiment, an IGF-1 comprises a polypeptide having, e.g., at most one, two, three, four, five, six, seven, eight, nine, 10 or 20 non-contiguous amino acid substitutions relative to amino acids 52-109 or amino acids 49-118 of SEQ ID NO: 33. In other aspects of this embodiment, an IGF-1 comprises a polypeptide having, e.g., at least one, two, three, four, five, six, seven, eight, nine, 10 or 20 non-contiguous amino acid substitutions relative to amino acids 52-109 or amino acids 49-118 of SEQ ID NO: 33. In yet other aspects of this embodiment, an IGF-1 comprises a polypeptide having, e.g., at most one, two, three, four, five, six, seven, eight, nine, 10 or 20 non-contiguous amino acid deletions relative to amino acids 52-109 or amino acids 49-118 of SEQ ID NO: 33. In other aspects of this embodiment, an IGF-1 comprises a polypeptide having, e.g., at least one, two, three, four, five, six, seven, eight, nine, 10 or 20 non-contiguous amino acid deletions relative to amino acids 52-109 or amino acids 49-118 of SEQ ID NO: 33. In still other aspects of this embodiment, an IGF-1 comprises a polypeptide having, e.g., at most one, two, three, four, five, six, seven, eight, nine, 10 or 20 non-contiguous amino acid additions relative to amino acids 52-109 or amino acids 49-118 of SEQ ID NO: 33. In other aspects of this embodiment, an IGF-1 comprises a polypeptide having, e.g., at least one, two, three, four, five, six, seven, eight, nine, 10 or 20 non-contiguous amino acid additions relative to amino acids 52-109 or amino acids 49-118 of SEQ ID NO: 33.

In other aspects of this embodiment, an IGF-1 comprises a polypeptide having, e.g., at most one, two, three, four, five, six, seven, eight, nine, 10 or 20 contiguous amino acid substitutions relative to amino acids 52-109 or amino acids 49-118 of SEQ ID NO: 33. In other aspects of this embodiment, an IGF-1 comprises a polypeptide having, e.g., at least one, two, three, four, five, six, seven, eight, nine, 10 or 20 contiguous amino acid substitutions relative to amino acids 52-109 or amino acids 49-118 of SEQ ID NO: 33. In yet other aspects of this embodiment, an IGF-1 comprises a polypeptide having, e.g., at most one, two, three, four, five, six, seven, eight, nine, 10 or 20 contiguous amino acid deletions relative to amino acids 52-109 or amino acids 49-118 of SEQ ID NO: 33. In other aspects of this embodiment, an IGF-1 comprises a polypeptide having, e.g., at least one, two, three, four, five, six, seven, eight, nine, 10 or 20 contiguous amino acid deletions relative to amino acids 52-109 or amino acids 49-118 of SEQ ID NO: 33. In still other aspects of this embodiment, an IGF-1 comprises a polypeptide having, e.g., at most one, two, three, four, five, six, seven, eight, nine, 10 or 20 contiguous amino acid additions relative to amino acids 52-109 or amino acids 49-118 of SEQ ID NO: 33. In other aspects of this embodiment, an IGF-1 comprises a polypeptide having, e.g., at least one, two, three, four, five, six, seven, eight, nine, 10 or 20 contiguous amino acid additions relative to amino acids 52-109 or amino acids 49-118 of SEQ ID NO: 33.

In another embodiment, an enhanced binding domain is derived from an IGF-2. In another embodiment, an enhanced binding domain is derived from an IGF-2 of SEQ ID NO: 34. In an aspect of this embodiment, an enhanced binding domain is derived from an IGF-2 comprises amino acids 31-84 or amino acids 25-180 of SEQ ID NO: 34.

In other aspects of this embodiment, an IGF-2 comprises a polypeptide having, e.g., at least 70% amino acid identity with amino acids 31-84 or amino acids 25-180 of SEQ ID NO: 34, at least 75% amino acid identity with amino acids 31-84 or amino acids 25-180 of SEQ ID NO: 34, at least 80% amino acid identity with amino acids 31-84 or amino acids 25-180 of SEQ ID NO: 34, at least 85% amino acid identity with amino acids 31-84 or amino acids 25-180 of SEQ ID NO: 34, at least 90% amino acid identity with amino acids 31-84 or amino acids 25-180 of SEQ ID NO: 34 or at least 95% amino acid identity with amino acids 31-84 or amino acids 25-180 of SEQ ID NO: 34. In yet other aspects of this embodiment, an IGF-2 comprises a polypeptide having, e.g., at most 70% amino acid identity with amino acids 31-84 or amino acids 25-180 of SEQ ID NO: 34, at most 75% amino acid identity with amino acids 31-84 or amino acids 25-180 of SEQ ID NO: 34, at most 80% amino acid identity with amino acids 31-84 or amino acids 25-180 of SEQ ID NO: 34, at most 85% amino acid identity with amino acids 31-84 or amino acids 25-180 of SEQ ID NO: 34, at most 90% amino acid identity with amino acids 31-84 or amino acids 25-180 of SEQ ID NO: 34 or at most 95% amino acid identity with amino acids 31-84 or amino acids 25-180 of SEQ ID NO: 34.

In other aspects of this embodiment, an IGF-2 comprises a polypeptide having, e.g., at most one, two, three, four, five, six, seven, eight, nine, 10 or 20 non-contiguous amino acid substitutions relative to amino acids 31-84 or amino acids 25-180 of SEQ ID NO: 34. In other aspects of this embodiment, an IGF-2 comprises a polypeptide having, e.g., at least one, two, three, four, five, six, seven, eight, nine, 10 or 20 non-contiguous amino acid substitutions relative to amino acids 31-84 or amino acids 25-180 of SEQ ID NO: 34. In yet other aspects of this embodiment, an IGF-2 comprises a polypeptide having, e.g., at most one, two, three, four, five, six, seven, eight, nine, 10 or 20 non-contiguous amino acid deletions relative to amino acids 31-84 or amino acids 25-180 of SEQ ID NO: 34. In other aspects of this embodiment, an IGF-2 comprises a polypeptide having, e.g., at least one, two, three, four, five, six, seven, eight, nine, 10 or 20 non-contiguous amino acid deletions relative to amino acids 31-84 or amino acids 25-180 of SEQ ID NO: 34. In still other aspects of this embodiment, an IGF-2 comprises a polypeptide having, e.g., at most one, two, three, four, five, six, seven, eight, nine, 10 or 20 non-contiguous amino acid additions relative to amino acids 31-84 or amino acids 25-180 of SEQ ID NO: 34. In other aspects of this embodiment, an IGF-2 comprises a polypeptide having, e.g., at least one, two, three, four, five, six, seven, eight, nine, 10 or 20 non-contiguous amino acid additions relative to amino acids 31-84 or amino acids 25-180 of SEQ ID NO: 34.

In other aspects of this embodiment, an IGF-2 comprises a polypeptide having, e.g., at most one, two, three, four, five, six, seven, eight, nine, 10 or 20 contiguous amino acid substitutions relative to amino acids 31-84 or amino acids 25-180 of SEQ ID NO: 34. In other aspects of this embodiment, an IGF-2 comprises a polypeptide having, e.g., at least one, two, three, four, five, six, seven, eight, nine, 10 or 20 contiguous amino acid substitutions relative to amino acids 31-84 or amino acids 25-180 of SEQ ID NO: 34. In yet other aspects of this embodiment, an IGF-2 comprises a polypeptide having, e.g., at most one, two, three, four, five, six, seven, eight, nine, 10 or 20 contiguous amino acid deletions relative to amino acids 31-84 or amino acids 25-180 of SEQ ID NO: 34. In other aspects of this embodiment, an IGF-2 comprises a polypeptide having, e.g., at least one, two, three, four, five, six, seven, eight, nine, 10 or 20 contiguous amino acid deletions relative to amino acids 31-84 or amino acids 25-180 of SEQ ID NO: 34. In still other aspects of this embodiment, an IGF-2 comprises a polypeptide having, e.g., at most one, two, three, four, five, six, seven, eight, nine, 10 or 20 contiguous amino acid additions relative to amino acids 31-84 or amino acids 25-180 of SEQ ID NO: 34. In other aspects of this embodiment, an IGF-2 comprises a polypeptide having, e.g., at least one, two, three, four, five, six, seven, eight, nine, 10 or 20 contiguous amino acid additions relative to amino acids 31-84 or amino acids 25-180 of SEQ ID NO: 34.

In another embodiment, an enhanced binding domain is derived from an EGF. In another embodiment, an enhanced binding domain is derived from an EGF of SEQ ID NO: 35. In aspects of this embodiment, an EGF comprises a polypeptide having, e.g., at least 70% amino acid identity with the amino acid sequence of SEQ ID NO: 35, at least 75% amino acid identity with the amino acid sequence of SEQ ID NO: 35, at least 80% amino acid identity with the amino acid sequence of SEQ ID NO: 35, at least 85% amino acid identity with the amino acid sequence of SEQ ID NO: 35, at least 90% amino acid identity with the amino acid sequence of SEQ ID NO: 35 or at least 95% amino acid identity with the amino acid sequence of SEQ ID NO: 35. In yet other aspects of this embodiment, an EGF comprises a polypeptide having, e.g., at most 70% amino acid identity with the amino acid sequence of SEQ ID NO: 35, at most 75% amino acid identity with the amino acid sequence of SEQ ID NO: 35, at most 80% amino acid identity with the amino acid sequence of SEQ ID NO: 35, at most 85% amino acid identity with the amino acid sequence of SEQ ID NO: 35, at most 90% amino acid identity with the amino acid sequence of SEQ ID NO: 35 or at most 95% amino acid identity with the amino acid sequence of SEQ ID NO: 35.

In other aspects of this embodiment, an EGF comprises a polypeptide having, e.g., at most one, two, three, four, five, six, seven, eight, nine, 10 or 20 non-contiguous amino acid substitutions relative to the amino acid sequence of SEQ ID NO: 35. In other aspects of this embodiment, an EGF comprises a polypeptide having, e.g., at least one, two, three, four, five, six, seven, eight, nine, 10 or 20 non-contiguous amino acid substitutions relative to the amino acid sequence of SEQ ID NO: 35. In yet other aspects of this embodiment, an EGF comprises a polypeptide having, e.g., at most one, two, three, four, five, six, seven, eight, nine, 10 or 20 non-contiguous amino acid deletions relative to the amino acid sequence of SEQ ID NO: 35. In other aspects of this embodiment, an EGF comprises a polypeptide having, e.g., at least one, two, three, four, five, six, seven, eight, nine, 10 or 20 non-contiguous amino acid deletions relative to the amino acid sequence of SEQ ID NO: 35. In still other aspects of this embodiment, an EGF comprises a polypeptide having, e.g., at most one, two, three, four, five, six, seven, eight, nine, 10 or 20 non-contiguous amino acid additions relative to the amino acid sequence of SEQ ID NO: 35. In other aspects of this embodiment, an EGF comprises a polypeptide having, e.g., at least one, two, three, four, five, six, seven, eight, nine, 10 or 20 non-contiguous amino acid additions relative to the amino acid sequence of SEQ ID NO: 35.

In other aspects of this embodiment, an EGF comprises a polypeptide having, e.g., at most one, two, three, four, five, six, seven, eight, nine, 10 or 20 contiguous amino acid substitutions relative to the amino acid sequence of SEQ ID NO: 35. In other aspects of this embodiment, an EGF comprises a polypeptide having, e.g., at least one, two, three, four, five, six, seven, eight, nine, 10 or 20 contiguous amino acid substitutions relative to the amino acid sequence of SEQ ID NO: 35. In yet other aspects of this embodiment, an EGF comprises a polypeptide having, e.g., at most one, two, three, four, five, six, seven, eight, nine, 10 or 20 contiguous amino acid deletions relative to the amino acid sequence of SEQ ID NO: 35. In other aspects of this embodiment, an EGF comprises a polypeptide having, e.g., at least one, two, three, four, five, six, seven, eight, nine, 10 or 20 contiguous amino acid deletions relative to the amino acid sequence of SEQ ID NO: 35. In still other aspects of this embodiment, an EGF comprises a polypeptide having, e.g., at most one, two, three, four, five, six, seven, eight, nine, 10 or 20 contiguous amino acid additions relative to the amino acid sequence of SEQ ID NO: 35. In other aspects of this embodiment, an EGF comprises a polypeptide having, e.g., at least one, two, three, four, five, six, seven, eight, nine, 10 or 20 contiguous amino acid additions relative to the amino acid sequence of SEQ ID NO: 35.

Another example of an enhanced targeting domain disclosed in the present specification is, e.g., a neurotrophin, such as, e.g., a NGF, a BDNF, a NT-3 or a NT-5.

Thus, in an embodiment, an enhanced binding domain is derived from a NGF. In another embodiment, an enhanced binding domain is derived from a NGF of SEQ ID NO: 36. In an aspect of this embodiment, an enhanced binding domain is derived from a NGF comprises amino acids 139-257 of SEQ ID NO: 36.

In other aspects of this embodiment, a NGF comprises a polypeptide having, e.g., at least 70% amino acid identity with amino acids 139-257 of SEQ ID NO: 36, at least 75% amino acid identity with amino acids 139-257 of SEQ ID NO: 36, at least 80% amino acid identity with amino acids 139-257 of SEQ ID NO: 36, at least 85% amino acid identity with amino acids 139-257 of SEQ ID NO: 36, at least 90% amino acid identity with amino acids 139-257 of SEQ ID NO: 36 or at least 95% amino acid identity with amino acids 139-257 of SEQ ID NO: 36. In yet other aspects of this embodiment, a NGF comprises a polypeptide having, e.g., at most 70% amino acid identity with amino acids 139-257 of SEQ ID NO: 36, at most 75% amino acid identity with amino acids 139-257 of SEQ ID NO: 36, at most 80% amino acid identity with amino acids 139-257 of SEQ ID NO: 36, at most 85% amino acid identity with amino acids 139-257 of SEQ ID NO: 36, at most 90% amino acid identity with amino acids 139-257 of SEQ ID NO: 36 or at most 95% amino acid identity with amino acids 139-257 of SEQ ID NO: 36.

In other aspects of this embodiment, a NGF comprises a polypeptide having, e.g., at most one, two, three, four, five, six, seven, eight, nine, 10 or 20 non-contiguous amino acid substitutions relative to amino acids 139-257 of SEQ ID NO: 36. In other aspects of this embodiment, a NGF comprises a polypeptide having, e.g., at least one, two, three, four, five, six, seven, eight, nine, 10 or 20 non-contiguous amino acid substitutions relative to amino acids 139-257 of SEQ ID NO: 36. In yet other aspects of this embodiment, a NGF comprises a polypeptide having, e.g., at most one, two, three, four, five, six, seven, eight, nine, 10 or 20 non-contiguous amino acid deletions relative to amino acids 139-257 of SEQ ID NO: 36. In other aspects of this embodiment, a NGF comprises a polypeptide having, e.g., at least one, two, three, four, five, six, seven, eight, nine, 10 or 20 non-contiguous amino acid deletions relative to amino acids 139-257 of SEQ ID NO: 36. In still other aspects of this embodiment, a NGF comprises a polypeptide having, e.g., at most one, two, three, four, five, six, seven, eight, nine, 10 or 20 non-contiguous amino acid additions relative to amino acids 139-257 of SEQ ID NO: 36. In other aspects of this embodiment, a NGF comprises a polypeptide having, e.g., at least one, two, three, four, five, six, seven, eight, nine, 10 or 20 non-contiguous amino acid additions relative to amino acids 139-257 of SEQ ID NO: 36.

In other aspects of this embodiment, a NGF comprises a polypeptide having, e.g., at most one, two, three, four, five, six, seven, eight, nine, 10 or 20 contiguous amino acid substitutions relative to amino acids 139-257 of SEQ ID NO: 36. In other aspects of this embodiment, a NGF comprises a polypeptide having, e.g., at least one, two, three, four, five, six, seven, eight, nine, 10 or 20 contiguous amino acid substitutions relative to amino acids 139-257 of SEQ ID NO: 36. In yet other aspects of this embodiment, a NGF comprises a polypeptide having, e.g., at most one, two, three, four, five, six, seven, eight, nine, 10 or 20 contiguous amino acid deletions relative to amino acids 139-257 of SEQ ID NO: 36. In other aspects of this embodiment, a NGF comprises a polypeptide having, e.g., at least one, two, three, four, five, six, seven, eight, nine, 10 or 20 contiguous amino acid deletions relative to amino acids 139-257 of SEQ ID NO: 36. In still other aspects of this embodiment, a NGF comprises a polypeptide having, e.g., at most one, two, three, four, five, six, seven, eight, nine, 10 or 20 contiguous amino acid additions relative to amino acids 139-257 of SEQ ID NO: 36. In other aspects of this embodiment, a NGF comprises a polypeptide having, e.g., at least one, two, three, four, five, six, seven, eight, nine, 10 or 20 contiguous amino acid additions relative to amino acids 139-257 of SEQ ID NO: 36.

In another embodiment, an enhanced binding domain is derived from a BDGF. In another embodiment, an enhanced binding domain is derived from a BDGF of SEQ ID NO: 37. In an aspect of this embodiment, an enhanced binding domain is derived from a BDGF comprises amino acids 133-240 or amino acids 129-247 of SEQ ID NO: 37.

In other aspects of this embodiment, a BDGF comprises a polypeptide having, e.g., at least 70% amino acid identity with amino acids 133-240 or amino acids 129-247 of SEQ ID NO: 37, at least 75% amino acid identity with amino acids 133-240 or amino acids 129-247 of SEQ ID NO: 37, at least 80% amino acid identity with amino acids 133-240 or amino acids 129-247 of SEQ ID NO: 37, at least 85% amino acid identity with amino acids 133-240 or amino acids 129-247 of SEQ ID NO: 37, at least 90% amino acid identity with amino acids 133-240 or amino acids 129-247 of SEQ ID NO: 37 or at least 95% amino acid identity with amino acids 133-240 or amino acids 129-247 of SEQ ID NO: 37. In yet other aspects of this embodiment, a BDGF comprises a polypeptide having, e.g., at most 70% amino acid identity with amino acids 133-240 or amino acids 129-247 of SEQ ID NO: 37, at most 75% amino acid identity with amino acids 133-240 or amino acids 129-247 of SEQ ID NO: 37, at most 80% amino acid identity with amino acids 133-240 or amino acids 129-247 of SEQ ID NO: 37, at most 85% amino acid identity with amino acids 133-240 or amino acids 129-247 of SEQ ID NO: 37, at most 90% amino acid identity with amino acids 133-240 or amino acids 129-247 of SEQ ID NO: 37 or at most 95% amino acid identity with amino acids 133-240 or amino acids 129-247 of SEQ ID NO: 37.

In other aspects of this embodiment, a BDGF comprises a polypeptide having, e.g., at most one, two, three, four, five, six, seven, eight, nine, 10 or 20 non-contiguous amino acid substitutions relative to amino acids 133-240 or amino acids 129-247 of SEQ ID NO: 37. In other aspects of this embodiment, a BDGF comprises a polypeptide having, e.g., at least one, two, three, four, five, six, seven, eight, nine, 10 or 20 non-contiguous amino acid substitutions relative to amino acids 133-240 or amino acids 129-247 of SEQ ID NO: 37. In yet other aspects of this embodiment, a BDGF comprises a polypeptide having, e.g., at most one, two, three, four, five, six, seven, eight, nine, 10 or 20 non-contiguous amino acid deletions relative to amino acids 133-240 or amino acids 129-247 of SEQ ID NO: 37. In other aspects of this embodiment, a BDGF comprises a polypeptide having, e.g., at least one, two, three, four, five, six, seven, eight, nine, 10 or 20 non-contiguous amino acid deletions relative to amino acids 133-240 or amino acids 129-247 of SEQ ID NO: 37. In still other aspects of this embodiment, a BDGF comprises a polypeptide having, e.g., at most one, two, three, four, five, six, seven, eight, nine, 10 or 20 non-contiguous amino acid additions relative to amino acids 133-240 or amino acids 129-247 of SEQ ID NO: 37. In other aspects of this embodiment, a BDGF comprises a polypeptide having, e.g., at least one, two, three, four, five, six, seven, eight, nine, 10 or 20 non-contiguous amino acid additions relative to amino acids 133-240 or amino acids 129-247 of SEQ ID NO: 37.

In other aspects of this embodiment, a BDGF comprises a polypeptide having, e.g., at most one, two, three, four, five, six, seven, eight, nine, 10 or 20 contiguous amino acid substitutions relative to amino acids 133-240 or amino acids 129-247 of SEQ ID NO: 37. In other aspects of this embodiment, a BDGF comprises a polypeptide having, e.g., at least one, two, three, four, five, six, seven, eight, nine, 10 or 20 contiguous amino acid substitutions relative to amino acids 133-240 or amino acids 129-247 of SEQ ID NO: 37. In yet other aspects of this embodiment, a BDGF comprises a polypeptide having, e.g., at most one, two, three, four, five, six, seven, eight, nine, 10 or 20 contiguous amino acid deletions relative to amino acids 133-240 or amino acids 129-247 of SEQ ID NO: 37. In other aspects of this embodiment, a BDGF comprises a polypeptide having, e.g., at least one, two, three, four, five, six, seven, eight, nine, 10 or 20 contiguous amino acid deletions relative to amino acids 133-240 or amino acids 129-247 of SEQ ID NO: 37. In still other aspects of this embodiment, a BDGF comprises a polypeptide having, e.g., at most one, two, three, four, five, six, seven, eight, nine, 10 or 20 contiguous amino acid additions relative to amino acids 133-240 or amino acids 129-247 of SEQ ID NO: 37. In other aspects of this embodiment, a BDGF comprises a polypeptide having, e.g., at least one, two, three, four, five, six, seven, eight, nine, 10 or 20 contiguous amino acid additions relative to amino acids 133-240 or amino acids 129-247 of SEQ ID NO: 37.

In another embodiment, an enhanced binding domain is derived from a NT-3. In another embodiment, an enhanced binding domain is derived from a NT-3 of SEQ ID NO: 38. In an aspect of this embodiment, an enhanced binding domain is derived from a NT-3 comprises amino acids 144-249 or amino acids 19-257 of SEQ ID NO: 38.

In other aspects of this embodiment, a NT-3 comprises a polypeptide having, e.g., at least 70% amino acid identity with amino acids 144-249 or amino acids 19-257 of SEQ ID NO: 38, at least 75% amino acid identity with amino acids 144-249 or amino acids 19-257 of SEQ ID NO: 38, at least 80% amino acid identity with amino acids 144-249 or amino acids 19-257 of SEQ ID NO: 38, at least 85% amino acid identity with amino acids 144-249 or amino acids 19-257 of SEQ ID NO: 38, at least 90% amino acid identity with amino acids 144-249 or amino acids 19-257 of SEQ ID NO: 38 or at least 95% amino acid identity with amino acids 144-249 or amino acids 19-257 of SEQ ID NO: 38. In yet other aspects of this embodiment, a NT-3 comprises a polypeptide having, e.g., at most 70% amino acid identity with amino acids 144-249 or amino acids 19-257 of SEQ ID NO: 38, at most 75% amino acid identity with amino acids 144-249 or amino acids 19-257 of SEQ ID NO: 38, at most 80% amino acid identity with amino acids 144-249 or amino acids 19-257 of SEQ ID NO: 38, at most 85% amino acid identity with amino acids 144-249 or amino acids 19-257 of SEQ ID NO: 38, at most 90% amino acid identity with amino acids 144-249 or amino acids 19-257 of SEQ ID NO: 38 or at most 95% amino acid identity with amino acids 144-249 or amino acids 19-257 of SEQ ID NO: 38.

In other aspects of this embodiment, a NT-3 comprises a polypeptide having, e.g., at most one, two, three, four, five, six, seven, eight, nine, 10 or 20 non-contiguous amino acid substitutions relative to amino acids 144-249 or amino acids 19-257 of SEQ ID NO: 38. In other aspects of this embodiment, a NT-3 comprises a polypeptide having, e.g., at least one, two, three, four, five, six, seven, eight, nine, 10 or 20 non-contiguous amino acid substitutions relative to amino acids 144-249 or amino acids 19-257 of SEQ ID NO: 38. In yet other aspects of this embodiment, a NT-3 comprises a polypeptide having, e.g., at most one, two, three, four, five, six, seven, eight, nine, 10 or 20 non-contiguous amino acid deletions relative to amino acids 144-249 or amino acids 19-257 of SEQ ID NO: 38. In other aspects of this embodiment, a NT-3 comprises a polypeptide having, e.g., at least one, two, three, four, five, six, seven, eight, nine, 10 or 20 non-contiguous amino acid deletions relative to amino acids 144-249 or amino acids 19-257 of SEQ ID NO: 38. In still other aspects of this embodiment, a NT-3 comprises a polypeptide having, e.g., at most one, two, three, four, five, six, seven, eight, nine, 10 or 20 non-contiguous amino acid additions relative to amino acids 144-249 or amino acids 19-257 of SEQ ID NO: 38. In other aspects of this embodiment, a NT-3 comprises a polypeptide having, e.g., at least one, two, three, four, five, six, seven, eight, nine, 10 or 20 non-contiguous amino acid additions relative to amino acids 144-249 or amino acids 19-257 of SEQ ID NO: 38.

In other aspects of this embodiment, a NT-3 comprises a polypeptide having, e.g., at most one, two, three, four, five, six, seven, eight, nine, 10 or 20 contiguous amino acid substitutions relative to amino acids 144-249 or amino acids 19-257 of SEQ ID NO: 38. In other aspects of this embodiment, a NT-3 comprises a polypeptide having, e.g., at least one, two, three, four, five, six, seven, eight, nine, 10 or 20 contiguous amino acid substitutions relative to amino acids 144-249 or amino acids 19-257 of SEQ ID NO: 38. In yet other aspects of this embodiment, a NT-3 comprises a polypeptide having, e.g., at most one, two, three, four, five, six, seven, eight, nine, 10 or 20 contiguous amino acid deletions relative to amino acids 144-249 or amino acids 19-257 of SEQ ID NO: 38. In other aspects of this embodiment, a NT-3 comprises a polypeptide having, e.g., at least one, two, three, four, five, six, seven, eight, nine, 10 or 20 contiguous amino acid deletions relative to amino acids 144-249 or amino acids 19-257 of SEQ ID NO: 38. In still other aspects of this embodiment, a NT-3 comprises a polypeptide having, e.g., at most one, two, three, four, five, six, seven, eight, nine, 10 or 20 contiguous amino acid additions relative to amino acids 144-249 or amino acids 19-257 of SEQ ID NO: 38. In other aspects of this embodiment, a NT-3 comprises a polypeptide having, e.g., at least one, two, three, four, five, six, seven, eight, nine, 10 or 20 contiguous amino acid additions relative to amino acids 144-249 or amino acids 19-257 of SEQ ID NO: 38.

In another embodiment, an enhanced binding domain is derived from a NT-4/5. In another embodiment, an enhanced binding domain is derived from a NT-4/5 of SEQ ID NO: 39. In an aspect of this embodiment, an enhanced binding domain is derived from a NT-4/5 comprises amino acids 89-202 or amino acids 81-210 of SEQ ID NO: 39.

In other aspects of this embodiment, a NT-4/5 comprises a polypeptide having, e.g., at least 70% amino acid identity with amino acids 89-202 or amino acids 81-210 of SEQ ID NO: 39, at least 75% amino acid identity with amino acids 89-202 or amino acids 81-210 of SEQ ID NO: 39, at least 80% amino acid identity with amino acids 89-202 or amino acids 81-210 of SEQ ID NO: 39, at least 85% amino acid identity with amino acids 89-202 or amino acids 81-210 of SEQ ID NO: 39, at least 90% amino acid identity with amino acids 89-202 or amino acids 81-210 of SEQ ID NO: 39 or at least 95% amino acid identity with amino acids 89-202 or amino acids 81-210 of SEQ ID NO: 39. In yet other aspects of this embodiment, a NT-4/5 comprises a polypeptide having, e.g., at most 70% amino acid identity with amino acids 89-202 or amino acids 81-210 of SEQ ID NO: 39, at most 75% amino acid identity with amino acids 89-202 or amino acids 81-210 of SEQ ID NO: 39, at most 80% amino acid identity with amino acids 89-202 or amino acids 81-210 of SEQ ID NO: 39, at most 85% amino acid identity with amino acids 89-202 or amino acids 81-210 of SEQ ID NO: 39, at most 90% amino acid identity with amino acids 89-202 or amino acids 81-210 of SEQ ID NO: 39 or at most 95% amino acid identity with amino acids 89-202 or amino acids 81-210 of SEQ ID NO: 39.

In other aspects of this embodiment, a NT-4/5 comprises a polypeptide having, e.g., at most one, two, three, four, five, six, seven, eight, nine, 10 or 20 non-contiguous amino acid substitutions relative to amino acids 89-202 or amino acids 81-210 of SEQ ID NO: 39. In other aspects of this embodiment, a NT-4/5 comprises a polypeptide having, e.g., at least one, two, three, four, five, six, seven, eight, nine, 10 or 20 non-contiguous amino acid substitutions relative to amino acids 89-202 or amino acids 81-210 of SEQ ID NO: 39. In yet other aspects of this embodiment, a NT-4/5 comprises a polypeptide having, e.g., at most one, two, three, four, five, six, seven, eight, nine, 10 or 20 non-contiguous amino acid deletions relative to amino acids 89-202 or amino acids 81-210 of SEQ ID NO: 39. In other aspects of this embodiment, a NT-4/5 comprises a polypeptide having, e.g., at least one, two, three, four, five, six, seven, eight, nine, 10 or 20 non-contiguous amino acid deletions relative to amino acids 89-202 or amino acids 81-210 of SEQ ID NO: 39. In still other aspects of this embodiment, a NT-4/5 comprises a polypeptide having, e.g., at most one, two, three, four, five, six, seven, eight, nine, 10 or 20 non-contiguous amino acid additions relative to amino acids 89-202 or amino acids 81-210 of SEQ ID NO: 39. In other aspects of this embodiment, a NT-4/5 comprises a polypeptide having, e.g., at least one, two, three, four, five, six, seven, eight, nine, 10 or 20 non-contiguous amino acid additions relative to amino acids 89-202 or amino acids 81-210 of SEQ ID NO: 39.

In other aspects of this embodiment, a NT-4/5 comprises a polypeptide having, e.g., at most one, two, three, four, five, six, seven, eight, nine, 10 or 20 contiguous amino acid substitutions relative to amino acids 89-202 or amino acids 81-210 of SEQ ID NO: 39. In other aspects of this embodiment, a NT-4/5 comprises a polypeptide having, e.g., at least one, two, three, four, five, six, seven, eight, nine, 10 or 20 contiguous amino acid substitutions relative to amino acids 89-202 or amino acids 81-210 of SEQ ID NO: 39. In yet other aspects of this embodiment, a NT-4/5 comprises a polypeptide having, e.g., at most one, two, three, four, five, six, seven, eight, nine, 10 or 20 contiguous amino acid deletions relative to amino acids 89-202 or amino acids 81-210 of SEQ ID NO: 39. In other aspects of this embodiment, a NT-4/5 comprises a polypeptide having, e.g., at least one, two, three, four, five, six, seven, eight, nine, 10 or 20 contiguous amino acid deletions relative to amino acids 89-202 or amino acids 81-210 of SEQ ID NO: 39. In still other aspects of this embodiment, a NT-4/5 comprises a polypeptide having, e.g., at most one, two, three, four, five, six, seven, eight, nine, 10 or 20 contiguous amino acid additions relative to amino acids 89-202 or amino acids 81-210 of SEQ ID NO: 39. In other aspects of this embodiment, a NT-4/5 comprises a polypeptide having, e.g., at least one, two, three, four, five, six, seven, eight, nine, 10 or 20 contiguous amino acid additions relative to amino acids 89-202 or amino acids 81-210 of SEQ ID NO: 39.

Another example of an enhanced targeting domain disclosed in the present specification is, e.g., a GDNF, a neurturin, a persephrin or an artemin.

Thus, in an embodiment, an enhanced binding domain is derived from a GDNF. In another embodiment, an enhanced binding domain is derived from a GDNF of SEQ ID NO: 40. In an aspect of this embodiment, an enhanced binding domain is derived from a GDNF comprises amino acids 118-211 of SEQ ID NO: 40.

In other aspects of this embodiment, a GDNF comprises a polypeptide having, e.g., at least 70% amino acid identity with amino acids 118-211 of SEQ ID NO: 40, at least 75% amino acid identity with amino acids 118-211 of SEQ ID NO: 40, at least 80% amino acid identity with amino acids 118-211 of SEQ ID NO: 40, at least 85% amino acid identity with amino acids 118-211 of SEQ ID NO: 40, at least 90% amino acid identity with amino acids 118-211 of SEQ ID NO: 40 or at least 95% amino acid identity with amino acids 118-211 of SEQ ID NO: 40. In yet other aspects of this embodiment, a GDNF comprises a polypeptide having, e.g., at most 70% amino acid identity with amino acids 118-211 of SEQ ID NO: 40, at most 75% amino acid identity with amino acids 118-211 of SEQ ID NO: 40, at most 80% amino acid identity with amino acids 118-211 of SEQ ID NO: 40, at most 85% amino acid identity with amino acids 118-211 of SEQ ID NO: 40, at most 90% amino acid identity with amino acids 118-211 of SEQ ID NO: 40 or at most 95% amino acid identity with amino acids 118-211 of SEQ ID NO: 40.

In other aspects of this embodiment, a GDNF comprises a polypeptide having, e.g., at most one, two, three, four, five, six, seven, eight, nine, 10 or 20 non-contiguous amino acid substitutions relative to amino acids 118-211 of SEQ ID NO: 40. In other aspects of this embodiment, a GDNF comprises a polypeptide having, e.g., at least one, two, three, four, five, six, seven, eight, nine, 10 or 20 non-contiguous amino acid substitutions relative to amino acids 118-211 of SEQ ID NO: 40. In yet other aspects of this embodiment, a GDNF comprises a polypeptide having, e.g., at most one, two, three, four, five, six, seven, eight, nine, 10 or 20 non-contiguous amino acid deletions relative to amino acids 118-211 of SEQ ID NO: 40. In other aspects of this embodiment, a GDNF comprises a polypeptide having, e.g., at least one, two, three, four, five, six, seven, eight, nine, 10 or 20 non-contiguous amino acid deletions relative to amino acids 118-211 of SEQ ID NO: 40. In still other aspects of this embodiment, a GDNF comprises a polypeptide having, e.g., at most one, two, three, four, five, six, seven, eight, nine, 10 or 20 non-contiguous amino acid additions relative to amino acids 118-211 of SEQ ID NO: 40. In other aspects of this embodiment, a GDNF comprises a polypeptide having, e.g., at least one, two, three, four, five, six, seven, eight, nine, 10 or 20 non-contiguous amino acid additions relative to amino acids 118-211 of SEQ ID NO: 40.

In other aspects of this embodiment, a GDNF comprises a polypeptide having, e.g., at most one, two, three, four, five, six, seven, eight, nine, 10 or 20 contiguous amino acid substitutions relative to amino acids 118-211 of SEQ ID NO: 40. In other aspects of this embodiment, a GDNF comprises a polypeptide having, e.g., at least one, two, three, four, five, six, seven, eight, nine, 10 or 20 contiguous amino acid substitutions relative to amino acids 118-211 of SEQ ID NO: 40. In yet other aspects of this embodiment, a GDNF comprises a polypeptide having, e.g., at most one, two, three, four, five, six, seven, eight, nine, 10 or 20 contiguous amino acid deletions relative to amino acids 118-211 of SEQ ID NO: 40. In other aspects of this embodiment, a GDNF comprises a polypeptide having, e.g., at least one, two, three, four, five, six, seven, eight, nine, 10 or 20 contiguous amino acid deletions relative to amino acids 118-211 of SEQ ID NO: 40. In still other aspects of this embodiment, a GDNF comprises a polypeptide having, e.g., at most one, two, three, four, five, six, seven, eight, nine, 10 or 20 contiguous amino acid additions relative to amino acids 118-211 of SEQ ID NO: 40. In other aspects of this embodiment, a GDNF comprises a polypeptide having, e.g., at least one, two, three, four, five, six, seven, eight, nine, 10 or 20 contiguous amino acid additions relative to amino acids 118-211 of SEQ ID NO: 40.

In another embodiment, an enhanced binding domain is derived from a Neurturin. In another embodiment, an enhanced binding domain is derived from a Neurturin of SEQ ID NO: 41. In an aspect of this embodiment, an enhanced binding domain is derived from a Neurturin comprises amino acids 107-196 or amino acids 96-197 of SEQ ID NO: 41.

In other aspects of this embodiment, a Neurturin comprises a polypeptide having, e.g., at least 70% amino acid identity with amino acids 107-196 or amino acids 96-197 of SEQ ID NO: 41, at least 75% amino acid identity with amino acids 107-196 or amino acids 96-197 of SEQ ID NO: 41, at least 80% amino acid identity with amino acids 107-196 or amino acids 96-197 of SEQ ID NO: 41, at least 85% amino acid identity with amino acids 107-196 or amino acids 96-197 of SEQ ID NO: 41, at least 90% amino acid identity with amino acids 107-196 or amino acids 96-197 of SEQ ID NO: 41 or at least 95% amino acid identity with amino acids 107-196 or amino acids 96-197 of SEQ ID NO: 41. In yet other aspects of this embodiment, a Neurturin comprises a polypeptide having, e.g., at most 70% amino acid identity with amino acids 107-196 or amino acids 96-197 of SEQ ID NO: 41, at most 75% amino acid identity with amino acids 107-196 or amino acids 96-197 of SEQ ID NO: 41, at most 80% amino acid identity with amino acids 107-196 or amino acids 96-197 of SEQ ID NO: 41, at most 85% amino acid identity with amino acids 107-196 or amino acids 96-197 of SEQ ID NO: 41, at most 90% amino acid identity with amino acids 107-196 or amino acids 96-197 of SEQ ID NO: 41 or at most 95% amino acid identity with amino acids 107-196 or amino acids 96-197 of SEQ ID NO: 41.

In other aspects of this embodiment, a Neurturin comprises a polypeptide having, e.g., at most one, two, three, four, five, six, seven, eight, nine, 10 or 20 non-contiguous amino acid substitutions relative to amino acids 107-196 or amino acids 96-197 of SEQ ID NO: 41. In other aspects of this embodiment, a Neurturin comprises a polypeptide having, e.g., at least one, two, three, four, five, six, seven, eight, nine, 10 or 20 non-contiguous amino acid substitutions relative to amino acids 107-196 or amino acids 96-197 of SEQ ID NO: 41. In yet other aspects of this embodiment, a Neurturin comprises a polypeptide having, e.g., at most one, two, three, four, five, six, seven, eight, nine, 10 or 20 non-contiguous amino acid deletions relative to amino acids 107-196 or amino acids 96-197 of SEQ ID NO: 41. In other aspects of this embodiment, a Neurturin comprises a polypeptide having, e.g., at least one, two, three, four, five, six, seven, eight, nine, 10 or 20 non-contiguous amino acid deletions relative to amino acids 107-196 or amino acids 96-197 of SEQ ID NO: 41. In still other aspects of this embodiment, a Neurturin comprises a polypeptide having, e.g., at most one, two, three, four, five, six, seven, eight, nine, 10 or 20 non-contiguous amino acid additions relative to amino acids 107-196 or amino acids 96-197 of SEQ ID NO: 41. In other aspects of this embodiment, a Neurturin comprises a polypeptide having, e.g., at least one, two, three, four, five, six, seven, eight, nine, 10 or 20 non-contiguous amino acid additions relative to amino acids 107-196 or amino acids 96-197 of SEQ ID NO: 41.

In other aspects of this embodiment, a Neurturin comprises a polypeptide having, e.g., at most one, two, three, four, five, six, seven, eight, nine, 10 or 20 contiguous amino acid substitutions relative to amino acids 107-196 or amino acids 96-197 of SEQ ID NO: 41. In other aspects of this embodiment, a Neurturin comprises a polypeptide having, e.g., at least one, two, three, four, five, six, seven, eight, nine, 10 or 20 contiguous amino acid substitutions relative to amino acids 107-196 or amino acids 96-197 of SEQ ID NO: 41. In yet other aspects of this embodiment, a Neurturin comprises a polypeptide having, e.g., at most one, two, three, four, five, six, seven, eight, nine, 10 or 20 contiguous amino acid deletions relative to amino acids 107-196 or amino acids 96-197 of SEQ ID NO: 41. In other aspects of this embodiment, a Neurturin comprises a polypeptide having, e.g., at least one, two, three, four, five, six, seven, eight, nine, 10 or 20 contiguous amino acid deletions relative to amino acids 107-196 or amino acids 96-197 of SEQ ID NO: 41. In still other aspects of this embodiment, a Neurturin comprises a polypeptide having, e.g., at most one, two, three, four, five, six, seven, eight, nine, 10 or 20 contiguous amino acid additions relative to amino acids 107-196 or amino acids 96-197 of SEQ ID NO: 41. In other aspects of this embodiment, a Neurturin comprises a polypeptide having, e.g., at least one, two, three, four, five, six, seven, eight, nine, 10 or 20 contiguous amino acid additions relative to amino acids 107-196 or amino acids 96-197 of SEQ ID NO: 41.

In another embodiment, an enhanced binding domain is derived from a Persephrin. In another embodiment, an enhanced binding domain is derived from a Persephrin of SEQ ID NO: 42. In an aspect of this embodiment, an enhanced binding domain is derived from a Persephrin comprises amino acids 66-155 of SEQ ID NO: 42.

In other aspects of this embodiment, a Persephrin comprises a polypeptide having, e.g., at least 70% amino acid identity with amino acids 66-155 of SEQ ID NO: 42, at least 75% amino acid identity with amino acids 66-155 of SEQ ID NO: 42, at least 80% amino acid identity with amino acids 66-155 of SEQ ID NO: 42, at least 85% amino acid identity with amino acids 66-155 of SEQ ID NO: 42, at least 90% amino acid identity with amino acids 66-155 of SEQ ID NO: 42 or at least 95% amino acid identity with amino acids 66-155 of SEQ ID NO: 42. In yet other aspects of this embodiment, a Persephrin comprises a polypeptide having, e.g., at most 70% amino acid identity with amino acids 66-155 of SEQ ID NO: 42, at most 75% amino acid identity with amino acids 66-155 of SEQ ID NO: 42, at most 80% amino acid identity with amino acids 66-155 of SEQ ID NO: 42, at most 85% amino acid identity with amino acids 66-155 of SEQ ID NO: 42, at most 90% amino acid identity with amino acids 66-155 of SEQ ID NO: 42 or at most 95% amino acid identity with amino acids 66-155 of SEQ ID NO: 42.

In other aspects of this embodiment, a Persephrin comprises a polypeptide having, e.g., at most one, two, three, four, five, six, seven, eight, nine, 10 or 20 non-contiguous amino acid substitutions relative to amino acids 66-155 of SEQ ID NO: 42. In other aspects of this embodiment, a Persephrin comprises a polypeptide having, e.g., at least one, two, three, four, five, six, seven, eight, nine, 10 or 20 non-contiguous amino acid substitutions relative to amino acids 66-155 of SEQ ID NO: 42. In yet other aspects of this embodiment, a Persephrin comprises a polypeptide having, e.g., at most one, two, three, four, five, six, seven, eight, nine, 10 or 20 non-contiguous amino acid deletions relative to amino acids 66-155 of SEQ ID NO: 42. In other aspects of this embodiment, a Persephrin comprises a polypeptide having, e.g., at least one, two, three, four, five, six, seven, eight, nine, 10 or 20 non-contiguous amino acid deletions relative to amino acids 66-155 of SEQ ID NO: 42. In still other aspects of this embodiment, a Persephrin comprises a polypeptide having, e.g., at most one, two, three, four, five, six, seven, eight, nine, 10 or 20 non-contiguous amino acid additions relative to amino acids 66-155 of SEQ ID NO: 42. In other aspects of this embodiment, a Persephrin comprises a polypeptide having, e.g., at least one, two, three, four, five, six, seven, eight, nine, 10 or 20 non-contiguous amino acid additions relative to amino acids 66-155 of SEQ ID NO: 42.

In other aspects of this embodiment, a Persephrin comprises a polypeptide having, e.g., at most one, two, three, four, five, six, seven, eight, nine, 10 or 20 contiguous amino acid substitutions relative to amino acids 66-155 of SEQ ID NO: 42. In other aspects of this embodiment, a Persephrin comprises a polypeptide having, e.g., at least one, two, three, four, five, six, seven, eight, nine, 10 or 20 contiguous amino acid substitutions relative to amino acids 66-155 of SEQ ID NO: 42. In yet other aspects of this embodiment, a Persephrin comprises a polypeptide having, e.g., at most one, two, three, four, five, six, seven, eight, nine, 10 or 20 contiguous amino acid deletions relative to amino acids 66-155 of SEQ ID NO: 42. In other aspects of this embodiment, a Persephrin comprises a polypeptide having, e.g., at least one, two, three, four, five, six, seven, eight, nine, 10 or 20 contiguous amino acid deletions relative to amino acids 66-155 of SEQ ID NO: 42. In still other aspects of this embodiment, a Persephrin comprises a polypeptide having, e.g., at most one, two, three, four, five, six, seven, eight, nine, 10 or 20 contiguous amino acid additions relative to amino acids 66-155 of SEQ ID NO: 42. In other aspects of this embodiment, a Persephrin comprises a polypeptide having, e.g., at least one, two, three, four, five, six, seven, eight, nine, 10 or 20 contiguous amino acid additions relative to amino acids 66-155 of SEQ ID NO: 42.

In another embodiment, an enhanced binding domain is derived from an Artemin. In another embodiment, an enhanced binding domain is derived from an Artemin of SEQ ID NO: 43. In an aspect of this embodiment, an enhanced binding domain is derived from an Artemin comprises amino acids 123-218 of SEQ ID NO: 43.

In other aspects of this embodiment, an Artemin comprises a polypeptide having, e.g., at least 70% amino acid identity with amino acids 123-218 of SEQ ID NO: 43, at least 75% amino acid identity with amino acids 123-218 of SEQ ID NO: 43, at least 80% amino acid identity with amino acids 123-218 of SEQ ID NO: 43, at least 85% amino acid identity with amino acids 123-218 of SEQ ID NO: 43, at least 90% amino acid identity with amino acids 123-218 of SEQ ID NO: 43 or at least 95% amino acid identity with amino acids 123-218 of SEQ ID NO: 43. In yet other aspects of this embodiment, an Artemin comprises a polypeptide having, e.g., at most 70% amino acid identity with amino acids 123-218 of SEQ ID NO: 43, at most 75% amino acid identity with amino acids 123-218 of SEQ ID NO: 43, at most 80% amino acid identity with amino acids 123-218 of SEQ ID NO: 43, at most 85% amino acid identity with amino acids 123-218 of SEQ ID NO: 43, at most 90% amino acid identity with amino acids 123-218 of SEQ ID NO: 43 or at most 95% amino acid identity with amino acids 123-218 of SEQ ID NO: 43.

In other aspects of this embodiment, an Artemin comprises a polypeptide having, e.g., at most one, two, three, four, five, six, seven, eight, nine, 10 or 20 non-contiguous amino acid substitutions relative to amino acids 123-218 of SEQ ID NO: 43. In other aspects of this embodiment, an Artemin comprises a polypeptide having, e.g., at least one, two, three, four, five, six, seven, eight, nine, 10 or 20 non-contiguous amino acid substitutions relative to amino acids 123-218 of SEQ ID NO: 43. In yet other aspects of this embodiment, an Artemin comprises a polypeptide having, e.g., at most one, two, three, four, five, six, seven, eight, nine, 10 or 20 non-contiguous amino acid deletions relative to amino acids 123-218 of SEQ ID NO: 43. In other aspects of this embodiment, an Artemin comprises a polypeptide having, e.g., at least one, two, three, four, five, six, seven, eight, nine, 10 or 20 non-contiguous amino acid deletions relative to amino acids 123-218 of SEQ ID NO: 43. In still other aspects of this embodiment, an Artemin comprises a polypeptide having, e.g., at most one, two, three, four, five, six, seven, eight, nine, 10 or 20 non-contiguous amino acid additions relative to amino acids 123-218 of SEQ ID NO: 43. In other aspects of this embodiment, an Artemin comprises a polypeptide having, e.g., at least one, two, three, four, five, six, seven, eight, nine, 10 or 20 non-contiguous amino acid additions relative to amino acids 123-218 of SEQ ID NO: 43.

In other aspects of this embodiment, an Artemin comprises a polypeptide having, e.g., at most one, two, three, four, five, six, seven, eight, nine, 10 or 20 contiguous amino acid substitutions relative to amino acids 123-218 of SEQ ID NO: 43. In other aspects of this embodiment, an Artemin comprises a polypeptide having, e.g., at least one, two, three, four, five, six, seven, eight, nine, 10 or 20 contiguous amino acid substitutions relative to amino acids 123-218 of SEQ ID NO: 43. In yet other aspects of this embodiment, an Artemin comprises a polypeptide having, e.g., at most one, two, three, four, five, six, seven, eight, nine, 10 or 20 contiguous amino acid deletions relative to amino acids 123-218 of SEQ ID NO: 43. In other aspects of this embodiment, an Artemin comprises a polypeptide having, e.g., at least one, two, three, four, five, six, seven, eight, nine, 10 or 20 contiguous amino acid deletions relative to amino acids 123-218 of SEQ ID NO: 43. In still other aspects of this embodiment, an Artemin comprises a polypeptide having, e.g., at most one, two, three, four, five, six, seven, eight, nine, 10 or 20 contiguous amino acid additions relative to amino acids 123-218 of SEQ ID NO: 43. In other aspects of this embodiment, an Artemin comprises a polypeptide having, e.g., at least one, two, three, four, five, six, seven, eight, nine, 10 or 20 contiguous amino acid additions relative to amino acids 123-218 of SEQ ID NO: 43.

Another example of an enhanced targeting domain disclosed in the present specification is, e.g., a TGFβs, such as, e.g., TGFβ1, TGFβ2, TGFβ3 or TGFβ4.

Thus, in an embodiment, an enhanced binding domain is derived from a TGFβ1. In another embodiment, an enhanced binding domain is derived from a TGFβ1 of SEQ ID NO: 44. In an aspect of this embodiment, an enhanced binding domain is derived from a TGFβ1 comprises amino acids 293-390 of SEQ ID NO: 44.

In other aspects of this embodiment, a TGFβ1 comprises a polypeptide having, e.g., at least 70% amino acid identity with amino acids 293-390 of SEQ ID NO: 44, at least 75% amino acid identity with amino acids 293-390 of SEQ ID NO: 44, at least 80% amino acid identity with amino acids 293-390 of SEQ ID NO: 44, at least 85% amino acid identity with amino acids 293-390 of SEQ ID NO: 44, at least 90% amino acid identity with amino acids 293-390 of SEQ ID NO: 44 or at least 95% amino acid identity with amino acids 293-390 of SEQ ID NO: 44. In yet other aspects of this embodiment, a TGFβ1 comprises a polypeptide having, e.g., at most 70% amino acid identity with amino acids 293-390 of SEQ ID NO: 44, at most 75% amino acid identity with amino acids 293-390 of SEQ ID NO: 44, at most 80% amino acid identity with amino acids 293-390 of SEQ ID NO: 44, at most 85% amino acid identity with amino acids 293-390 of SEQ ID NO: 44, at most 90% amino acid identity with amino acids 293-390 of SEQ ID NO: 44 or at most 95% amino acid identity with amino acids 293-390 of SEQ ID NO: 44.

In other aspects of this embodiment, a TGFβ1 comprises a polypeptide having, e.g., at most one, two, three, four, five, six, seven, eight, nine, 10 or 20 non-contiguous amino acid substitutions relative to amino acids 293-390 of SEQ ID NO: 44. In other aspects of this embodiment, a TGFβ1 comprises a polypeptide having, e.g., at least one, two, three, four, five, six, seven, eight, nine, 10 or 20 non-contiguous amino acid substitutions relative to amino acids 293-390 of SEQ ID NO: 44. In yet other aspects of this embodiment, a TGFβ1 comprises a polypeptide having, e.g., at most one, two, three, four, five, six, seven, eight, nine, 10 or 20 non-contiguous amino acid deletions relative to amino acids 293-390 of SEQ ID NO: 44. In other aspects of this embodiment, a TGFβ1 comprises a polypeptide having, e.g., at least one, two, three, four, five, six, seven, eight, nine, 10 or 20 non-contiguous amino acid deletions relative to amino acids 293-390 of SEQ ID NO: 44. In still other aspects of this embodiment, a TGFβ1 comprises a polypeptide having, e.g., at most one, two, three, four, five, six, seven, eight, nine, 10 or 20 non-contiguous amino acid additions relative to amino acids 293-390 of SEQ ID NO: 44. In other aspects of this embodiment, a TGFβ1 comprises a polypeptide having, e.g., at least one, two, three, four, five, six, seven, eight, nine, 10 or 20 non-contiguous amino acid additions relative to amino acids 293-390 of SEQ ID NO: 44.

In other aspects of this embodiment, a TGFβ1 comprises a polypeptide having, e.g., at most one, two, three, four, five, six, seven, eight, nine, 10 or 20 contiguous amino acid substitutions relative to amino acids 293-390 of SEQ ID NO: 44. In other aspects of this embodiment, a TGFβ1 comprises a polypeptide having, e.g., at least one, two, three, four, five, six, seven, eight, nine, 10 or 20 contiguous amino acid substitutions relative to amino acids 293-390 of SEQ ID NO: 44. In yet other aspects of this embodiment, a TGFβ1 comprises a polypeptide having, e.g., at most one, two, three, four, five, six, seven, eight, nine, 10 or 20 contiguous amino acid deletions relative to amino acids 293-390 of SEQ ID NO: 44. In other aspects of this embodiment, a TGFβ1 comprises a polypeptide having, e.g., at least one, two, three, four, five, six, seven, eight, nine, 10 or 20 contiguous amino acid deletions relative to amino acids 293-390 of SEQ ID NO: 44. In still other aspects of this embodiment, a TGFβ1 comprises a polypeptide having, e.g., at most one, two, three, four, five, six, seven, eight, nine, 10 or 20 contiguous amino acid additions relative to amino acids 293-390 of SEQ ID NO: 44. In other aspects of this embodiment, a TGFβ1 comprises a polypeptide having, e.g., at least one, two, three, four, five, six, seven, eight, nine, 10 or 20 contiguous amino acid additions relative to amino acids 293-390 of SEQ ID NO: 44.

In another embodiment, an enhanced binding domain is derived from a TGFβ2. In another embodiment, an enhanced binding domain is derived from a TGFβ2 of SEQ ID NO: 44. In an aspect of this embodiment, an enhanced binding domain is derived from a TGFβ2 comprises amino acids 317-414 of SEQ ID NO: 45.

In other aspects of this embodiment, a TGFβ2 comprises a polypeptide having, e.g., at least 70% amino acid identity with amino acids 317-414 of SEQ ID NO: 45, at least 75% amino acid identity with amino acids 317-414 of SEQ ID NO: 45, at least 80% amino acid identity with amino acids 317-414 of SEQ ID NO: 45, at least 85% amino acid identity with amino acids 317-414 of SEQ ID NO: 45, at least 90% amino acid identity with amino acids 317-414 of SEQ ID NO: 45 or at least 95% amino acid identity with amino acids 317-414 of SEQ ID NO: 45. In yet other aspects of this embodiment, a TGFβ2 comprises a polypeptide having, e.g., at most 70% amino acid identity with amino acids 317-414 of SEQ ID NO: 45, at most 75% amino acid identity with amino acids 317-414 of SEQ ID NO: 45, at most 80% amino acid identity with amino acids 317-414 of SEQ ID NO: 45, at most 85% amino acid identity with amino acids 317-414 of SEQ ID NO: 45, at most 90% amino acid identity with amino acids 317-414 of SEQ ID NO: 45 or at most 95% amino acid identity with amino acids 317-414 of SEQ ID NO: 45.

In other aspects of this embodiment, a TGFβ2 comprises a polypeptide having, e.g., at most one, two, three, four, five, six, seven, eight, nine, 10 or 20 non-contiguous amino acid substitutions relative to amino acids 317-414 of SEQ ID NO: 45. In other aspects of this embodiment, a TGFβ2 comprises a polypeptide having, e.g., at least one, two, three, four, five, six, seven, eight, nine, 10 or 20 non-contiguous amino acid substitutions relative to amino acids 317-414 of SEQ ID NO: 45. In yet other aspects of this embodiment, a TGFβ2 comprises a polypeptide having, e.g., at most one, two, three, four, five, six, seven, eight, nine, 10 or 20 non-contiguous amino acid deletions relative to amino acids 317-414 of SEQ ID NO: 45. In other aspects of this embodiment, a TGFβ2 comprises a polypeptide having, e.g., at least one, two, three, four, five, six, seven, eight, nine, 10 or 20 non-contiguous amino acid deletions relative to amino acids 317-414 of SEQ ID NO: 45. In still other aspects of this embodiment, a TGFβ2 comprises a polypeptide having, e.g., at most one, two, three, four, five, six, seven, eight, nine, 10 or 20 non-contiguous amino acid additions relative to amino acids 317-414 of SEQ ID NO: 45. In other aspects of this embodiment, a TGFβ2 comprises a polypeptide having, e.g., at least one, two, three, four, five, six, seven, eight, nine, 10 or 20 non-contiguous amino acid additions relative to amino acids 317-414 of SEQ ID NO: 45.

In other aspects of this embodiment, a TGFβ2 comprises a polypeptide having, e.g., at most one, two, three, four, five, six, seven, eight, nine, 10 or 20 contiguous amino acid substitutions relative to amino acids 317-414 of SEQ ID NO: 45. In other aspects of this embodiment, a TGFβ2 comprises a polypeptide having, e.g., at least one, two, three, four, five, six, seven, eight, nine, 10 or 20 contiguous amino acid substitutions relative to amino acids 317-414 of SEQ ID NO: 45. In yet other aspects of this embodiment, a TGFβ2 comprises a polypeptide having, e.g., at most one, two, three, four, five, six, seven, eight, nine, 10 or 20 contiguous amino acid deletions relative to amino acids 317-414 of SEQ ID NO: 45. In other aspects of this embodiment, a TGFβ2 comprises a polypeptide having, e.g., at least one, two, three, four, five, six, seven, eight, nine, 10 or 20 contiguous amino acid deletions relative to amino acids 317-414 of SEQ ID NO: 45. In still other aspects of this embodiment, a TGFβ2 comprises a polypeptide having, e.g., at most one, two, three, four, five, six, seven, eight, nine, 10 or 20 contiguous amino acid additions relative to amino acids 317-414 of SEQ ID NO: 45. In other aspects of this embodiment, a TGFβ2 comprises a polypeptide having, e.g., at least one, two, three, four, five, six, seven, eight, nine, 10 or 20 contiguous amino acid additions relative to amino acids 317-414 of SEQ ID NO: 45.

In another embodiment, an enhanced binding domain is derived from a TGFβ3. In another embodiment, an enhanced binding domain is derived from a TGFβ3 of SEQ ID NO: 44. In an aspect of this embodiment, an enhanced binding domain is derived from a TGFβ3 comprises amino acids 315-412 of SEQ ID NO: 46.

In other aspects of this embodiment, a TGFβ3 comprises a polypeptide having, e.g., at least 70% amino acid identity with amino acids 315-412 of SEQ ID NO: 46, at least 75% amino acid identity with amino acids 315-412 of SEQ ID NO: 46, at least 80% amino acid identity with amino acids 315-412 of SEQ ID NO: 46, at least 85% amino acid identity with amino acids 315-412 of SEQ ID NO: 46, at least 90% amino acid identity with amino acids 315-412 of SEQ ID NO: 46 or at least 95% amino acid identity with amino acids 315-412 of SEQ ID NO: 46. In yet other aspects of this embodiment, a TGFβ3 comprises a polypeptide having, e.g., at most 70% amino acid identity with amino acids 315-412 of SEQ ID NO: 46, at most 75% amino acid identity with amino acids 315-412 of SEQ ID NO: 46, at most 80% amino acid identity with amino acids 315-412 of SEQ ID NO: 46, at most 85% amino acid identity with amino acids 315-412 of SEQ ID NO: 46, at most 90% amino acid identity with amino acids 315-412 of SEQ ID NO: 46 or at most 95% amino acid identity with amino acids 315-412 of SEQ ID NO: 46.

In other aspects of this embodiment, a TGFβ3 comprises a polypeptide having, e.g., at most one, two, three, four, five, six, seven, eight, nine, 10 or 20 non-contiguous amino acid substitutions relative to amino acids 315-412 of SEQ ID NO: 46. In other aspects of this embodiment, a TGFβ3 comprises a polypeptide having, e.g., at least one, two, three, four, five, six, seven, eight, nine, 10 or 20 non-contiguous amino acid substitutions relative to amino acids 315-412 of SEQ ID NO: 46. In yet other aspects of this embodiment, a TGFβ3 comprises a polypeptide having, e.g., at most one, two, three, four, five, six, seven, eight, nine, 10 or 20 non-contiguous amino acid deletions relative to amino acids 315-412 of SEQ ID NO: 46. In other aspects of this embodiment, a TGFβ3 comprises a polypeptide having, e.g., at least one, two, three, four, five, six, seven, eight, nine, 10 or 20 non-contiguous amino acid deletions relative to amino acids 315-412 of SEQ ID NO: 46. In still other aspects of this embodiment, a TGFβ3 comprises a polypeptide having, e.g., at most one, two, three, four, five, six, seven, eight, nine, 10 or 20 non-contiguous amino acid additions relative to amino acids 315-412 of SEQ ID NO: 46. In other aspects of this embodiment, a TGFβ3 comprises a polypeptide having, e.g., at least one, two, three, four, five, six, seven, eight, nine, 10 or 20 non-contiguous amino acid additions relative to amino acids 315-412 of SEQ ID NO: 46.

In other aspects of this embodiment, a TGFβ3 comprises a polypeptide having, e.g., at most one, two, three, four, five, six, seven, eight, nine, 10 or 20 contiguous amino acid substitutions relative to amino acids 315-412 of SEQ ID NO: 46. In other aspects of this embodiment, a TGFβ3 comprises a polypeptide having, e.g., at least one, two, three, four, five, six, seven, eight, nine, 10 or 20 contiguous amino acid substitutions relative to amino acids 315-412 of SEQ ID NO: 46. In yet other aspects of this embodiment, a TGFβ3 comprises a polypeptide having, e.g., at most one, two, three, four, five, six, seven, eight, nine, 10 or 20 contiguous amino acid deletions relative to amino acids 315-412 of SEQ ID NO: 46. In other aspects of this embodiment, a TGFβ3 comprises a polypeptide having, e.g., at least one, two, three, four, five, six, seven, eight, nine, 10 or 20 contiguous amino acid deletions relative to amino acids 315-412 of SEQ ID NO: 46. In still other aspects of this embodiment, a TGFβ3 comprises a polypeptide having, e.g., at most one, two, three, four, five, six, seven, eight, nine, 10 or 20 contiguous amino acid additions relative to amino acids 315-412 of SEQ ID NO: 46. In other aspects of this embodiment, a TGFβ3 comprises a polypeptide having, e.g., at least one, two, three, four, five, six, seven, eight, nine, 10 or 20 contiguous amino acid additions relative to amino acids 315-412 of SEQ ID NO: 46.

In another embodiment, an enhanced binding domain is derived from a TGFβ4. In another embodiment, an enhanced binding domain is derived from a TGFβ4 of SEQ ID NO: 44. In an aspect of this embodiment, an enhanced binding domain is derived from a TGFβ4 comprises amino acids 276-373 of SEQ ID NO: 47.

In other aspects of this embodiment, a TGFβ4 comprises a polypeptide having, e.g., at least 70% amino acid identity with amino acids 276-373 of SEQ ID NO: 47, at least 75% amino acid identity with amino acids 276-373 of SEQ ID NO: 47, at least 80% amino acid identity with amino acids 276-373 of SEQ ID NO: 47, at least 85% amino acid identity with amino acids 276-373 of SEQ ID NO: 47, at least 90% amino acid identity with amino acids 276-373 of SEQ ID NO: 47 or at least 95% amino acid identity with amino acids 276-373 of SEQ ID NO: 47. In yet other aspects of this embodiment, a TGFβ4 comprises a polypeptide having, e.g., at most 70% amino acid identity with amino acids 276-373 of SEQ ID NO: 47, at most 75% amino acid identity with amino acids 276-373 of SEQ ID NO: 47, at most 80% amino acid identity with amino acids 276-373 of SEQ ID NO: 47, at most 85% amino acid identity with amino acids 276-373 of SEQ ID NO: 47, at most 90% amino acid identity with amino acids 276-373 of SEQ ID NO: 47 or at most 95% amino acid identity with amino acids 276-373 of SEQ ID NO: 47.

In other aspects of this embodiment, a TGFβ4 comprises a polypeptide having, e.g., at most one, two, three, four, five, six, seven, eight, nine, 10 or 20 non-contiguous amino acid substitutions relative to amino acids 276-373 of SEQ ID NO: 47. In other aspects of this embodiment, a TGFβ4 comprises a polypeptide having, e.g., at least one, two, three, four, five, six, seven, eight, nine, 10 or 20 non-contiguous amino acid substitutions relative to amino acids 276-373 of SEQ ID NO: 47. In yet other aspects of this embodiment, a TGFβ4 comprises a polypeptide having, e.g., at most one, two, three, four, five, six, seven, eight, nine, 10 or 20 non-contiguous amino acid deletions relative to amino acids 276-373 of SEQ ID NO: 47. In other aspects of this embodiment, a TGFβ4 comprises a polypeptide having, e.g., at least one, two, three, four, five, six, seven, eight, nine, 10 or 20 non-contiguous amino acid deletions relative to amino acids 276-373 of SEQ ID NO: 47. In still other aspects of this embodiment, a TGFβ4 comprises a polypeptide having, e.g., at most one, two, three, four, five, six, seven, eight, nine, 10 or 20 non-contiguous amino acid additions relative to amino acids 276-373 of SEQ ID NO: 47. In other aspects of this embodiment, a TGFβ4 comprises a polypeptide having, e.g., at least one, two, three, four, five, six, seven, eight, nine, 10 or 20 non-contiguous amino acid additions relative to amino acids 276-373 of SEQ ID NO: 47.

In other aspects of this embodiment, a TGFβ4 comprises a polypeptide having, e.g., at most one, two, three, four, five, six, seven, eight, nine, 10 or 20 contiguous amino acid substitutions relative to amino acids 276-373 of SEQ ID NO: 47. In other aspects of this embodiment, a TGFβ4 comprises a polypeptide having, e.g., at least one, two, three, four, five, six, seven, eight, nine, 10 or 20 contiguous amino acid substitutions relative to amino acids 276-373 of SEQ ID NO: 47. In yet other aspects of this embodiment, a TGFβ4 comprises a polypeptide having, e.g., at most one, two, three, four, five, six, seven, eight, nine, 10 or 20 contiguous amino acid deletions relative to amino acids 276-373 of SEQ ID NO: 47. In other aspects of this embodiment, a TGFβ4 comprises a polypeptide having, e.g., at least one, two, three, four, five, six, seven, eight, nine, 10 or 20 contiguous amino acid deletions relative to amino acids 276-373 of SEQ ID NO: 47. In still other aspects of this embodiment, a TGFβ4 comprises a polypeptide having, e.g., at most one, two, three, four, five, six, seven, eight, nine, 10 or 20 contiguous amino acid additions relative to amino acids 276-373 of SEQ ID NO: 47. In other aspects of this embodiment, a TGFβ4 comprises a polypeptide having, e.g., at least one, two, three, four, five, six, seven, eight, nine, 10 or 20 contiguous amino acid additions relative to amino acids 276-373 of SEQ ID NO: 47.

Another example of an enhanced targeting domain disclosed in the present specification is, e.g., a BMPs, such as, e.g., BMP2, BMP3, BMP4, BMP5, BMP6, BMP7, BMP8 or BMP10.

Thus, in an embodiment, an enhanced binding domain is derived from a BMP2. In another embodiment, an enhanced binding domain is derived from a BMP2 of SEQ ID NO: 48. In an aspect of this embodiment, an enhanced binding domain is derived from a BMP2 comprises amino acids 296-396 of SEQ ID NO: 48.

In other aspects of this embodiment, a BMP2 comprises a polypeptide having, e.g., at least 70% amino acid identity with amino acids 296-396 of SEQ ID NO: 48, at least 75% amino acid identity with amino acids 296-396 of SEQ ID NO: 48, at least 80% amino acid identity with amino acids 296-396 of SEQ ID NO: 48, at least 85% amino acid identity with amino acids 296-396 of SEQ ID NO: 48, at least 90% amino acid identity with amino acids 296-396 of SEQ ID NO: 48 or at least 95% amino acid identity with amino acids 296-396 of SEQ ID NO: 48. In yet other aspects of this embodiment, a BMP2 comprises a polypeptide having, e.g., at most 70% amino acid identity with amino acids 296-396 of SEQ ID NO: 48, at most 75% amino acid identity with amino acids 296-396 of SEQ ID NO: 48, at most 80% amino acid identity with amino acids 296-396 of SEQ ID NO: 48, at most 85% amino acid identity with amino acids 296-396 of SEQ ID NO: 48, at most 90% amino acid identity with amino acids 296-396 of SEQ ID NO: 48 or at most 95% amino acid identity with amino acids 296-396 of SEQ ID NO: 48.

In other aspects of this embodiment, a BMP2 comprises a polypeptide having, e.g., at most one, two, three, four, five, six, seven, eight, nine, 10 or 20 non-contiguous amino acid substitutions relative to amino acids 296-396 of SEQ ID NO: 48. In other aspects of this embodiment, a BMP2 comprises a polypeptide having, e.g., at least one, two, three, four, five, six, seven, eight, nine, 10 or 20 non-contiguous amino acid substitutions relative to amino acids 296-396 of SEQ ID NO: 48. In yet other aspects of this embodiment, a BMP2 comprises a polypeptide having, e.g., at most one, two, three, four, five, six, seven, eight, nine, 10 or 20 non-contiguous amino acid deletions relative to amino acids 296-396 of SEQ ID NO: 48. In other aspects of this embodiment, a BMP2 comprises a polypeptide having, e.g., at least one, two, three, four, five, six, seven, eight, nine, 10 or 20 non-contiguous amino acid deletions relative to amino acids 296-396 of SEQ ID NO: 48. In still other aspects of this embodiment, a BMP2 comprises a polypeptide having, e.g., at most one, two, three, four, five, six, seven, eight, nine, 10 or 20 non-contiguous amino acid additions relative to amino acids 296-396 of SEQ ID NO: 48. In other aspects of this embodiment, a BMP2 comprises a polypeptide having, e.g., at least one, two, three, four, five, six, seven, eight, nine, 10 or 20 non-contiguous amino acid additions relative to amino acids 296-396 of SEQ ID NO: 48.

In other aspects of this embodiment, a BMP2 comprises a polypeptide having, e.g., at most one, two, three, four, five, six, seven, eight, nine, 10 or 20 contiguous amino acid substitutions relative to amino acids 296-396 of SEQ ID NO: 48. In other aspects of this embodiment, a BMP2 comprises a polypeptide having, e.g., at least one, two, three, four, five, six, seven, eight, nine, 10 or 20 contiguous amino acid substitutions relative to amino acids 296-396 of SEQ ID NO: 48. In yet other aspects of this embodiment, a BMP2 comprises a polypeptide having, e.g., at most one, two, three, four, five, six, seven, eight, nine, 10 or 20 contiguous amino acid deletions relative to amino acids 296-396 of SEQ ID NO: 48. In other aspects of this embodiment, a BMP2 comprises a polypeptide having, e.g., at least one, two, three, four, five, six, seven, eight, nine, 10 or 20 contiguous amino acid deletions relative to amino acids 296-396 of SEQ ID NO: 48. In still other aspects of this embodiment, a BMP2 comprises a polypeptide having, e.g., at most one, two, three, four, five, six, seven, eight, nine, 10 or 20 contiguous amino acid additions relative to amino acids 296-396 of SEQ ID NO: 48. In other aspects of this embodiment, a BMP2 comprises a polypeptide having, e.g., at least one, two, three, four, five, six, seven, eight, nine, 10 or 20 contiguous amino acid additions relative to amino acids 296-396 of SEQ ID NO: 48.

In another embodiment, an enhanced binding domain is derived from a BMP3. In another embodiment, an enhanced binding domain is derived from a BMP3 of SEQ ID NO: 49. In an aspect of this embodiment, an enhanced binding domain is derived from a BMP3 comprises amino acids 370-472 of SEQ ID NO: 49.

In other aspects of this embodiment, a BMP3 comprises a polypeptide having, e.g., at least 70% amino acid identity with amino acids 370-472 of SEQ ID NO: 49, at least 75% amino acid identity with amino acids 370-472 of SEQ ID NO: 49, at least 80% amino acid identity with amino acids 370-472 of SEQ ID NO: 49, at least 85% amino acid identity with amino acids 370-472 of SEQ ID NO: 49, at least 90% amino acid identity with amino acids 370-472 of SEQ ID NO: 49 or at least 95% amino acid identity with amino acids 370-472 of SEQ ID NO: 49. In yet other aspects of this embodiment, a BMP3 comprises a polypeptide having, e.g., at most 70% amino acid identity with amino acids 370-472 of SEQ ID NO: 49, at most 75% amino acid identity with amino acids 370-472 of SEQ ID NO: 49, at most 80% amino acid identity with amino acids 370-472 of SEQ ID NO: 49, at most 85% amino acid identity with amino acids 370-472 of SEQ ID NO: 49, at most 90% amino acid identity with amino acids 370-472 of SEQ ID NO: 49 or at most 95% amino acid identity with amino acids 370-472 of SEQ ID NO: 49.

In other aspects of this embodiment, a BMP3 comprises a polypeptide having, e.g., at most one, two, three, four, five, six, seven, eight, nine, 10 or 20 non-contiguous amino acid substitutions relative to amino acids 370-472 of SEQ ID NO: 49. In other aspects of this embodiment, a BMP3 comprises a polypeptide having, e.g., at least one, two, three, four, five, six, seven, eight, nine, 10 or 20 non-contiguous amino acid substitutions relative to amino acids 370-472 of SEQ ID NO: 49. In yet other aspects of this embodiment, a BMP3 comprises a polypeptide having, e.g., at most one, two, three, four, five, six, seven, eight, nine, 10 or 20 non-contiguous amino acid deletions relative to amino acids 370-472 of SEQ ID NO: 49. In other aspects of this embodiment, a BMP3 comprises a polypeptide having, e.g., at least one, two, three, four, five, six, seven, eight, nine, 10 or 20 non-contiguous amino acid deletions relative to amino acids 370-472 of SEQ ID NO: 49. In still other aspects of this embodiment, a BMP3 comprises a polypeptide having, e.g., at most one, two, three, four, five, six, seven, eight, nine, 10 or 20 non-contiguous amino acid additions relative to amino acids 370-472 of SEQ ID NO: 49. In other aspects of this embodiment, a BMP3 comprises a polypeptide having, e.g., at least one, two, three, four, five, six, seven, eight, nine, 10 or 20 non-contiguous amino acid additions relative to amino acids 370-472 of SEQ ID NO: 49.

In other aspects of this embodiment, a BMP3 comprises a polypeptide having, e.g., at most one, two, three, four, five, six, seven, eight, nine, 10 or 20 contiguous amino acid substitutions relative to amino acids 370-472 of SEQ ID NO: 49. In other aspects of this embodiment, a BMP3 comprises a polypeptide having, e.g., at least one, two, three, four, five, six, seven, eight, nine, 10 or 20 contiguous amino acid substitutions relative to amino acids 370-472 of SEQ ID NO: 49. In yet other aspects of this embodiment, a BMP3 comprises a polypeptide having, e.g., at most one, two, three, four, five, six, seven, eight, nine, 10 or 20 contiguous amino acid deletions relative to amino acids 370-472 of SEQ ID NO: 49. In other aspects of this embodiment, a BMP3 comprises a polypeptide having, e.g., at least one, two, three, four, five, six, seven, eight, nine, 10 or 20 contiguous amino acid deletions relative to amino acids 370-472 of SEQ ID NO: 49. In still other aspects of this embodiment, a BMP3 comprises a polypeptide having, e.g., at most one, two, three, four, five, six, seven, eight, nine, 10 or 20 contiguous amino acid additions relative to amino acids 370-472 of SEQ ID NO: 49. In other aspects of this embodiment, a BMP3 comprises a polypeptide having, e.g., at least one, two, three, four, five, six, seven, eight, nine, 10 or 20 contiguous amino acid additions relative to amino acids 370-472 of SEQ ID NO: 49.

In another embodiment, an enhanced binding domain is derived from a BMP4. In another embodiment, an enhanced binding domain is derived from a BMP4 of SEQ ID NO: 50. In an aspect of this embodiment, an enhanced binding domain is derived from a BMP4 comprises amino acids 309-409 of SEQ ID NO: 50.

In other aspects of this embodiment, a BMP4 comprises a polypeptide having, e.g., at least 70% amino acid identity with amino acids 309-409 of SEQ ID NO: 50, at least 75% amino acid identity with amino acids 309-409 of SEQ ID NO: 50, at least 80% amino acid identity with amino acids 309-409 of SEQ ID NO: 50, at least 85% amino acid identity with amino acids 309-409 of SEQ ID NO: 50, at least 90% amino acid identity with amino acids 309-409 of SEQ ID NO: 50 or at least 95% amino acid identity with amino acids 309-409 of SEQ ID NO: 50. In yet other aspects of this embodiment, a BMP4 comprises a polypeptide having, e.g., at most 70% amino acid identity with amino acids 309-409 of SEQ ID NO: 50, at most 75% amino acid identity with amino acids 309-

409 of SEQ ID NO: 50, at most 80% amino acid identity with amino acids 309-409 of SEQ ID NO: 50, at most 85% amino acid identity with amino acids 309-409 of SEQ ID NO: 50, at most 90% amino acid identity with amino acids 309-409 of SEQ ID NO: 50 or at most 95% amino acid identity with amino acids 309-409 of SEQ ID NO: 50.

In other aspects of this embodiment, a BMP4 comprises a polypeptide having, e.g., at most one, two, three, four, five, six, seven, eight, nine, 10 or 20 non-contiguous amino acid substitutions relative to amino acids 309-409 of SEQ ID NO: 50. In other aspects of this embodiment, a BMP4 comprises a polypeptide having, e.g., at least one, two, three, four, five, six, seven, eight, nine, 10 or 20 non-contiguous amino acid substitutions relative to amino acids 309-409 of SEQ ID NO: 50. In yet other aspects of this embodiment, a BMP4 comprises a polypeptide having, e.g., at most one, two, three, four, five, six, seven, eight, nine, 10 or 20 non-contiguous amino acid deletions relative to amino acids 309-409 of SEQ ID NO: 50. In other aspects of this embodiment, a BMP4 comprises a polypeptide having, e.g., at least one, two, three, four, five, six, seven, eight, nine, 10 or 20 non-contiguous amino acid deletions relative to amino acids 309-409 of SEQ ID NO: 50. In still other aspects of this embodiment, a BMP4 comprises a polypeptide having, e.g., at most one, two, three, four, five, six, seven, eight, nine, 10 or 20 non-contiguous amino acid additions relative to amino acids 309-409 of SEQ ID NO: 50. In other aspects of this embodiment, a BMP4 comprises a polypeptide having, e.g., at least one, two, three, four, five, six, seven, eight, nine, 10 or 20 non-contiguous amino acid additions relative to amino acids 309-409 of SEQ ID NO: 50.

In other aspects of this embodiment, a BMP4 comprises a polypeptide having, e.g., at most one, two, three, four, five, six, seven, eight, nine, 10 or 20 contiguous amino acid substitutions relative to amino acids 309-409 of SEQ ID NO: 50. In other aspects of this embodiment, a BMP4 comprises a polypeptide having, e.g., at least one, two, three, four, five, six, seven, eight, nine, 10 or 20 contiguous amino acid substitutions relative to amino acids 309-409 of SEQ ID NO: 50. In yet other aspects of this embodiment, a BMP4 comprises a polypeptide having, e.g., at most one, two, three, four, five, six, seven, eight, nine, 10 or 20 contiguous amino acid deletions relative to amino acids 309-409 of SEQ ID NO: 50. In other aspects of this embodiment, a BMP4 comprises a polypeptide having, e.g., at least one, two, three, four, five, six, seven, eight, nine, 10 or 20 contiguous amino acid deletions relative to amino acids 309-409 of SEQ ID NO: 50. In still other aspects of this embodiment, a BMP4 comprises a polypeptide having, e.g., at most one, two, three, four, five, six, seven, eight, nine, 10 or 20 contiguous amino acid additions relative to amino acids 309-409 of SEQ ID NO: 50. In other aspects of this embodiment, a BMP4 comprises a polypeptide having, e.g., at least one, two, three, four, five, six, seven, eight, nine, 10 or 20 contiguous amino acid additions relative to amino acids 309-409 of SEQ ID NO: 50.

In another embodiment, an enhanced binding domain is derived from a BMP5. In another embodiment, an enhanced binding domain is derived from a BMP5 of SEQ ID NO: 51. In an aspect of this embodiment, an enhanced binding domain is derived from a BMP5 comprises amino acids 353-454 or amino acids 323-454 of SEQ ID NO: 51.

In other aspects of this embodiment, a BMP5 comprises a polypeptide having, e.g., at least 70% amino acid identity with amino acids 353-454 or amino acids 323-454 of SEQ ID NO: 51, at least 75% amino acid identity with amino acids 353-454 or amino acids 323-454 of SEQ ID NO: 51, at least 80% amino acid identity with amino acids 353-454 or amino acids 323-454 of SEQ ID NO: 51, at least 85% amino acid identity with amino acids 353-454 or amino acids 323-454 of SEQ ID NO: 51, at least 90% amino acid identity with amino acids 353-454 or amino acids 323-454 of SEQ ID NO: 51 or at least 95% amino acid identity with amino acids 353-454 or amino acids 323-454 of SEQ ID NO: 51. In yet other aspects of this embodiment, a BMP5 comprises a polypeptide having, e.g., at most 70% amino acid identity with amino acids 353-454 or amino acids 323-454 of SEQ ID NO: 51, at most 75% amino acid identity with amino acids 353-454 or amino acids 323-454 of SEQ ID NO: 51, at most 80% amino acid identity with amino acids 353-454 or amino acids 323-454 of SEQ ID NO: 51, at most 85% amino acid identity with amino acids 353-454 or amino acids 323-454 of SEQ ID NO: 51, at most 90% amino acid identity with amino acids 353-454 or amino acids 323-454 of SEQ ID NO: 51 or at most 95% amino acid identity with amino acids 353-454 or amino acids 323-454 of SEQ ID NO: 51.

In other aspects of this embodiment, a BMP5 comprises a polypeptide having, e.g., at most one, two, three, four, five, six, seven, eight, nine, 10 or 20 non-contiguous amino acid substitutions relative to amino acids 353-454 or amino acids 323-454 of SEQ ID NO: 51. In other aspects of this embodiment, a BMP5 comprises a polypeptide having, e.g., at least one, two, three, four, five, six, seven, eight, nine, 10 or 20 non-contiguous amino acid substitutions relative to amino acids 353-454 or amino acids 323-454 of SEQ ID NO: 51. In yet other aspects of this embodiment, a BMP5 comprises a polypeptide having, e.g., at most one, two, three, four, five, six, seven, eight, nine, 10 or 20 non-contiguous amino acid deletions relative to amino acids 353-454 or amino acids 323-454 of SEQ ID NO: 51. In other aspects of this embodiment, a BMP5 comprises a polypeptide having, e.g., at least one, two, three, four, five, six, seven, eight, nine, 10 or 20 non-contiguous amino acid deletions relative to amino acids 353-454 or amino acids 323-454 of SEQ ID NO: 51. In still other aspects of this embodiment, a BMP5 comprises a polypeptide having, e.g., at most one, two, three, four, five, six, seven, eight, nine, 10 or 20 non-contiguous amino acid additions relative to amino acids 353-454 or amino acids 323-454 of SEQ ID NO: 51. In other aspects of this embodiment, a BMP5 comprises a polypeptide having, e.g., at least one, two, three, four, five, six, seven, eight, nine, 10 or 20 non-contiguous amino acid additions relative to amino acids 353-454 or amino acids 323-454 of SEQ ID NO: 51.

In other aspects of this embodiment, a BMP5 comprises a polypeptide having, e.g., at most one, two, three, four, five, six, seven, eight, nine, 10 or 20 contiguous amino acid substitutions relative to amino acids 353-454 or amino acids 323-454 of SEQ ID NO: 51. In other aspects of this embodiment, a BMP5 comprises a polypeptide having, e.g., at least one, two, three, four, five, six, seven, eight, nine, 10 or 20 contiguous amino acid substitutions relative to amino acids 353-454 or amino acids 323-454 of SEQ ID NO: 51. In yet other aspects of this embodiment, a BMP5 comprises a polypeptide having, e.g., at most one, two, three, four, five, six, seven, eight, nine, 10 or 20 contiguous amino acid deletions relative to amino acids 353-454 or amino acids 323-454 of SEQ ID NO: 51. In other aspects of this embodiment, a BMP5 comprises a polypeptide having, e.g., at least one, two, three, four, five, six, seven, eight, nine, 10 or 20 contiguous amino acid deletions relative to amino acids 353-454 or amino acids 323-454 of SEQ ID NO: 51. In still other aspects of this embodiment, a BMP5 comprises a polypeptide having, e.g., at most one, two, three, four, five, six, seven, eight, nine, 10 or 20 contiguous amino acid additions relative to amino acids 353-454 or amino acids 323-454 of SEQ ID NO: 51. In other aspects of this embodiment, a BMP5 comprises a polypeptide having, e.g., at least one, two, three, four, five, six, seven, eight, nine, 10 or 20 contiguous amino acid additions relative to amino acids 353-454 or amino acids 323-454 of SEQ ID NO: 51.

In another embodiment, an enhanced binding domain is derived from a BMP6. In another embodiment, an enhanced binding domain is derived from a BMP6 of SEQ ID NO: 52. In an aspect of this embodiment, an enhanced binding domain is derived from a BMP6 comprises amino acids 412-513 or amino acids 374-513 of SEQ ID NO: 52.

In other aspects of this embodiment, a BMP6 comprises a polypeptide having, e.g., at least 70% amino acid identity with amino acids 412-513 or amino acids 374-513 of SEQ ID NO: 52, at least 75% amino acid identity with amino acids 412-513 or amino acids 374-513 of SEQ ID NO: 52, at least 80% amino acid identity with amino acids 412-513 or amino acids 374-513 of SEQ ID NO: 52, at least 85% amino acid identity with amino acids 412-513 or amino acids 374-513 of SEQ ID NO: 52, at least 90% amino acid identity with amino acids 412-513 or amino acids 374-513 of SEQ ID NO: 52 or at least 95% amino acid identity with amino acids 412-513 or amino acids 374-513 of SEQ ID NO: 52. In yet other aspects of this embodiment, a BMP6 comprises a polypeptide having, e.g., at most 70% amino acid identity with amino acids 412-513 or amino acids 374-513 of SEQ ID NO: 52, at most 75% amino acid identity with amino acids 412-513 or amino acids 374-513 of SEQ ID NO: 52, at most 80% amino acid identity with amino acids 412-513 or amino acids 374-513 of SEQ ID NO: 52, at most 85% amino acid identity with amino acids 412-513 or amino acids 374-513 of SEQ ID NO: 52, at most 90% amino acid identity with amino acids 412-513 or amino acids 374-513 of SEQ ID NO: 52 or at most 95% amino acid identity with amino acids 412-513 or amino acids 374-513 of SEQ ID NO: 52.

In other aspects of this embodiment, a BMP6 comprises a polypeptide having, e.g., at most one, two, three, four, five, six, seven, eight, nine, 10 or 20 non-contiguous amino acid substitutions relative to amino acids 412-513 or amino acids 374-513 of SEQ ID NO: 52. In other aspects of this embodiment, a BMP6 comprises a polypeptide having, e.g., at least one, two, three, four, five, six, seven, eight, nine, 10 or 20 non-contiguous amino acid substitutions relative to amino acids 412-513 or amino acids 374-513 of SEQ ID NO: 52. In yet other aspects of this embodiment, a BMP6 comprises a polypeptide having, e.g., at most one, two, three, four, five, six, seven, eight, nine, 10 or 20 non-contiguous amino acid deletions relative to amino acids 412-513 or amino acids 374-513 of SEQ ID NO: 52. In other aspects of this embodiment, a BMP6 comprises a polypeptide having, e.g., at least one, two, three, four, five, six, seven, eight, nine, 10 or 20 non-contiguous amino acid deletions relative to amino acids 412-513 or amino acids 374-513 of SEQ ID NO: 52. In still other aspects of this embodiment, a BMP6 comprises a polypeptide having, e.g., at most one, two, three, four, five, six, seven, eight, nine, 10 or 20 non-contiguous amino acid additions relative to amino acids 412-513 or amino acids 374-513 of SEQ ID NO: 52. In other aspects of this embodiment, a BMP6 comprises a polypeptide having, e.g., at least one, two, three, four, five, six, seven, eight, nine, 10 or 20 non-contiguous amino acid additions relative to amino acids 412-513 or amino acids 374-513 of SEQ ID NO: 52.

In other aspects of this embodiment, a BMP6 comprises a polypeptide having, e.g., at most one, two, three, four, five, six, seven, eight, nine, 10 or 20 contiguous amino acid substitutions relative to amino acids 412-513 or amino acids 374-513 of SEQ ID NO: 52. In other aspects of this embodiment, a BMP6 comprises a polypeptide having, e.g., at least one, two, three, four, five, six, seven, eight, nine, 10 or 20 contiguous amino acid substitutions relative to amino acids 412-513 or amino acids 374-513 of SEQ ID NO: 52. In yet other aspects of this embodiment, a BMP6 comprises a polypeptide having, e.g., at most one, two, three, four, five, six, seven, eight, nine, 10 or 20 contiguous amino acid deletions relative to amino acids 412-513 or amino acids 374-513 of SEQ ID NO: 52. In other aspects of this embodiment, a BMP6 comprises a polypeptide having, e.g., at least one, two, three, four, five, six, seven, eight, nine, 10 or 20 contiguous amino acid deletions relative to amino acids 412-513 or amino acids 374-513 of SEQ ID NO: 52. In still other aspects of this embodiment, a BMP6 comprises a polypeptide having, e.g., at most one, two, three, four, five, six, seven, eight, nine, 10 or 20 contiguous amino acid additions relative to amino acids 412-513 or amino acids 374-513 of SEQ ID NO: 52. In other aspects of this embodiment, a BMP6 comprises a polypeptide having, e.g., at least one, two, three, four, five, six, seven, eight, nine, 10 or 20 contiguous amino acid additions relative to amino acids 412-513 or amino acids 374-513 of SEQ ID NO: 52.

In another embodiment, an enhanced binding domain is derived from a BMP7. In another embodiment, an enhanced binding domain is derived from a BMP7 of SEQ ID NO: 53. In an aspect of this embodiment, an enhanced binding domain is derived from a BMP7 comprises amino acids 330-431 or amino acids 293-431 of SEQ ID NO: 53.

In other aspects of this embodiment, a BMP7 comprises a polypeptide having, e.g., at least 70% amino acid identity with amino acids 330-431 or amino acids 293-431 of SEQ ID NO: 53, at least 75% amino acid identity with amino acids 330-431 or amino acids 293-431 of SEQ ID NO: 53, at least 80% amino acid identity with amino acids 330-431 or amino acids 293-431 of SEQ ID NO: 53, at least 85% amino acid identity with amino acids 330-431 or amino acids 293-431 of SEQ ID NO: 53, at least 90% amino acid identity with amino acids 330-431 or amino acids 293-431 of SEQ ID NO: 53 or at least 95% amino acid identity with amino acids 330-431 or amino acids 293-431 of SEQ ID NO: 53. In yet other aspects of this embodiment, a BMP7 comprises a polypeptide having, e.g., at most 70% amino acid identity with amino acids 330-431 or amino acids 293-431 of SEQ ID NO: 53, at most 75% amino acid identity with amino acids 330-431 or amino acids 293-431 of SEQ ID NO: 53, at most 80% amino acid identity with amino acids 330-431 or amino acids 293-431 of SEQ ID NO: 53, at most 85% amino acid identity with amino acids 330-431 or amino acids 293-431 of SEQ ID NO: 53, at most 90% amino acid identity with amino acids 330-431 or amino acids 293-431 of SEQ ID NO: 53 or at most 95% amino acid identity with amino acids 330-431 or amino acids 293-431 of SEQ ID NO: 53.

In other aspects of this embodiment, a BMP7 comprises a polypeptide having, e.g., at most one, two, three, four, five, six, seven, eight, nine, 10 or 20 non-contiguous amino acid substitutions relative to amino acids 330-431 or amino acids 293-431 of SEQ ID NO: 53. In other aspects of this embodiment, a BMP7 comprises a polypeptide having, e.g., at least one, two, three, four, five, six, seven, eight, nine, 10 or 20 non-contiguous amino acid substitutions relative to amino acids 330-431 or amino acids 293-431 of SEQ ID NO: 53. In yet other aspects of this embodiment, a BMP7 comprises a polypeptide having, e.g., at most one, two, three, four, five, six, seven, eight, nine, 10 or 20 non-contiguous amino acid deletions relative to amino acids 330-431 or amino acids 293-431 of SEQ ID NO: 53. In other aspects of this embodiment, a BMP7 comprises a polypeptide having, e.g., at least one, two, three, four, five, six, seven, eight, nine, 10 or 20 non-contiguous amino acid deletions relative to amino acids 330-431 or amino acids 293-431 of SEQ ID NO: 53. In still other aspects of this embodiment, a BMP7 comprises a polypeptide having, e.g., at most one, two, three, four, five, six, seven, eight, nine, 10 or 20 non-contiguous amino acid additions relative to amino acids 330-431 or amino acids 293-431 of SEQ ID NO: 53. In other aspects of this embodiment, a BMP7 comprises a polypeptide having, e.g., at least one, two, three, four, five, six, seven, eight, nine, 10 or 20 non-contiguous amino acid additions relative to amino acids 330-431 or amino acids 293-431 of SEQ ID NO: 53.

In other aspects of this embodiment, a BMP7 comprises a polypeptide having, e.g., at most one, two, three, four, five, six, seven, eight, nine, 10 or 20 contiguous amino acid substitutions relative to amino acids 330-431 or amino acids 293-431 of SEQ ID NO: 53. In other aspects of this embodiment, a BMP7 comprises a polypeptide having, e.g., at least one, two, three, four, five, six, seven, eight, nine, 10 or 20 contiguous amino acid substitutions relative to amino acids 330-431 or amino acids 293-431 of SEQ ID NO: 53. In yet other aspects of this embodiment, a BMP7 comprises a polypeptide having, e.g., at most one, two, three, four, five, six, seven, eight, nine, 10 or 20 contiguous amino acid deletions relative to amino acids 330-431 or amino acids 293-431 of SEQ ID NO: 53. In other aspects of this embodiment, a BMP7 comprises a polypeptide having, e.g., at least one, two, three, four, five, six, seven, eight, nine, 10 or 20 contiguous amino acid deletions relative to amino acids 330-431 or amino acids 293-431 of SEQ ID NO: 53. In still other aspects of this embodiment, a BMP7 comprises a polypeptide having, e.g., at most one, two, three, four, five, six, seven, eight, nine, 10 or 20 contiguous amino acid additions relative to amino acids 330-431 or amino acids 293-431 of SEQ ID NO: 53. In other aspects of this embodiment, a BMP7 comprises a polypeptide having, e.g., at least one, two, three, four, five, six, seven, eight, nine, 10 or 20 contiguous amino acid additions relative to amino acids 330-431 or amino acids 293-431 of SEQ ID NO: 53.

In another embodiment, an enhanced binding domain is derived from a BMP8. In another embodiment, an enhanced binding domain is derived from a BMP8 of SEQ ID NO: 54. In an aspect of this embodiment, an enhanced binding domain is derived from a BMP8 comprises amino acids 301-402 of SEQ ID NO: 54.

In other aspects of this embodiment, a BMP8 comprises a polypeptide having, e.g., at least 70% amino acid identity with amino acids 301-402 of SEQ ID NO: 54, at least 75% amino acid identity with amino acids 301-402 of SEQ ID NO: 54, at least 80% amino acid identity with amino acids 301-402 of SEQ ID NO: 54, at least 85% amino acid identity with amino acids 301-402 of SEQ ID NO: 54, at least 90% amino acid identity with amino acids 301-402 of SEQ ID NO: 54 or at least 95% amino acid identity with amino acids 301-402 of SEQ ID NO: 54. In yet other aspects of this embodiment, a BMP8 comprises a polypeptide having, e.g., at most 70% amino acid identity with amino acids 301-402 of SEQ ID NO: 54, at most 75% amino acid identity with amino acids 301-402 of SEQ ID NO: 54, at most 80% amino acid identity with amino acids 301-402 of SEQ ID NO: 54, at most 85% amino acid identity with amino acids 301-402 of SEQ ID NO: 54, at most 90% amino acid identity with amino acids 301-402 of SEQ ID NO: 54 or at most 95% amino acid identity with amino acids 301-402 of SEQ ID NO: 54.

In other aspects of this embodiment, a BMP8 comprises a polypeptide having, e.g., at most one, two, three, four, five, six, seven, eight, nine, 10 or 20 non-contiguous amino acid substitutions relative to amino acids 301-402 of SEQ ID NO: 54. In other aspects of this embodiment, a BMP8 comprises a polypeptide having, e.g., at least one, two, three, four, five, six, seven, eight, nine, 10 or 20 non-contiguous amino acid substitutions relative to amino acids 301-402 of SEQ ID NO: 54. In yet other aspects of this embodiment, a BMP8 comprises a polypeptide having, e.g., at most one, two, three, four, five, six, seven, eight, nine, 10 or 20 non-contiguous amino acid deletions relative to amino acids 301-402 of SEQ ID NO: 54. In other aspects of this embodiment, a BMP8 comprises a polypeptide having, e.g., at least one, two, three, four, five, six, seven, eight, nine, 10 or 20 non-contiguous amino acid deletions relative to amino acids 301-402 of SEQ ID NO: 54. In still other aspects of this embodiment, a BMP8 comprises a polypeptide having, e.g., at most one, two, three, four, five, six, seven, eight, nine, 10 or 20 non-contiguous amino acid additions relative to amino acids 301-402 of SEQ ID NO: 54. In other aspects of this embodiment, a BMP8 comprises a polypeptide having, e.g., at least one, two, three, four, five, six, seven, eight, nine, 10 or 20 non-contiguous amino acid additions relative to amino acids 301-402 of SEQ ID NO: 54.

In other aspects of this embodiment, a BMP8 comprises a polypeptide having, e.g., at most one, two, three, four, five, six, seven, eight, nine, 10 or 20 contiguous amino acid substitutions relative to amino acids 301-402 of SEQ ID NO: 54. In other aspects of this embodiment, a BMP8 comprises a polypeptide having, e.g., at least one, two, three, four, five, six, seven, eight, nine, 10 or 20 contiguous amino acid substitutions relative to amino acids 301-402 of SEQ ID NO: 54. In yet other aspects of this embodiment, a BMP8 comprises a polypeptide having, e.g., at most one, two, three, four, five, six, seven, eight, nine, 10 or 20 contiguous amino acid deletions relative to amino acids 301-402 of SEQ ID NO: 54. In other aspects of this embodiment, a BMP8 comprises a polypeptide having, e.g., at least one, two, three, four, five, six, seven, eight, nine, 10 or 20 contiguous amino acid deletions relative to amino acids 301-402 of SEQ ID NO: 54. In still other aspects of this embodiment, a BMP8 comprises a polypeptide having, e.g., at most one, two, three, four, five, six, seven, eight, nine, 10 or 20 contiguous amino acid additions relative to amino acids 301-402 of SEQ ID NO: 54. In other aspects of this embodiment, a BMP8 comprises a polypeptide having, e.g., at least one, two, three, four, five, six, seven, eight, nine, 10 or 20 contiguous amino acid additions relative to amino acids 301-402 of SEQ ID NO: 54.

In another embodiment, an enhanced binding domain is derived from a BMP10. In another embodiment, an enhanced binding domain is derived from a BMP10 of SEQ ID NO: 55. In an aspect of this embodiment, an enhanced binding domain is derived from a BMP10 comprises amino acids 323-424 of SEQ ID NO: 55.

In other aspects of this embodiment, a BMP10 comprises a polypeptide having, e.g., at least 70% amino acid identity with amino acids 323-424 of SEQ ID NO: 55, at least 75% amino acid identity with amino acids 323-424 of SEQ ID NO: 55, at least 80% amino acid identity with amino acids 323-424 of SEQ ID NO: 55, at least 85% amino acid identity with amino acids 323-424 of SEQ ID NO: 55, at least 90% amino acid identity with amino acids 323-424 of SEQ ID NO: 55 or at least 95% amino acid identity with amino acids 323-424 of SEQ ID NO: 55. In yet other aspects of this embodiment, a BMP10 comprises a polypeptide having, e.g., at most 70% amino acid identity with amino acids 323-424 of SEQ ID NO: 55, at most 75% amino acid identity with amino acids 323-424 of SEQ ID NO: 55, at most 80% amino acid identity with amino acids 323-424 of SEQ ID NO: 55, at most 85% amino acid identity with amino acids 323-424 of SEQ ID NO: 55, at most 90% amino acid identity with amino acids 323-424 of SEQ ID NO: 55 or at most 95% amino acid identity with amino acids 323-424 of SEQ ID NO: 55.

In other aspects of this embodiment, a BMP10 comprises a polypeptide having, e.g., at most one, two, three, four, five, six, seven, eight, nine, 10 or 20 non-contiguous amino acid substitutions relative to amino acids 323-424 of SEQ ID NO: 55. In other aspects of this embodiment, a BMP10 comprises a polypeptide having, e.g., at least one, two, three, four, five, six, seven, eight, nine, 10 or 20 non-contiguous amino acid substitutions relative to amino acids 323-424 of SEQ ID NO: 55. In yet other aspects of this embodiment, a BMP10 comprises a polypeptide having, e.g., at most one, two, three, four, five, six, seven, eight, nine, 10 or 20 non-contiguous amino acid deletions relative to amino acids 323-424 of SEQ ID NO: 55. In other aspects of this embodiment, a BMP10 comprises a polypeptide having, e.g., at least one, two, three, four, five, six, seven, eight, nine, 10 or 20 non-contiguous amino acid deletions relative to amino acids 323-424 of SEQ ID NO: 55. In still other aspects of this embodiment, a BMP10 comprises a polypeptide having, e.g., at most one, two, three, four, five, six, seven, eight, nine, 10 or 20 non-contiguous amino acid additions relative to amino acids 323-424 of SEQ ID NO: 55. In other aspects of this embodiment, a BMP10 comprises a polypeptide having, e.g., at least one, two, three, four, five, six, seven, eight, nine, 10 or 20 non-contiguous amino acid additions relative to amino acids 323-424 of SEQ ID NO: 55.

In other aspects of this embodiment, a BMP10 comprises a polypeptide having, e.g., at most one, two, three, four, five, six, seven, eight, nine, 10 or 20 contiguous amino acid substitutions relative to amino acids 323-424 of SEQ ID NO: 55. In other aspects of this embodiment, a BMP10 comprises a polypeptide having, e.g., at least one, two, three, four, five, six, seven, eight, nine, 10 or 20 contiguous amino acid substitutions relative to amino acids 323-424 of SEQ ID NO: 55. In yet other aspects of this embodiment, a BMP10 comprises a polypeptide having, e.g., at most one, two, three, four, five, six, seven, eight, nine, 10 or 20 contiguous amino acid deletions relative to amino acids 323-424 of SEQ ID NO: 55. In other aspects of this embodiment, a BMP10 comprises a polypeptide having, e.g., at least one, two, three, four, five, six, seven, eight, nine, 10 or 20 contiguous amino acid deletions relative to amino acids 323-424 of SEQ ID NO: 55. In still other aspects of this embodiment, a BMP10 comprises a polypeptide having, e.g., at most one, two, three, four, five, six, seven, eight, nine, 10 or 20 contiguous amino acid additions relative to amino acids 323-424 of SEQ ID NO: 55. In other aspects of this embodiment, a BMP10 comprises a polypeptide having, e.g., at least one, two, three, four, five, six, seven, eight, nine, 10 or 20 contiguous amino acid additions relative to amino acids 323-424 of SEQ ID NO: 55.

Another example of an enhanced targeting domain disclosed in the present specification is, e.g., a GFPs, such as, e.g., GDF1, GDF2, GDF3, GDF5, GDF6, GDF7, GDF8, GDF10, GDF11 or GDF15.

Thus, in an embodiment, an enhanced binding domain is derived from a GDF1. In another embodiment, an enhanced binding domain is derived from a GDF1 of SEQ ID NO: 56. In an aspect of this embodiment, an enhanced binding domain is derived from a GDF1 comprises amino acids 267-372 of SEQ ID NO: 56.

In other aspects of this embodiment, a GDF1 comprises a polypeptide having, e.g., at least 70% amino acid identity with amino acids 267-372 of SEQ ID NO: 56, at least 75% amino acid identity with amino acids 267-372 of SEQ ID NO: 56, at least 80% amino acid identity with amino acids 267-372 of SEQ ID NO: 56, at least 85% amino acid identity with amino acids 267-372 of SEQ ID NO: 56, at least 90% amino acid identity with amino acids 267-372 of SEQ ID NO: 56 or at least 95% amino acid identity with amino acids 267-372 of SEQ ID NO: 56. In yet other aspects of this embodiment, a GDF1 comprises a polypeptide having, e.g., at most 70% amino acid identity with amino acids 267-372 of SEQ ID NO: 56, at most 75% amino acid identity with amino acids 267-372 of SEQ ID NO: 56, at most 80% amino acid identity with amino acids 267-372 of SEQ ID NO: 56, at most 85% amino acid identity with amino acids 267-372 of SEQ ID NO: 56, at most 90% amino acid identity with amino acids 267-372 of SEQ ID NO: 56 or at most 95% amino acid identity with amino acids 267-372 of SEQ ID NO: 56.

In other aspects of this embodiment, a GDF1 comprises a polypeptide having, e.g., at most one, two, three, four, five, six, seven, eight, nine, 10 or 20 non-contiguous amino acid substitutions relative to amino acids 267-372 of SEQ ID NO: 56. In other aspects of this embodiment, a GDF1 comprises a polypeptide having, e.g., at least one, two, three, four, five, six, seven, eight, nine, 10 or 20 non-contiguous amino acid substitutions relative to amino acids 267-372 of SEQ ID NO: 56. In yet other aspects of this embodiment, a GDF1 comprises a polypeptide having, e.g., at most one, two, three, four, five, six, seven, eight, nine, 10 or 20 non-contiguous amino acid deletions relative to amino acids 267-372 of SEQ ID NO: 56. In other aspects of this embodiment, a GDF1 comprises a polypeptide having, e.g., at least one, two, three, four, five, six, seven, eight, nine, 10 or 20 non-contiguous amino acid deletions relative to amino acids 267-372 of SEQ ID NO: 56. In still other aspects of this embodiment, a GDF1 comprises a polypeptide having, e.g., at most one, two, three, four, five, six, seven, eight, nine, 10 or 20 non-contiguous amino acid additions relative to amino acids 267-372 of SEQ ID NO: 56. In other aspects of this embodiment, a GDF1 comprises a polypeptide having, e.g., at least one, two, three, four, five, six, seven, eight, nine, 10 or 20 non-contiguous amino acid additions relative to amino acids 267-372 of SEQ ID NO: 56.

In other aspects of this embodiment, a GDF1 comprises a polypeptide having, e.g., at most one, two, three, four, five, six, seven, eight, nine, 10 or 20 contiguous amino acid substitutions relative to amino acids 267-372 of SEQ ID NO: 56. In other aspects of this embodiment, a GDF1 comprises a polypeptide having, e.g., at least one, two, three, four, five, six, seven, eight, nine, 10 or 20 contiguous amino acid substitutions relative to amino acids 267-372 of SEQ ID NO: 56. In yet other aspects of this embodiment, a GDF1 comprises a polypeptide having, e.g., at most one, two, three, four, five, six, seven, eight, nine, 10 or 20 contiguous amino acid deletions relative to amino acids 267-372 of SEQ ID NO: 56. In other aspects of this embodiment, a GDF1 comprises a polypeptide having, e.g., at least one, two, three, four, five, six, seven, eight, nine, 10 or 20 contiguous amino acid deletions relative to amino acids 267-372 of SEQ ID NO: 56. In still other aspects of this embodiment, a GDF1 comprises a polypeptide having, e.g., at most one, two, three, four, five, six, seven, eight, nine, 10 or 20 contiguous amino acid additions relative to amino acids 267-372 of SEQ ID NO: 56. In other aspects of this embodiment, a GDF1 comprises a polypeptide having, e.g., at least one, two, three, four, five, six, seven, eight, nine, 10 or 20 contiguous amino acid additions relative to amino acids 267-372 of SEQ ID NO: 56.

In another embodiment, an enhanced binding domain is derived from a GDF2. In another embodiment, an enhanced binding domain is derived from a GDF2 of SEQ ID NO: 57. In an aspect of this embodiment, an enhanced binding domain is derived from a GDF2 comprises amino acids 327-429 of SEQ ID NO: 57.

In other aspects of this embodiment, a GDF2 comprises a polypeptide having, e.g., at least 70% amino acid identity with amino acids 327-429 of SEQ ID NO: 57, at least 75% amino acid identity with amino acids 327-429 of SEQ ID NO: 57, at least 80% amino acid identity with amino acids 327-429 of SEQ ID NO: 57, at least 85% amino acid identity with amino acids 327-429 of SEQ ID NO: 57, at least 90% amino acid identity with amino acids 327-429 of SEQ ID NO: 57 or at least 95% amino acid identity with amino acids 327-429 of SEQ ID NO: 57. In yet other aspects of this embodiment, a GDF2 comprises a polypeptide having, e.g., at most 70% amino acid identity with amino acids 327-429 of SEQ ID NO: 57, at most 75% amino acid identity with amino acids 327-429 of SEQ ID NO: 57, at most 80% amino acid identity with amino acids 327-429 of SEQ ID NO: 57, at most 85% amino acid identity with amino acids 327-429 of SEQ ID NO: 57, at most 90% amino acid identity with amino acids 327-429 of SEQ ID NO: 57 or at most 95% amino acid identity with amino acids 327-429 of SEQ ID NO: 57.

In other aspects of this embodiment, a GDF2 comprises a polypeptide having, e.g., at most one, two, three, four, five, six, seven, eight, nine, 10 or 20 non-contiguous amino acid substitutions relative to amino acids 327-429 of SEQ ID NO: 57. In other aspects of this embodiment, a GDF2 comprises a polypeptide having, e.g., at least one, two, three, four, five, six, seven, eight, nine, 10 or 20 non-contiguous amino acid substitutions relative to amino acids 327-429 of SEQ ID NO: 57. In yet other aspects of this embodiment, a GDF2 comprises a polypeptide having, e.g., at most one, two, three, four, five, six, seven, eight, nine, 10 or 20 non-contiguous amino acid deletions relative to amino acids 327-429 of SEQ ID NO: 57. In other aspects of this embodiment, a GDF2 comprises a polypeptide having, e.g., at least one, two, three, four, five, six, seven, eight, nine, 10 or 20 non-contiguous amino acid deletions relative to amino acids 327-429 of SEQ ID NO: 57. In still other aspects of this embodiment, a GDF2 comprises a polypeptide having, e.g., at most one, two, three, four, five, six, seven, eight, nine, 10 or 20 non-contiguous amino acid additions relative to amino acids 327-429 of SEQ ID NO: 57. In other aspects of this embodiment, a GDF2 comprises a polypeptide having, e.g., at least one, two, three, four, five, six, seven, eight, nine, 10 or 20 non-contiguous amino acid additions relative to amino acids 327-429 of SEQ ID NO: 57.

In other aspects of this embodiment, a GDF2 comprises a polypeptide having, e.g., at most one, two, three, four, five, six, seven, eight, nine, 10 or 20 contiguous amino acid substitutions relative to amino acids 327-429 of SEQ ID NO: 57. In other aspects of this embodiment, a GDF2 comprises a polypeptide having, e.g., at least one, two, three, four, five, six, seven, eight, nine, 10 or 20 contiguous amino acid substitutions relative to amino acids 327-429 of SEQ ID NO: 57. In yet other aspects of this embodiment, a GDF2 comprises a polypeptide having, e.g., at most one, two, three, four, five, six, seven, eight, nine, 10 or 20 contiguous amino acid deletions relative to amino acids 327-429 of SEQ ID NO: 57. In other aspects of this embodiment, a GDF2 comprises a polypeptide having, e.g., at least one, two, three, four, five, six, seven, eight, nine, 10 or 20 contiguous amino acid deletions relative to amino acids 327-429 of SEQ ID NO: 57. In still other aspects of this embodiment, a GDF2 comprises a polypeptide having, e.g., at most one, two, three, four, five, six, seven, eight, nine, 10 or 20 contiguous amino acid additions relative to amino acids 327-429 of SEQ ID NO: 57. In other aspects of this embodiment, a GDF2 comprises a polypeptide having, e.g., at least one, two, three, four, five, six, seven, eight, nine, 10 or 20 contiguous amino acid additions relative to amino acids 327-429 of SEQ ID NO: 57.

In another embodiment, an enhanced binding domain is derived from a GDF3. In another embodiment, an enhanced binding domain is derived from a GDF3 of SEQ ID NO: 58. In an aspect of this embodiment, an enhanced binding domain is derived from a GDF3 comprises amino acids 264-364 of SEQ ID NO: 58.

In other aspects of this embodiment, a GDF3 comprises a polypeptide having, e.g., at least 70% amino acid identity with amino acids 264-364 of SEQ ID NO: 58, at least 75% amino acid identity with amino acids 264-364 of SEQ ID NO: 58, at least 80% amino acid identity with amino acids 264-364 of SEQ ID NO: 58, at least 85% amino acid identity with amino acids 264-364 of SEQ ID NO: 58, at least 90% amino acid identity with amino acids 264-364 of SEQ ID NO: 58 or at least 95% amino acid identity with amino acids 264-364 of SEQ ID NO: 58. In yet other aspects of this embodiment, a GDF3 comprises a polypeptide having, e.g., at most 70% amino acid identity with amino acids 264-364 of SEQ ID NO: 58, at most 75% amino acid identity with amino acids 264-364 of SEQ ID NO: 58, at most 80% amino acid identity with amino acids 264-364 of SEQ ID NO: 58, at most 85% amino acid identity with amino acids 264-364 of SEQ ID NO: 58, at most 90% amino acid identity with amino acids 264-364 of SEQ ID NO: 58 or at most 95% amino acid identity with amino acids 264-364 of SEQ ID NO: 58.

In other aspects of this embodiment, a GDF3 comprises a polypeptide having, e.g., at most one, two, three, four, five, six, seven, eight, nine, 10 or 20 non-contiguous amino acid substitutions relative to amino acids 264-364 of SEQ ID NO: 58. In other aspects of this embodiment, a GDF3 comprises a polypeptide having, e.g., at least one, two, three, four, five, six, seven, eight, nine, 10 or 20 non-contiguous amino acid substitutions relative to amino acids 264-364 of SEQ ID NO: 58. In yet other aspects of this embodiment, a GDF3 comprises a polypeptide having, e.g., at most one, two, three, four, five, six, seven, eight, nine, 10 or 20 non-contiguous amino acid deletions relative to amino acids 264-364 of SEQ ID NO: 58. In other aspects of this embodiment, a GDF3 comprises a polypeptide having, e.g., at least one, two, three, four, five, six, seven, eight, nine, 10 or 20 non-contiguous amino acid deletions relative to amino acids 264-364 of SEQ ID NO: 58. In still other aspects of this embodiment, a GDF3 comprises a polypeptide having, e.g., at most one, two, three, four, five, six, seven, eight, nine, 10 or 20 non-contiguous amino acid additions relative to amino acids 264-364 of SEQ ID NO: 58. In other aspects of this embodiment, a GDF3 comprises a polypeptide having, e.g., at least one, two, three, four, five, six, seven, eight, nine, 10 or 20 non-contiguous amino acid additions relative to amino acids 264-364 of SEQ ID NO: 58.

In other aspects of this embodiment, a GDF3 comprises a polypeptide having, e.g., at most one, two, three, four, five, six, seven, eight, nine, 10 or 20 contiguous amino acid substitutions relative to amino acids 264-364 of SEQ ID NO: 58. In other aspects of this embodiment, a GDF3 comprises a polypeptide having, e.g., at least one, two, three, four, five, six, seven, eight, nine, 10 or 20 contiguous amino acid substitutions relative to amino acids 264-364 of SEQ ID NO: 58. In yet other aspects of this embodiment, a GDF3 comprises a polypeptide having, e.g., at most one, two, three, four, five, six, seven, eight, nine, 10 or 20 contiguous amino acid deletions relative to amino acids 264-364 of SEQ ID NO: 58. In other aspects of this embodiment, a GDF3 comprises a polypeptide having, e.g., at least one, two, three, four, five, six, seven, eight, nine, 10 or 20 contiguous amino acid deletions relative to amino acids 264-364 of SEQ ID NO: 58. In still other aspects of this embodiment, a GDF3 comprises a polypeptide having, e.g., at most one, two, three, four, five, six, seven, eight, nine, 10 or 20 contiguous amino acid additions relative to amino acids 264-364 of SEQ ID NO: 58. In other aspects of this embodiment, a GDF3 comprises a polypeptide having, e.g., at least one, two, three, four, five, six, seven, eight, nine, 10 or 20 contiguous amino acid additions relative to amino acids 264-364 of SEQ ID NO: 58.

In another embodiment, an enhanced binding domain is derived from a GDF5. In another embodiment, an enhanced binding domain is derived from a GDF5 of SEQ ID NO: 59. In an aspect of this embodiment, an enhanced binding domain is derived from a GDF5 comprises amino acids 400-501 of SEQ ID NO: 59.

In other aspects of this embodiment, a GDF5 comprises a polypeptide having, e.g., at least 70% amino acid identity with amino acids 400-501 of SEQ ID NO: 59, at least 75% amino acid identity with amino acids 400-501 of SEQ ID NO: 59, at least 80% amino acid identity with amino acids 400-501 of SEQ ID NO: 59, at least 85% amino acid identity with amino acids 400-501 of SEQ ID NO: 59, at least 90% amino acid identity with amino acids 400-501 of SEQ ID NO: 59 or at least 95% amino acid identity with amino acids 400-501 of SEQ ID NO: 59. In yet other aspects of this embodiment, a GDF5 comprises a polypeptide having, e.g., at most 70% amino acid identity with amino acids 400-501 of SEQ ID NO: 59, at most 75% amino acid identity with amino acids 400-501 of SEQ ID NO: 59, at most 80% amino acid identity with amino acids 400-501 of SEQ ID NO: 59, at most 85% amino acid identity with amino acids 400-501 of SEQ ID NO: 59, at most 90% amino acid identity with amino acids 400-501 of SEQ ID NO: 59 or at most 95% amino acid identity with amino acids 400-501 of SEQ ID NO: 59.

In other aspects of this embodiment, a GDF5 comprises a polypeptide having, e.g., at most one, two, three, four, five, six, seven, eight, nine, 10 or 20 non-contiguous amino acid substitutions relative to amino acids 400-501 of SEQ ID NO: 59. In other aspects of this embodiment, a GDF5 comprises a polypeptide having, e.g., at least one, two, three, four, five, six, seven, eight, nine, 10 or 20 non-contiguous amino acid substitutions relative to amino acids 400-501 of SEQ ID NO: 59. In yet other aspects of this embodiment, a GDF5 comprises a polypeptide having, e.g., at most one, two, three, four, five, six, seven, eight, nine, 10 or 20 non-contiguous amino acid deletions relative to amino acids 400-501 of SEQ ID NO: 59. In other aspects of this embodiment, a GDF5 comprises a polypeptide having, e.g., at least one, two, three, four, five, six, seven, eight, nine, 10 or 20 non-contiguous amino acid deletions relative to amino acids 400-501 of SEQ ID NO: 59. In still other aspects of this embodiment, a GDF5 comprises a polypeptide having, e.g., at most one, two, three, four, five, six, seven, eight, nine, 10 or 20 non-contiguous amino acid additions relative to amino acids 400-501 of SEQ ID NO: 59. In other aspects of this embodiment, a GDF5 comprises a polypeptide having, e.g., at least one, two, three, four, five, six, seven, eight, nine, 10 or 20 non-contiguous amino acid additions relative to amino acids 400-501 of SEQ ID NO: 59.

In other aspects of this embodiment, a GDF5 comprises a polypeptide having, e.g., at most one, two, three, four, five, six, seven, eight, nine, 10 or 20 contiguous amino acid substitutions relative to amino acids 400-501 of SEQ ID NO: 59. In other aspects of this embodiment, a GDF5 comprises a polypeptide having, e.g., at least one, two, three, four, five, six, seven, eight, nine, 10 or 20 contiguous amino acid substitutions relative to amino acids 400-501 of SEQ ID NO: 59. In yet other aspects of this embodiment, a GDF5 comprises a polypeptide having, e.g., at most one, two, three, four, five, six, seven, eight, nine, 10 or 20 contiguous amino acid deletions relative to amino acids 400-501 of SEQ ID NO: 59. In other aspects of this embodiment, a GDF5 comprises a polypeptide having, e.g., at least one, two, three, four, five, six, seven, eight, nine, 10 or 20 contiguous amino acid deletions relative to amino acids 400-501 of SEQ ID NO: 59. In still other aspects of this embodiment, a GDF5 comprises a polypeptide having, e.g., at most one, two, three, four, five, six, seven, eight, nine, 10 or 20 contiguous amino acid additions relative to amino acids 400-501 of SEQ ID NO: 59. In other aspects of this embodiment, a GDF5 comprises a polypeptide having, e.g., at least one, two, three, four, five, six, seven, eight, nine, 10 or 20 contiguous amino acid additions relative to amino acids 400-501 of SEQ ID NO: 59.

In another embodiment, an enhanced binding domain is derived from a GDF6. In another embodiment, an enhanced binding domain is derived from a GDF6 of SEQ ID NO: 60. In an aspect of this embodiment, an enhanced binding domain is derived from a GDF6 comprises amino acids 354-455 of SEQ ID NO: 60.

In other aspects of this embodiment, a GDF6 comprises a polypeptide having, e.g., at least 70% amino acid identity with amino acids 354-455 of SEQ ID NO: 60, at least 75% amino acid identity with amino acids 354-455 of SEQ ID NO: 60, at least 80% amino acid identity with amino acids 354-455 of SEQ ID NO: 60, at least 85% amino acid identity with amino acids 354-455 of SEQ ID NO: 60, at least 90% amino acid identity with amino acids 354-455 of SEQ ID NO: 60 or at least 95% amino acid identity with amino acids 354-455 of SEQ ID NO: 60. In yet other aspects of this embodiment, a GDF6 comprises a polypeptide having, e.g., at most 70% amino acid identity with amino acids 354-455 of SEQ ID NO: 60, at most 75% amino acid identity with amino acids 354-455 of SEQ ID NO: 60, at most 80% amino acid identity with amino acids 354-455 of SEQ ID NO: 60, at most 85% amino acid identity with amino acids 354-455 of SEQ ID NO: 60, at most 90% amino acid identity with amino acids 354-455 of SEQ ID NO: 60 or at most 95% amino acid identity with amino acids 354-455 of SEQ ID NO: 60.

In other aspects of this embodiment, a GDF6 comprises a polypeptide having, e.g., at most one, two, three, four, five, six, seven, eight, nine, 10 or 20 non-contiguous amino acid substitutions relative to amino acids 354-455 of SEQ ID NO: 60. In other aspects of this embodiment, a GDF6 comprises a polypeptide having, e.g., at least one, two, three, four, five, six, seven, eight, nine, 10 or 20 non-contiguous amino acid substitutions relative to amino acids 354-455 of SEQ ID NO: 60. In yet other aspects of this embodiment, a GDF6 comprises a polypeptide having, e.g., at most one, two, three, four, five, six, seven, eight, nine, 10 or 20 non-contiguous amino acid deletions relative to amino acids 354-455 of SEQ ID NO: 60. In other aspects of this embodiment, a GDF6 comprises a polypeptide having, e.g., at least one, two, three, four, five, six, seven, eight, nine, 10 or 20 non-contiguous amino acid deletions relative to amino acids 354-455 of SEQ ID NO: 60. In still other aspects of this embodiment, a GDF6 comprises a polypeptide having, e.g., at most one, two, three, four, five, six, seven, eight, nine, 10 or 20 non-contiguous amino acid additions relative to amino acids 354-455 of SEQ ID NO: 60. In other aspects of this embodiment, a GDF6 comprises a polypeptide having, e.g., at least one, two, three, four, five, six, seven, eight, nine, 10 or 20 non-contiguous amino acid additions relative to amino acids 354-455 of SEQ ID NO: 60.

In other aspects of this embodiment, a GDF6 comprises a polypeptide having, e.g., at most one, two, three, four, five, six, seven, eight, nine, 10 or 20 contiguous amino acid substitutions relative to amino acids 354-455 of SEQ ID NO: 60. In other aspects of this embodiment, a GDF6 comprises a polypeptide having, e.g., at least one, two, three, four, five, six, seven, eight, nine, 10 or 20 contiguous amino acid substitutions relative to amino acids 354-455 of SEQ ID NO: 60. In yet other aspects of this embodiment, a GDF6 comprises a polypeptide having, e.g., at most one, two, three, four, five, six, seven, eight, nine, 10 or 20 contiguous amino acid deletions relative to amino acids 354-455 of SEQ ID NO: 60. In other aspects of this embodiment, a GDF6 comprises a polypeptide having, e.g., at least one, two, three, four, five, six, seven, eight, nine, 10 or 20 contiguous amino acid deletions relative to amino acids 354-455 of SEQ ID NO: 60. In still other aspects of this embodiment, a GDF6 comprises a polypeptide having, e.g., at most one, two, three, four, five, six, seven, eight, nine, 10 or 20 contiguous amino acid additions relative to amino acids 354-455 of SEQ ID NO: 60. In other aspects of this embodiment, a GDF6 comprises a polypeptide having, e.g., at least one, two, three, four, five, six, seven, eight, nine, 10 or 20 contiguous amino acid additions relative to amino acids 354-455 of SEQ ID NO: 60.

In another embodiment, an enhanced binding domain is derived from a GDF7. In another embodiment, an enhanced binding domain is derived from a GDF7 of SEQ ID NO: 61. In an aspect of this embodiment, an enhanced binding domain is derived from a GDF7 comprises amino acids 352-450 of SEQ ID NO: 61.

In other aspects of this embodiment, a GDF7 comprises a polypeptide having, e.g., at least 70% amino acid identity with amino acids 352-450 of SEQ ID NO: 61, at least 75% amino acid identity with amino acids 352-450 of SEQ ID NO: 61, at least 80% amino acid identity with amino acids 352-450 of SEQ ID NO: 61, at least 85% amino acid identity with amino acids 352-450 of SEQ ID NO: 61, at least 90% amino acid identity with amino acids 352-450 of SEQ ID NO: 61 or at least 95% amino acid identity with amino acids 352-450 of SEQ ID NO: 61. In yet other aspects of this embodiment, a GDF7 comprises a polypeptide having, e.g., at most 70% amino acid identity with amino acids 352-450 of SEQ ID NO: 61, at most 75% amino acid identity with amino acids 352-450 of SEQ ID NO: 61, at most 80% amino acid identity with amino acids 352-450 of SEQ ID NO: 61, at most 85% amino acid identity with amino acids 352-450 of SEQ ID NO: 61, at most 90% amino acid identity with amino acids 352-450 of SEQ ID NO: 61 or at most 95% amino acid identity with amino acids 352-450 of SEQ ID NO: 61.

In other aspects of this embodiment, a GDF7 comprises a polypeptide having, e.g., at most one, two, three, four, five, six, seven, eight, nine, 10 or 20 non-contiguous amino acid substitutions relative to amino acids 352-450 of SEQ ID NO: 61. In other aspects of this embodiment, a GDF7 comprises a polypeptide having, e.g., at least one, two, three, four, five, six, seven, eight, nine, 10 or 20 non-contiguous amino acid substitutions relative to amino acids 352-450 of SEQ ID NO: 61. In yet other aspects of this embodiment, a GDF7 comprises a polypeptide having, e.g., at most one, two, three, four, five, six, seven, eight, nine, 10 or 20 non-contiguous amino acid deletions relative to amino acids 352-450 of SEQ ID NO: 61. In other aspects of this embodiment, a GDF7 comprises a polypeptide having, e.g., at least one, two, three, four, five, six, seven, eight, nine, 10 or 20 non-contiguous amino acid deletions relative to amino acids 352-450 of SEQ ID NO: 61. In still other aspects of this embodiment, a GDF7 comprises a polypeptide having, e.g., at most one, two, three, four, five, six, seven, eight, nine, 10 or 20 non-contiguous amino acid additions relative to amino acids 352-450 of SEQ ID NO: 61. In other aspects of this embodiment, a GDF7 comprises a polypeptide having, e.g., at least one, two, three, four, five, six, seven, eight, nine, 10 or 20 non-contiguous amino acid additions relative to amino acids 352-450 of SEQ ID NO: 61.

In other aspects of this embodiment, a GDF7 comprises a polypeptide having, e.g., at most one, two, three, four, five, six, seven, eight, nine, 10 or 20 contiguous amino acid substitutions relative to amino acids 352-450 of SEQ ID NO: 61. In other aspects of this embodiment, a GDF7 comprises a polypeptide having, e.g., at least one, two, three, four, five, six, seven, eight, nine, 10 or 20 contiguous amino acid substitutions relative to amino acids 352-450 of SEQ ID NO: 61. In yet other aspects of this embodiment, a GDF7 comprises a polypeptide having, e.g., at most one, two, three, four, five, six, seven, eight, nine, 10 or 20 contiguous amino acid deletions relative to amino acids 352-450 of SEQ ID NO: 61. In other aspects of this embodiment, a GDF7 comprises a polypeptide having, e.g., at least one, two, three, four, five, six, seven, eight, nine, 10 or 20 contiguous amino acid deletions relative to amino acids 352-450 of SEQ ID NO: 61. In still other aspects of this embodiment, a GDF7 comprises a polypeptide having, e.g., at most one, two, three, four, five, six, seven, eight, nine, 10 or 20 contiguous amino acid additions relative to amino acids 352-450 of SEQ ID NO: 61. In other aspects of this embodiment, a GDF7 comprises a polypeptide having, e.g., at least one, two, three, four, five, six, seven, eight, nine, 10 or 20 contiguous amino acid additions relative to amino acids 352-450 of SEQ ID NO: 61.

In another embodiment, an enhanced binding domain is derived from a GDF8. In another embodiment, an enhanced binding domain is derived from a GDF8 of SEQ ID NO: 62. In an aspect of this embodiment, an enhanced binding domain is derived from a GDF8 comprises amino acids 281-375 of SEQ ID NO: 62.

In other aspects of this embodiment, a GDF8 comprises a polypeptide having, e.g., at least 70% amino acid identity with amino acids 281-375 of SEQ ID NO: 62, at least 75% amino acid identity with amino acids 281-375 of SEQ ID NO: 62, at least 80% amino acid identity with amino acids 281-375 of SEQ ID NO: 62, at least 85% amino acid identity with amino acids 281-375 of SEQ ID NO: 62, at least 90% amino acid identity with amino acids 281-375 of SEQ ID NO: 62 or at least 95% amino acid identity with amino acids 281-375 of SEQ ID NO: 62. In yet other aspects of this embodiment, a GDF8 comprises a polypeptide having, e.g., at most 70% amino acid identity with amino acids 281-375 of SEQ ID NO: 62, at most 75% amino acid identity with amino acids 281-375 of SEQ ID NO: 62, at most 80% amino acid identity with amino acids 281-375 of SEQ ID NO: 62, at most 85% amino acid identity with amino acids 281-375 of SEQ ID NO: 62, at most 90% amino acid identity with amino acids 281-375 of SEQ ID NO: 62 or at most 95% amino acid identity with amino acids 281-375 of SEQ ID NO: 62.

In other aspects of this embodiment, a GDF8 comprises a polypeptide having, e.g., at most one, two, three, four, five, six, seven, eight, nine, 10 or 20 non-contiguous amino acid substitutions relative to amino acids 281-375 of SEQ ID NO: 62. In other aspects of this embodiment, a GDF8 comprises a polypeptide having, e.g., at least one, two, three, four, five, six, seven, eight, nine, 10 or 20 non-contiguous amino acid substitutions relative to amino acids 281-375 of SEQ ID NO: 62. In yet other aspects of this embodiment, a GDF8 comprises a polypeptide having, e.g., at most one, two, three, four, five, six, seven, eight, nine, 10 or 20 non-contiguous amino acid deletions relative to amino acids 281-375 of SEQ ID NO: 62. In other aspects of this embodiment, a GDF8 comprises a polypeptide having, e.g., at least one, two, three, four, five, six, seven, eight, nine, 10 or 20 non-contiguous amino acid deletions relative to amino acids 281-375 of SEQ ID NO: 62. In still other aspects of this embodiment, a GDF8 comprises a polypeptide having, e.g., at most one, two, three, four, five, six, seven, eight, nine, 10 or 20 non-contiguous amino acid additions relative to amino acids 281-375 of SEQ ID NO: 62. In other aspects of this embodiment, a GDF8 comprises a polypeptide having, e.g., at least one, two, three, four, five, six, seven, eight, nine, 10 or 20 non-contiguous amino acid additions relative to amino acids 281-375 of SEQ ID NO: 62.

In other aspects of this embodiment, a GDF8 comprises a polypeptide having, e.g., at most one, two, three, four, five, six, seven, eight, nine, 10 or 20 contiguous amino acid substitutions relative to amino acids 281-375 of SEQ ID NO: 62. In other aspects of this embodiment, a GDF8 comprises a polypeptide having, e.g., at least one, two, three, four, five, six, seven, eight, nine, 10 or 20 contiguous amino acid substitutions relative to amino acids 281-375 of SEQ ID NO: 62. In yet other aspects of this embodiment, a GDF8 comprises a polypeptide having, e.g., at most one, two, three, four, five, six, seven, eight, nine, 10 or 20 contiguous amino acid deletions relative to amino acids 281-375 of SEQ ID NO: 62. In other aspects of this embodiment, a GDF8 comprises a polypeptide having, e.g., at least one, two, three, four, five, six, seven, eight, nine, 10 or 20 contiguous amino acid deletions relative to amino acids 281-375 of SEQ ID NO: 62. In still other aspects of this embodiment, a GDF8 comprises a polypeptide having, e.g., at most one, two, three, four, five, six, seven, eight, nine, 10 or 20 contiguous amino acid additions relative to amino acids 281-375 of SEQ ID NO: 62. In other aspects of this embodiment, a GDF8 comprises a polypeptide having, e.g., at least one, two, three, four, five, six, seven, eight, nine, 10 or 20 contiguous amino acid additions relative to amino acids 281-375 of SEQ ID NO: 62.

In another embodiment, an enhanced binding domain is derived from a GDF10. In another embodiment, an enhanced binding domain is derived from a GDF10 of SEQ ID NO: 63. In an aspect of this embodiment, an enhanced binding domain is derived from a GDF10 comprises amino acids 376-478 of SEQ ID NO: 63.

In other aspects of this embodiment, a GDF10 comprises a polypeptide having, e.g., at least 70% amino acid identity with amino acids 376-478 of SEQ ID NO: 63, at least 75% amino acid identity with amino acids 376-478 of SEQ ID NO: 63, at least 80% amino acid identity with amino acids 376-478 of SEQ ID NO: 63, at least 85% amino acid identity with amino acids 376-478 of SEQ ID NO: 63, at least 90% amino acid identity with amino acids 376-478 of SEQ ID NO: 63 or at least 95% amino acid identity with amino acids 376-478 of SEQ ID NO: 63. In yet other aspects of this embodiment, a GDF10 comprises a polypeptide having, e.g., at most 70% amino acid identity with amino acids 376-478 of SEQ ID NO: 63, at most 75% amino acid identity with amino acids 376-478 of SEQ ID NO: 63, at most 80% amino acid identity with amino acids 376-478 of SEQ ID NO: 63, at most 85% amino acid identity with amino acids 376-478 of SEQ ID NO: 63, at most 90% amino acid identity with amino acids 376-478 of SEQ ID NO: 63 or at most 95% amino acid identity with amino acids 376-478 of SEQ ID NO: 63.

In other aspects of this embodiment, a GDF10 comprises a polypeptide having, e.g., at most one, two, three, four, five, six, seven, eight, nine, 10 or 20 non-contiguous amino acid substitutions relative to amino acids 376-478 of SEQ ID NO: 63. In other aspects of this embodiment, a GDF10 comprises a polypeptide having, e.g., at least one, two, three, four, five, six, seven, eight, nine, 10 or 20 non-contiguous amino acid substitutions relative to amino acids 376-478 of SEQ ID NO: 63. In yet other aspects of this embodiment, a GDF10 comprises a polypeptide having, e.g., at most one, two, three, four, five, six, seven, eight, nine, 10 or 20 non-contiguous amino acid deletions relative to amino acids 376-478 of SEQ ID NO: 63. In other aspects of this embodiment, a GDF10 comprises a polypeptide having, e.g., at least one, two, three, four, five, six, seven, eight, nine, 10 or 20 non-contiguous amino acid deletions relative to amino acids 376-478 of SEQ ID NO: 63. In still other aspects of this embodiment, a GDF10 comprises a polypeptide having, e.g., at most one, two, three, four, five, six, seven, eight, nine, 10 or 20 non-contiguous amino acid additions relative to amino acids 376-478 of SEQ ID NO: 63. In other aspects of this embodiment, a GDF10 comprises a polypeptide having, e.g., at least one, two, three, four, five, six, seven, eight, nine, 10 or 20 non-contiguous amino acid additions relative to amino acids 376-478 of SEQ ID NO: 63.

In other aspects of this embodiment, a GDF10 comprises a polypeptide having, e.g., at most one, two, three, four, five, six, seven, eight, nine, 10 or 20 contiguous amino acid substitutions relative to amino acids 376-478 of SEQ ID NO: 63. In other aspects of this embodiment, a GDF10 comprises a polypeptide having, e.g., at least one, two, three, four, five, six, seven, eight, nine, 10 or 20 contiguous amino acid substitutions relative to amino acids 376-478 of SEQ ID NO: 63. In yet other aspects of this embodiment, a GDF10 comprises a polypeptide having, e.g., at most one, two, three, four, five, six, seven, eight, nine, 10 or 20 contiguous amino acid deletions relative to amino acids 376-478 of SEQ ID NO: 63. In other aspects of this embodiment, a GDF10 comprises a polypeptide having, e.g., at least one, two, three, four, five, six, seven, eight, nine, 10 or 20 contiguous amino acid deletions relative to amino acids 376-478 of SEQ ID NO: 63. In still other aspects of this embodiment, a GDF10 comprises a polypeptide having, e.g., at most one, two, three, four, five, six, seven, eight, nine, 10 or 20 contiguous amino acid additions relative to amino acids 376-478 of SEQ ID NO: 63. In other aspects of this embodiment, a GDF10 comprises a polypeptide having, e.g., at least one, two, three, four, five, six, seven, eight, nine, 10 or 20 contiguous amino acid additions relative to amino acids 376-478 of SEQ ID NO: 63.

In another embodiment, an enhanced binding domain is derived from a GDF11. In another embodiment, an enhanced binding domain is derived from a GDF11 of SEQ ID NO: 64. In an aspect of this embodiment, an enhanced binding domain is derived from a GDF11 comprises amino acids 313-407 of SEQ ID NO: 64.

In other aspects of this embodiment, a GDF11 comprises a polypeptide having, e.g., at least 70% amino acid identity with amino acids 313-407 of SEQ ID NO: 64, at least 75% amino acid identity with amino acids 313-407 of SEQ ID NO: 64, at least 80% amino acid identity with amino acids 313-407 of SEQ ID NO: 64, at least 85% amino acid identity with amino acids 313-407 of SEQ ID NO: 64, at least 90% amino acid identity with amino acids 313-407 of SEQ ID NO: 64 or at least 95% amino acid identity with amino acids 313-407 of SEQ ID NO: 64. In yet other aspects of this embodiment, a GDF11 comprises a polypeptide having, e.g., at most 70% amino acid identity with amino acids 313-407 of SEQ ID NO: 64, at most 75% amino acid identity with amino acids 313-407 of SEQ ID NO: 64, at most 80% amino acid identity with amino acids 313-407 of SEQ ID NO: 64, at most 85% amino acid identity with amino acids 313-407 of SEQ ID NO: 64, at most 90% amino acid identity with amino acids 313-407 of SEQ ID NO: 64 or at most 95% amino acid identity with amino acids 313-407 of SEQ ID NO: 64.

In other aspects of this embodiment, a GDF11 comprises a polypeptide having, e.g., at most one, two, three, four, five, six, seven, eight, nine, 10 or 20 non-contiguous amino acid substitutions relative to amino acids 313-407 of SEQ ID NO: 64. In other aspects of this embodiment, a GDF11 comprises a polypeptide having, e.g., at least one, two, three, four, five, six, seven, eight, nine, 10 or 20 non-contiguous amino acid substitutions relative to amino acids 313-407 of SEQ ID NO: 64. In yet other aspects of this embodiment, a GDF11 comprises a polypeptide having, e.g., at most one, two, three, four, five, six, seven, eight, nine, 10 or 20 non-contiguous amino acid deletions relative to amino acids 313-407 of SEQ ID NO: 64. In other aspects of this embodiment, a GDF11 comprises a polypeptide having, e.g., at least one, two, three, four, five, six, seven, eight, nine, 10 or 20 non-contiguous amino acid deletions relative to amino acids 313-407 of SEQ ID NO: 64. In still other aspects of this embodiment, a GDF11 comprises a polypeptide having, e.g., at most one, two, three, four, five, six, seven, eight, nine, 10 or 20 non-contiguous amino acid additions relative to amino acids 313-407 of SEQ ID NO: 64. In other aspects of this embodiment, a GDF11 comprises a polypeptide having, e.g., at least one, two, three, four, five, six, seven, eight, nine, 10 or 20 non-contiguous amino acid additions relative to amino acids 313-407 of SEQ ID NO: 64.

In other aspects of this embodiment, a GDF11 comprises a polypeptide having, e.g., at most one, two, three, four, five, six, seven, eight, nine, 10 or 20 contiguous amino acid substitutions relative to amino acids 313-407 of SEQ ID NO: 64. In other aspects of this embodiment, a GDF11 comprises a polypeptide having, e.g., at least one, two, three, four, five, six, seven, eight, nine, 10 or 20 contiguous amino acid substitutions relative to amino acids 313-407 of SEQ ID NO: 64. In yet other aspects of this embodiment, a GDF11 comprises a polypeptide having, e.g., at most one, two, three, four, five, six, seven, eight, nine, 10 or 20 contiguous amino acid deletions relative to amino acids 313-407 of SEQ ID NO: 64. In other aspects of this embodiment, a GDF11 comprises a polypeptide having, e.g., at least one, two, three, four, five, six, seven, eight, nine, 10 or 20 contiguous amino acid deletions relative to amino acids 313-407 of SEQ ID NO: 64. In still other aspects of this embodiment, a GDF11 comprises a polypeptide having, e.g., at most one, two, three, four, five, six, seven, eight, nine, 10 or 20 contiguous amino acid additions relative to amino acids 313-407 of SEQ ID NO: 64. In other aspects of this embodiment, a GDF11 comprises a polypeptide having, e.g., at least one, two, three, four, five, six, seven, eight, nine, 10 or 20 contiguous amino acid additions relative to amino acids 313-407 of SEQ ID NO: 64.

In another embodiment, an enhanced binding domain is derived from a GDF15. In another embodiment, an enhanced binding domain is derived from a GDF15 of SEQ ID NO: 65. In an aspect of this embodiment, an enhanced binding domain is derived from a GDF15 comprises amino acids 211-308 of SEQ ID NO: 65.

In other aspects of this embodiment, a GDF15 comprises a polypeptide having, e.g., at least 70% amino acid identity with amino acids 211-308 of SEQ ID NO: 65, at least 75% amino acid identity with amino acids 211-308 of SEQ ID NO: 65, at least 80% amino acid identity with amino acids 211-308 of SEQ ID NO: 65, at least 85% amino acid identity with amino acids 211-308 of SEQ ID NO: 65, at least 90% amino acid identity with amino acids 211-308 of SEQ ID NO: 65 or at least 95% amino acid identity with amino acids 211-308 of SEQ ID NO: 65. In yet other aspects of this embodiment, a GDF15 comprises a polypeptide having, e.g., at most 70% amino acid identity with amino acids 211-308 of SEQ ID NO: 65, at most 75% amino acid identity with amino acids 211-308 of SEQ ID NO: 65, at most 80% amino acid identity with amino acids 211-308 of SEQ ID NO: 65, at most 85% amino acid identity with amino acids 211-308 of SEQ ID NO: 65, at most 90% amino acid identity with amino acids 211-308 of SEQ ID NO: 65 or at most 95% amino acid identity with amino acids 211-308 of SEQ ID NO: 65.

In other aspects of this embodiment, a GDF15 comprises a polypeptide having, e.g., at most one, two, three, four, five, six, seven, eight, nine, 10 or 20 non-contiguous amino acid substitutions relative to amino acids 211-308 of SEQ ID NO: 65. In other aspects of this embodiment, a GDF15 comprises a polypeptide having, e.g., at least one, two, three, four, five, six, seven, eight, nine, 10 or 20 non-contiguous amino acid substitutions relative to amino acids 211-308 of SEQ ID NO: 65. In yet other aspects of this embodiment, a GDF15 comprises a polypeptide having, e.g., at most one, two, three, four, five, six, seven, eight, nine, 10 or 20 non-contiguous amino acid deletions relative to amino acids 211-308 of SEQ ID NO: 65. In other aspects of this embodiment, a GDF15 comprises a polypeptide having, e.g., at least one, two, three, four, five, six, seven, eight, nine, 10 or 20 non-contiguous amino acid deletions relative to amino acids 211-308 of SEQ ID NO: 65. In still other aspects of this embodiment, a GDF15 comprises a polypeptide having, e.g., at most one, two, three, four, five, six, seven, eight, nine, 10 or 20 non-contiguous amino acid additions relative to amino acids 211-308 of SEQ ID NO: 65. In other aspects of this embodiment, a GDF15 comprises a polypeptide having, e.g., at least one, two, three, four, five, six, seven, eight, nine, 10 or 20 non-contiguous amino acid additions relative to amino acids 211-308 of SEQ ID NO: 65.

In other aspects of this embodiment, a GDF15 comprises a polypeptide having, e.g., at most one, two, three, four, five, six, seven, eight, nine, 10 or 20 contiguous amino acid substitutions relative to amino acids 211-308 of SEQ ID NO: 65. In other aspects of this embodiment, a GDF15 comprises a polypeptide having, e.g., at least one, two, three, four, five, six, seven, eight, nine, 10 or 20 contiguous amino acid substitutions relative to amino acids 211-308 of SEQ ID NO: 65. In yet other aspects of this embodiment, a GDF15 comprises a polypeptide having, e.g., at most one, two, three, four, five, six, seven, eight, nine, 10 or 20 contiguous amino acid deletions relative to amino acids 211-308 of SEQ ID NO: 65. In other aspects of this embodiment, a GDF15 comprises a polypeptide having, e.g., at least one, two, three, four, five, six, seven, eight, nine, 10 or 20 contiguous amino acid deletions relative to amino acids 211-308 of SEQ ID NO: 65. In still other aspects of this embodiment, a GDF15 comprises a polypeptide having, e.g., at most one, two, three, four, five, six, seven, eight, nine, 10 or 20 contiguous amino acid additions relative to amino acids 211-308 of SEQ ID NO: 65. In other aspects of this embodiment, a GDF15 comprises a polypeptide having, e.g., at least one, two, three, four, five, six, seven, eight, nine, 10 or 20 contiguous amino acid additions relative to amino acids 211-308 of SEQ ID NO: 65.

Another example of an enhanced targeting domain disclosed in the present specification is, e.g., an activin A, an activin B, an activin C, an activin E or an inhibin A.

In another embodiment, an enhanced binding domain is derived from an Activin A. In another embodiment, an enhanced binding domain is derived from an Activin A of SEQ ID NO: 66. In an aspect of this embodiment, an enhanced binding domain is derived from an Activin A comprises amino acids 321-426 of SEQ ID NO: 66.

In other aspects of this embodiment, an Activin A comprises a polypeptide having, e.g., at least 70% amino acid identity with amino acids 321-426 of SEQ ID NO: 66, at least 75% amino acid identity with amino acids 321-426 of SEQ ID NO: 66, at least 80% amino acid identity with amino acids 321-426 of SEQ ID NO: 66, at least 85% amino acid identity with amino acids 321-426 of SEQ ID NO: 66, at least 90% amino acid identity with amino acids 321-426 of SEQ ID NO: 66 or at least 95% amino acid identity with amino acids 321-426 of SEQ ID NO: 66. In yet other aspects of this embodiment, an Activin A comprises a polypeptide having, e.g., at most 70% amino acid identity with amino acids 321-426 of SEQ ID NO: 66, at most 75% amino acid identity with amino acids 321-426 of SEQ ID NO: 66, at most 80% amino acid identity with amino acids 321-426 of SEQ ID NO: 66, at most 85% amino acid identity with amino acids 321-426 of SEQ ID NO: 66, at most 90% amino acid identity with amino acids 321-426 of SEQ ID NO: 66 or at most 95% amino acid identity with amino acids 321-426 of SEQ ID NO: 66.

In other aspects of this embodiment, an Activin A comprises a polypeptide having, e.g., at most one, two, three, four, five, six, seven, eight, nine, 10 or 20 non-contiguous amino acid substitutions relative to amino acids 321-426 of SEQ ID NO: 66. In other aspects of this embodiment, an Activin A comprises a polypeptide having, e.g., at least one, two, three, four, five, six, seven, eight, nine, 10 or 20 non-contiguous amino acid substitutions relative to amino acids 321-426 of SEQ ID NO: 66. In yet other aspects of this embodiment, an Activin A comprises a polypeptide having, e.g., at most one, two, three, four, five, six, seven, eight, nine, 10 or 20 non-contiguous amino acid deletions relative to amino acids 321-426 of SEQ ID NO: 66. In other aspects of this embodiment, an Activin A comprises a polypeptide having, e.g., at least one, two, three, four, five, six, seven, eight, nine, 10 or 20 non-contiguous amino acid deletions relative to amino acids 321-426 of SEQ ID NO: 66. In still other aspects of this embodiment, an Activin A comprises a polypeptide having, e.g., at most one, two, three, four, five, six, seven, eight, nine, 10 or 20 non-contiguous amino acid additions relative to amino acids 321-426 of SEQ ID NO: 66. In other aspects of this embodiment, an Activin A comprises a polypeptide having, e.g., at least one, two, three, four, five, six, seven, eight, nine, 10 or 20 non-contiguous amino acid additions relative to amino acids 321-426 of SEQ ID NO: 66.

In other aspects of this embodiment, an Activin A comprises a polypeptide having, e.g., at most one, two, three, four, five, six, seven, eight, nine, 10 or 20 contiguous amino acid substitutions relative to amino acids 321-426 of SEQ ID NO: 66. In other aspects of this embodiment, an Activin A comprises a polypeptide having, e.g., at least one, two, three, four, five, six, seven, eight, nine, 10 or 20 contiguous amino acid substitutions relative to amino acids 321-426 of SEQ ID NO: 66. In yet other aspects of this embodiment, an Activin A comprises a polypeptide having, e.g., at most one, two, three, four, five, six, seven, eight, nine, 10 or 20 contiguous amino acid deletions relative to amino acids 321-426 of SEQ ID NO: 66. In other aspects of this embodiment, an Activin A comprises a polypeptide having, e.g., at least one, two, three, four, five, six, seven, eight, nine, 10 or 20 contiguous amino acid deletions relative to amino acids 321-426 of SEQ ID NO: 66. In still other aspects of this embodiment, an Activin A comprises a polypeptide having, e.g., at most one, two, three, four, five, six, seven, eight, nine, 10 or 20 contiguous amino acid additions relative to amino acids 321-426 of SEQ ID NO: 66. In other aspects of this embodiment, an Activin A comprises a polypeptide having, e.g., at least one, two, three, four, five, six, seven, eight, nine, 10 or 20 contiguous amino acid additions relative to amino acids 321-426 of SEQ ID NO: 66.

In another embodiment, an enhanced binding domain is derived from an Activin B. In another embodiment, an enhanced binding domain is derived from an Activin B of SEQ ID NO: 67. In an aspect of this embodiment, an enhanced binding domain is derived from an Activin B comprises amino acids 303-406 of SEQ ID NO: 67.

In other aspects of this embodiment, an Activin B comprises a polypeptide having, e.g., at least 70% amino acid identity with amino acids 303-406 of SEQ ID NO: 67, at least 75% amino acid identity with amino acids 303-406 of SEQ ID NO: 67, at least 80% amino acid identity with amino acids 303-406 of SEQ ID NO: 67, at least 85% amino acid identity with amino acids 303-406 of SEQ ID NO: 67, at least 90% amino acid identity with amino acids 303-406 of SEQ ID NO: 67 or at least 95% amino acid identity with amino acids 303-406 of SEQ ID NO: 67. In yet other aspects of this embodiment, an Activin B comprises a polypeptide having, e.g., at most 70% amino acid identity with amino acids 303-406 of SEQ ID NO: 67, at most 75% amino acid identity with amino acids 303-406 of SEQ ID NO: 67, at most 80% amino acid identity with amino acids 303-406 of SEQ ID NO: 67, at most 85% amino acid identity with amino acids 303-406 of SEQ ID NO: 67, at most 90% amino acid identity with amino acids 303-406 of SEQ ID NO: 67 or at most 95% amino acid identity with amino acids 303-406 of SEQ ID NO: 67.

In other aspects of this embodiment, an Activin B comprises a polypeptide having, e.g., at most one, two, three, four, five, six, seven, eight, nine, 10 or 20 non-contiguous amino acid substitutions relative to amino acids 303-406 of SEQ ID NO: 67. In other aspects of this embodiment, an Activin B comprises a polypeptide having, e.g., at least one, two, three, four, five, six, seven, eight, nine, 10 or 20 non-contiguous amino acid substitutions relative to amino acids 303-406 of SEQ ID NO: 67. In yet other aspects of this embodiment, an Activin B comprises a polypeptide having, e.g., at most one, two, three, four, five, six, seven, eight, nine, 10 or 20 non-contiguous amino acid deletions relative to amino acids 303-406 of SEQ ID NO: 67. In other aspects of this embodiment, an Activin B comprises a polypeptide having, e.g., at least one, two, three, four, five, six, seven, eight, nine, 10 or 20 non-contiguous amino acid deletions relative to amino acids 303-406 of SEQ ID NO: 67. In still other aspects of this embodiment, an Activin B comprises a polypeptide having, e.g., at most one, two, three, four, five, six, seven, eight, nine, 10 or 20 non-contiguous amino acid additions relative to amino acids 303-406 of SEQ ID NO: 67. In other aspects of this embodiment, an Activin B comprises a polypeptide having, e.g., at least one, two, three, four, five, six, seven, eight, nine, 10 or 20 non-contiguous amino acid additions relative to amino acids 303-406 of SEQ ID NO: 67.

In other aspects of this embodiment, an Activin B comprises a polypeptide having, e.g., at most one, two, three, four, five, six, seven, eight, nine, 10 or 20 contiguous amino acid substitutions relative to amino acids 303-406 of SEQ ID NO: 67. In other aspects of this embodiment, an Activin B comprises a polypeptide having, e.g., at least one, two, three, four, five, six, seven, eight, nine, 10 or 20 contiguous amino acid substitutions relative to amino acids 303-406 of SEQ ID NO: 67. In yet other aspects of this embodiment, an Activin B comprises a polypeptide having, e.g., at most one, two, three, four, five, six, seven, eight, nine, 10 or 20 contiguous amino acid deletions relative to amino acids 303-406 of SEQ ID NO: 67. In other aspects of this embodiment, an Activin B comprises a polypeptide having, e.g., at least one, two, three, four, five, six, seven, eight, nine, 10 or 20 contiguous amino acid deletions relative to amino acids 303-406 of SEQ ID NO: 67. In still other aspects of this embodiment, an Activin B comprises a polypeptide having, e.g., at most one, two, three, four, five, six, seven, eight, nine, 10 or 20 contiguous amino acid additions relative to amino acids 303-406 of SEQ ID NO: 67. In other aspects of this embodiment, an Activin B comprises a polypeptide having, e.g., at least one, two, three, four, five, six, seven, eight, nine, 10 or 20 contiguous amino acid additions relative to amino acids 303-406 of SEQ ID NO: 67.

In another embodiment, an enhanced binding domain is derived from an Activin C. In another embodiment, an enhanced binding domain is derived from an Activin C of SEQ ID NO: 68. In an aspect of this embodiment, an enhanced binding domain is derived from an Activin C comprises amino acids 247-352 or amino acids 237-352 of SEQ ID NO: 68.

In other aspects of this embodiment, an Activin C comprises a polypeptide having, e.g., at least 70% amino acid identity with amino acids 247-352 or amino acids 237-352 of SEQ ID NO: 68, at least 75% amino acid identity with amino acids 247-352 or amino acids 237-352 of SEQ ID NO: 68, at least 80% amino acid identity with amino acids 247-352 or amino acids 237-352 of SEQ ID NO: 68, at least 85% amino acid identity with amino acids 247-352 or amino acids 237-352 of SEQ ID NO: 68, at least 90% amino acid identity with amino acids 247-352 or amino acids 237-352 of SEQ ID NO: 68 or at least 95% amino acid identity with amino acids 247-352 or amino acids 237-352 of SEQ ID NO: 68. In yet other aspects of this embodiment, an Activin C comprises a polypeptide having, e.g., at most 70% amino acid identity with amino acids 247-352 or amino acids 237-352 of SEQ ID NO: 68, at most 75% amino acid identity with amino acids 247-352 or amino acids 237-352 of SEQ ID NO: 68, at most 80% amino acid identity with amino acids 247-352 or amino acids 237-352 of SEQ ID NO: 68, at most 85% amino acid identity with amino acids 247-352 or amino acids 237-352 of SEQ ID NO: 68, at most 90% amino acid identity with amino acids 247-352 or amino acids 237-352 of SEQ ID NO: 68 or at most 95% amino acid identity with amino acids 247-352 or amino acids 237-352 of SEQ ID NO: 68.

In other aspects of this embodiment, an Activin C comprises a polypeptide having, e.g., at most one, two, three, four, five, six, seven, eight, nine, 10 or 20 non-contiguous amino acid substitutions relative to amino acids 247-352 or amino acids 237-352 of SEQ ID NO: 68. In other aspects of this embodiment, an Activin C comprises a polypeptide having, e.g., at least one, two, three, four, five, six, seven, eight, nine, 10 or 20 non-contiguous amino acid substitutions relative to amino acids 247-352 or amino acids 237-352 of SEQ ID NO: 68. In yet other aspects of this embodiment, an Activin C comprises a polypeptide having, e.g., at most one, two, three, four, five, six, seven, eight, nine, 10 or 20 non-contiguous amino acid deletions relative to amino acids 247-352 or amino acids 237-352 of SEQ ID NO: 68. In other aspects of this embodiment, an Activin C comprises a polypeptide having, e.g., at least one, two, three, four, five, six, seven, eight, nine, 10 or 20 non-contiguous amino acid deletions relative to amino acids 247-352 or amino acids 237-352 of SEQ ID NO: 68. In still other aspects of this embodiment, an Activin C comprises a polypeptide having, e.g., at most one, two, three, four, five, six, seven, eight, nine, 10 or 20 non-contiguous amino acid additions relative to amino acids 247-352 or amino acids 237-352 of SEQ ID NO: 68. In other aspects of this embodiment, an Activin C comprises a polypeptide having, e.g., at least one, two, three, four, five, six, seven, eight, nine, 10 or 20 non-contiguous amino acid additions relative to amino acids 247-352 or amino acids 237-352 of SEQ ID NO: 68.

In other aspects of this embodiment, an Activin C comprises a polypeptide having, e.g., at most one, two, three, four, five, six, seven, eight, nine, 10 or 20 contiguous amino acid substitutions relative to amino acids 247-352 or amino acids 237-352 of SEQ ID NO: 68. In other aspects of this embodiment, an Activin C comprises a polypeptide having, e.g., at least one, two, three, four, five, six, seven, eight, nine, 10 or 20 contiguous amino acid substitutions relative to amino acids 247-352 or amino acids 237-352 of SEQ ID NO: 68. In yet other aspects of this embodiment, an Activin C comprises a polypeptide having, e.g., at most one, two, three, four, five, six, seven, eight, nine, 10 or 20 contiguous amino acid deletions relative to amino acids 247-352 or amino acids 237-352 of SEQ ID NO: 68. In other aspects of this embodiment, an Activin C comprises a polypeptide having, e.g., at least one, two, three, four, five, six, seven, eight, nine, 10 or 20 contiguous amino acid deletions relative to amino acids 247-352 or amino acids 237-352 of SEQ ID NO: 68. In still other aspects of this embodiment, an Activin C comprises a polypeptide having, e.g., at most one, two, three, four, five, six, seven, eight, nine, 10 or 20 contiguous amino acid additions relative to amino acids 247-352 or amino acids 237-352 of SEQ ID NO: 68. In other aspects of this embodiment, an Activin C comprises a polypeptide having, e.g., at least one, two, three, four, five, six, seven, eight, nine, 10 or 20 contiguous amino acid additions relative to amino acids 247-352 or amino acids 237-352 of SEQ ID NO: 68.

In another embodiment, an enhanced binding domain is derived from an Activin E. In another embodiment, an enhanced binding domain is derived from an Activin E of SEQ ID NO: 69. In an aspect of this embodiment, an enhanced binding domain is derived from an Activin E comprises amino acids 247-350 of SEQ ID NO: 69.

In other aspects of this embodiment, an Activin E comprises a polypeptide having, e.g., at least 70% amino acid identity with amino acids 247-350 of SEQ ID NO: 69, at least 75% amino acid identity with amino acids 247-350 of SEQ ID NO: 69, at least 80% amino acid identity with amino acids 247-350 of SEQ ID NO: 69, at least 85% amino acid identity with amino acids 247-350 of SEQ ID NO: 69, at least 90% amino acid identity with amino acids 247-350 of SEQ ID NO: 69 or at least 95% amino acid identity with amino acids 247-350 of SEQ ID NO: 69. In yet other aspects of this embodiment, an Activin E comprises a polypeptide having, e.g., at most 70% amino acid identity with amino acids 247-350 of SEQ ID NO: 69, at most 75% amino acid identity with amino acids 247-350 of SEQ ID NO: 69, at most 80% amino acid identity with amino acids 247-350 of SEQ ID NO: 69, at most 85% amino acid identity with amino acids 247-350 of SEQ ID NO: 69, at most 90% amino acid identity with amino acids 247-350 of SEQ ID NO: 69 or at most 95% amino acid identity with amino acids 247-350 of SEQ ID NO: 69.

In other aspects of this embodiment, an Activin E comprises a polypeptide having, e.g., at most one, two, three, four, five, six, seven, eight, nine, 10 or 20 non-contiguous amino acid substitutions relative to amino acids 247-350 of SEQ ID NO: 69. In other aspects of this embodiment, an Activin E comprises a polypeptide having, e.g., at least one, two, three, four, five, six, seven, eight, nine, 10 or 20 non-contiguous amino acid substitutions relative to amino acids 247-350 of SEQ ID NO: 69. In yet other aspects of this embodiment, an Activin E comprises a polypeptide having, e.g., at most one, two, three, four, five, six, seven, eight, nine, 10 or 20 non-contiguous amino acid deletions relative to amino acids 247-350 of SEQ ID NO: 69. In other aspects of this embodiment, an Activin E comprises a polypeptide having, e.g., at least one, two, three, four, five, six, seven, eight, nine, 10 or 20 non-contiguous amino acid deletions relative to amino acids 247-350 of SEQ ID NO: 69. In still other aspects of this embodiment, an Activin E comprises a polypeptide having, e.g., at most one, two, three, four, five, six, seven, eight, nine, 10 or 20 non-contiguous amino acid additions relative to amino acids 247-350 of SEQ ID NO: 69. In other aspects of this embodiment, an Activin E comprises a polypeptide having, e.g., at least one, two, three, four, five, six, seven, eight, nine, 10 or 20 non-contiguous amino acid additions relative to amino acids 247-350 of SEQ ID NO: 69.

In other aspects of this embodiment, an Activin E comprises a polypeptide having, e.g., at most one, two, three, four, five, six, seven, eight, nine, 10 or 20 contiguous amino acid substitutions relative to amino acids 247-350 of SEQ ID NO: 69. In other aspects of this embodiment, an Activin E comprises a polypeptide having, e.g., at least one, two, three, four, five, six, seven, eight, nine, 10 or 20 contiguous amino acid substitutions relative to amino acids 247-350 of SEQ ID NO: 69. In yet other aspects of this embodiment, an Activin E comprises a polypeptide having, e.g., at most one, two, three, four, five, six, seven, eight, nine, 10 or 20 contiguous amino acid deletions relative to amino acids 247-350 of SEQ ID NO: 69. In other aspects of this embodiment, an Activin E comprises a polypeptide having, e.g., at least one, two, three, four, five, six, seven, eight, nine, 10 or 20 contiguous amino acid deletions relative to amino acids 247-350 of SEQ ID NO: 69. In still other aspects of this embodiment, an Activin E comprises a polypeptide having, e.g., at most one, two, three, four, five, six, seven, eight, nine, 10 or 20 contiguous amino acid additions relative to amino acids 247-350 of SEQ ID NO: 69. In other aspects of this embodiment, an Activin E comprises a polypeptide having, e.g., at least one, two, three, four, five, six, seven, eight, nine, 10 or 20 contiguous amino acid additions relative to amino acids 247-350 of SEQ ID NO: 69.

In another embodiment, an enhanced binding domain is derived from an Inhibin A. In another embodiment, an enhanced binding domain is derived from an Inhibin A of SEQ ID NO: 70. In an aspect of this embodiment, an enhanced binding domain is derived from an Inhibin A comprises amino acids 262-366 or amino acids 233-366 of SEQ ID NO: 70.

In other aspects of this embodiment, an Inhibin A comprises a polypeptide having, e.g., at least 70% amino acid identity with amino acids 262-366 or amino acids 233-366 of SEQ ID NO: 70, at least 75% amino acid identity with amino acids 262-366 or amino acids 233-366 of SEQ ID NO: 70, at least 80% amino acid identity with amino acids 262-366 or amino acids 233-366 of SEQ ID NO: 70, at least 85% amino acid identity with amino acids 262-366 or amino acids 233-366 of SEQ ID NO: 70, at least 90% amino acid identity with amino acids 262-366 or amino acids 233-366 of SEQ ID NO: 70 or at least 95% amino acid identity with amino acids 262-366 or amino acids 233-366 of SEQ ID NO: 70. In yet other aspects of this embodiment, an Inhibin A comprises a polypeptide having, e.g., at most 70% amino acid identity with amino acids 262-366 or amino acids 233-366 of SEQ ID NO: 70, at most 75% amino acid identity with amino acids 262-366 or amino acids 233-366 of SEQ ID NO: 70, at most 80% amino acid identity with amino acids 262-366 or amino acids 233-366 of SEQ ID NO: 70, at most 85% amino acid identity with amino acids 262-366 or amino acids 233-366 of SEQ ID NO: 70, at most 90% amino acid identity with amino acids 262-366 or amino acids 233-366 of SEQ ID NO: 70 or at most 95% amino acid identity with amino acids 262-366 or amino acids 233-366 of SEQ ID NO: 70.

In other aspects of this embodiment, an Inhibin A comprises a polypeptide having, e.g., at most one, two, three, four, five, six, seven, eight, nine, 10 or 20 non-contiguous amino acid substitutions relative to amino acids 262-366 or amino acids 233-366 of SEQ ID NO: 70. In other aspects of this embodiment, an Inhibin A comprises a polypeptide having, e.g., at least one, two, three, four, five, six, seven, eight, nine, 10 or 20 non-contiguous amino acid substitutions relative to amino acids 262-366 or amino acids 233-366 of SEQ ID NO: 70. In yet other aspects of this embodiment, an Inhibin A comprises a polypeptide having, e.g., at most one, two, three, four, five, six, seven, eight, nine, 10 or 20 non-contiguous amino acid deletions relative to amino acids 262-366 or amino acids 233-366 of SEQ ID NO: 70. In still other aspects of this embodiment, an Inhibin A comprises a polypeptide having, e.g., at most one, two, three, four, five, six, seven, eight, nine, 10 or 20 non-contiguous amino acid additions relative to amino acids 262-366 or amino acids 233-366 of SEQ ID NO: 70. In other aspects of this embodiment, an Inhibin A comprises a polypeptide having, e.g., at least one, two, three, four, five, six, seven, eight, nine, 10 or 20 non-contiguous amino acid additions relative to amino acids 262-366 or amino acids 233-366 of SEQ ID NO: 70.

In other aspects of this embodiment, an Inhibin A comprises a polypeptide having, e.g., at most one, two, three, four, five, six, seven, eight, nine, 10 or 20 contiguous amino acid substitutions relative to amino acids 262-366 or amino acids 233-366 of SEQ ID NO: 70. In other aspects of this embodiment, an Inhibin A comprises a polypeptide having, e.g., at least one, two, three, four, five, six, seven, eight, nine, 10 or 20 contiguous amino acid substitutions relative to amino acids 262-366 or amino acids 233-366 of SEQ ID NO: 70. In yet other aspects of this embodiment, an Inhibin A comprises a polypeptide having, e.g., at most one, two, three, four, five, six, seven, eight, nine, 10 or 20 contiguous amino acid deletions relative to amino acids 262-366 or amino acids 233-366 of SEQ ID NO: 70. In other aspects of this embodiment, an Inhibin A comprises a polypeptide having, e.g., at least one, two, three, four, five, six, seven, eight, nine, 10 or 20 contiguous amino acid deletions relative to amino acids 262-366 or amino acids 233-366 of SEQ ID NO: 70. In still other aspects of this embodiment, an Inhibin A comprises a polypeptide having, e.g., at most one, two, three, four, five, six, seven, eight, nine, 10 or 20 contiguous amino acid additions relative to amino acids 262-366 or amino acids 233-366 of SEQ ID NO: 70. In other aspects of this embodiment, an Inhibin A comprises a polypeptide having, e.g., at least one, two, three, four, five, six, seven, eight, nine, 10 or 20 contiguous amino acid additions relative to amino acids 262-366 or amino acids 233-366 of SEQ ID NO: 70.

An enhanced targeting domain disclosed in the present specification replaces the binding activity of the Clostridial toxin binding domain found in naturally occurring Clostridial toxins. As used herein, the term "Clostridial toxin binding domain" is synonomous with "Clostridial toxin $H_C$ region" and means any naturally occurring Clostridial toxin polypeptide that can execute the cell binding step of the intoxication process, including, e.g., the binding of the Clostridial toxin to a Clostridial toxin-specific receptor system located on the plasma membrane surface of a target cell. It is envisioned that replacement of the binding activity can be achieved by, e.g., replacing the entire Clostridial toxin binding domain with an enhanced targeting domain; replacing a portion of a Clostridial toxin binding domain with an enhanced targeting domain, with the proviso that the portion of a Clostridial toxin binding domain remaining cannot selectively bind to its Clostridial toxin receptor system; and operationally-linking an enhanced targeting domain to a Clostridial toxin comprising a Clostridial toxin binding domain, with the proviso that the a Clostridial toxin binding domain is altered so that it cannot selectively bind to its Clostridial toxin receptor system.

The three-dimensional crystal structures of BoNT/A, BoNT/B and the $H_C$ domain of TeNT indicate that the three functional domains of Clostridial neurotoxins are structurally distinct. The HEXXH consensus motif of the light chain forms the tetrahedral zinc binding pocket of the catalytic site located in a deep cleft on the protein surface that is accessible by a channel. The structure of the $H_N$ and $H_C$ domains consists primarily of β-sheet topologies that are linked by a single α-helix. The cylindrical-shaped $H_N$ domain comprises two long amphipathic α-helices that resemble the coiled-coil motif found in some viral proteins. The $H_N$ domain also forms a long unstructured loop called the 'translocation belt,' which wraps around a large negatively charged cleft of the light chain that blocks access of the zinc atom to the catalytic-binding pocket of active site. The $H_C$ domain comprises two distinct structural features of roughly equal size that indicate function. The first, designated the $H_{CN}$ subdomain, is located in the amino half of the $H_C$ domain. The $H_{CN}$ subdomain forms a β-barrel, jelly-roll fold. The $H_{CC}$ subdomain is the second subdomain that comprises the $H_C$ domain. This carboxy-terminal subdomain comprises a modified β-trefoil domain which forms three distinct carbohydrate binding regions that resembles the carbohydrate binding moiety found in many sugar-binding proteins, such as, e.g., serum amyloid P, sialidase, cryia, insecticidal ϑ-endotoxin and lectins. Biochemical studies indicate that the β-trefoil domain structure of the $H_{CC}$ subdomain appears to mediate the binding to specific carbohydrate containing components of the Clostridial toxin receptor system on the cell surface, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site*, 482(1-2) FEBS Lett. 119-124 (2000). The $H_C$ domain tilts away from the $H_N$ domain exposing the surface loops and making them accessible for binding. No contacts occur between the light chain and the $H_C$ domain.

Proteins containing the structural β-trefoil domain represents a diverse group of proteins, see, e.g., C. A. Orengo et al., *Protein Superfamilies and Domain Superfolds*, 372 Nature 631-634 (1994). The β-trefoil domain comprises a six-stranded β-barrel closed off at one end by three β-hairpin structures that exhibits a characteristic pseudo-threefold axis symmetry. The monomeric structural unit of this three-fold symmetry is referred to as the β-trefoil fold that contains four β-sheets organized as a pair of antiparallel β-sheets. Dividing each of these β-trefoil folds is a β-hairpin turn. Therefore, in a linear fashion, a β-trefoil domain comprises four β-sheets of the first β-trefoil fold, a β-hairpin turn, four β-sheets of the second β-trefoil fold, a second β-hairpin turn four β-sheets of the third β-trefoil fold. Because the first hairpin turn is located between the fourth and fifth β-sheets of the β-trefoil domain, it is designated the β4/β5 β-hairpin turn. Likewise, since the second hairpin turn is located between the eight and ninth β-sheets of the β-trefoil domain, it is designated the β8/β9 β-hairpin turn.

As is typical for proteins containing a β-trefoil fold, the overall amino acid sequence identity of the $H_{CC}$ subdomain between Clostridial toxins is low. However, key residues essential for binding activity have been identified by structural analysis and mutagenesis experiments, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site*, 482(1-2) FEBS Lett. 119-124 (2000); and Andreas Rummel et al., *The $H_{CC}$-Domain of Botulinum Neurotoxins A and B Exhibits a Singular Ganglioside Binding Site Displaying Serotype Specific Carbohydrate Interaction*, 51(3) Mol. Microbiol. 631-643 (2004). Additionally, research has elucidated that β4/β5 and β8/β9 β-hairpin turns are important in conferring the proper pseudo-threefold axis symmetry observed in the β-trefoil domain and that these turns are important for β-trefoil domain stability, see, e.g., Stephen R. Brych et al., *Structure and Stability Effects of Mutations Designed to Increase the Primary Sequence Symmetry Within the Core Region of a β-trefoil*, 10 Protein Sci. 2587-2599 (2001); Jaewon Kim et al., *Alternative Type I and I' Turn Conformations in the β8/β9 β-hairpin of Human Acidic Fibroblast Growth Factor*, 11 Protein Sci. 459-466 (2002); Jaewon Kim et al., *Sequence swapping Does Not Result in Conformation Swapping for the β4/β5 and β8/β9 β-hairpin Turns in Human Acidic Fibroblast Growth Factor*, 14 Protein Sci. 351-359 (2005). The amino acid sequences comprising the β-trefoil domains found in various Clostridial toxins are shown in Table 2.

TABLE 2

β-trefoil Domains of Clostridial Toxins

| | | Amino Acid Sequence Region of Carbohydrate Binding Moieties | | | | |
|---|---|---|---|---|---|---|
| Protein | SEQ ID NO: | α-fold | β4/β5 β-hairpin turn | β-fold | β8/β9 β-hairpin turn | γ-fold |
| BoNT/A | 1 | 1111-1162 | 1163-1178 | 1179-1223 | 1224-1236 | 1237-1296 |
| BoNT/B | 2 | 1098-1147 | 1148-1165 | 1166-1210 | 1211-1222 | 1223-1291 |
| BoNT/C1 | 3 | 1112-1150 | 1151-1166 | 1167-1218 | 1219-1229 | 1230-1291 |
| BoNT/D | 4 | 1099-1137 | 1138-1153 | 1154-1207 | 1208-1218 | 1219-1276 |
| BoNT/E | 5 | 1086-1129 | 1130-1146 | 1147-1190 | 1191-1198 | 1199-1252 |
| BoNT/F | 6 | 1106-1152 | 1153-1171 | 1172-1213 | 1214-1221 | 1222-1274 |
| BoNT/G | 7 | 1106-1153 | 1154-1172 | 1173-1218 | 1219-1230 | 1231-1297 |
| TeNT | 8 | 1128-1177 | 1178-1194 | 1195-1240 | 1241-1254 | 1255-1315 |

Thus, in one embodiment, a Clostridial toxin binding domain comprising an $H_C$ region can be replaced with an enhance binding domain disclosed in the present specification. In aspects of this embodiment, a BoNT/A $H_C$ region can be replaced with an enhanced targeting domain, a BoNT/B $H_C$ region can be replaced with an enhanced targeting domain, a BoNT/C1 $H_C$ region can be replaced with an enhanced targeting domain, a BoNT/D $H_C$ region can be replaced with an enhanced targeting domain, a BoNT/E $H_C$ region can be replaced with an enhanced targeting domain, a BoNT/F $H_C$ region can be replaced with an enhanced targeting domain, a BoNT/G $H_C$ region can be replaced with an enhanced targeting domain and a TeNT $H_C$ region can be replaced with an enhanced targeting domain. In other aspects of this embodiment, a BoNT/A $H_C$ region comprising amino acids 872-1296 of SEQ ID NO: 1 can be replaced with an enhanced targeting domain, a BoNT/B $H_C$ region comprising amino acids 859-1291 of SEQ ID NO: 2 can be replaced with an enhanced targeting domain, a BoNT/C1 $H_C$ region comprising amino acids 867-1291 of SEQ ID NO: 3 can be replaced with an enhanced targeting domain, a BoNT/D $H_C$ region comprising amino acids 863-1276 of SEQ ID NO: 4 can be replaced with an enhanced targeting domain, a BoNT/E $H_C$ region comprising amino acids 846-1252 of SEQ ID NO: 5 can be replaced with an enhanced targeting domain, a BoNT/F $H_C$ region comprising amino acids 865-1274 of SEQ ID NO: 6 can be replaced with an enhanced targeting domain, a BoNT/G $H_C$ region comprising amino acids 864-1297 of SEQ ID NO: 7 can be replaced with an enhanced targeting domain and a TeNT $H_C$ region comprising amino acids 880-1315 of SEQ ID NO: 8 can be replaced with an enhanced targeting domain.

In another embodiment, a Clostridial toxin binding domain comprising an $H_{CC}$ region can be replaced with an enhance binding domain disclosed in the present specification. In aspects of this embodiment, a BoNT/A $H_{CC}$ region can be replaced with an enhanced targeting domain, a BoNT/B $H_{CC}$ region can be replaced with an enhanced targeting domain, a BoNT/C1 $H_{CC}$ region can be replaced with an enhanced targeting domain, a BoNT/D $H_{CC}$ region can be replaced with an enhanced targeting domain, a BoNT/E $H_{CC}$ region can be replaced with an enhanced targeting domain, a BoNT/F $H_{CC}$ region can be replaced with an enhanced targeting domain, a BoNT/G $H_{CC}$ region can be replaced with an enhanced targeting domain and a TeNT $H_{CC}$ region can be replaced with an enhanced targeting domain. In other aspects of this embodiment, a BoNT/A $H_{CC}$ region comprising amino acids 1092-1296 of SEQ ID NO: 1 can be replaced with an enhanced targeting domain, a BoNT/B $H_{CC}$ region comprising amino acids 1079-1291 of SEQ ID NO: 2 can be replaced with an enhanced targeting domain, a BoNT/C1 $H_{CC}$ region comprising amino acids 1093-1291 of SEQ ID NO: 3 can be replaced with an enhanced targeting domain, a BoNT/D $H_{CC}$ region comprising amino acids 1080-1276 of SEQ ID NO: 4 can be replaced with an enhanced targeting domain, a BoNT/E $H_{CC}$ region comprising amino acids 1067-1252 of SEQ ID NO: 5 can be replaced with an enhanced targeting domain, a BoNT/F $H_{CC}$ region comprising amino acids 1087-1274 of SEQ ID NO: 6 can be replaced with an enhanced targeting domain, a BoNT/G $H_{CC}$ region comprising amino acids 1087-1297 of SEQ ID NO: 7 can be replaced with an enhanced targeting domain and a TeNT $H_{CC}$ region comprising amino acids 1109-1315 of SEQ ID NO: 8 can be replaced with an enhanced targeting domain.

In another embodiment, an enhance binding domain disclosed in the present specification is operationally-linked to a Clostridial toxin comprising a Clostridial toxin binding domain altered so that it cannot selectively bind to its Clostridial toxin receptor system. As used herein, the term "altered," when referring to a Clostridial toxin binding domain, means a naturally occurring Clostridial toxin binding domain modified to eliminate or reduce the binding activity of the Clostridial toxin binding domain so that the domain can no longer selectively bind to a Clostridial toxin receptor system. By definition, an altered Clostridial toxin binding domain has at least one amino acid change from the corresponding region of the disclosed reference sequences (see Table 1) and can be described in percent identity to the corresponding region of that reference sequence. As non-limiting examples, a modified BoNT/A $H_C$ region comprising amino acids 872-1296 of SEQ ID NO: 1 will have at least one amino acid difference, such as, e.g., an amino acid substitution, deletion or addition, as compared to the amino acid region 872-1296 of SEQ ID NO: 1; a modified BoNT/B $H_C$ region comprising amino acids 859-1291 of SEQ ID NO: 2 will have at least one amino acid difference, such as, e.g., an amino acid substitution, deletion or addition, as compared to the amino acid region 859-1291 of SEQ ID NO: 2; a modified BoNT/C1 $H_C$ region comprising amino acids 867-1291 of SEQ ID NO: 3 will have at least one amino acid difference, such as, e.g., an amino acid substitution, deletion or addition, as compared to the amino acid region 867-1291 of SEQ ID NO: 3; a modified BoNT/D $H_C$ region comprising amino acids 863-1276 of SEQ ID NO: 4 will have at least one amino acid difference, such as, e.g., an amino acid substitution, deletion or addition, as compared to the amino acid region 863-1276 of SEQ ID NO: 4; a modified BoNT/E $H_C$ region comprising amino acids 846-1252 of SEQ ID NO: 5 will have at least one amino acid difference, such as, e.g., an amino acid substitution, deletion or addition, as compared to the amino acid region 846-1252 of SEQ ID NO: 5; a modified BoNT/F $H_C$ region comprising amino acids 865-1274 of SEQ ID NO: 6 will have at least one amino acid difference, such as, e.g., an amino acid substitution, deletion or addition, as compared to the amino acid region 865-1274 of SEQ ID NO: 6; a modified BoNT/G $H_C$ region comprising amino acids 864-1297 of SEQ ID NO: 7 will have at least one amino acid difference, such as, e.g., an amino acid substitution, deletion or addition, as compared to the amino acid region 864-1297 of SEQ ID NO: 7; and a modified TeNT $H_C$ region comprising amino acids 880-1315 of SEQ ID NO: 8 will have at least one amino acid difference, such as, e.g., an amino acid substitution, deletion or addition, as compared to the amino acid region 880-1315 of SEQ ID NO: 8.

In aspects of this embodiment, an altered Clostridial toxin $H_C$ region comprises a polypeptide having, e.g., at least 70% amino acid identity with its reference sequence, at least 75% amino acid identity with its reference sequence, at least 80% amino acid identity with its reference sequence, at least 85% amino acid identity with its reference sequence, at least 90% amino acid identity with its reference sequence or at least 95% amino acid identity with its reference sequence. In yet other aspects of this embodiment, an altered Clostridial toxin $H_C$ region comprises a polypeptide having, e.g., at most 70% amino acid identity with its reference sequence, at most 75% amino acid identity with its reference sequence, at most 80% amino acid identity with its reference sequence, at most 85% amino acid identity with its reference sequence, at most 90% amino acid identity with its reference sequence or at most 95% amino acid identity with its reference sequence.

In other aspects of this embodiment, an altered Clostridial toxin $H_C$ region comprises a polypeptide having, e.g., at most one, two, three, four, five, six, seven, eight, nine, 10, 20, 30, 40, 50, 100, or 200 non-contiguous amino acid substitutions relative to its reference sequence. In other aspects of this embodiment, an altered Clostridial toxin $H_C$ region comprises a polypeptide having, e.g., at least one, two, three, four, five, six, seven, eight, nine, 10, 20, 30, 40, 50, 100 or 200 non-contiguous amino acid substitutions relative to its reference sequence. In yet other aspects of this embodiment, an altered Clostridial toxin $H_C$ region comprises a polypeptide having, e.g., at most one, two, three, four, five, six, seven, eight, nine, 10, 20, 30, 40, 50, 100 or 200 non-contiguous amino acid deletions relative to its reference sequence. In other aspects of this embodiment, an altered Clostridial toxin $H_C$ region comprises a polypeptide having, e.g., at least one, two, three, four, five, six, seven, eight, nine, 10, 20, 30, 40, 50, 100 or 200 non-contiguous amino acid deletions relative to its reference sequence. In still other aspects of this embodiment, an altered Clostridial toxin $H_C$ region comprises a polypeptide having, e.g., at most one, two, three, four, five, six, seven, eight, nine, 10, 20, 30, 40, 50, 100 or 200 non-contiguous amino acid additions relative to its reference sequence. In other aspects of this embodiment, an altered Clostridial toxin $H_C$ region comprises a polypeptide having, e.g., at least one, two, three, four, five, six, seven, eight, nine, 10, 20, 30, 40, 50, 100 or 200 non-contiguous amino acid additions relative to its reference sequence.

In other aspects of this embodiment, an altered Clostridial toxin $H_C$ region comprises a polypeptide having, e.g., at most one, two, three, four, five, six, seven, eight, nine, 10, 20, 30, 40, 50, 100 or 200 contiguous amino acid substitutions relative to its reference sequence. In other aspects of this embodiment, an altered Clostridial toxin $H_C$ region comprises a polypeptide having, e.g., at least one, two, three, four, five, Clostridial toxin into the di-chain form. Non-limiting examples of a Clostridial toxin di-chain loop region, include, a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; and a di-chain loop region of TeNT comprising amino acids 439-467 of SEQ ID NO: 8 (Table 3).

TABLE 3

Di-chain Loop Region of Clostridial Toxins

| Toxin | SEQ ID NO: | Light Chain Region | Di-chain Loop Region Containing the Naturally-occurring Protease Cleavage Site | Heavy Chain Region |
| --- | --- | --- | --- | --- |
| BoNT/A | 1 | NMNFTKLKNFTGLFEFYKLL | CVRGIITSKTKSLDKGYNK----ALNDLC | IKVNNWDL |
| BoNT/B | 2 | KQAYEEISKEHLAVYKIQM | CKSVK*-----------------APGIC | IDVDNEDL |
| BoNT/C1 | 3 | PALRKVNPENMLYLFTKF | CHKAIDGRSLYNK*------------TLDC | RELLVKNTDL |
| BoNT/D | 4 | PALQKLSSESVVDLFTKV | CLRLTKNSR*---------------DDSTC | IKVKNNRL |
| BoNT/E | 5 | IITPITGRGLVKKIIRF | CKNIVSVKGIR*--------------KSIC | IEINNGEL |
| BoNT/F | 6 | IIDSIPDKGLVEKIVKF | CKSVIPRKGTK*------------APPRLC | IRVNNSEL |
| BoNT/G | 7 | KEAYEEISLEHLVIYRIAM | CKPVMYKNTGK*--------------SEQC | IIVNNEDL |
| TeNT | 8 | TNAFRNVDGSGLVSKLIGL | CKKIIPPTNIRENLYNRTA*SLTDLGGELC | IKIKNEDL |

The amino acid sequence displayed are as follows: BoNT/A, residues 325-462 of SEQ ID No: 1; BoNT/B, residues 332-454 of SEQ ID No: 2; BoNT/C1, residues 334-463 of SEQ ID No: 3; BoNT/D, residues 334-458 of SEQ ID No: 4; BoNT/E, residues 311-434 of SEQ ID No: 5; BoNT/F, residues 328-453 of SEQ ID No: 6; BoNT/G, residues 331-458 of SEQ ID No: 7; and TeNT, residues 334-474 of SEQ ID No: 8. An asterisks (*) indicates the peptide bond that is cleaved by a Clostridial toxin protease.

six, seven, eight, nine, 10, 20, 30, 40, 50, 100 or 200 contiguous amino acid substitutions relative to its reference sequence. In yet other aspects of this embodiment, an altered Clostridial toxin $H_C$ region comprises a polypeptide having, e.g., at most one, two, three, four, five, six, seven, eight, nine, 10, 20, 30, 40, 50, 100 or 200 contiguous amino acid deletions relative to its reference sequence. In other aspects of this embodiment, an altered Clostridial toxin $H_C$ region comprises a polypeptide having, e.g., at least one, two, three, four, five, six, seven, eight, nine, 10, 20, 30, 40, 50, 100 or 200 contiguous amino acid deletions relative to its reference sequence. In still other aspects of this embodiment, an altered Clostridial toxin $H_C$ region comprises a polypeptide having, e.g., at most one, two, three, four, five, six, seven, eight, nine, 10, 20, 30, 40, 50, 100 or 200 contiguous amino acid additions relative to its reference sequence. In other aspects of this embodiment, an altered Clostridial toxin $H_C$ region comprises a polypeptide having, e.g., at least one, two, three, four, five, six, seven, eight, nine, 10, 20, 30, 40, 50, 100 or 200 contiguous amino acid additions relative to its reference sequence.

In another aspect of the invention, a modified Clostridial toxin with enhanced binding activity comprises, in part, a protease cleavage site is located within a di-chain loop region. As used herein, the term "di-chain loop region" means the amino acid sequence of a Clostridial toxin containing a protease cleavage site used to convert the single-chain form of a In is envisioned that any and all protease cleavage sites can be used to convert the single-chain polypeptide form of a Clostridial toxin into the di-chain form, including, without limitation, endogenous di-chain loop protease cleavage sites and exogenous protease cleavage sites.

As used herein, the term "endogenous di-chain loop protease cleavage site" is synonymous with a "naturally occurring di-chain loop protease cleavage site" and means a naturally occurring protease cleavage site found within the di-chain loop region of a naturally occurring Clostridial toxin and includes, without limitation, naturally occurring Clostridial toxin di-chain loop protease cleavage site variants, such as, e.g., Clostridial toxin di-chain loop protease cleavage site isoforms and Clostridial toxin di-chain loop protease cleavage site subtypes. Non-limiting examples of an endogenous protease cleavage site, include, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

As mentioned above, Clostridial toxins are translated as a single-chain polypeptide of approximately 150 kDa that is subsequently cleaved by proteolytic scission within a disulfide loop by a naturally-occurring protease. This posttranslational processing yields a di-chain molecule comprising an approximately 50 kDa light chain (LC) and an approximately 100 kDa heavy chain (HC) held together by a single disulphide bond and noncovalent interactions. While the identity of the protease is currently unknown, the di-chain loop protease cleavage site for many Clostridial toxins has been determined. In BoNTs, cleavage at K448-A449 converts the single polypeptide form of BoNT/A into the di-chain form; cleavage at K441-A442 converts the single polypeptide form of BoNT/B into the di-chain form; cleavage at K449-T450 converts the single polypeptide form of BoNT/C1 into the di-chain form; cleavage at R445-D446 converts the single polypeptide form of BoNT/D into the di-chain form; cleavage at R422-K423 converts the single polypeptide form of BoNT/E into the di-chain form; cleavage at K439-A440 converts the single polypeptide form of BoNT/F into the di-chain form; and cleavage at K446-S447 converts the single polypeptide form of BoNT/G into the di-chain form. Proteolytic cleavage of the single polypeptide form of TeNT at A457-S458 results in the di-chain form. Such a di-chain loop protease cleavage site is operably-linked in-frame to a modified Clostridial toxin as a fusion protein. However, it should also be noted that additional cleavage sites within the di-chain loop also appear to be cleaved resulting in the generation of a small peptide fragment being lost. As a non-limiting example, BoNT/A single-chain polypeptide cleave ultimately results in the loss of a ten amino acid fragment within the di-chain loop.

Thus, in an embodiment, a protease cleavage site comprising an endogenous Clostridial toxin di-chain loop protease cleavage site is used to convert the single-chain toxin into the di-chain form. In aspects of this embodiment, conversion into the di-chain form by proteolytic cleavage occurs from a site comprising, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site or a TeNT di-chain loop protease cleavage site.

In other aspects of this embodiment, conversion into the di-chain form by proteolytic cleavage occurs from a site comprising, e.g., a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; or a di-chain loop region of TeNT comprising amino acids 439-467 of SEQ ID NO: 8.

It is also envisioned that an exogenous protease cleavage site can be used to convert the single-chain polypeptide form of a modified Clostridial toxin disclosed in the present specification into the di-chain form. As used herein, the term "exogenous protease cleavage site" is synonymous with a "non-naturally occurring protease cleavage site" and means a protease cleavage site that is not normally present in a di-chain loop region from a naturally occurring Clostridial toxin. Non-limiting examples of exogenous protease cleavage sites include, e.g., an enterokinase cleavage site (Table 4); a Thrombin cleavage site (Table 4); a Factor Xa cleavage site (Table 4); a human rhinovirus 3C protease cleavage site (Table 4); a tobacco etch virus (TEV) protease cleavage site (Table 4); a dipeptidyl aminopeptidase cleavage site; a small ubiquitin-like modifier (SUMO)/ubiquitin-like protein-1 (ULP-1) protease cleavage site, such as, e.g., MADSEVNQEAKPEVKPEVKPETHINLKVSDGSSEIFFKIKKTTPLRRLMEAFAKRQGK EMDSLRFLYDGIRIQADQTPEDLDMEDNDIIEAHREQIGG (SEQ ID. NO: 57); and a Clostridial toxin substrate cleavage site.

TABLE 4

Exogenous Protease Cleavage Sites

| Protease Cleavage Site | Consensus Sequence | Non-limiting Examples | SEQ ID NO: |
|---|---|---|---|
| Bovine enterokinase | DDDDK* | DDDDK* | 71 |
| Tobacco Etch Virus (TEV) | E P⁵P⁴YP²Q*(G/S), where P², P⁴ and P⁵ can be any amino acid | ENLYFQ*G<br>ENLYFQ*S<br>ENIYTQ*G<br>ENIYTQ*S<br>ENIYLQ*G<br>ENIYLQ*S<br>ENVYFQ*G<br>ENVYSQ*S<br>ENVYSQ*G<br>ENVYSQ*S | 72<br>73<br>74<br>75<br>76<br>77<br>78<br>79<br>80<br>81 |
| Human Rhinovirus 3C | P⁵P⁴LFQ*GP where P⁴ is G, A, V, L, I, M, S or T and P⁵ can any amino acid, with D or E preferred. | EALFQ*GP<br>EVLFQ*GP<br>ELLFQ*GP<br>DALFQ*GP<br>DVLFQ*GP<br>DLLFQ*GP | 82<br>83<br>84<br>85<br>86<br>87 |
| SUMO/ULP-1 | Tertiary structure | polypeptide-G* | 88 |
| Thrombin | P³P²(R/K)*P¹', where P³ is any amino acid and P² or P¹' is G with the other position being any amino acid | GVR*G<br>SAR*G<br>SLR*G<br>DGR*I<br>QGK*I | 89<br>90<br>91<br>92<br>93 |
| Thrombin | P⁴P³P(R/K)*P¹' P²' where P¹' and P²' can be any amino acid except for acidic amino acids like D or E; and P³ and P⁴ are hydrophobic amino acids like F, L, I, Y, W, V, M, P, C or A | LVPR*GS<br>LVPK*GS<br>FIPR*TF<br>VLPR*SF<br>IVPR*SF<br>IVPR*GY<br>VVPR*GV<br>VLPR*LI<br>VMPR*SL<br>MFPR*SL | 94<br>95<br>96<br>97<br>98<br>99<br>100<br>101<br>102<br>103 |
| Coagulation Factor Xa | I(E/D)GR* | IDGR*<br>IEGR* | 104<br>105 |

An asterisks (*) indicates the peptide bond that is cleaved by the indicated protease.

As mentioned above, a Clostridial toxin is converted from a single polypeptide form into a di-chain molecule by proteolytic cleavage. While the naturally-occurring protease is currently not known, cleavage occurs within the di-chain loop region between the two cysteine residues that form the disulfide bridge (see Table 3). Replacement of an endogenous protease cleavage site with an exogenous protease cleavage site will enable cleavage of a modified Clostridial toxin disclosed in the present specification when expressed in an organism that does not produce the naturally-occurring protease used to cleave the di-chain loop region of a toxin. Similarly, an addition of an exogenous protease cleavage site in the di-chain loop region will also enable cleavage of a modified Clostridial toxin disclosed in the present specification when expressed in an organism that does not produce the naturally-occurring protease used to cleave the di-chain loop region of a toxin.

It is envisioned that an exogenous protease cleavage site of any and all lengths can be useful in aspects of the present invention with the proviso that the exogenous protease cleavage site is capable of being cleaved by its respective protease. Thus, in aspects of this embodiment, an exogenous protease cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, an exogenous protease cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

In aspects of this embodiment, a di-chain loop region can be modified to substitute a naturally-occurring protease cleavage site for an exogenous protease cleavage site. In this type of modification, the naturally-occurring protease cleavage site is made inoperable and thus can not be cleaved by its protease. Only the exogenous protease cleavage site can be cleaved by its corresponding exogenous protease. In this type of modification, the exogenous protease site is operably-linked in-frame to a modified Clostridial toxin as a fusion protein and the site can be cleaved by its respective exogenous protease. As a non-limiting example, a single-chain modified BoNT/A comprising an exogenous protease cleavage site in the di-chain loop region can be cleaved by its respective exogenous protease to produce the di-chain form of the toxin.

In other aspects of this embodiment, a di-chain loop region can be modified to include an exogenous protease cleavage site in addition to the naturally-occurring protease cleavage site. In this type of modification, both cleavage sites are operably-linked in-frame to a modified Clostridial toxin as a fusion protein and both sites can be cleaved by their respective proteases. As a non-limiting example, a single-chain modified BoNT/A that comprises a di-chain loop containing both the naturally-occurring BoNT/A di-chain loop protease cleavage site and an exogenous protease cleavage site can be cleaved by either the naturally occurring di-chain loop protease or by the appropriate exogenous protease to produce the di-chain form of the toxin.

A naturally-occurring protease cleavage site can be made inoperable by altering at least the two amino acids flanking the peptide bond cleaved by the naturally-occurring di-chain loop protease. More extensive alterations can be made, with the proviso that the two cysteine residues of the di-chain loop region remain intact and can still form the disulfide bridge. Non-limiting examples of an amino acid alteration include deletion of an amino acid or replacement of the original amino acid with a different amino acid. Thus, in one embodiment, a naturally-occurring protease cleavage site is made inoperable by altering the two amino acids flanking the peptide bond cleaved by a naturally-occurring protease. In other aspects of this embodiment, a naturally-occurring protease cleavage site is made inoperable by altering, e.g., at least three amino acids including the two amino acids flanking the peptide bond cleaved by a naturally-occurring protease; at least four amino acids including the two amino acids flanking the peptide bond cleaved by a naturally-occurring protease; at least five amino acids including the two amino acids flanking the peptide bond cleaved by a naturally-occurring protease; at least six amino acids including the two amino acids flanking the peptide bond cleaved by a naturally-occurring protease; at least seven amino acids including the two amino acids flanking the peptide bond cleaved by a naturally-occurring protease; at least eight amino acids including the two amino acids flanking the peptide bond cleaved by a naturally-occurring protease; at least nine amino acids including the two amino acids flanking the peptide bond cleaved by a naturally-occurring protease; at least ten amino acids including the two amino acids flanking the peptide bond cleaved by a naturally-occurring protease; at least 15 amino acids including the two amino acids flanking the peptide bond cleaved by a naturally-occurring protease; or at least 20 amino acids including the two amino acids flanking the peptide bond cleaved by a naturally-occurring protease.

In still other aspects of this embodiment, a naturally-occurring di-chain protease cleavage site is made inoperable by altering, e.g., at most three amino acids including the two amino acids flanking the peptide bond cleaved by a naturally-occurring protease; at most four amino acids including the two amino acids flanking the peptide bond cleaved by a naturally-occurring protease; at most five amino acids including the two amino acids flanking the peptide bond cleaved by a naturally-occurring protease; at most six amino acids including the two amino acids flanking the peptide bond cleaved by a naturally-occurring protease; at most seven amino acids including the two amino acids flanking the peptide bond cleaved by a naturally-occurring protease; at most eight amino acids including the two amino acids flanking the peptide bond cleaved by a naturally-occurring protease; at most nine amino acids including the two amino acids flanking the peptide bond cleaved by a naturally-occurring protease; at most ten amino acids including the two amino acids flanking the peptide bond cleaved by a naturally-occurring protease; at most 15 amino acids including the two amino acids flanking the peptide bond cleaved by a naturally-occurring protease; or at most 20 amino acids including the two amino acids flanking the peptide bond cleaved by a naturally-occurring protease.

In an embodiment, an exogenous protease cleavage site is located within the di-chain loop of a modified Clostridial toxin. In aspects of this embodiment, a modified Clostridial toxin comprises an exogenous protease cleavage site comprises, e.g., a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site or a Factor Xa protease cleavage site. In other aspects of this embodiment, an exogenous protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In an aspect of this embodiment, an exogenous protease cleavage site can be, e.g., a bovine enterokinase cleavage site is located within the di-chain loop of a modified Clostridial toxin. In other aspects of the embodiment, an exogenous protease cleavage site can be, e.g., a bovine enterokinase protease cleavage site located within the di-chain loop of a modified Clostridial toxin comprises SEQ ID NO: 71. Is still other aspects of this embodiment, a bovine enterokinase protease cleavage site is located within the di-chain loop of, e.g., a modified BoNT/A, a modified BoNT/B, a modified BoNT/

C1, a modified BoNT/D, a modified BoNT/E, a modified BoNT/F, a modified BoNT/G or a modified TeNT.

In another aspect of this embodiment, an exogenous protease cleavage site can be, e.g., a Tobacco Etch Virus protease cleavage site is located within the di-chain loop of a modified Clostridial toxin. In other aspects of the embodiment, an exogenous protease cleavage site can be, e.g., a Tobacco Etch Virus protease cleavage site located within the di-chain loop of a modified Clostridial toxin comprises SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80 or SEQ ID NO: 81. Is still other aspects of this embodiment, a Tobacco Etch Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In still another aspect of this embodiment, an exogenous protease cleavage site can be, e.g., a Human Rhinovirus 3C protease cleavage site is located within the di-chain loop of a modified Clostridial toxin. In other aspects of the embodiment, an exogenous protease cleavage site can be, e.g., a Human Rhinovirus 3C protease cleavage site located within the di-chain loop of a modified Clostridial toxin comprises SEQ ID NO: 82, SEQ ID NO: 83, SEQ ID NO: 84, SEQ ID NO: 85, SEQ ID NO: 86 or SEQ ID NO: 87. Is still other aspects of this embodiment, a Human Rhinovirus 3C protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In yet another aspect of this embodiment, an exogenous protease cleavage site can be, e.g., a SUMO/ULP-1 protease cleavage site is located within the di-chain loop of a modified Clostridial toxin. In other aspects of the embodiment, an exogenous protease cleavage site can be, e.g., a SUMO/ULP-1 protease cleavage site located within the di-chain loop of a modified Clostridial toxin comprises SEQ ID NO: 88. Is still other aspects of this embodiment, a SUMO/ULP-1 protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In a further aspect of this embodiment, an exogenous protease cleavage site can be, e.g., a Thrombin protease cleavage site is located within the di-chain loop of a modified Clostridial toxin. In other aspects of the embodiment, an exogenous protease cleavage site can be, e.g., a Thrombin protease cleavage site located within the di-chain loop of a modified Clostridial toxin comprises SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102 or SEQ ID NO: 103. Is still other aspects of this embodiment, a Thrombin protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another aspect of this embodiment, an exogenous protease cleavage site can be, e.g., a Coagulation Factor Xa protease cleavage site is located within the di-chain loop of a modified Clostridial toxin. In other aspects of the embodiment, an exogenous protease cleavage site can be, e.g., a Coagulation Factor Xa protease cleavage site located within the di-chain loop of a modified Clostridial toxin comprises SEQ ID NO: 104 or SEQ ID NO: 105. Is still other aspects of this embodiment, a Coagulation Factor Xa protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another embodiment, an exogenous protease site comprises a Clostridial toxin substrate cleavage site. As used herein, the term "Clostridial toxin substrate cleavage site" means a scissile bond together with adjacent or non-adjacent recognition elements, or both, sufficient for detectable proteolysis at the scissile bond by a Clostridial toxin under conditions suitable for Clostridial toxin protease activity. By definition, a Clostridial toxin substrate cleavage site is susceptible to cleavage by at least one Clostridial toxin under conditions suitable for Clostridial toxin protease activity. Non-limiting examples of Clostridial toxin substrate cleavage site are disclosed in, e.g., Steward, L. E. et al., Self-Activating Clostridial Toxins, U.S. Patent Application 60/718,616 (Sep. 19, 2005).

It is understood that a modified Clostridial toxin disclosed in the present specification can optionally include one or more additional components. As a non-limiting example of an optional component, a modified Clostridial toxin can further comprise a flexible region comprising a flexible spacer. Non-limiting examples of a flexible spacer include, e.g., a G-spacer GGGGS (SEQ ID NO: 106) or an A-spacer EAAAK (SEQ ID NO: 107). A flexible region comprising flexible spacers can be used to adjust the length of a polypeptide region in order to optimize a characteristic, attribute or property of a polypeptide. Such a flexible region is operably-linked in-frame to the modified Clostridial toxin as a fusion protein. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present an enhanced targeting domain, thereby facilitating the binding of that enhanced targeting domain to its receptor system.

Thus, in an embodiment, a modified Clostridial toxin disclosed in the present specification can further comprise a flexible region comprising a flexible spacer. In another embodiment, a modified Clostridial toxin disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a modified Clostridial toxin can comprise a flexible region comprising one or more copies of the same flexible spacers, one or more copies of different flexible-spacer regions, or any combination thereof.

In aspects of this embodiment, a modified Clostridial toxin comprising a flexible spacer can be, e.g., a modified BoNT/A, a modified BoNT/B, a modified BoNT/C1, a modified BoNT/D, a modified BoNT/E, a modified BoNT/F, a modified BoNT/G or a modified TeNT.

It is envisioned that a modified Clostridial toxin disclosed in the present specification can comprise a flexible spacer in any and all locations with the proviso that modified Clostridial toxin is capable of performing the intoxication process. In aspects of this embodiment, a flexible spacer is positioned between, e.g., an enzymatic domain and a translocation domain, an enzymatic domain and an enhanced targeting domain, an enzymatic domain and a protease cleavage site. In other aspects of this embodiment, a G-spacer is positioned between, e.g., an enzymatic domain and a translocation domain, an enzymatic domain and an enhanced targeting domain, an enzymatic domain and a protease cleavage site. In other aspects of this embodiment, a A-spacer is positioned between, e.g., an enzymatic domain and a translocation domain, an enzymatic domain and an enhanced targeting domain, an enzymatic domain and a protease cleavage site.

In other aspects of this embodiment, a flexible spacer is positioned between, e.g., an enhanced targeting domain and a translocation domain, an enhanced targeting domain and an enzymatic domain, an enhanced targeting domain and a protease cleavage site. In other aspects of this embodiment, a G-spacer is positioned between, e.g., an enhanced targeting domain and a translocation domain, an enhanced targeting domain and an enzymatic domain, an enhanced targeting domain and a protease cleavage site. In other aspects of this embodiment, a A-spacer is positioned between, e.g., an enhanced targeting domain and a translocation domain, an enhanced targeting domain and an enzymatic domain, an enhanced targeting domain and a protease cleavage site.

In yet other aspects of this embodiment, a flexible spacer is positioned between, e.g., a translocation domain and an enzymatic domain, an translocation domain and an enhanced targeting domain, an translocation domain and a protease cleavage site. In other aspects of this embodiment, a G-spacer is positioned between, e.g., a translocation domain and an enzymatic domain, an translocation domain and an enhanced targeting domain, an translocation domain and a protease cleavage site. In other aspects of this embodiment, a A-spacer is positioned between, e.g., a translocation domain and an enzymatic domain, an translocation domain and an enhanced targeting domain, a translocation domain and a protease cleavage site.

As another non-limiting example of an optional component, a modified Clostridial toxin can further comprise an epitope-binding region. An epitope-binding region can be used in a wide variety of procedures involving, e.g., protein purification and protein visualization. Such an epitope-binding region is operably-linked in-frame to a modified Clostridial toxin as a fusion protein. Non-limiting examples of an epitope-binding region include, e.g., FLAG, Express™ (SEQ ID NO: 108), human Influenza virus hemagluttinin (HA) (SEQ ID NO: 109), human p62$^{c\text{-}Myc}$ protein (c-MYC) (SEQ ID NO: 110), Vesicular Stomatitis Virus Glycoprotein (VSV-G) (SEQ ID NO: 111), Substance P (SEQ ID NO: 112), glycoprotein-D precursor of Herpes simplex virus (HSV) (SEQ ID NO: 113), V5 (SEQ ID NO: 114), AU1 (SEQ ID NO: 115) and AU5 (SEQ ID NO: 116); affinity-binding, such as. e.g., polyhistidine (HIS) (SEQ ID NO: 117), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual: Portable Protocol No. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a modified Clostridial toxin disclosed in the present specification can further comprise an epitope-binding region. In another embodiment, a modified Clostridial toxin disclosed in the present specification can further comprises a plurality of epitope-binding regions. In aspects of this embodiment, a modified Clostridial toxin can comprise, e.g., at least 1 epitope-binding region, at least 2 epitope-binding regions, at least 3 epitope-binding regions, at least 4 epitope-binding regions or at least 5 epitope-binding regions. In other aspects of this embodiment, a modified Clostridial toxin can comprise, e.g., at most 1 epitope-binding region, at most 2 epitope-binding regions, at most 3 epitope-binding regions, at most 4 epitope-binding regions or at most 5 epitope-binding regions. In another aspect of this embodiment, a modified Clostridial toxin can comprise one or more copies of the same epitope-binding region, one or more copies of different epitope-binding regions, or any combination thereof.

The location of an epitope-binding region can be in various positions, including, without limitation, at the amino terminus of a modified Clostridial toxin, within a modified Clostridial toxin, or at the carboxyl terminus of a modified Clostridial toxin. Thus, in an embodiment, an epitope-binding region is located at the amino-terminus of a modified Clostridial toxin. In such a location, a start methionine should be placed in front of the epitope-binding region. In addition, it is known in the art that when adding a polypeptide that is operationally-linked to the amino terminus of another polypeptide comprising the start methionine that the original methionine residue can be deleted. This is due to the fact that the added polypeptide will contain a new start methionine and that the original start methionine may reduce optimal expression of the fusion protein. In aspects of this embodiment, an epitope-binding region located at the amino-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In another embodiment, an epitope-binding region is located at the carboxyl-terminus of a modified Clostridial toxin. In aspects of this embodiment, an epitope-binding region located at the carboxyl-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

As another non-limiting example of an optional component, a modified Clostridial toxin can further comprise an epitope-binding region. An epitope-binding region can be used in a wide variety of procedures involving, e.g., protein purification and protein visualization. Such an epitope-binding region is operably-linked in-frame to a modified Clostridial toxin as a fusion protein. Non-limiting examples of an epitope-binding region include, e.g., FLAG, Express™ (SEQ ID NO: 108), human Influenza virus hemagluttinin (HA) (SEQ ID NO: 109), human p62$^{c\text{-}Myc}$ protein (c-MYC) (SEQ ID NO: 110), Vesicular Stomatitis Virus Glycoprotein (VSV-G) (SEQ ID NO: 111), Substance P (SEQ ID NO: 112), glycoprotein-D precursor of Herpes simplex virus (HSV) (SEQ ID NO: 113), V5 (SEQ ID NO: 114), AU1 (SEQ ID NO: 115) and AU5 (SEQ ID NO: 116); affinity-binding, such as. e.g., polyhistidine (HIS) (SEQ ID NO: 117), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual: Portable Protocol No. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a modified Clostridial toxin disclosed in the present specification can further comprise an epitope-binding region. In another embodiment, a modified Clostridial toxin disclosed in the present specification can further comprises a plurality of epitope-binding regions. In aspects of this embodiment, a modified Clostridial toxin can comprise, e.g., at least 1 epitope-binding region, at least 2 epitope-binding regions, at least 3 epitope-binding regions, at least 4 epitope-binding regions or at least 5 epitope-binding regions. In other aspects of this embodiment, a modified Clostridial toxin can comprise, e.g., at most 1 epitope-binding region, at most 2 epitope-binding regions, at most 3 epitope-binding regions, at most 4 epitope-binding regions or at most 5 epitope-binding regions. In another aspect of this embodiment, a modified Clostridial toxin can comprise one or more copies of the same epitope-binding region, one or more copies of different epitope-binding regions, or any combination thereof.

The location of an epitope-binding region can be in various positions, including, without limitation, at the amino terminus of a modified Clostridial toxin, within a modified Clostridial toxin, or at the carboxyl terminus of a modified Clostridial toxin. Thus, in an embodiment, an epitope-binding region is located at the amino-terminus of a modified Clostridial toxin. In such a location, a start methionine should be placed in front of the epitope-binding region. In addition, it is known in the art that when adding a polypeptide that is operationally-linked to the amino terminus of another polypeptide comprising the start methionine that the original methionine residue can be deleted. This is due to the fact that the added polypeptide will contain a new start methionine and that the original start methionine may reduce optimal expression of the fusion protein. In aspects of this embodiment, an epitope-binding region located at the amino-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In another embodiment, an epitope-binding region is located at the carboxyl-terminus of a modified Clostridial toxin. In aspects of this embodiment, an epitope-binding region located at the carboxyl-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

Figure 3A:
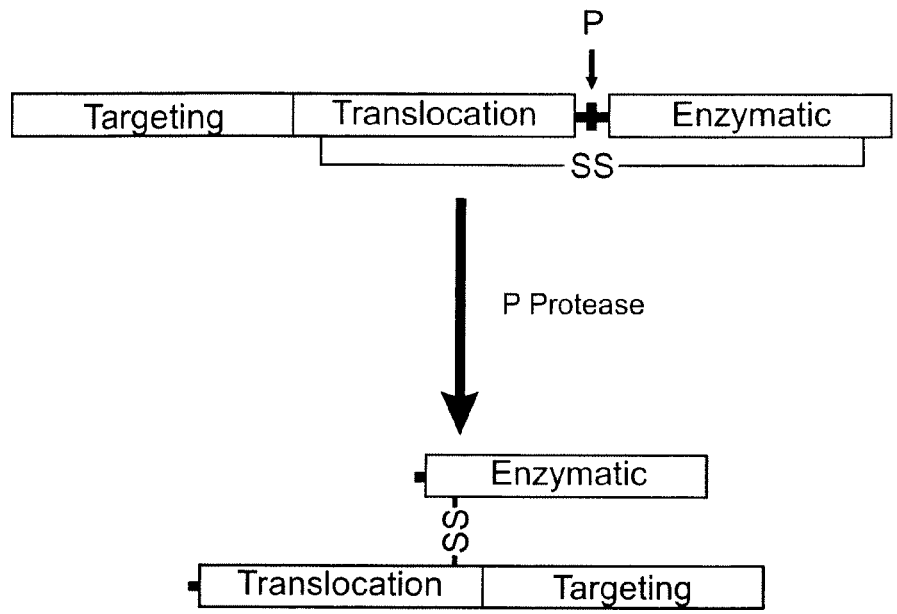
FIG. 3A depicts the single polypeptide form of a modified Clostridial toxin with an amino to carboxyl linear organization comprising an enhanced targeting domain, an enzymatic domain and a translocation domain, with the di-chain loop region depicted by the double SS bracket. A proteolytic cleavage site (P) within a di-chain loop region is located between the translocation and enzymatic domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the targeting and translocation domains, the translocation and enzymatic domains or any combination thereof.
Figure 3B:
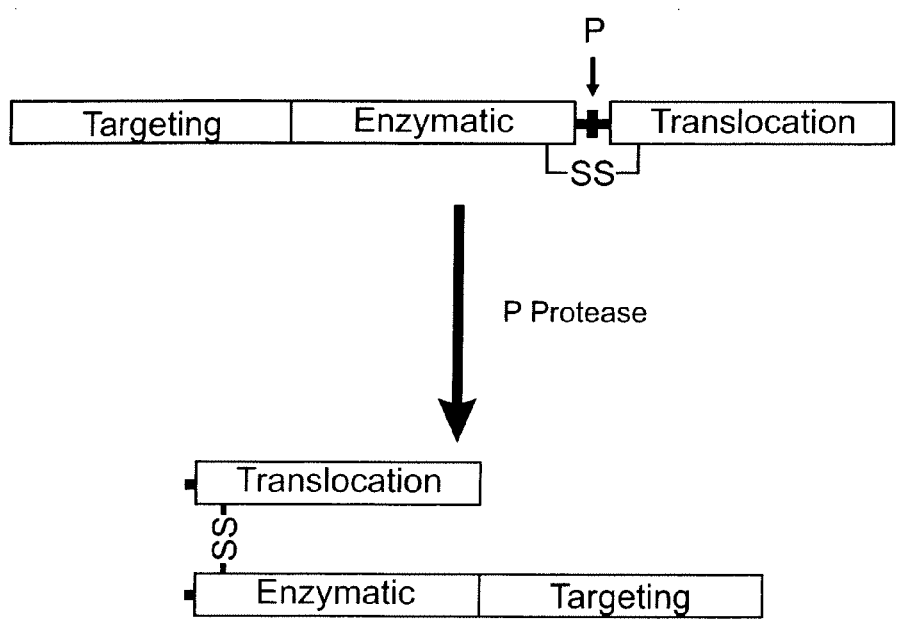
FIG. 3B depicts the single polypeptide form of a modified Clostridial toxin with an amino to carboxyl linear organization comprising an enhanced targeting domain, an enzymatic domain and a translocation domain, with the di-chain loop region depicted by the double SS bracket. A proteolytic cleavage site (P) within a di-chain loop region is located between the enzymatic and translocation domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the targeting and enzymatic domains, the enzymatic and translocation domains or any combination thereof.
Figure 4A:
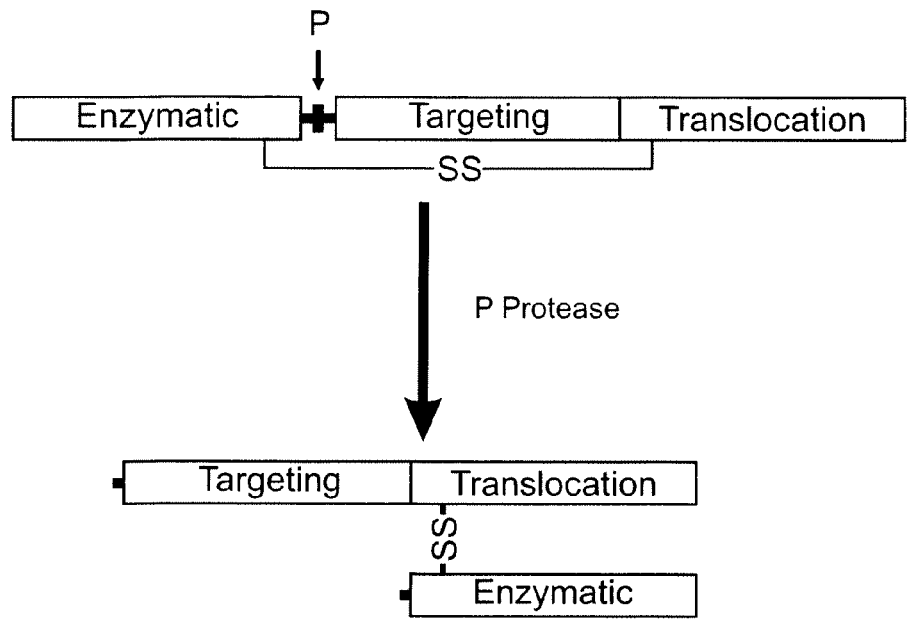
FIG. 4A depicts the single polypeptide form of a modified Clostridial toxin with an amino to carboxyl linear organization comprising an enzymatic domain, an enhanced targeting domain and a translocation domain, with the di-chain loop region depicted by the double SS bracket. A proteolytic cleavage site (P) within a di-chain loop region is located between the enzymatic and targeting domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic and targeting domains, the targeting and translocation domains or any combination thereof.
Figure 4B:
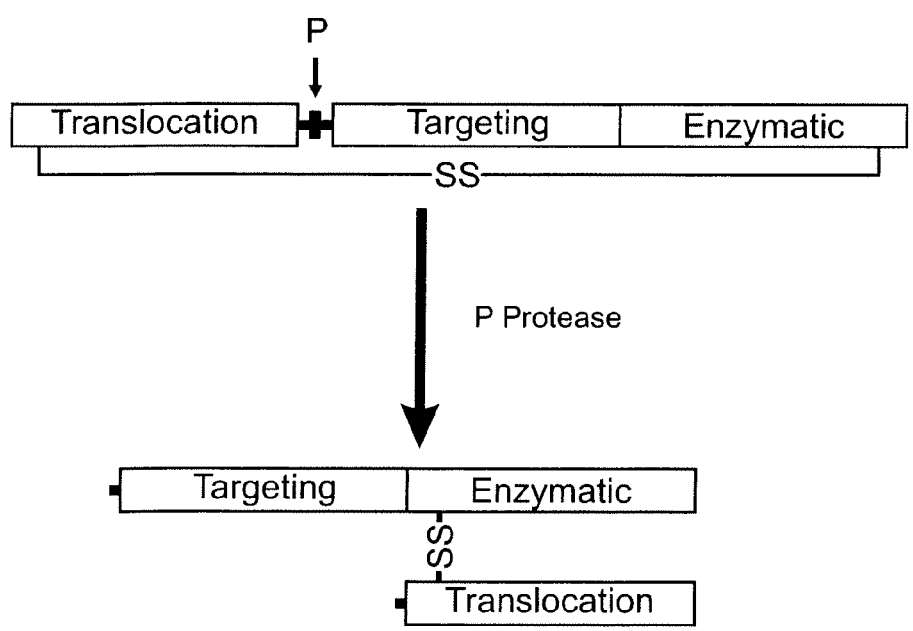
FIG. 4B depicts the single polypeptide form of a modified Clostridial toxin with an amino to carboxyl linear organization comprising a translocation domain, an enhanced targeting domain and an enzymatic domain, with the di-chain loop region depicted by the double SS bracket. A proteolytic cleavage site (P) within a di-chain loop region is located between the translocation and targeting domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the translocation and targeting domains, the targeting and enzymatic domains or any combination thereof.
Figure 5A:
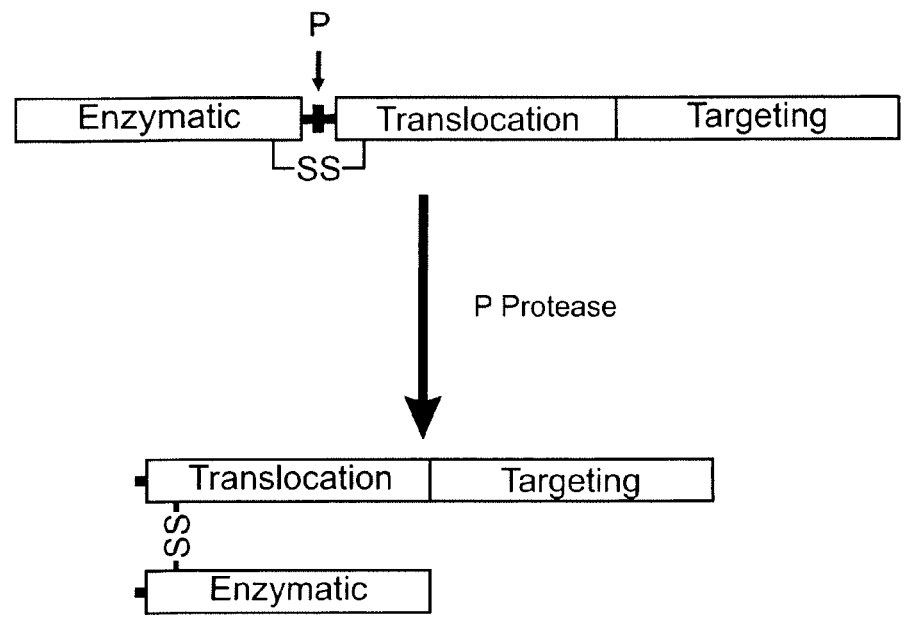
FIG. 5A depicts the single polypeptide form of a modified Clostridial toxin with an amino to carboxyl linear organization comprising an enzymatic domain, a translocation domain and an enhanced targeting domain, with the di-chain loop region depicted by the double SS bracket. A proteolytic cleavage site (P) within a di-chain loop region is located between the enzymatic and translocation domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic and translocation domains, the translocation and targeting domains or any combination thereof.
Figure 5B:
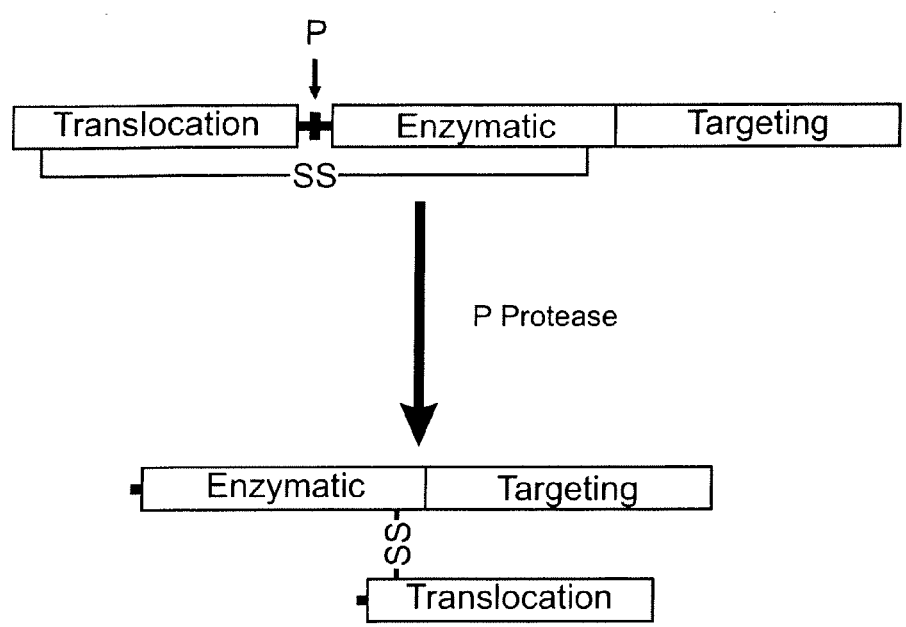
FIG. 5B depicts the single polypeptide form of a modified Clostridial toxin with an amino to carboxyl linear organization comprising a translocation domain, an enzymatic domain and an enhanced targeting domain, with the di-chain loop region depicted by the double SS bracket. A proteolytic cleavage site (P) within a di-chain loop region is located between the translocation and enzymatic domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the translocation and enzymatic domains, the enzymatic and targeting domains or any combination thereof.

It is envisioned that a modified Clostridial toxin disclosed in the present specification can comprise an enhance binding domain in any and all locations with the proviso that modified Clostridial toxin is capable of performing the intoxication process. Non-limiting examples include, locating an enhance binding domain at the amino terminus of a modified Clostridial toxin (FIG. 3); locating an enhance binding domain between a Clostridial toxin enzymatic domain and a Clostridial toxin translocation domain of a modified Clostridial toxin (FIG. 4); and locating an enhance binding domain at the carboxyl terminus of a modified Clostridial toxin (FIG. 5).

Thus, in an embodiment, a modified Clostridial toxin can comprise an amino to carboxyl single polypeptide linear order comprising a Clostridial toxin enzymatic domain, a Clostridial toxin translocation domain and an enhanced targeting domain. In an aspect of this embodiment, a modified Clostridial toxin can comprise an amino to carboxyl single polypeptide linear order comprising a Clostridial toxin enzymatic domain, a protease cleavage site, a Clostridial toxin translocation domain and an enhanced targeting domain. In another aspect of this embodiment, a modified Clostridial toxin can comprise an amino to carboxyl single polypeptide linear order comprising a Clostridial toxin enzymatic domain, an endogenous protease cleavage site, a Clostridial toxin translocation domain and an enhanced targeting domain. In another aspect of this embodiment, a modified Clostridial toxin can comprise an amino to carboxyl single polypeptide linear order comprising a Clostridial toxin enzymatic domain, an exogenous protease cleavage site, a Clostridial toxin translocation domain and an enhanced targeting domain.

In another embodiment, a modified Clostridial toxin can comprise an amino to carboxyl single polypeptide linear order comprising a Clostridial toxin enzymatic domain, an enhanced targeting domain and a Clostridial toxin translocation domain. In an aspect of this embodiment, a modified Clostridial toxin can comprise an amino to carboxyl single polypeptide linear order comprising a Clostridial toxin enzymatic domain, a protease cleavage site, an enhanced targeting domain and a Clostridial toxin translocation domain. In another aspect of this embodiment, a modified Clostridial toxin can comprise an amino to carboxyl single polypeptide linear order comprising a Clostridial toxin enzymatic domain, an endogenous protease cleavage site, an enhanced targeting domain and a Clostridial toxin translocation domain. In another aspect of this embodiment, a modified Clostridial toxin can comprise an amino to carboxyl single polypeptide linear order comprising a Clostridial toxin enzymatic domain, an exogenous protease cleavage site, an enhanced targeting domain and a Clostridial toxin translocation domain.

In another embodiment, a modified Clostridial toxin can comprise an amino to carboxyl single polypeptide linear order comprising an enhanced targeting domain, a Clostridial toxin translocation domain, and a Clostridial toxin enzymatic domain. In an aspect of this embodiment, a modified Clostridial toxin can comprise an amino to carboxyl single polypeptide linear order comprising an enhanced targeting domain, a Clostridial toxin translocation domain, a protease cleavage site and a Clostridial toxin enzymatic domain. In another aspect of this embodiment, a modified Clostridial toxin can comprise an amino to carboxyl single polypeptide linear order comprising an enhanced targeting domain, a Clostridial toxin translocation domain, an endogenous protease cleavage site and a Clostridial toxin enzymatic domain. In another aspect of this embodiment, a modified Clostridial toxin can comprise an amino to carboxyl single polypeptide linear order comprising an enhanced targeting domain, a Clostridial toxin translocation domain, an exogenous protease cleavage site and a Clostridial toxin enzymatic domain.

In another embodiment, a modified Clostridial toxin can comprise an amino to carboxyl single polypeptide linear order comprising an enhanced targeting domain, a Clostridial toxin enzymatic domain and a Clostridial toxin translocation domain. In an aspect of this embodiment, a modified Clostridial toxin can comprise an amino to carboxyl single polypeptide linear order comprising an enhanced targeting domain, a Clostridial toxin enzymatic domain, a protease cleavage site and a Clostridial toxin translocation domain. In another aspect of this embodiment, a modified Clostridial toxin can comprise an amino to carboxyl single polypeptide linear order comprising an enhanced targeting domain, a Clostridial toxin enzymatic domain, an endogenous protease cleavage site and a Clostridial toxin translocation domain. In another aspect of this embodiment, a modified Clostridial toxin can comprise an amino to carboxyl single polypeptide linear order comprising an enhanced targeting domain, a Clostridial toxin enzymatic domain, an exogenous protease cleavage site and a Clostridial toxin translocation domain.

In another embodiment, a modified Clostridial toxin can comprise an amino to carboxyl single polypeptide linear order comprising a Clostridial toxin translocation domain, a Clostridial toxin enzymatic domain and an enhanced targeting domain. In an aspect of this embodiment, a modified Clostridial toxin can comprise an amino to carboxyl single polypeptide linear order comprising a Clostridial toxin translocation domain, a protease cleavage site, a Clostridial toxin enzymatic domain and an enhanced targeting domain. In another aspect of this embodiment, a modified Clostridial toxin can comprise an amino to carboxyl single polypeptide linear order comprising a Clostridial toxin translocation domain, an endogenous protease cleavage site, a Clostridial toxin enzymatic domain and an enhanced targeting domain. In another aspect of this embodiment, a modified Clostridial toxin can comprise an amino to carboxyl single polypeptide linear order comprising a Clostridial toxin translocation domain, an exogenous protease cleavage site, a Clostridial toxin enzymatic domain and an enhanced targeting domain.

Aspects of the present invention provide, in part modified Clostridial toxins. Non-limiting examples of Clostridial toxin modifications disclosed in the present specification include, e.g., addition of an enhanced targeting domain, addition of a protease cleavage site, rearrangement of the enzymatic, translocation and binding domains and addition of a spacer region. It is understood that all such modifications do not substantially affect the ability of a modified Clostridial toxin to intoxicate a cell. As used herein, the term "do not substantially affect" means a modified Clostridial toxin can still execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. In aspects of this embodiment, the modified Clostridial toxin is, e.g., at least 10% as toxic as a naturally-occurring Clostridial toxin, at least 20% as toxic as a naturally-occurring Clostridial toxin, at least 30% as toxic as a naturally-occurring Clostridial toxin, at least 40% as toxic as a naturally-occurring Clostridial toxin, at least 50% as toxic as a naturally-occurring Clostridial toxin, at least 60% as toxic as a naturally-occurring Clostridial toxin, at least 70% as toxic as a naturally-occurring Clostridial toxin, at least 80% as toxic as a naturally-occurring Clostridial toxin, at least 90% as toxic as a naturally-occurring Clostridial toxin or at least 95% as toxic as a naturally-occurring Clostridial toxin. In aspects of this embodiment, the modified Clostridial toxin is, e.g., at most 10% as toxic as a naturally-occurring Clostridial toxin, at most 20% as toxic as a naturally-occurring Clostridial toxin, at most 30% as toxic as a naturally-occurring Clostridial toxin, at most 40% as toxic as a naturally-occurring Clostridial toxin, at most 50% as toxic as a naturally-occurring Clostridial toxin, at most 60% as toxic as a naturally-occurring Clostridial toxin, at most 70% as toxic as a naturally-occurring Clostridial toxin, at most 80% as toxic as a naturally-occurring Clostridial toxin, at most 90% as toxic as a naturally-occurring Clostridial toxin or at most 95% as toxic as a naturally-occurring Clostridial toxin.

Another aspect of the present invention provides polynucleotide molecules encoding modified Clostridial toxins disclosed in the present specification. It is envisioned that any and all modified Clostridial toxin disclosed in the present specification can be encoded by a polynucleotide molecule.

Aspects of the present invention provide, in part polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a modified Clostridial toxin disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Thus, in an embodiment, a polynucleotide molecule encodes a modified Clostridial toxin disclosed in the present specification.

In another embodiment, a polynucleotide molecule encodes, in part, a modified Clostridial toxin comprising a Clostridial toxin enzymatic domain disclosed in the present specification. In an aspect of this embodiment, a polynucleotide molecule encoding a modified Clostridial toxin enzymatic domain comprises a naturally occurring Clostridial toxin enzymatic domain variant, such as, e.g., a Clostridial toxin enzymatic domain isoform or a Clostridial toxin enzymatic domain subtype. In another aspect of this embodiment, a polynucleotide molecule encoding a Clostridial toxin enzymatic domain comprises a non-naturally occurring Clostridial toxin enzymatic domain variant, such as, e.g., a conservative Clostridial toxin enzymatic domain variant, a non-conservative Clostridial toxin enzymatic domain variant or an active Clostridial toxin enzymatic domain fragment, or any combination thereof. In other aspects of this embodiment, a polynucleotide molecule encoding a Clostridial toxin enzymatic domain comprises a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, or active fragment thereof.

In another embodiment, a polynucleotide molecule encodes, in part, a modified Clostridial toxin comprising a Clostridial toxin translocation domain disclosed in the present specification. In an aspect of this embodiment, a polynucleotide molecule encoding a modified Clostridial toxin translocation domain comprises a naturally occurring Clostridial toxin translocation domain variant, such as, e.g., a Clostridial toxin translocation domain isoform or a Clostridial toxin translocation domain subtype. In another aspect of this embodiment, a polynucleotide molecule encoding a Clostridial toxin translocation domain comprises a non-naturally occurring Clostridial toxin translocation domain variant, such as, e.g., a conservative Clostridial toxin translocation domain variant, a non-conservative Clostridial toxin translocation domain variant or an active Clostridial toxin translocation domain fragment, or any combination thereof. In other aspects of this embodiment, a polynucleotide molecule encoding a Clostridial toxin translocation domain comprises a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, or active fragment thereof.

In another embodiment, a polynucleotide molecule encodes, in part, a modified Clostridial toxin comprising an enhanced targeting domain disclosed in the present specification. In an aspect of this embodiment, a polynucleotide molecule encoding an enhanced targeting domain comprises a polypeptide that selectively binds to a non-Clostridial toxin receptor system present on a presynaptic membrane of a Clostridial toxin target cell. In an aspect of this embodiment, a polynucleotide molecule encoding a polypeptide that selectively binds to a non-Clostridial toxin receptor system present on a presynaptic membrane of a Clostridial toxin target cell comprises a naturally occurring variant, such as, e.g., an isoform or a subtype. In another aspect of this embodiment, a polynucleotide molecule encoding a polypeptide that selectively binds to a non-Clostridial toxin receptor system present on a presynaptic membrane of a Clostridial toxin target cell comprises a non-naturally occurring variant, such as, e.g., a conservative variant, a non-conservative variant or an active fragment, or any combination thereof. In other aspects of this embodiment, a polynucleotide molecule encoding a polypeptide that selectively binds to a non-Clostridial toxin receptor system present on a presynaptic membrane of a Clostridial toxin target cell comprises a TGFβ superfamily polypeptide, such as, e.g., a TGFβ, a BMPs, a GDF and an activin; a neurotrophin, such as, e.g., a NGF, a BDNF, a NT-3 and a NT-4/5; an axon guidance signaling molecule, such as, e.g., a netrin, a semaphroring and an ephrin; a neuroregulatory cytokine, such as, e.g., a CNTF, a GPA, a LIF, an interleukin, an onostatin M, a CT-1 and a CLC; a sugar binding protein, such as, e.g., a serum amyloid P, a β-glucanase, a sialidase, a lectin, a cryia, an insecticidal delta-endotoxin, an agglutinin, an abrin and a ricin; an IGF, such as, e.g., a IGF-1 and a IGF-2; a neurexin; a neuroleukin/AMF/MF; a TrkB; an EGF; a visceral gut peptide such as, e.g., a gastrin, a VIP, a bombesin; and a WNT, such as, e.g., a Frizzled.

In another embodiment, a polynucleotide molecule encodes, in part, a modified Clostridial toxin comprising an enhanced targeting domain disclosed in the present specification. In an aspect of this embodiment, a polynucleotide molecule encoding an enhanced targeting domain comprises a polypeptide that selectively binds to a non-Clostridial toxin receptor system present on a postsynaptic membrane of a Clostridial toxin target cell. In an aspect of this embodiment, a polynucleotide molecule encoding a polypeptide that selectively binds to a non-Clostridial toxin receptor system present on a postsynaptic membrane of a Clostridial toxin target cell comprises a naturally occurring variant, such as, e.g., an isoform or a subtype. In another aspect of this embodiment, a polynucleotide molecule encoding a polypeptide that selectively binds to a non-Clostridial toxin receptor system present on a postsynaptic membrane of a Clostridial toxin target cell comprises a non-naturally occurring variant, such as, e.g., a conservative variant, a non-conservative variant or an active fragment, or any combination thereof. In other aspects of this embodiment, a polynucleotide molecule encoding a polypeptide that selectively binds to a non-Clostridial toxin receptor system present on a postsynaptic membrane of a Clostridial toxin target cell comprises a Ng-CAM(L1), a N-CAM, a N-cadherin, an agrin-MUSK, and a basement membrane polypeptide, such as, e.g., laminin β-2.

In another embodiment, a polynucleotide molecule encodes, in part, a modified Clostridial toxin comprising a protease cleavage site disclosed in the present specification. In an aspect of this embodiment, a polynucleotide molecule encoding a protease cleavage site comprises an endogenous Clostridial toxin protease site. In aspects of this embodiment, a polynucleotide molecule encoding an endogenous Clostridial toxin protease site can be, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site or a TeNT di-chain loop protease cleavage site. In another aspect of this embodiment, a polynucleotide molecule encoding a protease cleavage site comprises an exogenous Clostridial toxin protease site. In aspects of this embodiment, a polynucleotide molecule encoding an exogenous Clostridial toxin protease site can be, e.g., a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site, a Coagulation Factor Xa protease cleavage site or a Clostridial toxin substrate cleavage site, such as, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site or a TeNT substrate cleavage site.

In another embodiment, a polynucleotide molecule encodes, in part, a modified Clostridial toxin comprising a flexible spacer disclosed in the present specification. In an aspect of this embodiment, a polynucleotide molecule encoding a flexible spacer a G-spacer, a A-spacer of any combination thereof.

Well-established molecular biology techniques that may be necessary to make a polynucleotide molecule encoding a modified Clostridial toxin disclosed in the present specification including, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine procedures well within the scope of one skilled in the art and from the teaching herein. Non-limiting examples of specific protocols necessary to make a polynucleotide molecule encoding a modified Clostridial toxin are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a modified Clostridial toxin are widely available. These protocols are routine procedures well within the scope of one skilled in the art and from the teaching herein.

Another aspect of the present invention provides a method of producing a modified Clostridial toxin disclosed in the present specification, such method comprising the step of expressing a polynucleotide molecule encoding a modified Clostridial toxin in a cell. Another aspect of the present invention provides a method of producing a modified Clostridial toxin disclosed in the present specification, such method comprising the steps of introducing an expression construct comprising a polynucleotide molecule encoding a modified Clostridial toxin into a cell and expressing the expression construct in the cell.

The methods disclosed in the present specification include, in part, a modified Clostridial toxin. It is envisioned that any and all modified Clostridial toxins disclosed in the present specification can be produced using the methods disclosed in the present specification. It is also envisioned that any and all polynucleotide molecules encoding a modified Clostridial toxins disclosed in the present specification can be useful in producing a modified Clostridial toxins disclosed in the present specification using the methods disclosed in the present specification.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a modified Clostridial toxin, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a modified Clostridial toxin under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Thus, aspects of this embodiment include, without limitation, a viral expression vector operably-linked to a polynucleotide molecule encoding a modified Clostridial toxin; a prokaryotic expression vector operably-linked to a polynucleotide molecule encoding a modified Clostridial toxin; a yeast expression vector operably-linked to a polynucleotide molecule encoding a modified Clostridial toxin; an insect expression vector operably-linked to a polynucleotide molecule encoding a modified Clostridial toxin; and a mammalian expression vector operably-linked to a polynucleotide molecule encoding a modified Clostridial toxin. Other aspects of this embodiment include, without limitation, expression constructs suitable for expressing a modified Clostridial toxin disclosed in the present specification using a cell-free extract comprising a cell-free extract expression vector operably linked to a polynucleotide molecule encoding a modified Clostridial toxin.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia per-*

*fringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, 4$^{th}$ ed. 2000); ANIMAL CELL CULTURE: A PRACTICAL APPROACH (John R. W. Masters ed., Oxford University Press, 3$^{rd}$ ed. 2000); MOLECULAR CLONING A LABORATORY MANUAL, supra, (2001); BASIC CELL CULTURE: A PRACTICAL APPROACH (John M. Davis, Oxford Press, 2$^{nd}$ ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell a polynucleotide molecule. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a nucleic acid molecule into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated tranfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, 3$^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a polynucleotide molecule encoding a modified Clostridial toxin into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, Transfection of adherent and suspended cells by calcium phosphate, 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., Polyethylenimine strategies for plasmid delivery to brain-derived cells, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a polynucleotide molecule encoding a modified Clostridial toxin into a cell. Physical techniques include, without limitation, electroporation, biolistic and microinjection. Biolistics and microinjection techniques perforate the cell wall in order to introduce the nucleic acid molecule into the cell, see, e.g., Jeike E. Biewenga et al., Plasmid-mediated gene transfer in neurons using the biolistics technique, 71(1) J. Neurosci. Methods. 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the nucleic acid molecules enter and can be used effectively for stable and transient transfections of all cell types, see, e.g., M. Golzio et al., In vitro and in vivo electric field-mediated permeabilization, gene transfer, and expression, 33(2) Methods 126-135 (2004); and Oliver Greschet al., New non-viral method for gene transfer into primary cells, 33(2) Methods 151-163 (2004).

In another aspect of this embodiment, a viral-mediated method, termed transduction, is used to introduce a polynucleotide molecule encoding a modified Clostridial toxin into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, Lentiviral and MLV based retroviral vectors for ex vivo and in vivo gene transfer, 33(2) Methods 164-172 (2004); and Maurizio Federico, From lentiviruses to lentivirus vectors, 229 Methods Mol. Biol. 3-15 (2003); E. M. Poeschla, Non-primate lentiviral vectors, 5(5) Curr. Opin. Mol. Ther. 529-540 (2003); Karim Benihoud et al, Adenovirus vectors for gene delivery, 10(5) Curr. Opin. Biotechnol. 440-447 (1999); H. Bueler, Adeno-associated viral vectors for gene transfer and gene therapy, 380(6) Biol. Chem. 613-622 (1999); Chooi M. Lai et al., Adenovirus and adeno-associated virus vectors, 21(12) DNA Cell Biol. 895-913 (2002); Edward A. Burton et al., Gene delivery using herpes simplex virus vectors, 21(12) DNA Cell Biol. 915-936 (2002); Paola Grandi et al., Targeting HSV amplicon vectors, 33(2) Methods 179-186 (2004); Ilya Frolov et al., Alphavirusbased expression vectors: strategies and applications, 93(21) Proc. Natl. Acad. Sci. U.S.A. 11371-11377 (1996); Markus U. Ehrengruber, Alphaviral gene transfer in neurobiology, 59(1) Brain Res. Bull. 13-22 (2002); Thomas A. Kost & J. Patrick Condreay, Recombinant baculoviruses as mammalian cell gene-delivery vectors, 20(4) Trends Biotechnol. 173-180 (2002); and A. Huser & C. Hofmann, Baculovirus vectors: novel mammalian cell gene-delivery vehicles and their applications, 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71(1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenoviral vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEasy™ Adenoviral Vector System (Stratagene, Inc., La Jolla, Calif.) and AdEasy™ Adenoviral Vector System Instruction Manual 064004f, Stratagene, Inc.

Nucleic acid molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., Transient production of retroviral- and lentiviral-based vectors for the transduction of Mammalian cells, 285 Methods Mol. Biol. 141-148 (2004); Armin Blesch, Lentiviral and MLV based retroviral vectors for ex vivo and in vivo gene transfer, 33(2) Methods 164-172 (2004); Félix Recillas-Targa, Gene transfer and expression in mammalian cell lines and transgenic animals, 267 Methods Mol. Biol. 417-433 (2004); and Roland Wolkowicz et al., Lentiviral vectors for the delivery of DNA into mammalian cells, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., In vivo gene delivery and stable transduction of non-dividing cells by a lentiviral vector, 272 (5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. Patent Nos. Manfred Gossen & Hermann Bujard, Tight control of gene expression in eukaryotic cells by tetracycline-responsive promoters, U.S. Pat. No. 5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

The methods disclosed in the present specification include, in part, expressing a modified Clostridial toxin from a polynucleotide molecule. It is envisioned that any of a variety of expression systems may be useful for expressing a modified Clostridial toxin from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and E. coli extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins*, 80(9) CURRENT SCIENCE 1121-1128, (2001). These protocols are routine procedures well within the scope of one skilled in the art and from the teaching herein.

A variety of cell-based expression procedures are useful for expressing a modified Clostridial toxin encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the ViraPower™ Lentiviral (Invitrogen, Inc., Carlsbad, Calif.), the Adenoviral Expression Systems (Invitrogen, Inc., Carlsbad, Calif.), the AdEasy™ XL Adenoviral Vector System (Stratagene, La Jolla, Calif.) and the ViraPort® Retroviral Gene Expression System (Stratagene, La Jolla, Calif.). Non-limiting examples of prokaryotic expression systems include the Champion™ pET Expression System (EMD Biosciences-Novagen, Madison, Wis.), the TriEx™ Bacterial Expression System (EMD Biosciences-Novagen, Madison, Wis.), the QIAexpress® Expression System (QIAGEN, Inc.), and the Affinity® Protein Expression and Purification System (Stratagene, La Jolla, Calif.). Yeast expression systems include, without limitation, the EasySelect™ *Pichia* Expression Kit (Invitrogen, Inc., Carlsbad, Calif.), the YES-Echo™ Expression Vector Kits (Invitrogen, Inc., Carlsbad, Calif.) and the SPECTRA™ *S. pombe* Expression System (Invitrogen, Inc., Carlsbad, Calif.). Non-limiting examples of baculoviral expression systems include the BaculoDirect™ (Invitrogen, Inc., Carlsbad, Calif.), the Bac-to-Bac® (Invitrogen, Inc., Carlsbad, Calif.), and the BD BaculoGold™ (BD Biosciences-Pharmigen, San Diego, Calif.). Insect expression systems include, without limitation, the *Drosophila* Expression System (DES®) (Invitrogen, Inc., Carlsbad, Calif.), InsectSelect™ System (Invitrogen, Inc., Carlsbad, Calif.) and InsectDirect™ System (EMD Biosciences-Novagen, Madison, Wis.). Non-limiting examples of mammalian expression systems include the T-REx™ (Tetracycline-Regulated Expression) System (Invitrogen, Inc., Carlsbad, Calif.), the Flp-In™ T-REx™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the Exchanger® System, InterPlay™ Mammalian TAP System (Stratagene, La Jolla, Calif.), Complete Control® Inducible Mammalian Expression System (Stratagene, La Jolla, Calif.) and LacSwitch® II Inducible Mammalian Expression System (Stratagene, La Jolla, Calif.).

Another procedure of expressing a modified Clostridial toxin encoded by polynucleotide molecule disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ActivePro In Vitro Translation Kit (Ambion, Inc., Austin, Tex.), the EcoPro™ System (EMD Biosciences-Novagen, Madison, Wis.) and the Expressway™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TnT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINscript® II System (Ambion, Inc., Austin, Tex.) and the TnT® Coupled Reticulocyte Lysate Systems (Promega Corp., Madison, Wis.).

EXAMPLES

The following non-limiting examples are provided for illustrative purposes only in order to facilitate a more complete understanding of disclosed embodiments and are in no way intended to limit any of the embodiments disclosed in the present specification.

Example 1

Construction of a Modified Clostridial Toxin Comprising an Amino-terminally Presented Enhanced Targeting Domain This example illustrates how to make a modified Clostridial toxin disclosed in the present specification comprising an enhanced targeting domain located at the amino terminus of the modified toxin.

1a. A Targeting-translocation-enzymatic Domain Organization.

A polynucleotide molecule based on BoNT/A-AP4A-GRPP (SEQ ID NO: 118) will be synthesized using standard procedures (BlueHeron® Biotechnology, Bothell, Wash.). This polynucleotide molecule encodes a BoNT/A modified to replace amino acids 1111-1296 of SEQ ID NO: 1, a BoNT/A $H_{CC}$ targeting domain, with amino acids 21-50 of SEQ ID NO: 9, a GRPP targeting domain, and has the general domain arrangement of FIG. 4A. Oligonucleotides of 20 to 50 bases in length are synthesized using standard phosphoramidite synthesis. These oligonucleotides will be hybridized into double stranded duplexes that are ligated together to assemble the full-length polynucleotide molecule. This polynucleotide molecule will be cloned using standard molecular biology methods into a pUCBHB1 vector at the SmaI site to generate pUCBHB1/BoNT/A-AP4A-GRPP. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule based on BoNT/A-AP4A-GRPP (SEQ ID NO: 118) can be synthesized in order to improve expression in an *Escherichia coli* strain. The polynucleotide molecule encoding the BoNT/A-AP4A-GRPP will be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al., *Optimizing Expression of Active Botulinum Toxin Type E*, International Patent Publication WO 2006/011966 (Feb. 2, 2006); Lance E. Steward et al., *Optimizing Expression of Active Botulinum Toxin Type A*, International Patent Publication WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-AP4A-GRPP. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, expression optimization to a different organism, such as, e.g., a yeast strain, an insect cell-line or a mammalian cell line, can be done, see, e.g., Steward, supra, (Feb. 2, 2006); and Steward, supra, (Feb. 16, 2006).

A similar cloning strategy will be used to make pUCBHB1 cloning constructs for BoNT/B-AP4A-GRPP, a modified BoNT/B where amino acids 1098-1291 of SEQ ID NO: 2 are replaced with amino acids 21-50 of SEQ ID NO: 9; BoNT/C1-AP4A-GRPP, a modified BoNT/C1 where amino acids 1112-1291 of SEQ ID NO: 3 are replaced with amino acids 21-50 of SEQ ID NO: 9; BoNT/D-AP4A-GRPP, a modified BoNT/D where amino acids 1099-1276 of SEQ ID NO: 4 are replaced with amino acids 21-50 of SEQ ID NO: 9; BoNT/E-AP4A-GRPP, a modified BoNT/E where amino acids 1086-1252 of SEQ ID NO: 5 are replaced with amino acids 21-50 of SEQ ID NO: 9; BoNT/F-AP4A-GRPP, a modified BoNT/F where amino acids 1106-1274 of SEQ ID NO: 6 are replaced with amino acids 21-50 of SEQ ID NO: 9; BoNT/G-AP4A-GRPP, a modified BoNT/G where amino acids 1106-1297 of SEQ ID NO: 7 are replaced with amino acids 21-50 of SEQ ID NO: 9; and TeNT-AP4A-GRPP, a modified TeNT where amino acids 1128-1315 of SEQ ID NO: 8 are replaced with amino acids 21-50 of SEQ ID NO: 9.

Likewise, a similar cloning strategy will be used to make pUCBHB1 cloning constructs comprising a polynucleotide molecule encoding a modified Clostridial toxin-AP4A that will replace the $H_{CC}$-targeting domain from a Clostridial toxin the with an enhanced targeting domain comprising, e.g., amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

To construct pET29/BoNT/A-AP4A-GRPP, a pUCBHB1/BoNT/A-AP4A-GRPP construct will be digested with restriction endonucleases that 1) will excise the polynucleotide molecule encoding the open reading frame of BoNT/A-AP4A-GRPP; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-AP4A-GRPP. The ligation mixture will be transformed into chemically competent *E. coli* DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-AP4A-GRPP operably-linked to a carboxyl terminal polyhistidine affinity binding peptide.

A similar cloning strategy will be used to make pET29 expression constructs for other modified Clostridial toxin-AP4A-GRPP toxins, such as, e.g., BoNT/B-AP4A-GRPP, BoNT/C1-AP4A-GRPP, BoNT/D-AP4A-GRPP, BoNT/E-AP4A-GRPP, BoNT/F-AP4A-GRPP, BoNT/G-AP4A-GRPP or TeNT-AP4A-GRPP. Likewise, a similar cloning strategy will be used to make pET29 expression constructs comprising a polynucleotide molecule encoding a modified Clostridial toxin-AP4A comprising an enhanced targeting domain such as, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

1b. A Targeting-enzymatic-translocation Domain Organization.

A polynucleotide molecule based on BoNT/A-AP4B-GRPP (SEQ ID NO: 119) will be synthesized and cloned into a pUCBHB1 vector as described in Example 1a. This polynucleotide molecule encodes a BoNT/A modified to replace amino acids 1111-1296 of SEQ ID NO: 1, a BoNT/A $H_{CC}$ targeting domain, with amino acids 21-50 of SEQ ID NO: 9, a GRPP targeting domain, and has the general domain arrangement of FIG. 4B. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

Likewise, a similar cloning strategy will be used to make pUCBHB1 cloning constructs comprising a polynucleotide molecule encoding a modified Clostridial toxin-AP4B that will replace the $H_{CC}$ targeting domain from a Clostridial toxin the with an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

In addition, similar cloning strategy will be used to produce a modified Clostridial toxin-AP4B, such as, e.g., BoNT/B-AP4B, BoNT/C1-AP4B, BoNT/D-AP4B, BoNT/E-AP4B, BoNT/F-AP4B, BoNT/G-AP4B or TeNT-AP4B, to comprise an enhanced targeting domain comprising, e.g., amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

To construct pET29/BoNT/A-AP4B-GRPP, a similar cloning strategy will be used as described in Example 1a. This cloning strategy will yield a pET29 expression construct comprising the polynucleotide molecule encoding the BoNT/A-AP4B-GRPP operably-linked to a carboxyl terminal polyhistidine affinity binding peptide. A similar cloning strategy will be used to make pET29 expression constructs for other modified Clostridial toxin-AP4B-GRPP toxins, such as, e.g., BoNT/B-AP4B-GRPP, BoNT/C1-AP4B-GRPP, BoNT/D-AP4B-GRPP, BoNT/E-AP4B-GRPP, BoNT/F-AP4B-GRPP, BoNT/G-AP4B-GRPP or TeNT-AP4B-GRPP. Likewise, a similar cloning strategy will be used to make pET29 expression constructs comprising a polynucleotide molecule encoding a modified Clostridial toxin-AP4B comprising an enhanced targeting domain such as, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

Example 2

Construction of a Modified Clostridial Toxin Comprising a Centrally Presented Enhanced Targeting Domain This example illustrates how to make a modified Clostridial toxin disclosed in the present specification comprising an enhanced targeting domain located between two other domains of the modified toxin.

2a. An Enzymatic-targeting-translocation Domain Organization.

A polynucleotide molecule based on BoNT/A-CP5A-GRPP (SEQ ID NO: 196) will be synthesized using standard procedures (BlueHeron® Biotechnology, Bothell, Wash.). This polynucleotide molecule encodes a BoNT/A modified to replace amino acids 1111-1296 of SEQ ID NO: 1, a BoNT/A $H_{CC}$ targeting domain, with amino acids 21-50 of SEQ ID NO: 9, a GRPP targeting domain, and has the general domain arrangement of FIG. 5A. Cleavage of an enterokinse cleavage site used to form the di-chain toxin also exposes the first amino acid of the GRPP targeting domain. Oligonucleotides of 20 to 50 bases in length are synthesized using standard phosphoramidite synthesis. These oligonucleotides will be hybridized into double stranded duplexes that are ligated together to assemble the full-length polynucleotide molecule. This polynucleotide molecule will be cloned using standard molecular biology methods into a pUCBHB1 vector at the SmaI site to generate pUCBHB1/BoNT/A-CP5A-GRPP. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule based on BoNT/A-CP5A-GRPP (SEQ ID NO: 196) can be synthesized in order to improve expression in an *Escherichia coli* strain. The polynucleotide molecule encoding the BoNT/A-CP5A-GRPP will be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al., Optimizing Expression of Active Botulinum Toxin Type E, International Patent Publication WO 2006/011966 (Feb. 2, 2006); Lance E. Steward et al., Optimizing Expression of Active Botulinum Toxin Type A, International Patent Publication WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-CP5A-GRPP. The synthesized polynucleotide molecule is verified by sequencing using Big Dye Terminator™ Chemistry 3.1 (CP5Aplied Biosystems, Foster City, Calif.) and an ABI 3100 sequencer (CP5Aplied Biosystems, Foster City, Calif.). If so desired, expression optimization to a different organism, such as, e.g., a yeast strain, an insect cell-line or a mammalian cell line, can be done, see, e.g., Steward, supra, (Feb. 2, 2006); and Steward, supra, (Feb. 16, 2006).

A similar cloning strategy will be used to make pUCBHB1 cloning constructs for BoNT/B-CP5A-GRPP, a modified BoNT/B where amino acids 1098-1291 of SEQ ID NO: 2 are replaced with amino acids 21-50 of SEQ ID NO: 9; BoNT/C1-CP5A-GRPP, a modified BoNT/C1 where amino acids 1112-1291 of SEQ ID NO: 3 are replaced with amino acids 21-50 of SEQ ID NO: 9; BoNT/D-CP5A-GRPP, a modified BoNT/D where amino acids 1099-1276 of SEQ ID NO: 4 are replaced with amino acids 21-50 of SEQ ID NO: 9; BoNT/E-CP5A-GRPP, a modified BoNT/E where amino acids 1086-1252 of SEQ ID NO: 5 are replaced with amino acids 21-50 of SEQ ID NO: 9; BoNT/F-CP5A-GRPP, a modified BoNT/F where amino acids 1106-1274 of SEQ ID NO: 6 are replaced with amino acids 21-50 of SEQ ID NO: 9; BoNT/G-CP5A-GRPP, a modified BoNT/G where amino acids 1106-1297 of SEQ ID NO: 7 are replaced with amino acids 21-50 of SEQ ID NO: 9; and TeNT-CP5A-GRPP, a modified TeNT where amino acids 1128-1315 of SEQ ID NO: 8 are replaced with amino acids 21-50 of SEQ ID NO: 9.

Likewise, a similar cloning strategy will be used to make pUCBHB1 cloning constructs comprising a polynucleotide molecule encoding a modified Clostridial toxin-CP5A that will replace the $H_{CC}$ targeting domain from a Clostridial toxin the with an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

To construct pET29/BoNT/A-CP5A-GRPP, a pUCBHB1/BoNT/A-CP5A-GRPP construct will be digested with restriction endonucleases that 1) will excise the polynucleotide molecule encoding the open reading frame of BoNT/A-CP5A-GRPP; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-CP5A-GRPP. The ligation mixture will be transformed into chemically competent *E. coli* DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-CP5A-GRPP operably-linked to a carboxyl terminal polyhistidine affinity binding peptide.

A similar cloning strategy will be used to make pET29 expression constructs for other modified Clostridial toxin-CP5A-GRPP toxins, such as, e.g., BoNT/B-CP5A-GRPP, BoNT/C1-CP5A-GRPP, BoNT/D-CP5A-GRPP, BoNT/E-CP5A-GRPP, BoNT/F-CP5A-GRPP, BoNT/G-CP5A-GRPP or TeNT-CP5A-GRPP. Likewise, a similar cloning strategy will be used to make pET29 expression constructs comprising a polynucleotide molecule encoding a modified Clostridial toxin-CP5A comprising an enhanced targeting domain such as, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

2b. A Translocation-targeting-enzymatic Domain Organization.

A polynucleotide molecule based on BoNT/A-CP5B-GRPP (SEQ ID NO: 120) will be synthesized and cloned into a pUCBHB1 vector as described in Example 1a. This polynucleotide molecule encodes a BoNT/A modified to replace amino acids 1111-1296 of SEQ ID NO: 1, a BoNT/A $H_{CC}$ targeting domain, with amino acids 21-50 of SEQ ID NO: 9, a GRPP targeting domain, and has the general domain arrangement of FIG. 5B. Cleavage of an enterokinse cleavage site used to form the di-chain toxin also exposes the first amino acid of the GRPP targeting domain. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

Likewise, a similar cloning strategy will be used to make pUCBHB1 cloning constructs comprising a polynucleotide molecule encoding a modified Clostridial toxin-CP5B that will replace the $H_{CC}$ targeting domain from a Clostridial toxin the with an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

In addition, similar cloning strategy will be used to produce a modified Clostridial toxin-XP6B, such as, e.g., BoNT/B-CP5B, BoNT/C1-CP5B, BoNT/D-CP5B, BoNT/E-CP5B, BoNT/F-CP5B, BoNT/G-CP5B or TeNT-CP5B, to comprise an enhanced targeting domain comprising, e.g., amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

To construct pET29/BoNT/A-CP5B-GRPP, a similar cloning strategy will be used as described in Example 1a. This cloning strategy will yield a pET29 expression construct comprising the polynucleotide molecule encoding the BoNT/A-CP5B-GRPP operably-linked to a carboxyl terminal polyhistidine affinity binding peptide. A similar cloning strategy will be used to make pET29 expression constructs for other modified Clostridial toxin-CP5B-GRPP toxins, such as, e.g., BoNT/B-CP5B-GRPP, BoNT/C1-CP5B-GRPP, BoNT/D-CP5B-GRPP, BoNT/E-CP5B-GRPP, BoNT/F-CP5B-GRPP, BoNT/G-CP5B-GRPP or TeNT-CP5B-GRPP. Likewise, a similar cloning strategy will be used to make pET29 expression constructs comprising a polynucleotide molecule encoding a modified Clostridial toxin-CP5B with an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

Example 3

Construction of a Modified Clostridial Toxin Comprising a Carboxyl-terminally Presented Enhanced Targeting Domain This example illustrates how to make a modified Clostridial toxin disclosed in the present specification comprising an enhanced targeting domain located at the carboxyl terminus of the modified toxin.

3a. An Enzymatic-translocation-targeting Domain Organization.

A polynucleotide molecule based on BoNT/A-XP6A-GRPP (SEQ ID NO: 121) will be synthesized using standard procedures (BlueHeron® Biotechnology, Bothell, Wash.). This polynucleotide molecule encodes a BoNT/A modified to replace amino acids 1111-1296 of SEQ ID NO: 1, a BoNT/A $H_{CC}$ targeting domain, with amino acids 21-50 of SEQ ID NO: 9, a GRPP targeting domain, and has the general domain arrangement of FIG. 6A. Oligonucleotides of 20 to 50 bases in length are synthesized using standard phosphoramidite synthesis. These oligonucleotides will be hybridized into double stranded duplexes that are ligated together to assemble the full-length polynucleotide molecule. This polynucleotide molecule will be cloned using standard molecular biology methods into a pUCBHB1 vector at the SmaI site to generate pUCBHB1/BoNT/A-XP6A-GRPP. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule based on BoNT/A-XP6A-GRPP (SEQ ID NO: 121) can be synthesized in order to improve expression in an *Escherichia coli* strain. The polynucleotide molecule encoding the BoNT/A-XP6A-GRPP will be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al., Optimizing Expression of Active Botulinum Toxin Type E, International Patent Publication WO 2006/011966 (Feb. 2, 2006); Lance E. Steward et al., Optimizing Expression of Active Botulinum Toxin Type A, International Patent Publication WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-XP6A-GRPP. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, expression optimization to a different organism, such as, e.g., a yeast strain, an insect cell-line or a mammalian cell line, can be done, see, e.g., Steward, supra, (Feb. 2, 2006); and Steward, supra, (Feb. 16, 2006).

A similar cloning strategy will be used to make pUCBHB1 cloning constructs for BoNT/B-XP6A-GRPP, a modified BoNT/B where amino acids 1098-1291 of SEQ ID NO: 2 are replaced with amino acids 21-50 of SEQ ID NO: 9; BoNT/C1-XP6A-GRPP, a modified BoNT/C1 where amino acids 1112-1291 of SEQ ID NO: 3 are replaced with amino acids 21-50 of SEQ ID NO: 9; BoNT/D-XP6A-GRPP, a modified BoNT/D where amino acids 1099-1276 of SEQ ID NO: 4 are replaced with amino acids 21-50 of SEQ ID NO: 9; BoNT/E-XP6A-GRPP, a modified BoNT/E where amino acids 1086-1252 of SEQ ID NO: 5 are replaced with amino acids 21-50 of SEQ ID NO: 9; BoNT/F-XP6A-GRPP, a modified BoNT/F where amino acids 1106-1274 of SEQ ID NO: 6 are replaced with amino acids 21-50 of SEQ ID NO: 9; BoNT/G-XP6A-GRPP, a modified BoNT/G where amino acids 1106-1297 of SEQ ID NO: 7 are replaced with amino acids 21-50 of SEQ ID NO: 9; and TeNT-XP6A-GRPP, a modified TeNT where amino acids 1128-1315 of SEQ ID NO: 8 are replaced with amino acids 21-50 of SEQ ID NO: 9. Likewise, a similar cloning strategy will be used to make pUCBHB1 cloning constructs comprising a polynucleotide molecule encoding a modified Clostridial toxin-XP6A with an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

To construct pET29/BoNT/A-XP6A-GRPP, a pUCBHB1/BoNT/A-XP6A-GRPP construct will be digested with restriction endonucleases that 1) will excise the polynucleotide molecule encoding the open reading frame of BoNT/A-XP6A-GRPP; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-XP6A-GRPP. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-XP6A-GRPP operably-linked to a carboxyl terminal polyhistidine affinity binding peptide.

A similar cloning strategy will be used to make pET29 expression constructs for other modified Clostridial toxin-XP6A-GRPP toxins, such as, e.g., BoNT/B-XP6A-GRPP, BoNT/C1-XP6A-GRPP, BoNT/D-XP6A-GRPP, BoNT/E-XP6A-GRPP, BoNT/F-XP6A-GRPP, BoNT/G-XP6A-GRPP or TeNT-XP6A-GRPP. Likewise, a similar cloning strategy will be used to make pET29 expression constructs comprising a polynucleotide molecule encoding a modified Clostridial toxin-XP6A with an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

3b. A Translocation-Enzymatic-Targeting Domain Organization.

A polynucleotide molecule based on BoNT/A-XP6B-GRPP (SEQ ID NO: 122) will be synthesized and cloned into a pUCBHB1 vector as described in Example 1a. This polynucleotide molecule encodes a BoNT/A modified to replace amino acids 1111-1296 of SEQ ID NO: 1, a BoNT/A $H_{CC}$ targeting domain, with amino acids 21-50 of SEQ ID NO: 9, a GRPP targeting domain, and has the general domain arrangement of FIG. 6B. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

Likewise, a similar cloning strategy will be used to make pUCBHB1 cloning constructs comprising a polynucleotide molecule encoding a modified BoNT/A-XP6B comprising an enhanced targeting domain comprising, e.g, amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33;

amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

In addition, similar cloning strategy will be used to produce a modified Clostridial toxin-XP6B, such as, e.g., BoNT/B-XP6B, BoNT/C1-XP6B, BoNT/D-XP6B, BoNT/E-XP6B, BoNT/F-XP6B, BoNT/G-XP6B or TeNT-XP6B, to comprise an enhanced targeting domain comprising, e.g., amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

To construct pET29/BoNT/A-XP6B-GRPP, a similar cloning strategy will be used as described in Example 1a. This cloning strategy will yield a pET29 expression construct comprising the polynucleotide molecule encoding the BoNT/A-XP6B-GRPP operably-linked to a carboxyl terminal polyhistidine affinity binding peptide. A similar cloning strategy will be used to make pET29 expression constructs for other modified Clostridial toxin-XP6B-GRPP toxins, such as, e.g., BoNT/B-XP6B-GRPP, BoNT/C1-XP6B-GRPP, BoNT/D-XP6B-GRPP, BoNT/E-XP6B-GRPP, BoNT/F-XP6B-GRPP, BoNT/G-XP6B-GRPP or TeNT-XP6B-GRPP. Likewise, a similar cloning strategy will be used to make pET29 expression constructs comprising a polynucleotide molecule encoding a modified Clostridial toxin-XP6B with an enhanced targeting domain comprising, e.g., amino acids 53-81 of SEQ ID NO: 9; amino acids 53-89 of SEQ ID NO: 9; amino acids 98-124 of SEQ ID NO: 9; amino acids 146-178 of SEQ ID NO: 9; amino acids 132-158 of SEQ ID NO: 10; amino acids 32-58 of SEQ ID NO: 11; amino acids 32-75 of SEQ ID NO: 11; amino acids 81-107 of SEQ ID NO: 12; amino acids 125-151 of SEQ ID NO: 12; amino acids 81-107 of SEQ ID NO: 13; amino acids 124-150 of SEQ ID NO: 13; amino acids 52-78 of SEQ ID NO: 14; amino acids 52-93 of SEQ ID NO: 14; amino acids 28-54 of SEQ ID NO: 15; amino acids 76-92 of SEQ ID NO: 16; amino acids 59-92 of SEQ ID NO: 16; amino acids 41-50 of SEQ ID NO: 17; amino acids 24-50 of SEQ ID NO: 17; amino acids 99-112 of SEQ ID NO: 18; amino acids 159-193 of SEQ ID NO: 19; amino acids 154-194 of SEQ ID NO: 19; amino acids 35-70 of SEQ ID NO: 20; amino acids 145-177 of SEQ ID NO: 20; amino acids 1-200 of SEQ ID NO: 21; amino acids 1-150 of SEQ ID NO: 22; amino acids 1-202 of SEQ ID NO: 23; amino acids 1-201 of SEQ ID NO: 24; amino acids 1-225 of SEQ ID NO: 25; amino acids 123-265 of SEQ ID NO: 26; amino acids 21-153 of SEQ ID NO: 27; amino acids 57-210 of SEQ ID NO: 28; amino acids 21-99 of SEQ ID NO: 29; amino acids 31-94 of SEQ ID NO: 29; amino acids 19-178 of SEQ ID NO: 30; amino acids 1-558 of SEQ ID NO: 31; amino acids 1-371 of SEQ ID NO: 32; amino acids 49-118 of SEQ ID NO: 33; amino acids 25-180 of SEQ ID NO: 34; amino acids 1-54 of SEQ ID NO: 35; amino acids 139-257 of SEQ ID NO: 36; amino acids 129-247 of SEQ ID NO: 37; amino acids 19-257 of SEQ ID NO: 38; amino acids 81-210 of SEQ ID NO: 39; amino acids 118-211 of SEQ ID NO: 40; amino acids 107-196 of SEQ ID NO: 41; amino acids 96-197 of SEQ ID NO: 41; amino acids 66-155 of SEQ ID NO: 42; amino acids 123-218 of SEQ ID NO: 43; amino acids 293-390 of SEQ ID NO: 44; amino acids 317-414 of SEQ ID NO: 45; amino acids 315-412 of SEQ ID NO: 46; amino acids 276-373 of SEQ ID NO: 47; amino acids 296-396 of SEQ ID NO: 48; amino acids 370-472 of SEQ ID NO: 49; amino acids 309-409 of SEQ ID NO: 50; amino acids 323-454 of SEQ ID NO: 51; amino acids 412-513 of SEQ ID NO: 52; amino acids 374-513 of SEQ ID NO: 52; amino acids 330-431 of SEQ ID NO: 53; amino acids 293-431 of SEQ ID NO: 53; amino acids 301-402 of SEQ ID NO: 54; amino acids 323-424 of SEQ ID NO: 55; amino acids 267-372 of SEQ ID NO: 56; amino acids 327-429 of SEQ ID NO: 57; amino acids 264-364 of SEQ ID NO: 58; amino acids 400-501 of SEQ ID NO: 59; amino acids 354-455 of SEQ ID NO: 60; amino acids 352-450 of SEQ ID NO: 61; amino acids 281-375 of SEQ ID NO: 62; amino acids 376-478 of SEQ ID NO: 63; amino acids 313-407 of SEQ ID NO: 64; amino acids 211-308 of SEQ ID NO: 65; amino acids 321-426 of SEQ ID NO: 66; amino acids 303-406 of SEQ ID NO: 67; amino acids 247-352 of SEQ ID NO: 68; amino acids 237-352 of SEQ ID NO: 68; amino acids 247-350 of SEQ ID NO: 69; amino acids 262-366 of SEQ ID NO: 70; or amino acids 233-366 of SEQ ID NO: 70.

Example 4

Expression of Modified Clostridial Toxins in a Bacterial Cell

The following example illustrates a procedure useful for expressing any of the modified Clostridial toxins disclosed in the present specification in a bacterial cell.

An expression construct, such as, e.g., any of the expression constructs in Examples 1-5, is introduced into chemically competent E. coli BL21 (DE3) cells (Invitrogen, Inc, Carlsbad, Calif.) using a heat-shock transformation protocol. The heat-shock reaction is plated onto 1.5% Luria-Bertani agar plates (pH 7.0) containing 50 µg/mL of Kanamycin and is placed in a 37° C. incubator for overnight growth. Kanamycin-resistant colonies of transformed E. coli containing the expression construct are used to inoculate a baffled flask containing 3.0 mL of PA-0.5G media containing 50 µg/mL of Kanamycin which is then placed in a 37° C. incubator, shaking at 250 rpm, for overnight growth. The resulting overnight starter culture is in turn used to inoculate a 3 L baffled flask containing ZYP-5052 autoinducing media containing 50 µg/mL of Kanamycin at a dilution of 1:1000. Culture volumes ranged from about 600 mL (20% flask volume) to about 750 mL (25% flask volume). These cultures are grown in a 37° C. incubator shaking at 250 rpm for approximately 5.5 hours and are then transferred to a 16° C. incubator shaking at 250 rpm for overnight expression. Cells are harvested by centrifugation (4,000 rpm at 4° C. for 20-30 minutes) and are used immediately, or stored dry at −80° C. until needed.

Example 5

Purification and Quantification of Modified Clostridial Toxins

The following example illustrates methods useful for purification and quantification of any modified Clostridial toxins disclosed in the present specification.

For immobilized metal affinity chromatography (IMAC) protein purification, E. coli BL21 (DE3) cell pellets used to express a modified Clostridial toxin, as described in Example 7, are resuspended in Column Binding Buffer (25 mM N-(2-hydroxyethyl)piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) Triton-X® 100, 4-octylphenol polyethoxylate; 10% (v/v) glycerol), and then are transferred to a cold Oakridge centrifuge tube. The cell suspension is sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column is prepared using a 20 mL Econo-Pac column support (Bio-Rad Laboratories, Hercules, Calif.) packed with 2.5-5.0 mL of TALON™ SuperFlow $C^{2+}$ affinity resin (BD Biosciences-Clontech, Palo Alto, Calif.), which is then equilibrated by rinsing with 5 column volumes of deionized, distilled water, followed by 5 column volumes of Column Binding Buffer. The clarified lysate is applied slowly to the equilibrated column by gravity flow (approximately 0.25-0.3 mL/minute). The column is then washed with 5 column volumes of Column Wash Buffer (N-(2-hydroxyethyl)piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The modified Clostridial toxin is eluted with 20-30 mL of Column Elution Buffer (25 mM N-(2-hydroxyethyl) piperazine-N'-(2-ethanesulfonic acid) (HEPES), pH 7.8; 500 mM sodium chloride; 500 mM imidazole; 0.1% (v/v) Triton-X® 100, 4-octylphenol polyethoxylate; 10% (v/v) glycerol) and is collected in approximately twelve 1 mL fractions. The amount of modified Clostridial toxin contained in each elution fraction is determined by a Bradford dye assay. In this procedure, 20 µL aliquots of each 1.0 mL fraction is combined with 200 µL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered the elution peak and are combined together. Total protein yield is determined by estimating the total protein concentration of the pooled peak elution fractions using bovine gamma globulin as a standard (Bio-Rad Laboratories, Hercules, Calif.).

For purification of a modified Clostridial toxin using a FPLC desalting column, a HiPrep™ 26/10 size exclusion column (Amersham Biosciences, Piscataway, N.J.) is pre-equilibrated with 80 mL of 4° C. Column Buffer (50 mM sodium phosphate, pH 6.5). After the column is equilibrated, a modified Clostridial toxin sample is applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified Clostridial toxin sample is collected as a single fraction of approximately 7-12 mL.

For purification of a modified Clostridial toxin using a FPLC ion exchange column, a modified Clostridial toxin sample that has been desalted following elution from an IMAC column is applied to a 1 mL Q1™ anion exchange column (Bio-Rad Laboratories, Hercules, Calif.) using a BioLogic DuoFlow chromatography system (Bio-Rad Laboratories, Hercules, Calif.). The sample is applied to the column in 4° C. Column Buffer (50 mM sodium phosphate, pH 6.5) and is eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of modified Clostridial toxin from the column is monitored at 280, 260, and 214 nm, and peaks absorbing above a minimum threshold (0.01 au) at 280 nm are collected. Most of the modified Clostridial toxin will elute at a sodium chloride concentration of approximately 100 to 200 mM. Average total yields of modified Clostridial toxin will be determined by a Bradford assay.

Expression of a modified Clostridial toxin is analyzed by polyacrylamide gel electrophoresis. Samples purified using the procedure described above are added to 2× LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels are stained with SYPRO® Ruby (Bio-Rad Laboratories, Hercules, Calif.) and the separated polypeptides are imaged using a Fluor-S MAX MultiImager (Bio-Rad Laboratories, Hercules, Calif.) for quantification of modified Clostridial toxin expression levels. The size and amount of modified Clostridial toxin is determined by comparison to MagicMark™ protein molecular weight standards (Invitrogen, Inc, Carlsbad, Calif.).

Expression of modified Clostridial toxin is also analyzed by Western blot analysis. Protein samples purified using the procedure described above are added to 2× LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots are washed three times for 15 minutes each time in Tris-Buffered Saline TWEEN-20®. Washed membranes are incubated at room temperature for 2 hours in Tris-Buffered Saline TWEEN-20® containing an appropriate immunoglobulin G antibody conjugated to horseradish peroxidase as a secondary antibody. Secondary antibody-probed blots are washed three times for 15 minutes each time in Tris-Buffered Saline TWEEN-20®. Signal detection of the labeled modified Clostridial toxin are visualized using the ECL Plus™ Western Blot Detection System (Amersham Biosciences, Piscataway, N.J.) and are imaged with a Typhoon 9410 Variable Mode Imager (Amersham Biosciences, Piscataway, N.J.) for quantification of modified Clostridial toxin expression levels.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

SEQUENCE LISTING

```
<160> NUMBER OF SEQ ID NOS: 123

<210> SEQ ID NO 1
<211> LENGTH: 1296
<212> TYPE: PRT
<213> ORGANISM: Clostridium botulinum serotype A

<400> SEQUENCE: 1

Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
                 20                  25                  30

Val Lys Ala Phe Lys Ile His Asn Lys Ile Trp Val Ile Pro Glu Arg
             35                  40                  45

Asp Thr Phe Thr Asn Pro Glu Glu Gly Asp Leu Asn Pro Pro Pro Glu
         50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140
```

-continued

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
```

```
                    565                 570                 575
Leu Asn Pro Ser Arg Val Tyr Thr Phe Phe Ser Ser Asp Tyr Val Lys
                580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
        610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Thr Glu Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
            820                 825                 830
Gln Val Asp Arg Leu Lys Asp Lys Val Asn Asn Thr Leu Ser Thr Asp
        835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
            900                 905                 910
Gln Ile Gln Leu Phe Asn Leu Glu Ser Ser Lys Ile Glu Val Ile Leu
        915                 920                 925
Lys Asn Ala Ile Val Tyr Asn Ser Met Tyr Glu Asn Phe Ser Thr Ser
    930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
            980                 985                 990
```

```
Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
            1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Ile Lys Asp Leu Tyr
    1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
                1140                1145                1150

Ser Leu Tyr Arg Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
                1220                1225                1230

Asn Lys Cys Lys Met Asn Leu Gln Asp Asn Asn Gly Asn Asp Ile Gly
            1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
            1285                1290                1295

<210> SEQ ID NO 2
<211> LENGTH: 1291
<212> TYPE: PRT
<213> ORGANISM: Clostridium botulinum serotype B

<400> SEQUENCE: 2

Met Pro Val Thr Ile Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80
```

-continued

```
Thr Asn Asp Lys Lys Asn Ile Phe Leu Gln Thr Met Ile Lys Leu Phe
                 85                  90                  95
Asn Arg Ile Lys Ser Lys Pro Leu Gly Glu Lys Leu Leu Glu Met Ile
                100                 105                 110
Ile Asn Gly Ile Pro Tyr Leu Gly Asp Arg Val Pro Leu Glu Glu
            115                 120                 125
Phe Asn Thr Asn Ile Ala Ser Val Thr Val Asn Lys Leu Ile Ser Asn
            130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Gly Thr Ile Asp Ile Gly
                165                 170                 175
Ile Gln Asn His Phe Ala Ser Arg Glu Gly Phe Gly Gly Ile Met Gln
            180                 185                 190
Met Lys Phe Cys Pro Glu Tyr Val Ser Val Phe Asn Asn Val Gln Glu
        195                 200                 205
Asn Lys Gly Ala Ser Ile Phe Asn Arg Arg Gly Tyr Phe Ser Asp Pro
    210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Thr Pro Ser Thr Asp Lys Ser Ile
        275                 280                 285
Tyr Asp Lys Val Leu Gln Asn Phe Arg Gly Ile Val Asp Arg Leu Asn
    290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
        355                 360                 365
Thr Arg Ala Ser Tyr Phe Ser Asp Ser Leu Pro Pro Val Lys Ile Lys
    370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
        435                 440                 445
Val Asp Asn Glu Asp Leu Phe Phe Ile Ala Asp Lys Asn Ser Phe Ser
    450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
```

-continued

```
Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
```

```
                930             935             940
Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu Ser
    1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
                1060                1065                1070

Glu Arg Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Thr Tyr Lys
    1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
                1220                1225                1230

Asp Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr Leu
    1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290

<210> SEQ ID NO 3
<211> LENGTH: 1291
<212> TYPE: PRT
<213> ORGANISM: Clostridium botulinum serotype C1

<400> SEQUENCE: 3

Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
```

-continued

```
                 20                  25                  30
Pro Glu Lys Ala Phe Arg Ile Thr Gly Asn Ile Trp Val Ile Pro Asp
             35                  40                  45

Arg Phe Ser Arg Asn Ser Asn Pro Asn Leu Asn Lys Pro Pro Arg Val
         50                  55                  60

Thr Ser Pro Lys Ser Gly Tyr Tyr Asp Pro Asn Tyr Leu Ser Thr Asp
 65                  70                  75                  80

Ser Asp Lys Asp Pro Phe Leu Lys Glu Ile Ile Lys Leu Phe Lys Arg
                 85                  90                  95

Ile Asn Ser Arg Glu Ile Gly Glu Leu Ile Tyr Arg Leu Ser Thr
            100                 105                 110

Asp Ile Pro Phe Pro Gly Asn Asn Thr Pro Ile Asn Thr Phe Asp
            115                 120                 125

Phe Asp Val Asp Phe Asn Ser Val Asp Val Lys Thr Arg Gln Gly Asn
            130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
            195                 200                 205

Val Gly Glu Gly Arg Phe Ser Lys Ser Glu Phe Cys Met Asp Pro Ile
            210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
            290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
            370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
            435                 440                 445
```

```
Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
                515                 520                 525

Glu Asn Gln Val Phe Tyr Asp Asn Arg Thr Gln Asn Val Asp Tyr Leu
530                 535                 540

Asn Ser Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
                580                 585                 590

Val Gln Gly Gly Leu Phe Leu Met Trp Ala Asn Asp Val Val Glu Asp
                595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
                675                 680                 685

Thr Ile Asp Asn Cys Leu Glu Gln Arg Ile Lys Arg Trp Lys Asp Ser
                690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
                755                 760                 765

Asp Val Lys Ile Ser Glu Ala Met Asn Asn Ile Asn Lys Phe Ile Arg
                770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
                835                 840                 845

Phe Ser Tyr Thr Asn Asn Ser Leu Leu Lys Asp Ile Ile Asn Glu Tyr
                850                 855                 860

Phe Asn Asn Ile Asn Asp Ser Lys Ile Leu Ser Leu Gln Asn Arg Lys
865                 870                 875                 880
```

```
Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
            930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
                980                 985                 990

Phe Ser Tyr Asp Ile Ser Asn Asn Ala Pro Gly Tyr Asn Lys Trp Phe
                995                 1000                1005

Phe Val Thr Val Thr Asn Asn Met Met Gly Asn Met Lys Ile Tyr Ile
                1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
                1045                1050                1055

Gly Leu Ile Thr Ser Asp Ser Asp Asn Ile Asn Met Trp Ile Arg Asp
                1060                1065                1070

Phe Tyr Ile Phe Ala Lys Glu Leu Asp Gly Lys Asp Ile Asn Ile Leu
                1075                1080                1085

Phe Asn Ser Leu Gln Tyr Thr Asn Val Val Lys Asp Tyr Trp Gly Asn
                1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135

Arg Asn Asn Asn Asp Phe Asn Glu Gly Tyr Lys Ile Ile Ile Lys Arg
                1140                1145                1150

Ile Arg Gly Asn Thr Asn Asp Thr Arg Val Arg Gly Gly Asp Ile Leu
                1155                1160                1165

Tyr Phe Asp Met Thr Ile Asn Asn Lys Ala Tyr Asn Leu Phe Met Lys
                1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Tyr Ala Ser Gln Ile Phe
                1220                1225                1230

Lys Ser Asn Phe Asn Gly Glu Asn Ile Ser Gly Ile Cys Ser Ile Gly
                1235                1240                1245

Thr Tyr Arg Phe Arg Leu Gly Gly Asp Trp Tyr Arg His Asn Tyr Leu
                1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290
```

```
<210> SEQ ID NO 4
<211> LENGTH: 1276
<212> TYPE: PRT
<213> ORGANISM: Clostridium botulinum serotype D

<400> SEQUENCE: 4

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
```

-continued

```
            385                 390                 395                 400
Leu Thr Asn Lys Gly Phe Asn Ile Glu Asn Ser Gly Gln Asn Ile Glu
                    405                 410                 415

Arg Asn Pro Ala Leu Gln Lys Leu Ser Ser Glu Ser Val Val Asp Leu
                    420                 425                 430

Phe Thr Lys Val Cys Leu Arg Leu Thr Lys Asn Ser Arg Asp Asp Ser
                    435                 440                 445

Thr Cys Ile Lys Val Lys Asn Asn Arg Leu Pro Tyr Val Ala Asp Lys
            450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                    485                 490                 495

Leu Asp Gly Gln Val Pro Ile Asn Pro Glu Ile Val Asp Pro Leu Leu
                    500                 505                 510

Pro Asn Val Asn Met Glu Pro Leu Asn Leu Pro Gly Glu Glu Ile Val
                    515                 520                 525

Phe Tyr Asp Asp Ile Thr Lys Tyr Val Asp Tyr Leu Asn Ser Tyr Tyr
            530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                    565                 570                 575

Phe Leu Pro Ser Leu Ala Glu Lys Val Asn Lys Gly Val Gln Ala Gly
                    580                 585                 590

Leu Phe Leu Asn Trp Ala Asn Glu Val Val Glu Asp Phe Thr Thr Asn
                    595                 600                 605

Ile Met Lys Lys Asp Thr Leu Asp Lys Ile Ser Asp Val Ser Val Ile
            610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                    645                 650                 655

Glu Gly Phe Pro Glu Phe Thr Ile Pro Ala Leu Gly Val Phe Thr Phe
                    660                 665                 670

Tyr Ser Ser Ile Gln Glu Arg Glu Lys Ile Ile Lys Thr Ile Glu Asn
                    675                 680                 685

Cys Leu Glu Gln Arg Val Lys Arg Trp Lys Asp Ser Tyr Gln Trp Met
            690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                    725                 730                 735

Lys Ile Asp Leu Glu Tyr Lys Lys Tyr Ser Gly Ser Asp Lys Glu Asn
                    740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
            770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                    805                 810                 815
```

-continued

His Asn Ile Ile Leu Val Gly Glu Val Asp Arg Leu Lys Ala Lys Val
             820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
            915                 920                 925

Glu Asn Ser Ser Val Ser Phe Trp Ile Lys Ile Ser Lys Asp Leu Thr
        930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu Lys
    1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
            1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
    1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
            1140                1145                1150

Asp Asn Ile Ile Leu His Met Leu Tyr Asn Ser Arg Lys Tyr Met Ile
        1155                1160                1165

Ile Arg Asp Thr Asp Thr Ile Tyr Ala Thr Gln Gly Gly Glu Cys Ser
    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                1205                1210                1215

Cys Ser Gln Ile Phe Ser Ser Phe Arg Glu Asn Thr Met Leu Leu Ala
            1220                1225                1230

Asp Ile Tyr Lys Pro Trp Arg Phe Ser Phe Lys Asn Ala Tyr Thr Pro
        1235                1240                1245

```
Val Ala Val Thr Asn Tyr Glu Thr Lys Leu Leu Ser Thr Ser Ser Phe
    1250                1255                1260

Trp Lys Phe Ile Ser Arg Asp Pro Gly Trp Val Glu
1265            1270                1275

<210> SEQ ID NO 5
<211> LENGTH: 1252
<212> TYPE: PRT
<213> ORGANISM: Clostridium botulinum serotype E

<400> SEQUENCE: 5

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350
```

-continued

```
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Asn Asn Leu Lys Val Asn Phe
            370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
            405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
            435                 440                 445
Asn Thr Pro Lys Glu Ile Asp Asp Thr Val Thr Ser Asn Asn Asn Tyr
            450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
            485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
            530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
            565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
            610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
            645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
            675                 680                 685
Trp Met Thr Lys Ile Asn Thr Gln Phe Asn Lys Arg Lys Glu Gln Met
            690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
            725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
```

```
            770           775           780
Tyr Asp Glu Asn Val Lys Thr Tyr Leu Leu Asn Tyr Ile Ile Gln His
785           790           795           800

Gly Ser Ile Leu Gly Glu Ser Gln Gln Glu Leu Asn Ser Met Val Thr
              805           810           815

Asp Thr Leu Asn Asn Ser Ile Pro Phe Lys Leu Ser Ser Tyr Thr Asp
              820           825           830

Asp Lys Ile Leu Ile Ser Tyr Phe Asn Lys Phe Phe Lys Arg Ile Lys
              835           840           845

Ser Ser Ser Val Leu Asn Met Arg Tyr Lys Asn Asp Lys Tyr Val Asp
850           855           860

Thr Ser Gly Tyr Asp Ser Asn Ile Asn Ile Asn Gly Asp Val Tyr Lys
865           870           875           880

Tyr Pro Thr Asn Lys Asn Gln Phe Gly Ile Tyr Asn Asp Lys Leu Ser
              885           890           895

Glu Val Asn Ile Ser Gln Asn Asp Tyr Ile Ile Tyr Asp Asn Lys Tyr
              900           905           910

Lys Asn Phe Ser Ile Ser Phe Trp Val Arg Ile Pro Asn Tyr Asp Asn
              915           920           925

Lys Ile Val Asn Val Asn Asn Glu Tyr Thr Ile Ile Asn Cys Met Arg
930           935           940

Asp Asn Asn Ser Gly Trp Lys Val Ser Leu Asn His Asn Glu Ile Ile
945           950           955           960

Trp Thr Leu Gln Asp Asn Ala Gly Ile Asn Gln Lys Leu Ala Phe Asn
              965           970           975

Tyr Gly Asn Ala Asn Gly Ile Ser Asp Tyr Ile Asn Lys Trp Ile Phe
              980           985           990

Val Thr Ile Thr Asn Asp Arg Leu Gly Asp Ser Lys Leu Tyr Ile Asn
              995          1000          1005

Gly Asn Leu Ile Asp Gln Lys Ser Ile Leu Asn Leu Gly Asn Ile His
             1010          1015          1020

Val Ser Asp Asn Ile Leu Phe Lys Ile Val Asn Cys Ser Tyr Thr Arg
1025          1030          1035          1040

Tyr Ile Gly Ile Arg Tyr Phe Asn Ile Phe Asp Lys Glu Leu Asp Glu
              1045          1050          1055

Thr Glu Ile Gln Thr Leu Tyr Ser Asn Glu Pro Asn Thr Asn Ile Leu
              1060          1065          1070

Lys Asp Phe Trp Gly Asn Tyr Leu Leu Tyr Asp Lys Glu Tyr Tyr Leu
              1075          1080          1085

Leu Asn Val Leu Lys Pro Asn Asn Phe Ile Asp Arg Arg Lys Asp Ser
1090          1095          1100

Thr Leu Ser Ile Asn Asn Ile Arg Ser Thr Ile Leu Leu Ala Asn Arg
1105          1110          1115          1120

Leu Tyr Ser Gly Ile Lys Val Lys Ile Gln Arg Val Asn Asn Ser Ser
              1125          1130          1135

Thr Asn Asp Asn Leu Val Arg Lys Asn Asp Gln Val Tyr Ile Asn Phe
              1140          1145          1150

Val Ala Ser Lys Thr His Leu Phe Pro Leu Tyr Ala Asp Thr Ala Thr
              1155          1160          1165

Thr Asn Lys Glu Lys Thr Ile Lys Ile Ser Ser Ser Gly Asn Arg Phe
              1170          1175          1180

Asn Gln Val Val Val Met Asn Ser Val Gly Asn Asn Cys Thr Met Asn
1185          1190          1195          1200
```

-continued

```
Phe Lys Asn Asn Asn Gly Asn Ile Gly Leu Leu Gly Phe Lys Ala
            1205                1210                1215

Asp Thr Val Val Ala Ser Thr Trp Tyr Tyr Thr His Met Arg Asp His
            1220                1225                1230

Thr Asn Ser Asn Gly Cys Phe Trp Asn Phe Ile Ser Glu Glu His Gly
        1235                1240                1245

Trp Gln Glu Lys
    1250

<210> SEQ ID NO 6
<211> LENGTH: 1274
<212> TYPE: PRT
<213> ORGANISM: Clostridium botulinum serotype F

<400> SEQUENCE: 6

Met Pro Val Ala Ile Asn Ser Phe Asn Tyr Asn Asp Pro Val Asn Asp
  1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
     50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320
```

-continued

```
Gln Trp Lys Tyr Gly Leu Asp Lys Asn Ala Asp Gly Ser Tyr Thr Val
            325                 330                 335
Asn Glu Asn Lys Phe Asn Glu Ile Tyr Lys Lys Leu Tyr Ser Phe Thr
            340                 345                 350
Glu Ser Asp Leu Ala Asn Lys Phe Lys Val Lys Cys Arg Asn Thr Tyr
            355                 360                 365
Phe Ile Lys Tyr Glu Phe Leu Lys Val Pro Asn Leu Leu Asp Asp Asp
            370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
            405                 410                 415
Pro Asp Lys Gly Leu Val Glu Lys Ile Val Lys Phe Cys Lys Ser Val
            420                 425                 430
Ile Pro Arg Lys Gly Thr Lys Ala Pro Pro Arg Leu Cys Ile Arg Val
            435                 440                 445
Asn Asn Ser Glu Leu Phe Phe Val Ala Ser Glu Ser Ser Tyr Asn Glu
            450                 455                 460
Asn Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
            485                 490                 495
Gln Thr Ile Pro Gln Ile Ser Asn Arg Thr Leu Asn Thr Leu Val Gln
            500                 505                 510
Asp Asn Ser Tyr Val Pro Arg Tyr Asp Ser Asn Gly Thr Ser Glu Ile
            515                 520                 525
Glu Glu Tyr Asp Val Val Asp Phe Asn Val Phe Phe Tyr Leu His Ala
            530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Asp Ile Phe Phe Ser Ser Glu
            565                 570                 575
Phe Ile Asp Thr Ile Asn Lys Pro Val Asn Ala Ala Leu Phe Ile Asp
            580                 585                 590
Trp Ile Ser Lys Val Ile Arg Asp Phe Thr Thr Glu Ala Thr Gln Lys
            595                 600                 605
Ser Thr Val Asp Lys Ile Ala Asp Ile Ser Leu Ile Val Pro Tyr Val
            610                 615                 620
Gly Leu Ala Leu Asn Ile Ile Glu Ala Glu Lys Gly Asn Phe Glu
625                 630                 635                 640
Glu Ala Phe Glu Leu Leu Gly Val Gly Ile Leu Leu Glu Phe Val Pro
            645                 650                 655
Glu Leu Thr Ile Pro Val Ile Leu Val Phe Thr Ile Lys Ser Tyr Ile
            660                 665                 670
Asp Ser Tyr Glu Asn Lys Asn Lys Ala Ile Lys Ala Ile Asn Asn Ser
            675                 680                 685
Leu Ile Glu Arg Glu Ala Lys Trp Lys Glu Ile Tyr Ser Trp Ile Val
            690                 695                 700
Ser Asn Trp Leu Thr Arg Ile Asn Thr Gln Phe Asn Lys Arg Lys Glu
705                 710                 715                 720
Gln Met Tyr Gln Ala Leu Gln Asn Gln Val Asp Ala Ile Lys Thr Ala
            725                 730                 735
Ile Glu Tyr Lys Tyr Asn Asn Tyr Thr Ser Asp Glu Lys Asn Arg Leu
            740                 745                 750
```

```
Glu Ser Glu Tyr Asn Ile Asn Asn Ile Glu Glu Leu Asn Lys Lys
            755                 760                 765

Val Ser Leu Ala Met Lys Asn Ile Glu Arg Phe Met Thr Glu Ser Ser
770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
                835                 840                 845

Thr Asn Asp Lys Ile Leu Ile Ile Tyr Phe Asn Arg Leu Tyr Lys Lys
                850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
                900                 905                 910

Leu Ser Glu Val Asn Ile Ala Gln Asn Asn Asp Ile Ile Tyr Asn Ser
                915                 920                 925

Arg Tyr Gln Asn Phe Ser Ile Ser Phe Trp Val Arg Ile Pro Lys His
                930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
                980                 985                 990

Leu Ile Phe Arg Tyr Glu Glu Leu Asn Arg Ile Ser Asn Tyr Ile Asn
                995                 1000                1005

Lys Trp Ile Phe Val Thr Ile Thr Asn Asn Arg Leu Gly Asn Ser Arg
                1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
                1060                1065                1070

Glu Leu Asp Lys Thr Glu Ile Glu Thr Leu Tyr Ser Asn Glu Pro Asp
                1075                1080                1085

Pro Ser Ile Leu Lys Asn Tyr Trp Gly Asn Tyr Leu Leu Tyr Asn Lys
                1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                1125                1130                1135

Ser Val Phe Leu Asn Tyr Lys Leu Tyr Glu Gly Val Glu Val Ile Ile
                1140                1145                1150

Arg Lys Asn Gly Pro Ile Asp Ile Ser Asn Thr Asp Asn Phe Val Arg
                1155                1160                1165

Lys Asn Asp Leu Ala Tyr Ile Asn Val Val Asp Arg Gly Val Glu Tyr
```

```
                1170                1175                1180
Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
                1205                1210                1215

Gly Asn Asn Cys Thr Met Asn Phe Gln Asn Asn Gly Ser Asn Ile
                1220                1225                1230

Gly Leu Leu Gly Phe His Ser Asn Asn Leu Val Ala Ser Ser Trp Tyr
                1235                1240                1245

Tyr Asn Asn Ile Arg Arg Asn Thr Ser Ser Asn Gly Cys Phe Trp Ser
                1250                1255                1260

Ser Ile Ser Lys Glu Asn Gly Trp Lys Glu
1265                1270

<210> SEQ ID NO 7
<211> LENGTH: 1297
<212> TYPE: PRT
<213> ORGANISM: Clostridium botulinum serotype G

<400> SEQUENCE: 7

Met Pro Val Asn Ile Lys Asn Phe Asn Tyr Asn Asp Pro Ile Asn Asn
  1               5                  10                  15

Asp Asp Ile Ile Met Met Glu Pro Phe Asn Asp Pro Gly Pro Gly Thr
                 20                  25                  30

Tyr Tyr Lys Ala Phe Arg Ile Ile Asp Arg Ile Trp Ile Val Pro Glu
             35                  40                  45

Arg Phe Thr Tyr Gly Phe Gln Pro Asp Gln Phe Asn Ala Ser Thr Gly
 50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
                 85                  90                  95

Asn Arg Ile Asn Ser Lys Pro Ser Gly Gln Arg Leu Leu Asp Met Ile
                100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
                180                 185                 190

Ile Arg Phe Cys Pro Ser Cys Leu Asn Val Phe Asn Asn Val Gln Glu
            195                 200                 205

Asn Lys Asp Thr Ser Ile Phe Ser Arg Arg Ala Tyr Phe Ala Asp Pro
210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
                260                 265                 270

Gly Gly His Asp Pro Ser Val Ile Ser Pro Ser Thr Asp Met Asn Ile
```

```
              275                 280                 285
Tyr Asn Lys Ala Leu Gln Asn Phe Gln Asp Ile Ala Asn Arg Leu Asn
    290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                325                 330                 335
Tyr Ser Val Asp Lys Asp Lys Phe Asp Lys Leu Tyr Lys Ala Leu Met
                340                 345                 350
Phe Gly Phe Thr Glu Thr Asn Leu Ala Gly Glu Tyr Gly Ile Lys Thr
            355                 360                 365
Arg Tyr Ser Tyr Phe Ser Glu Tyr Leu Pro Pro Ile Lys Thr Glu Lys
    370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
                420                 425                 430
Ile Ala Met Cys Lys Pro Val Met Tyr Lys Asn Thr Gly Lys Ser Glu
            435                 440                 445
Gln Cys Ile Ile Val Asn Asn Glu Asp Leu Phe Ile Ala Asn Lys
    450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
            515                 520                 525
Gln Ser Ala Leu Lys Lys Ile Phe Val Asp Gly Asp Ser Leu Phe Glu
    530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
                580                 585                 590
Ser Leu Phe Val Asn Trp Val Lys Gly Val Ile Asp Asp Phe Thr Ser
            595                 600                 605
Glu Ser Thr Gln Lys Ser Thr Ile Asp Lys Val Ser Asp Val Ser Ile
    610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
                660                 665                 670
Leu Glu Ser Tyr Val Gly Asn Lys Gly His Ile Ile Met Thr Ile Ser
            675                 680                 685
Asn Ala Leu Lys Lys Arg Asp Gln Lys Trp Thr Asp Met Tyr Gly Leu
    690                 695                 700
```

```
Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
        995                 1000                1005

Trp Phe Ser Ile Thr Ile Thr Asn Asp Arg Leu Gly Asn Ala Asn Ile
    1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
                1045                1050                1055

Asp Thr Thr Lys Phe Val Trp Ile Lys Asp Phe Asn Ile Phe Gly Arg
            1060                1065                1070

Glu Leu Asn Ala Thr Glu Val Ser Ser Leu Tyr Trp Ile Gln Ser Ser
        1075                1080                1085

Thr Asn Thr Leu Lys Asp Phe Trp Gly Asn Pro Leu Arg Tyr Asp Thr
    1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
                1125                1130                1135
```

Asn Ala Ala Ile Asn Tyr Gln Asn Leu Tyr Leu Gly Leu Arg Phe Ile
            1140                1145                1150

Ile Lys Lys Ala Ser Asn Ser Arg Asn Ile Asn Asn Asp Asn Ile Val
            1155                1160                1165

Arg Glu Gly Asp Tyr Ile Tyr Leu Asn Ile Asp Asn Ile Ser Asp Glu
            1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
            1205                1210                1215

Gln Ile Lys Lys Tyr Tyr Glu Lys Thr Thr Tyr Asn Cys Gln Ile Leu
            1220                1225                1230

Cys Glu Lys Asp Thr Lys Thr Phe Gly Leu Phe Gly Ile Gly Lys Phe
            1235                1240                1245

Val Lys Asp Tyr Gly Tyr Val Trp Asp Thr Tyr Asp Asn Tyr Phe Cys
            1250                1255                1260

Ile Ser Gln Trp Tyr Leu Arg Arg Ile Ser Glu Asn Ile Asn Lys Leu
1265                1270                1275                1280

Arg Leu Gly Cys Asn Trp Gln Phe Ile Pro Val Asp Glu Gly Trp Thr
            1285                1290                1295

Glu

<210> SEQ ID NO 8
<211> LENGTH: 1315
<212> TYPE: PRT
<213> ORGANISM: Clostridium tetani

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
            85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
            165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
            195                 200                 205

-continued

Val Ile Glu Asn Ile Thr Ser Leu Thr Ile Gly Lys Ser Lys Tyr Phe
210                215                220

Gln Asp Pro Ala Leu Leu Met His Glu Leu Ile His Val Leu His
225                230                235                240

Gly Leu Tyr Gly Met Gln Val Ser Ser His Glu Ile Ile Pro Ser Lys
                245                250                255

Gln Glu Ile Tyr Met Gln His Thr Tyr Pro Ile Ser Ala Glu Glu Leu
        260                265                270

Phe Thr Phe Gly Gly Gln Asp Ala Asn Leu Ile Ser Ile Asp Ile Lys
            275                280                285

Asn Asp Leu Tyr Glu Lys Thr Leu Asn Asp Tyr Lys Ala Ile Ala Asn
290                295                300

Lys Leu Ser Gln Val Thr Ser Cys Asn Asp Pro Asn Ile Asp Ile Asp
305                310                315                320

Ser Tyr Lys Gln Ile Tyr Gln Gln Lys Tyr Gln Phe Asp Lys Asp Ser
                325                330                335

Asn Gly Gln Tyr Ile Val Asn Glu Asp Lys Phe Gln Ile Leu Tyr Asn
            340                345                350

Ser Ile Met Tyr Gly Phe Thr Glu Ile Glu Leu Gly Lys Lys Phe Asn
            355                360                365

Ile Lys Thr Arg Leu Ser Tyr Phe Ser Met Asn His Asp Pro Val Lys
370                375                380

Ile Pro Asn Leu Leu Asp Asp Thr Ile Tyr Asn Asp Thr Glu Gly Phe
385                390                395                400

Asn Ile Glu Ser Lys Asp Leu Lys Ser Glu Tyr Lys Gly Gln Asn Met
                405                410                415

Arg Val Asn Thr Asn Ala Phe Arg Asn Val Asp Gly Ser Gly Leu Val
            420                425                430

Ser Lys Leu Ile Gly Leu Cys Lys Lys Ile Ile Pro Pro Thr Asn Ile
        435                440                445

Arg Glu Asn Leu Tyr Asn Arg Thr Ala Ser Leu Thr Asp Leu Gly Gly
    450                455                460

Glu Leu Cys Ile Lys Ile Lys Asn Glu Asp Leu Thr Phe Ile Ala Glu
465                470                475                480

Lys Asn Ser Phe Ser Glu Glu Pro Phe Gln Asp Glu Ile Val Ser Tyr
                485                490                495

Asn Thr Lys Asn Lys Pro Leu Asn Phe Asn Tyr Ser Leu Asp Lys Ile
            500                505                510

Ile Val Asp Tyr Asn Leu Gln Ser Lys Ile Thr Leu Pro Asn Asp Arg
        515                520                525

Thr Thr Pro Val Thr Lys Gly Ile Pro Tyr Ala Pro Glu Tyr Lys Ser
530                535                540

Asn Ala Ala Ser Thr Ile Glu Ile His Asn Ile Asp Asp Asn Thr Ile
545                550                555                560

Tyr Gln Tyr Leu Tyr Ala Gln Lys Ser Pro Thr Thr Leu Gln Arg Ile
                565                570                575

Thr Met Thr Asn Ser Val Asp Asp Ala Leu Ile Asn Ser Thr Lys Ile
            580                585                590

Tyr Ser Tyr Phe Pro Ser Val Ile Ser Lys Val Asn Gln Gly Ala Gln
        595                600                605

Gly Ile Leu Phe Leu Gln Trp Val Arg Asp Ile Asp Asp Phe Thr
    610                615                620

Asn Glu Ser Ser Gln Lys Thr Thr Ile Asp Lys Ile Ser Asp Val Ser
625                630                635                640

```
Thr Ile Val Pro Tyr Ile Gly Pro Ala Leu Asn Ile Val Lys Gln Gly
            645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
            690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                    725                 730                 735

Arg Ser Tyr Gln Met Tyr Arg Ser Leu Glu Tyr Gln Val Asp Ala Ile
                740                 745                 750

Lys Lys Ile Ile Asp Tyr Glu Tyr Lys Ile Tyr Ser Gly Pro Asp Lys
            755                 760                 765

Glu Gln Ile Ala Asp Glu Ile Asn Asn Leu Lys Asn Lys Leu Glu Glu
            770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                    805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
            850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                    885                 890                 895

Ser Asp Ile Ser Gly Phe Asn Ser Ser Val Ile Thr Tyr Pro Asp Ala
                900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
            930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                    965                 970                 975

Ile Ser Ser Met Lys Lys His Ser Leu Ser Ile Gly Ser Gly Trp Ser
                980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe Asn
            1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
                    1045                1050                1055

Glu Ile Thr Gly Leu Gly Ala Ile Arg Glu Asp Asn Asn Ile Thr Leu
```

```
                            1060                1065                1070
Lys Leu Asp Arg Cys Asn Asn Asn Gln Tyr Val Ser Ile Asp Lys
            1075                1080                1085

Phe Arg Ile Phe Cys Lys Ala Leu Asn Pro Lys Glu Ile Glu Lys Leu
        1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
            1125                1130                1135

Ser Lys Asp Val Gln Leu Lys Asn Ile Thr Asp Tyr Met Tyr Leu Thr
        1140                1145                1150

Asn Ala Pro Ser Tyr Thr Asn Gly Lys Leu Asn Ile Tyr Tyr Arg Arg
            1155                1160                1165

Leu Tyr Asn Gly Leu Lys Phe Ile Ile Lys Arg Tyr Thr Pro Asn Asn
            1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
            1205                1210                1215

Ala Phe Asn Asn Leu Asp Arg Ile Leu Arg Val Gly Tyr Asn Ala Pro
            1220                1225                1230

Gly Ile Pro Leu Tyr Lys Lys Met Glu Ala Val Lys Leu Arg Asp Leu
            1235                1240                1245

Lys Thr Tyr Ser Val Gln Leu Lys Leu Tyr Asp Asp Lys Asn Ala Ser
        1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
            1285                1290                1295

Lys Ile Leu Gly Cys Asp Trp Tyr Phe Val Pro Thr Asp Glu Gly Trp
            1300                1305                1310

Thr Asn Asp
        1315

<210> SEQ ID NO 9
<211> LENGTH: 180
<212> TYPE: PRT
<213> ORGANISM: Homo sapiens

<400> SEQUENCE: 9

Met Lys Ser Ile Tyr Phe Val Ala Gly Leu Phe Val Met Leu Val Gln
  1               5                  10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
```

```
                115                 120                 125
Arg Arg Asp Phe Pro Glu Glu Val Ala Ile Val Glu Glu Leu Gly Arg
130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 10
<211> LENGTH: 176
<212> TYPE: PRT
<213> ORGANISM: Homo sapiens

<400> SEQUENCE: 10

Met Thr Met Cys Ser Gly Ala Arg Leu Ala Leu Leu Val Tyr Gly Ile
1               5                   10                  15

Ile Met His Ser Ser Val Tyr Ser Ser Pro Ala Ala Gly Leu Arg
                20                  25                  30

Phe Pro Gly Ile Arg Pro Glu Glu Ala Tyr Gly Glu Asp Gly Asn
            35                  40                  45

Pro Leu Pro Asp Phe Asp Gly Ser Glu Pro Gly Ala Gly Ser Pro
50                  55                  60

Ala Ser Ala Pro Arg Ala Ala Ala Trp Tyr Arg Pro Ala Gly Arg
65                  70                  75                  80

Arg Asp Val Ala His Gly Ile Leu Asn Glu Ala Tyr Arg Lys Val Leu
                85                  90                  95

Asp Gln Leu Ser Ala Gly Lys His Leu Gln Ser Leu Val Ala Arg Gly
            100                 105                 110

Val Gly Gly Ser Leu Gly Gly Gly Ala Gly Asp Asp Ala Glu Pro Leu
        115                 120                 125

Ser Lys Arg His Ser Asp Gly Ile Phe Thr Asp Ser Tyr Ser Arg Tyr
130                 135                 140

Arg Lys Gln Met Ala Val Lys Lys Tyr Leu Ala Ala Val Leu Gly Lys
145                 150                 155                 160

Arg Tyr Lys Gln Arg Val Lys Asn Lys Gly Arg Arg Ile Ala Tyr Leu
                165                 170                 175

<210> SEQ ID NO 11
<211> LENGTH: 108
<212> TYPE: PRT
<213> ORGANISM: Homo sapiens

<400> SEQUENCE: 11

Met Pro Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg Tyr
                20                  25                  30

Ala Asp Ala Ile Phe Thr Asn Ser Tyr Arg Lys Val Leu Gly Gln Leu
            35                  40                  45

Ser Ala Arg Lys Leu Leu Gln Asp Ile Met Ser Arg Gln Gln Gly Glu
50                  55                  60

Ser Asn Gln Glu Arg Gly Ala Arg Ala Arg Leu Gly Arg Gln Val Asp
65                  70                  75                  80

Ser Met Trp Ala Glu Gln Lys Gln Met Glu Leu Glu Ser Ile Leu Val
                85                  90                  95
```

Ala Leu Leu Gln Lys His Ser Arg Asn Ser Gln Gly
            100                 105

<210> SEQ ID NO 12
<211> LENGTH: 170
<212> TYPE: PRT
<213> ORGANISM: Homo sapiens

<400> SEQUENCE: 12

Met Asp Thr Arg Asn Lys Ala Gln Leu Leu Val Leu Thr Leu Leu
 1               5                  10                  15

Ser Val Leu Phe Ser Gln Thr Ser Ala Trp Pro Leu Tyr Arg Ala Pro
                20                  25                  30

Ser Ala Leu Arg Leu Gly Asp Arg Ile Pro Phe Glu Gly Ala Asn Glu
            35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Ser Asn Ile Ser Glu Asp Pro Val Pro Val Lys Arg His Ser Asp Ala
            115                 120                 125

Val Phe Thr Asp Asn Tyr Thr Arg Leu Arg Lys Gln Met Ala Val Lys
130                 135                 140

Lys Tyr Leu Asn Ser Ile Leu Asn Gly Lys Ser Ser Glu Gly Glu
145                 150                 155                 160

Ser Pro Asp Phe Pro Glu Glu Leu Glu Lys
                165                 170

<210> SEQ ID NO 13
<211> LENGTH: 169
<212> TYPE: PRT
<213> ORGANISM: Homo sapiens

<400> SEQUENCE: 13

Met Asp Thr Arg Asn Lys Ala Gln Leu Leu Val Leu Thr Leu Leu
 1               5                  10                  15

Ser Val Leu Phe Ser Gln Thr Ser Ala Trp Pro Leu Tyr Arg Ala Pro
                20                  25                  30

Ser Ala Leu Arg Leu Gly Asp Arg Ile Pro Phe Glu Gly Ala Asn Glu
            35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Asn Ile Ser Glu Asp Pro Val Pro Val Lys Arg His Ser Asp Ala Val
            115                 120                 125

Phe Thr Asp Asn Tyr Thr Arg Leu Arg Lys Gln Met Ala Val Lys Lys
130                 135                 140

```
Tyr Leu Asn Ser Ile Leu Asn Gly Lys Arg Ser Ser Glu Gly Glu Ser
145                 150                 155                 160

Pro Asp Phe Pro Glu Glu Leu Glu Lys
                165

<210> SEQ ID NO 14
<211> LENGTH: 153
<212> TYPE: PRT
<213> ORGANISM: Homo sapiens

<400> SEQUENCE: 14

Met Val Ala Thr Lys Thr Phe Ala Leu Leu Leu Ser Leu Phe Leu
 1               5                  10                  15

Ala Val Gly Leu Gly Glu Lys Lys Glu Gly His Phe Ser Ala Leu Pro
                20                  25                  30

Ser Leu Pro Val Gly Ser His Ala Lys Val Ser Ser Pro Gln Pro Arg
                35                  40                  45

Gly Pro Arg Tyr Ala Glu Gly Thr Phe Ile Ser Asp Tyr Ser Ile Ala
                50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
                100                 105                 110

Val Glu Pro Gln Ser Ser Pro Ala Lys Asn Pro Ser Asp Glu Asp Leu
                115                 120                 125

Leu Arg Asp Leu Leu Ile Gln Glu Leu Leu Ala Cys Leu Leu Asp Gln
                130                 135                 140

Thr Asn Leu Cys Arg Leu Arg Ser Arg
145                 150

<210> SEQ ID NO 15
<211> LENGTH: 121
<212> TYPE: PRT
<213> ORGANISM: Homo sapiens

<400> SEQUENCE: 15

Met Ala Pro Arg Pro Leu Leu Leu Leu Leu Leu Leu Gly Gly Ser
 1               5                  10                  15

Ala Ala Arg Pro Ala Pro Pro Arg Ala Arg Arg His Ser Asp Gly Thr
                20                  25                  30

Phe Thr Ser Glu Leu Ser Arg Leu Arg Glu Gly Ala Arg Leu Gln Arg
                35                  40                  45

Leu Leu Gln Gly Leu Val Gly Lys Arg Ser Glu Gln Asp Ala Glu Asn
                50                  55                  60

Ser Met Ala Trp Thr Arg Leu Ser Ala Gly Leu Leu Cys Pro Ser Gly
65                  70                  75                  80

Ser Asn Met Pro Ile Leu Gln Ala Trp Met Pro Leu Asp Gly Thr Trp
                85                  90                  95

Ser Pro Trp Leu Pro Pro Gly Pro Met Val Ser Glu Pro Ala Gly Ala
                100                 105                 110

Ala Ala Glu Gly Thr Leu Arg Pro Arg
                115                 120

<210> SEQ ID NO 16
<211> LENGTH: 101
<212> TYPE: PRT
```

<213> ORGANISM: Homo sapiens

<400> SEQUENCE: 16

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 17
<211> LENGTH: 148
<212> TYPE: PRT
<213> ORGANISM: Homo sapiens

<400> SEQUENCE: 17

Met Arg Gly Arg Glu Leu Pro Leu Val Leu Leu Ala Leu Val Leu Cys
1               5                   10                  15

Leu Ala Pro Arg Gly Arg Ala Val Pro Leu Pro Ala Gly Gly Gly Thr
            20                  25                  30

Val Leu Thr Lys Met Tyr Pro Arg Gly Asn His Trp Ala Val Gly His
        35                  40                  45

Leu Met Gly Lys Lys Ser Thr Gly Glu Ser Ser Ser Val Ser Glu Arg
    50                  55                  60

Gly Ser Leu Lys Gln Gln Leu Arg Glu Tyr Ile Arg Trp Glu Glu Ala
65                  70                  75                  80

Ala Arg Asn Leu Leu Gly Leu Ile Glu Ala Lys Glu Asn Arg Asn His
                85                  90                  95

Gln Pro Pro Gln Pro Lys Ala Leu Gly Asn Gln Gln Pro Ser Trp Asp
            100                 105                 110

Ser Glu Asp Ser Ser Asn Phe Lys Asp Val Gly Ser Lys Gly Lys Val
        115                 120                 125

Gly Arg Leu Ser Ala Pro Gly Ser Gln Arg Glu Gly Arg Asn Pro Gln
    130                 135                 140

Leu Asn Gln Gln
145

<210> SEQ ID NO 18
<211> LENGTH: 115
<212> TYPE: PRT
<213> ORGANISM: Homo sapiens

<400> SEQUENCE: 18

Met Asn Ser Gly Val Cys Leu Cys Val Leu Met Ala Val Leu Ala Ala
1               5                   10                  15

Gly Ala Leu Thr Gln Pro Val Pro Pro Ala Asp Pro Ala Gly Ser Gly
            20                  25                  30

Leu Gln Arg Ala Glu Glu Ala Pro Arg Arg Gln Leu Arg Val Ser Gln
        35                  40                  45

```
Arg Thr Asp Gly Glu Ser Arg Ala His Leu Gly Ala Leu Leu Ala Arg
 50                  55                  60

Tyr Ile Gln Gln Ala Arg Lys Ala Pro Ser Gly Arg Met Ser Ile Val
 65                  70                  75                  80

Lys Asn Leu Gln Asn Leu Asp Pro Ser His Arg Ile Ser Asp Arg Asp
                 85                  90                  95

Tyr Met Gly Trp Met Asp Phe Gly Arg Arg Ser Ala Glu Glu Tyr Glu
                100                 105                 110

Tyr Pro Ser
        115

<210> SEQ ID NO 19
<211> LENGTH: 196
<212> TYPE: PRT
<213> ORGANISM: Homo sapiens

<400> SEQUENCE: 19

Met Arg Leu Pro Leu Leu Val Ser Ala Gly Val Leu Leu Val Ala Leu
 1               5                  10                  15

Leu Pro Cys Pro Pro Cys Arg Ala Leu Leu Ser Arg Gly Pro Val Pro
                 20                  25                  30

Gly Ala Arg Gln Ala Pro Gln His Pro Gln Pro Leu Asp Phe Phe Gln
                 35                  40                  45

Pro Pro Pro Gln Ser Glu Gln Pro Gln Gln Pro Gln Ala Arg Pro Val
 50                  55                  60

Leu Leu Arg Met Gly Glu Glu Tyr Phe Leu Arg Leu Gly Asn Leu Asn
 65                  70                  75                  80

Lys Ser Pro Ala Ala Pro Leu Ser Pro Ala Ser Ser Leu Leu Ala Gly
                 85                  90                  95

Gly Ser Gly Ser Arg Pro Ser Pro Glu Gln Ala Thr Ala Asn Phe Phe
                100                 105                 110

Arg Val Leu Leu Gln Gln Leu Leu Pro Arg Arg Ser Leu Asp Ser
                115                 120                 125

Pro Ala Ala Leu Ala Glu Arg Gly Ala Arg Asn Ala Leu Gly Gly His
                130                 135                 140

Gln Glu Ala Pro Glu Arg Glu Arg Ser Glu Gly Pro Pro Ile Ser
145                 150                 155                 160

Leu Asp Leu Thr Phe His Leu Leu Arg Glu Val Leu Glu Met Ala Arg
                165                 170                 175

Ala Glu Gln Leu Ala Gln Gln Ala His Ser Asn Arg Lys Leu Met Glu
                180                 185                 190

Ile Ile Gly Lys
        195

<210> SEQ ID NO 20
<211> LENGTH: 177
<212> TYPE: PRT
<213> ORGANISM: Homo sapiens

<400> SEQUENCE: 20

Met Gln Arg Arg Leu Val Gln Trp Ser Val Ala Val Phe Leu Leu
 1               5                  10                  15

Ser Tyr Ala Val Pro Ser Cys Gly Arg Ser Val Glu Gly Leu Ser Arg
                 20                  25                  30

Arg Leu Lys Arg Ala Val Ser Glu His Gln Leu Leu His Asp Lys Gly
                 35                  40                  45

Lys Ser Ile Gln Asp Leu Arg Arg Arg Phe Phe Leu His His Leu Ile
```

```
                50                  55                  60
Ala Glu Ile His Thr Ala Glu Ile Arg Ala Thr Ser Glu Val Ser Pro
 65                  70                  75                  80

Asn Ser Lys Pro Ser Pro Asn Thr Lys Asn His Pro Val Arg Phe Gly
                 85                  90                  95

Ser Asp Asp Glu Gly Arg Tyr Leu Thr Gln Glu Thr Asn Lys Val Glu
                100                 105                 110

Thr Tyr Lys Glu Gln Pro Leu Lys Thr Pro Gly Lys Lys Lys Lys Gly
                115                 120                 125

Lys Pro Gly Lys Arg Lys Glu Gln Glu Lys Lys Arg Arg Thr Arg
130                 135                 140

Ser Ala Trp Leu Asp Ser Gly Val Thr Gly Ser Gly Leu Glu Gly Asp
145                 150                 155                 160

His Leu Ser Asp Thr Ser Thr Ser Leu Glu Leu Asp Ser Arg Arg
                165                 170                 175

His
```

<210> SEQ ID NO 21
<211> LENGTH: 200
<212> TYPE: PRT
<213> ORGANISM: Homo sapiens

<400> SEQUENCE: 21

```
Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Thr Glu Ser Tyr Val Lys His Gln Gly Leu Asn Lys Asn Ile
                 35                  40                  45

Asn Leu Asp Ser Ala Asp Gly Met Pro Val Ala Ser Thr Asp Gln Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
                115                 120                 125

Leu Leu Glu Tyr Lys Ile Pro Arg Asn Glu Ala Asp Gly Met Pro Ile
                130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
                195                 200
```

<210> SEQ ID NO 22
<211> LENGTH: 150
<212> TYPE: PRT
<213> ORGANISM: Homo sapiens

<400> SEQUENCE: 22

```
Met Tyr Gly Lys Ile Ile Phe Val Leu Leu Leu Ser Ala Ile Val Ser
1               5                   10                  15

Ile Ser Ala Ser Ser Thr Thr Gly Val Ala Met His Thr Ser Thr Ser
            20                  25                  30

Ser Ser Val Thr Lys Ser Tyr Ile Ser Ser Gln Thr Asn Asp Thr His
        35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
                100                 105                 110

Gly Ile Arg Arg Leu Ile Lys Lys Ser Pro Ser Asp Val Lys Pro Leu
            115                 120                 125

Pro Ser Pro Asp Thr Asp Val Pro Leu Ser Ser Val Glu Ile Glu Asn
        130                 135                 140

Pro Glu Thr Ser Asp Gln
145                 150

<210> SEQ ID NO 23
<211> LENGTH: 202
<212> TYPE: PRT
<213> ORGANISM: Homo sapiens

<400> SEQUENCE: 23

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
                100                 105                 110

Gly Thr Ser Leu Gly Asn Ile Thr Arg Asp Gln Lys Ile Leu Asn Pro
            115                 120                 125

Ser Ala Leu Ser Leu His Ser Lys Leu Asn Ala Thr Ala Asp Ile Leu
        130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
                180                 185                 190

Gln Ile Ile Ala Val Leu Ala Gln Ala Phe
            195                 200

<210> SEQ ID NO 24
<211> LENGTH: 201
```

<212> TYPE: PRT
<213> ORGANISM: Homo sapiens

<400> SEQUENCE: 24

```
Met Ser Arg Arg Glu Gly Ser Leu Glu Asp Pro Gln Thr Asp Ser Ser
1               5                   10                  15

Val Ser Leu Leu Pro His Leu Glu Ala Lys Ile Arg Gln Thr His Ser
            20                  25                  30

Leu Ala His Leu Leu Thr Lys Tyr Ala Glu Gln Leu Leu Gln Glu Tyr
        35                  40                  45

Val Gln Leu Gln Gly Asp Pro Phe Gly Leu Pro Ser Phe Ser Pro Pro
    50                  55                  60

Arg Leu Pro Val Ala Gly Leu Ser Ala Pro Ala Pro Ser His Ala Gly
65                  70                  75                  80

Leu Pro Val His Glu Arg Leu Arg Leu Asp Ala Ala Leu Ala Ala
                85                  90                  95

Leu Pro Pro Leu Leu Asp Ala Val Cys Arg Arg Gln Ala Glu Leu Asn
                100                 105                 110

Pro Arg Ala Pro Arg Leu Leu Arg Arg Leu Glu Asp Ala Ala Arg Gln
            115                 120                 125

Ala Arg Ala Leu Gly Ala Ala Val Glu Ala Leu Leu Ala Ala Leu Gly
    130                 135                 140

Ala Ala Asn Arg Gly Pro Arg Ala Glu Pro Ala Ala Thr Ala Ser
145                 150                 155                 160

Ala Ala Ser Ala Thr Gly Val Phe Pro Ala Lys Val Leu Gly Leu Arg
                165                 170                 175

Val Cys Gly Leu Tyr Arg Glu Trp Leu Ser Arg Thr Glu Gly Asp Leu
            180                 185                 190

Gly Gln Leu Leu Pro Gly Gly Ser Ala
        195                 200
```

<210> SEQ ID NO 25
<211> LENGTH: 225
<212> TYPE: PRT
<213> ORGANISM: Homo sapiens

<400> SEQUENCE: 25

```
Met Asp Leu Arg Ala Gly Asp Ser Trp Gly Met Leu Ala Cys Leu Cys
1               5                   10                  15

Thr Val Leu Trp His Leu Pro Ala Val Pro Ala Leu Asn Arg Thr Gly
            20                  25                  30

Asp Pro Gly Pro Gly Pro Ser Ile Gln Lys Thr Tyr Asp Leu Thr Arg
        35                  40                  45

Tyr Leu Glu His Gln Leu Arg Ser Leu Ala Gly Thr Tyr Leu Asn Tyr
    50                  55                  60

Leu Gly Pro Pro Phe Asn Glu Pro Asp Phe Asn Pro Pro Arg Leu Gly
65                  70                  75                  80

Ala Glu Thr Leu Pro Arg Ala Thr Val Asp Leu Glu Val Trp Arg Ser
                85                  90                  95

Leu Asn Asp Lys Leu Arg Leu Thr Gln Asn Tyr Glu Ala Tyr Ser His
                100                 105                 110

Leu Leu Cys Tyr Leu Arg Gly Leu Asn Arg Gln Ala Ala Thr Ala Glu
            115                 120                 125

Leu Arg Arg Ser Leu Ala His Phe Cys Thr Ser Leu Gln Gly Leu Leu
    130                 135                 140

Gly Ser Ile Ala Gly Val Met Ala Ala Leu Gly Tyr Pro Leu Pro Gln
```

```
                145                 150                 155                 160
Pro Leu Pro Gly Thr Glu Pro Thr Trp Thr Pro Gly Pro Ala His Ser
                    165                 170                 175

Asp Phe Leu Gln Lys Met Asp Asp Phe Trp Leu Leu Lys Glu Leu Gln
                180                 185                 190

Thr Trp Leu Trp Arg Ser Ala Lys Asp Phe Asn Arg Leu Lys Lys Lys
            195                 200                 205

Met Gln Pro Pro Ala Ala Ala Val Thr Leu His Leu Gly Ala His Gly
        210                 215                 220

Phe
225

<210> SEQ ID NO 26
<211> LENGTH: 269
<212> TYPE: PRT
<213> ORGANISM: Homo sapiens

<400> SEQUENCE: 26

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 27
<211> LENGTH: 153
<212> TYPE: PRT
```

<213> ORGANISM: Homo sapiens

<400> SEQUENCE: 27

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 28
<211> LENGTH: 212
<212> TYPE: PRT
<213> ORGANISM: Homo sapiens

<400> SEQUENCE: 28

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 29
<211> LENGTH: 99
<212> TYPE: PRT
<213> ORGANISM: Homo sapiens

<400> SEQUENCE: 29

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 30
<211> LENGTH: 178
<212> TYPE: PRT
<213> ORGANISM: Homo sapiens

<400> SEQUENCE: 30

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 31
<211> LENGTH: 558
<212> TYPE: PRT
<213> ORGANISM: Homo sapiens

<400> SEQUENCE: 31

```
Met Ala Ala Leu Thr Arg Asp Pro Gln Phe Gln Lys Leu Gln Gln Trp
1               5                   10                  15

Tyr Arg Glu His Arg Ser Glu Leu Asn Leu Arg Arg Leu Phe Asp Ala
            20                  25                  30

Asn Lys Asp Arg Phe Asn His Phe Ser Leu Thr Leu Asn Thr Asn His
        35                  40                  45

Gly His Ile Leu Val Asp Tyr Ser Lys Asn Leu Val Thr Glu Asp Val
    50                  55                  60

Met Arg Met Leu Val Asp Leu Ala Lys Ser Arg Gly Val Glu Ala Ala
65                  70                  75                  80

Arg Glu Arg Met Phe Asn Gly Glu Lys Ile Asn Tyr Thr Glu Gly Arg
                85                  90                  95

Ala Val Leu His Val Ala Leu Arg Asn Arg Ser Asn Thr Pro Ile Leu
            100                 105                 110

Val Asp Gly Lys Asp Val Met Pro Glu Val Asn Lys Val Leu Asp Lys
        115                 120                 125

Met Lys Ser Phe Cys Gln Arg Val Arg Ser Gly Asp Trp Lys Gly Tyr
130                 135                 140

Thr Gly Lys Thr Ile Thr Asp Val Ile Asn Ile Gly Ile Gly Gly Ser
145                 150                 155                 160

Asp Leu Gly Pro Leu Met Val Thr Glu Ala Leu Lys Pro Tyr Ser Ser
                165                 170                 175

Gly Gly Pro Arg Val Trp Tyr Val Ser Asn Ile Asp Gly Thr His Ile
            180                 185                 190

Ala Lys Thr Leu Ala Gln Leu Asn Pro Glu Ser Ser Leu Phe Ile Ile
        195                 200                 205

Ala Ser Lys Thr Phe Thr Thr Gln Glu Thr Ile Thr Asn Ala Glu Thr
    210                 215                 220

Ala Lys Glu Trp Phe Leu Gln Ala Ala Lys Asp Pro Ser Ala Val Ala
225                 230                 235                 240

Lys His Phe Val Ala Leu Ser Thr Asn Thr Thr Lys Val Lys Glu Phe
                245                 250                 255

Gly Ile Asp Pro Gln Asn Met Phe Glu Phe Trp Asp Trp Val Gly Gly
            260                 265                 270

Arg Tyr Ser Leu Trp Ser Ala Ile Gly Leu Ser Ile Ala Leu His Val
        275                 280                 285

Gly Phe Asp Asn Phe Glu Gln Leu Leu Ser Gly Ala His Trp Met Asp
    290                 295                 300

Gln His Phe Arg Thr Thr Pro Leu Glu Lys Asn Ala Pro Val Leu Leu
305                 310                 315                 320

Ala Leu Leu Gly Ile Trp Tyr Ile Asn Cys Phe Gly Cys Glu Thr His
                325                 330                 335

Ala Met Leu Pro Tyr Asp Gln Tyr Leu His Arg Phe Ala Ala Tyr Phe
            340                 345                 350

Gln Gln Gly Asp Met Glu Ser Asn Gly Lys Tyr Ile Thr Lys Ser Gly
        355                 360                 365

Thr Arg Val Asp His Gln Thr Gly Pro Ile Val Trp Gly Glu Pro Gly
    370                 375                 380

Thr Asn Gly Gln His Ala Phe Tyr Gln Leu Ile His Gln Gly Thr Lys
385                 390                 395                 400

Met Ile Pro Cys Asp Phe Leu Ile Pro Val Gln Thr Gln His Pro Ile
                405                 410                 415
```

Arg Lys Gly Leu His His Lys Ile Leu Leu Ala Asn Phe Leu Ala Gln
            420                 425                 430

Thr Glu Ala Leu Met Arg Gly Lys Ser Thr Glu Glu Ala Arg Lys Glu
            435                 440                 445

Leu Gln Ala Ala Gly Lys Ser Pro Glu Asp Leu Glu Arg Leu Leu Pro
450                 455                 460

His Lys Val Phe Glu Gly Asn Arg Pro Thr Asn Ser Ile Val Phe Thr
465                 470                 475                 480

Lys Leu Thr Pro Phe Met Leu Gly Ala Leu Val Ala Met Tyr Glu His
                485                 490                 495

Lys Ile Phe Val Gln Gly Ile Ile Trp Asp Ile Asn Ser Phe Asp Gln
                500                 505                 510

Trp Gly Val Glu Leu Gly Lys Gln Leu Ala Lys Lys Ile Glu Pro Glu
            515                 520                 525

Leu Asp Gly Ser Ala Gln Val Thr Ser His Asp Ala Ser Thr Asn Gly
530                 535                 540

Leu Ile Asn Phe Ile Lys Gln Gln Arg Glu Ala Arg Val Gln
545                 550                 555

<210> SEQ ID NO 32
<211> LENGTH: 371
<212> TYPE: PRT
<213> ORGANISM: Homo sapiens

<400> SEQUENCE: 32

Met Thr Asp Arg Gln Thr Asp Thr Ala Pro Ser Pro Ser Tyr His Leu
 1               5                  10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

```
Ile Phe Gln Glu Tyr Pro Asp Glu Ile Glu Tyr Ile Phe Lys Pro Ser
                245                 250                 255

Cys Val Pro Leu Met Arg Cys Gly Cys Cys Asn Asp Glu Gly Leu
            260                 265                 270

Glu Cys Val Pro Thr Glu Ser Asn Ile Thr Met Gln Ile Met Arg
        275                 280                 285

Ile Lys Pro His Gln Gly Gln His Ile Gly Glu Met Ser Phe Leu Gln
            290                 295                 300

His Asn Lys Cys Glu Cys Arg Pro Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
                340                 345                 350

Lys Ala Arg Gln Leu Glu Leu Asn Glu Arg Thr Cys Arg Ser Leu Thr
                355                 360                 365

Arg Lys Asp
    370

<210> SEQ ID NO 33
<211> LENGTH: 153
<212> TYPE: PRT
<213> ORGANISM: Homo sapiens

<400> SEQUENCE: 33

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
                35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65              70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
                115                 120                 125

Met Pro Lys Thr Gln Lys Glu Val His Leu Lys Asn Ala Ser Arg Gly
            130                 135                 140

Ser Ala Gly Asn Lys Asn Tyr Arg Met
145                 150

<210> SEQ ID NO 34
<211> LENGTH: 180
<212> TYPE: PRT
<213> ORGANISM: Homo sapiens

<400> SEQUENCE: 34

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
                20                  25                  30
```

```
Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Ser Arg
 50                  55                  60

Gly Ile Val Glu Cys Cys Phe Arg Ser Cys Asp Leu Ala Leu Leu
 65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
                100                 105                 110

Phe Phe Gln Tyr Asp Thr Trp Lys Gln Ser Thr Gln Arg Leu Arg Arg
                115                 120                 125

Gly Leu Pro Ala Leu Leu Arg Ala Arg Arg Gly His Val Leu Ala Lys
            130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 35
<211> LENGTH: 54
<212> TYPE: PRT
<213> ORGANISM: Homo sapiens

<400> SEQUENCE: 35

Met Asn Ser Asp Ser Glu Cys Pro Leu Ser His Asp Gly Tyr Cys Leu
 1                5                  10                  15

His Asp Gly Val Cys Met Tyr Ile Glu Ala Leu Asp Lys Tyr Ala Cys
                20                  25                  30

Asn Cys Val Val Gly Tyr Ile Gly Glu Arg Cys Gln Tyr Arg Asp Leu
            35                  40                  45

Lys Trp Trp Glu Leu Arg
    50

<210> SEQ ID NO 36
<211> LENGTH: 257
<212> TYPE: PRT
<213> ORGANISM: Homo sapiens

<400> SEQUENCE: 36

Met Ser Ile Leu Phe Tyr Val Ile Phe Leu Ala Tyr Leu Arg Gly Ile
 1                5                  10                  15

Gln Gly Asn Asn Met Asp Gln Arg Ser Leu Pro Glu Asp Ser Leu Asn
                20                  25                  30

Ser Leu Ile Ile Lys Leu Ile Gln Ala Asp Ile Leu Lys Asn Lys Leu
            35                  40                  45

Ser Lys Gln Met Val Asp Val Lys Glu Asn Tyr Gln Ser Thr Leu Pro
 50                  55                  60

Lys Ala Glu Ala Pro Arg Glu Pro Glu Arg Gly Gly Pro Ala Lys Ser
 65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
                100                 105                 110

Glu Pro Pro Pro Leu Tyr Leu Met Glu Asp Tyr Val Gly Ser Pro Val
```

```
            115                 120                 125
Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 37
<211> LENGTH: 247
<212> TYPE: PRT
<213> ORGANISM: Homo sapiens

<400> SEQUENCE: 37

Met Thr Ile Leu Phe Leu Thr Met Val Ile Ser Tyr Phe Gly Cys Met
  1               5                  10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240
```

```
Leu Thr Ile Lys Arg Gly Arg
            245

<210> SEQ ID NO 38
<211> LENGTH: 257
<212> TYPE: PRT
<213> ORGANISM: Homo sapiens

<400> SEQUENCE: 38

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
    130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 39
<211> LENGTH: 210
<212> TYPE: PRT
<213> ORGANISM: Homo sapiens

<400> SEQUENCE: 39

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Ser Thr Leu Pro
            20                  25                  30

Pro Phe Leu Ala Pro Glu Trp Asp Leu Leu Ser Pro Arg Val Val Leu
        35                  40                  45

Ser Arg Gly Ala Pro Ala Gly Pro Pro Leu Leu Phe Leu Leu Glu Ala
```

```
            50                  55                  60
Gly Ala Phe Arg Glu Ser Ala Gly Ala Pro Ala Asn Arg Ser Arg Arg
 65                  70                  75                  80

Gly Val Ser Glu Thr Ala Pro Ala Ser Arg Arg Gly Glu Leu Ala Val
                 85                  90                  95

Cys Asp Ala Val Ser Gly Trp Val Thr Asp Arg Arg Thr Ala Val Asp
                100                 105                 110

Leu Arg Gly Arg Glu Val Glu Val Leu Gly Val Pro Ala Ala Gly
            115                 120                 125

Gly Ser Pro Leu Arg Gln Tyr Phe Glu Thr Arg Cys Lys Ala Asp
    130                 135                 140

Asn Ala Glu Glu Gly Gly Pro Gly Ala Gly Gly Gly Cys Arg Gly
145                 150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
                180                 185                 190

Ile Arg Ile Asp Thr Ala Cys Val Cys Thr Leu Leu Ser Arg Thr Gly
                195                 200                 205

Arg Ala
    210

<210> SEQ ID NO 40
<211> LENGTH: 211
<212> TYPE: PRT
<213> ORGANISM: Homo sapiens

<400> SEQUENCE: 40

Met Lys Leu Trp Asp Val Val Ala Val Cys Leu Val Leu Leu His Thr
  1               5                  10                  15

Ala Ser Ala Phe Pro Leu Pro Ala Gly Lys Arg Pro Pro Glu Ala Pro
                 20                  25                  30

Ala Glu Asp Arg Ser Leu Gly Arg Arg Arg Ala Pro Phe Ala Leu Ser
             35                  40                  45

Ser Asp Ser Asn Met Pro Glu Asp Tyr Pro Asp Gln Phe Asp Asp Val
 50                  55                  60

Met Asp Phe Ile Gln Ala Thr Ile Lys Arg Leu Lys Arg Ser Pro Asp
 65                  70                  75                  80

Lys Gln Met Ala Val Leu Pro Arg Arg Glu Arg Asn Arg Gln Ala Ala
                 85                  90                  95

Ala Ala Asn Pro Glu Asn Ser Arg Gly Lys Gly Arg Arg Gly Gln Arg
                100                 105                 110

Gly Lys Asn Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
                180                 185                 190

Asp Asn Leu Val Tyr His Ile Leu Arg Lys His Ser Ala Lys Arg Cys
                195                 200                 205

Gly Cys Ile
```

```
<210> SEQ ID NO 41
<211> LENGTH: 197
<212> TYPE: PRT
<213> ORGANISM: Homo sapiens

<400> SEQUENCE: 41

Met Gln Arg Trp Lys Ala Ala Leu Ala Ser Val Leu Cys Ser Ser
  1               5                  10                  15

Val Leu Ser Ile Trp Met Cys Arg Glu Gly Leu Leu Leu Ser His Arg
             20                  25                  30

Leu Gly Pro Ala Leu Val Pro Leu His Arg Leu Pro Arg Thr Leu Asp
         35                  40                  45

Ala Arg Ile Ala Arg Leu Ala Gln Tyr Arg Ala Leu Leu Gln Gly Ala
     50                  55                  60

Pro Asp Ala Met Glu Leu Arg Glu Leu Thr Pro Trp Ala Gly Arg Pro
 65                  70                  75                  80

Pro Gly Pro Arg Arg Arg Ala Gly Pro Arg Arg Arg Ala Arg Ala
                 85                  90                  95

Arg Leu Gly Ala Arg Pro Cys Gly Leu Arg Glu Leu Glu Arg Val
                100                 105                 110

Ser Glu Leu Gly Leu Gly Tyr Ala Ser Asp Glu Thr Val Leu Phe Arg
            115                 120                 125

Tyr Cys Ala Gly Ala Cys Glu Ala Ala Arg Val Tyr Asp Leu Gly
        130                 135                 140

Leu Arg Arg Leu Arg Gln Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
            180                 185                 190

Glu Cys Ala Cys Val
            195

<210> SEQ ID NO 42
<211> LENGTH: 156
<212> TYPE: PRT
<213> ORGANISM: Homo sapiens

<400> SEQUENCE: 42

Met Ala Val Gly Lys Phe Leu Leu Gly Ser Leu Leu Leu Ser Leu
  1               5                  10                  15

Gln Leu Gly Gln Gly Trp Gly Pro Asp Ala Arg Gly Val Pro Val Ala
             20                  25                  30

Asp Gly Glu Phe Ser Ser Glu Gln Val Ala Lys Ala Gly Gly Thr Trp
         35                  40                  45

Leu Gly Thr His Arg Pro Leu Ala Arg Leu Arg Arg Ala Leu Ser Gly
     50                  55                  60

Pro Cys Gln Leu Trp Ser Leu Thr Leu Ser Val Ala Glu Leu Gly Leu
 65                  70                  75                  80

Gly Tyr Ala Ser Glu Glu Lys Val Ile Phe Arg Tyr Cys Ala Gly Ser
                 85                  90                  95

Cys Pro Arg Gly Ala Arg Thr Gln His Gly Leu Ala Leu Ala Arg Leu
                100                 105                 110

Gln Gly Gln Gly Arg Ala His Gly Gly Pro Cys Cys Arg Pro Thr Arg
            115                 120                 125
```

```
Tyr Thr Asp Val Ala Phe Leu Asp Asp Arg His Arg Trp Gln Arg Leu
    130                 135                 140

Pro Gln Leu Ser Ala Ala Ala Cys Gly Cys Gly Gly
145                 150                 155

<210> SEQ ID NO 43
<211> LENGTH: 220
<212> TYPE: PRT
<213> ORGANISM: Homo sapiens

<400> SEQUENCE: 43

Met Glu Leu Gly Leu Gly Gly Leu Ser Thr Leu Ser His Cys Pro Trp
1               5                   10                  15

Pro Arg Gln Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Val Leu Ala Ser Pro Ala Gly His
    50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
                100                 105                 110

Ser Arg Ala Arg Ala Ala Gly Ala Arg Gly Cys Arg Leu Arg Ser Gln
            115                 120                 125

Leu Val Pro Val Arg Ala Leu Gly Leu Gly His Arg Ser Asp Glu Leu
    130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
                180                 185                 190

Tyr Glu Ala Val Ser Phe Met Asp Val Asn Ser Thr Trp Arg Thr Val
            195                 200                 205

Asp Arg Leu Ser Ala Thr Ala Cys Gly Cys Leu Gly
    210                 215                 220

<210> SEQ ID NO 44
<211> LENGTH: 390
<212> TYPE: PRT
<213> ORGANISM: Homo sapiens

<400> SEQUENCE: 44

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80
```

```
Tyr Asn Ser Thr Arg Asp Arg Val Ala Gly Glu Ser Ala Glu Pro Glu
                85                  90                  95

Pro Glu Pro Glu Ala Asp Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 45
<211> LENGTH: 413
<212> TYPE: PRT
<213> ORGANISM: Homo sapiens

<400> SEQUENCE: 45

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60
```

Pro Glu Val Ile Ser Ile Tyr Asn Ser Thr Arg Asp Leu Leu Gln Glu
65                  70                  75                  80

Lys Ala Ser Arg Arg Ala Ala Cys Glu Arg Glu Arg Ser Asp Glu
            85                  90                  95

Glu Tyr Tyr Ala Lys Glu Val Tyr Lys Ile Asp Met Pro Pro Phe Phe
            100                 105                 110

Pro Ser Glu Ala Ile Pro Pro Thr Phe Tyr Arg Pro Tyr Phe Arg Ile
            115                 120                 125

Val Arg Phe Asp Val Ser Ala Met Glu Lys Asn Ala Ser Asn Leu Val
130                 135                 140

Lys Ala Glu Phe Arg Val Phe Arg Leu Gln Asn Pro Lys Ala Arg Val
145                 150                 155                 160

Pro Glu Gln Arg Ile Glu Leu Tyr Gln Ile Leu Lys Ser Lys Asp Leu
            165                 170                 175

Thr Ser Pro Thr Gln Arg Tyr Ile Asp Ser Lys Val Val Lys Thr Arg
            180                 185                 190

Ala Glu Gly Glu Trp Leu Ser Phe Asp Val Thr Asp Ala Val His Glu
            195                 200                 205

Trp Leu His His Lys Asp Arg Asn Leu Gly Phe Lys Ile Ser Leu His
210                 215                 220

Cys Pro Cys Cys Thr Phe Val Pro Ser Asn Asn Tyr Ile Ile Pro Asn
225                 230                 235                 240

Lys Ser Glu Glu Leu Glu Ala Arg Phe Ala Gly Ile Asp Gly Thr Ser
            245                 250                 255

Thr Tyr Thr Ser Gly Asp Gln Lys Thr Ile Lys Ser Thr Arg Lys Lys
            260                 265                 270

Asn Ser Gly Lys Thr Pro His Leu Leu Leu Met Leu Leu Pro Ser Tyr
            275                 280                 285

Arg Leu Glu Ser Gln Gln Thr Asn Arg Arg Lys Lys Arg Ala Leu Asp
290                 295                 300

Ala Ala Tyr Cys Phe Arg Asn Val Gln Asp Asn Cys Cys Leu Arg Pro
305                 310                 315                 320

Leu Tyr Ile Asp Phe Lys Arg Asp Leu Gly Trp Lys Trp Ile His Glu
            325                 330                 335

Pro Lys Gly Tyr Asn Ala Asn Phe Cys Ala Gly Ala Cys Pro Tyr Leu
            340                 345                 350

Trp Ser Ser Asp Thr Gln His Ser Arg Val Leu Ser Leu Tyr Asn Thr
            355                 360                 365

Ile Asn Pro Glu Ala Ser Ala Ser Pro Cys Cys Val Ser Gln Asp Leu
            370                 375                 380

Glu Pro Leu Thr Ile Leu Tyr Tyr Ile Gly Lys Thr Pro Lys Ile Glu
385                 390                 395                 400

Gln Leu Ser Asn Met Ile Val Lys Ser Cys Lys Cys Ser
                405                 410

<210> SEQ ID NO 46
<211> LENGTH: 412
<212> TYPE: PRT
<213> ORGANISM: Homo sapiens

<400> SEQUENCE: 46

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
 50                  55                  60

Val Pro Tyr Gln Val Leu Ala Leu Tyr Asn Ser Thr Arg Glu Leu Leu
 65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
                115                 120                 125

Ser Lys Val Phe Arg Phe Asn Val Ser Ser Val Glu Lys Asn Arg Thr
 130                 135                 140

Asn Leu Phe Arg Ala Glu Phe Arg Val Leu Arg Val Pro Asn Pro Ser
 145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
 210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
                260                 265                 270

His His Asn Pro His Leu Ile Leu Met Met Ile Pro Pro His Arg Leu
            275                 280                 285

Asp Asn Pro Gly Gln Gly Gln Arg Lys Lys Arg Ala Leu Asp Thr
 290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
 370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 47
<211> LENGTH: 304
<212> TYPE: PRT
<213> ORGANISM: Homo sapiens

<400> SEQUENCE: 47

Met Asp Pro Met Ser Ile Gly Pro Lys Ser Cys Gly Ser Pro Trp
1               5                   10                  15

Arg Pro Pro Gly Thr Ala Pro Trp Ser Ile Gly Ser Arg Arg Ala Thr
            20                  25                  30

Ala Ser Ser Ser Cys Ser Thr Ser Ser Arg Val Arg Ala Glu Val Gly
        35                  40                  45

Gly Arg Ala Leu Leu His Arg Ala Glu Leu Arg Met Leu Arg Gln Lys
    50                  55                  60

Ala Ala Ala Asp Ser Ala Gly Thr Glu Gln Arg Leu Glu Leu Tyr Gln
65              70                  75                  80

Gly Tyr Gly Asn Ala Ser Trp Arg Tyr Leu His Gly Ser Val Arg
                85                  90                  95

Ala Thr Ala Asp Asp Glu Trp Leu Ser Phe Asp Val Thr Asp Ala Val
            100                 105                 110

His Gln Trp Leu Ser Gly Ser Glu Leu Leu Gly Val Phe Lys Leu Ser
            115                 120                 125

Val His Cys Pro Cys Glu Met Gly Pro Gly His Ala Asp Glu Met Arg
    130                 135                 140

Ile Ser Ile Glu Gly Phe Glu Gln Gln Arg Gly Asp Met Gln Ser Ile
145                 150                 155                 160

Ala Lys Lys His Arg Arg Val Pro Tyr Val Leu Ala Met Ala Leu Pro
                165                 170                 175

Ala Glu Arg Ala Asn Glu Leu His Ser Ala Arg Arg Arg Asp Leu
            180                 185                 190

Asp Thr Asp Tyr Cys Phe Gly Pro Gly Thr Asp Glu Lys Asn Cys Cys
    195                 200                 205

Val Arg Pro Leu Tyr Ile Asp Phe Arg Lys Asp Leu Gln Trp Lys Trp
210                 215                 220

Ile His Glu Pro Lys Gly Tyr Met Ala Asn Phe Cys Met Gly Pro Cys
225                 230                 235                 240

Pro Tyr Ile Trp Ser Ala Asp Thr Gln Tyr Thr Lys Val Leu Ala Leu
                245                 250                 255

Tyr Asn Gln His Asn Pro Gly Ala Ser Ala Ala Pro Cys Cys Val Pro
            260                 265                 270

Gln Thr Leu Asp Pro Leu Pro Ile Ile Tyr Tyr Val Gly Arg Asn Val
    275                 280                 285

Arg Val Glu Gln Leu Ser Asn Met Val Val Arg Ala Cys Lys Cys Ser
    290                 295                 300

<210> SEQ ID NO 48
<211> LENGTH: 396
<212> TYPE: PRT
<213> ORGANISM: Homo sapiens

<400> SEQUENCE: 48

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65              70                  75                  80

```
Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 49
<211> LENGTH: 472
<212> TYPE: PRT
<213> ORGANISM: Homo sapiens

<400> SEQUENCE: 49

Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45

Glu Leu Gln Pro Gln Asp Lys Val Ser Glu His Met Leu Arg Leu Tyr
    50                  55                  60
```

-continued

```
Asp Arg Tyr Ser Thr Val Gln Ala Ala Arg Thr Pro Gly Ser Leu Glu
 65                  70                  75                  80

Gly Gly Ser Gln Pro Trp Arg Pro Arg Leu Arg Glu Gly Asn Thr
                 85                  90                  95

Val Arg Ser Phe Arg Ala Ala Ala Ala Glu Thr Leu Glu Arg Lys Gly
                100                 105                 110

Leu Tyr Ile Phe Asn Leu Thr Ser Leu Thr Lys Ser Glu Asn Ile Leu
                115                 120                 125

Ser Ala Thr Leu Tyr Phe Cys Ile Gly Glu Leu Gly Asn Ile Ser Leu
130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
                180                 185                 190

Asp Ile Met Ser Trp Leu Ser Lys Asp Ile Thr Gln Phe Leu Arg Lys
                195                 200                 205

Ala Lys Glu Asn Glu Glu Phe Leu Ile Gly Phe Asn Ile Thr Ser Lys
210                 215                 220

Gly Arg Gln Leu Pro Lys Arg Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
                260                 265                 270

Trp Asp Ser His Ile Arg Ala Ala Leu Ser Ile Glu Arg Arg Lys Lys
                275                 280                 285

Arg Ser Thr Gly Val Leu Leu Pro Leu Gln Asn Asn Glu Leu Pro Gly
                290                 295                 300

Ala Glu Tyr Gln Tyr Lys Lys Asp Glu Val Trp Glu Glu Arg Lys Pro
305                 310                 315                 320

Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
                340                 345                 350

Glu Gln Thr Leu Lys Lys Ala Arg Arg Lys Gln Trp Ile Glu Pro Arg
                355                 360                 365

Asn Cys Ala Arg Arg Tyr Leu Lys Val Asp Phe Ala Asp Ile Gly Trp
                370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
                420                 425                 430

Pro Glu Pro Cys Cys Val Pro Glu Lys Met Ser Ser Leu Ser Ile Leu
                435                 440                 445

Phe Phe Asp Glu Asn Lys Asn Val Val Leu Lys Val Tyr Pro Asn Met
450                 455                 460

Thr Val Glu Ser Cys Ala Cys Arg
465                 470
```

<210> SEQ ID NO 50

```
<211> LENGTH: 408
<212> TYPE: PRT
<213> ORGANISM: Homo sapiens

<400> SEQUENCE: 50
```

| | | | | | | | | | | | | | | |
|---|---|---|---|---|---|---|---|---|---|---|---|---|---|---|
| Met | Ile | Pro | Gly | Asn | Arg | Met | Leu | Met | Val | Val | Leu | Leu | Cys | Gln | Val |
| 1 | | | | 5 | | | | | 10 | | | | | 15 | |
| Leu | Leu | Gly | Gly | Ala | Ser | His | Ala | Ser | Leu | Ile | Pro | Glu | Thr | Gly | Lys |
| | | | 20 | | | | | 25 | | | | | 30 | | |
| Lys | Lys | Val | Ala | Glu | Ile | Gln | Gly | His | Ala | Gly | Gly | Arg | Arg | Ser | Gly |
| | | 35 | | | | | 40 | | | | | 45 | | | |
| Gln | Ser | His | Glu | Leu | Leu | Arg | Asp | Phe | Glu | Ala | Thr | Leu | Leu | Gln | Met |
| | 50 | | | | | 55 | | | | | 60 | | | | |
| Phe | Gly | Leu | Arg | Arg | Pro | Gln | Pro | Ser | Lys | Ser | Ala | Val | Ile | Pro | |
| 65 | | | | | 70 | | | | | 75 | | | | | 80 |
| Asp | Tyr | Met | Arg | Asp | Leu | Tyr | Arg | Leu | Gln | Ser | Gly | Glu | Glu | Glu | |
| | | | | 85 | | | | | 90 | | | | | 95 | |
| Glu | Gln | Ile | His | Ser | Thr | Gly | Leu | Glu | Tyr | Pro | Glu | Arg | Pro | Ala | Ser |
| | | | 100 | | | | | 105 | | | | | 110 | | |
| Arg | Ala | Asn | Thr | Val | Arg | Ser | Phe | His | His | Glu | Glu | His | Leu | Glu | Asn |
| | | 115 | | | | | 120 | | | | | 125 | | | |
| Ile | Pro | Gly | Thr | Ser | Glu | Asn | Ser | Ala | Phe | Arg | Phe | Leu | Phe | Asn | Leu |
| 130 | | | | | 135 | | | | | 140 | | | | | |
| Ser | Ser | Ile | Pro | Glu | Asn | Glu | Val | Ile | Ser | Ser | Ala | Glu | Leu | Arg | Leu |
| 145 | | | | | 150 | | | | | 155 | | | | | 160 |
| Phe | Arg | Glu | Gln | Val | Asp | Gln | Gly | Pro | Asp | Trp | Glu | Arg | Gly | Phe | His |
| | | | | 165 | | | | | 170 | | | | | 175 | |
| Arg | Ile | Asn | Ile | Tyr | Glu | Val | Met | Lys | Pro | Pro | Ala | Glu | Val | Val | Pro |
| | | | 180 | | | | | 185 | | | | | 190 | | |
| Gly | His | Leu | Ile | Thr | Arg | Leu | Leu | Asp | Thr | Arg | Leu | Val | His | His | Asn |
| | | 195 | | | | | 200 | | | | | 205 | | | |
| Val | Thr | Arg | Trp | Glu | Thr | Phe | Asp | Val | Ser | Pro | Ala | Val | Leu | Arg | Trp |
| 210 | | | | | 215 | | | | | 220 | | | | | |
| Thr | Arg | Glu | Lys | Gln | Pro | Asn | Tyr | Gly | Leu | Ala | Ile | Glu | Val | Thr | His |
| 225 | | | | | 230 | | | | | 235 | | | | | 240 |
| Leu | His | Gln | Thr | Arg | Thr | His | Gln | Gly | Gln | His | Val | Arg | Ile | Ser | Arg |
| | | | | 245 | | | | | 250 | | | | | 255 | |
| Ser | Leu | Pro | Gln | Gly | Ser | Gly | Asn | Trp | Ala | Gln | Leu | Arg | Pro | Leu | Leu |
| | | | 260 | | | | | 265 | | | | | 270 | | |
| Val | Thr | Phe | Gly | His | Asp | Gly | Arg | Gly | His | Ala | Leu | Thr | Arg | Arg | Arg |
| | | 275 | | | | | 280 | | | | | 285 | | | |
| Arg | Ala | Lys | Arg | Ser | Pro | Lys | His | His | Ser | Gln | Arg | Ala | Arg | Lys | Lys |
| 290 | | | | | 295 | | | | | 300 | | | | | |
| Asn | Lys | Asn | Cys | Arg | Arg | His | Ser | Leu | Tyr | Val | Asp | Phe | Ser | Asp | Val |
| 305 | | | | 310 | | | | | 315 | | | | | 320 | |
| Gly | Trp | Asn | Asp | Trp | Ile | Val | Ala | Pro | Pro | Gly | Tyr | Gln | Ala | Phe | Tyr |
| | | | 325 | | | | | 330 | | | | | 335 | | |
| Cys | His | Gly | Asp | Cys | Pro | Phe | Pro | Leu | Ala | Asp | His | Leu | Asn | Ser | Thr |
| | | | 340 | | | | | 345 | | | | | 350 | | |
| Asn | His | Ala | Ile | Val | Gln | Thr | Leu | Val | Asn | Ser | Val | Asn | Ser | Ser | Ile |
| | | 355 | | | | | 360 | | | | | 365 | | | |
| Pro | Lys | Ala | Cys | Cys | Val | Pro | Thr | Glu | Leu | Ser | Ala | Ile | Ser | Met | Leu |
| 370 | | | | | 375 | | | | | 380 | | | | | |
| Tyr | Leu | Asp | Glu | Tyr | Asp | Lys | Val | Val | Leu | Lys | Asn | Tyr | Gln | Glu | Met |
| 385 | | | | | 390 | | | | | 395 | | | | | 400 |

Val Val Glu Gly Cys Gly Cys Arg
            405

<210> SEQ ID NO 51
<211> LENGTH: 454
<212> TYPE: PRT
<213> ORGANISM: Homo sapiens

<400> SEQUENCE: 51

Met His Leu Thr Val Phe Leu Leu Lys Gly Ile Val Gly Phe Leu Trp
  1               5                  10                  15

Ser Cys Trp Val Leu Val Gly Tyr Ala Lys Gly Gly Leu Gly Asp Asn
                 20                  25                  30

His Val His Ser Ser Phe Ile Tyr Arg Arg Leu Arg Asn His Glu Arg
             35                  40                  45

Arg Glu Ile Gln Arg Glu Ile Leu Ser Ile Leu Gly Leu Pro His Arg
         50                  55                  60

Pro Arg Pro Phe Ser Pro Gly Lys Gln Ala Ser Ser Ala Pro Leu Phe
 65                  70                  75                  80

Met Leu Asp Leu Tyr Asn Ala Met Thr Asn Glu Glu Asn Pro Glu Glu
                 85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Asp Trp Ile Ile Ala Pro Glu Gly Tyr Ala Phe Tyr Cys Asp Gly
        370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
            405                 410                 415

Pro Cys Cys Ala Pro Thr Lys Leu Asn Ala Ile Ser Val Leu Tyr Phe
                420                 425                 430

Asp Asp Ser Ser Asn Val Ile Leu Lys Lys Tyr Arg Asn Met Val Val
            435                 440                 445

Arg Ser Cys Gly Cys His
        450

<210> SEQ ID NO 52
<211> LENGTH: 513
<212> TYPE: PRT
<213> ORGANISM: Homo sapiens

<400> SEQUENCE: 52

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Pro Ser Pro Gln Ser Ser Ser
50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285

```
Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Phe Lys Val Ser Glu Val
        355                 360                 365

His Val Arg Thr Thr Arg Ser Ala Ser Ser Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
        435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His

<210> SEQ ID NO 53
<211> LENGTH: 431
<212> TYPE: PRT
<213> ORGANISM: Homo sapiens

<400> SEQUENCE: 53

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140
```

Glu Phe Phe His Pro Arg Tyr His Arg Glu Arg Phe Asp Leu
145                 150                 155                 160

Ser Lys Ile Pro Glu Gly Glu Ala Val Thr Ala Ala Glu Phe Arg Ile
            165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 54
<211> LENGTH: 402
<212> TYPE: PRT
<213> ORGANISM: Homo sapiens

<400> SEQUENCE: 54

Met Thr Ala Leu Pro Gly Pro Leu Trp Leu Leu Gly Leu Ala Leu Cys
1               5                   10                  15

Ala Leu Gly Gly Gly Gly Pro Gly Leu Arg Pro Pro Gly Cys Pro
                20                  25                  30

Gln Arg Arg Leu Gly Ala Arg Glu Arg Arg Asp Val Gln Arg Glu Ile
            35                  40                  45

Leu Ala Val Leu Gly Leu Pro Gly Arg Pro Arg Pro Arg Ala Pro Pro
50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95

```
Arg Arg Leu Gly Arg Ala Asp Leu Val Met Ser Phe Val Asn Met Val
        100                 105                 110

Glu Arg Asp Arg Ala Leu Gly His Gln Glu Pro His Trp Lys Glu Phe
            115                 120                 125

Arg Phe Asp Leu Thr Gln Ile Pro Ala Gly Glu Ala Val Thr Ala Ala
130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
    210                 215                 220

Gly His Ser Val Asp Pro Gly Leu Ala Gly Leu Gly Gln Arg Ala
225                 230                 235                 240

Pro Arg Ser Gln Gln Pro Phe Val Thr Phe Phe Arg Ala Ser Pro
                245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
    275                 280                 285

Phe Asp Asp Val His Gly Ser His Gly Arg Gln Val Cys Arg Arg His
290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
        355                 360                 365

Pro Thr Lys Leu Ser Ala Thr Ser Val Leu Tyr Tyr Asp Ser Ser Asn
370                 375                 380

Asn Val Ile Leu Arg Lys His Arg Asn Met Val Val Lys Ala Cys Gly
385                 390                 395                 400

Cys His

<210> SEQ ID NO 55
<211> LENGTH: 424
<212> TYPE: PRT
<213> ORGANISM: Homo sapiens

<400> SEQUENCE: 55

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly
        35                  40                  45

Val Asp Phe Asn Thr Leu Leu Gln Ser Met Lys Asp Glu Phe Leu Lys
50                  55                  60

Thr Leu Asn Leu Ser Asp Ile Pro Thr Gln Asp Ser Ala Lys Val Asp
```

```
                65                  70                  75                  80
        Pro Pro Glu Tyr Met Leu Glu Leu Tyr Asn Lys Phe Ala Thr Asp Arg
                            85                  90                  95

Thr Ser Met Pro Ser Ala Asn Ile Ile Arg Ser Phe Lys Asn Glu Asp
                        100                 105                 110

Leu Phe Ser Gln Pro Val Ser Phe Asn Gly Leu Arg Lys Tyr Pro Leu
                    115                 120                 125

Leu Phe Asn Val Ser Ile Pro His His Glu Val Ile Met Ala Glu
                130                 135                 140

Leu Arg Leu Tyr Thr Leu Val Gln Arg Asp Arg Met Ile Tyr Asp Gly
        145                 150                 155                 160

Val Asp Arg Lys Ile Thr Ile Phe Glu Val Leu Glu Ser Lys Gly Asp
                            165                 170                 175

Asn Glu Gly Glu Arg Asn Met Leu Val Leu Val Ser Gly Glu Ile Tyr
                        180                 185                 190

Gly Thr Asn Ser Glu Trp Glu Thr Phe Asp Val Thr Asp Ala Ile Arg
                    195                 200                 205

Arg Trp Gln Lys Ser Gly Ser Ser Thr His Gln Leu Glu Val His Ile
                210                 215                 220

Glu Ser Lys His Asp Glu Ala Glu Asp Ala Ser Ser Gly Arg Leu Glu
        225                 230                 235                 240

Ile Asp Thr Ser Ala Gln Asn Lys His Asn Pro Leu Leu Ile Val Phe
                            245                 250                 255

Ser Asp Asp Gln Ser Ser Asp Lys Glu Arg Lys Glu Glu Leu Asn Glu
                        260                 265                 270

Met Ile Ser His Glu Gln Leu Pro Glu Leu Asp Asn Leu Gly Leu Asp
                    275                 280                 285

Ser Phe Ser Ser Gly Pro Gly Glu Glu Ala Leu Leu Gln Met Arg Ser
                290                 295                 300

Asn Ile Ile Tyr Asp Ser Thr Ala Arg Ile Arg Arg Asn Ala Lys Gly
        305                 310                 315                 320

Asn Tyr Cys Lys Arg Thr Pro Leu Tyr Ile Asp Phe Lys Glu Ile Gly
                            325                 330                 335

Trp Asp Ser Trp Ile Ile Ala Pro Pro Gly Tyr Glu Ala Tyr Glu Cys
                        340                 345                 350

Arg Gly Val Cys Asn Tyr Pro Leu Ala Glu His Leu Thr Pro Thr Lys
                    355                 360                 365

His Ala Ile Ile Gln Ala Leu Val His Leu Lys Asn Ser Gln Lys Ala
                370                 375                 380

Ser Lys Ala Cys Cys Val Pro Thr Lys Leu Glu Pro Ile Ser Ile Leu
        385                 390                 395                 400

Tyr Leu Asp Lys Gly Val Val Thr Tyr Lys Phe Lys Tyr Glu Gly Met
                            405                 410                 415

Ala Val Ser Glu Cys Gly Cys Arg
                        420

<210> SEQ ID NO 56
        <211> LENGTH: 372
        <212> TYPE: PRT
        <213> ORGANISM: Homo sapiens

<400> SEQUENCE: 56

Met Pro Pro Gln Gln Gly Pro Cys Gly His His Leu Leu Leu
        1                   5                   10                  15

Leu Ala Leu Leu Leu Pro Ser Leu Pro Leu Thr Arg Ala Pro Val Pro
```

```
                      20                  25                  30
Pro Gly Pro Ala Ala Ala Leu Leu Gln Ala Leu Gly Leu Arg Asp Glu
        35                  40                  45
Pro Gln Gly Ala Pro Arg Leu Arg Pro Val Pro Val Met Trp Arg
50                  55                  60
Leu Phe Arg Arg Arg Asp Pro Gln Glu Thr Arg Ser Gly Ser Arg Arg
65                  70                  75                  80
Thr Ser Pro Gly Val Thr Leu Gln Pro Cys His Val Glu Glu Leu Gly
                        85                  90                  95
Val Ala Gly Asn Ile Val Arg His Ile Pro Asp Arg Gly Ala Pro Thr
                100                 105                 110
Arg Ala Ser Glu Pro Ala Ser Ala Ala Gly His Cys Pro Glu Trp Thr
            115                 120                 125
Val Val Phe Asp Leu Ser Ala Val Glu Pro Ala Glu Arg Pro Ser Arg
        130                 135                 140
Ala Arg Leu Glu Leu Arg Phe Ala Ala Ala Ala Ala Ala Pro Glu
145                 150                 155                 160
Gly Gly Trp Glu Leu Ser Val Ala Gln Ala Gly Gln Gly Ala Gly Ala
                    165                 170                 175
Asp Pro Gly Pro Val Leu Leu Arg Gln Leu Val Pro Ala Leu Gly Pro
                180                 185                 190
Pro Val Arg Ala Glu Leu Leu Gly Ala Ala Trp Ala Arg Asn Ala Ser
            195                 200                 205
Trp Pro Arg Ser Leu Arg Leu Ala Leu Ala Leu Arg Pro Arg Ala Pro
        210                 215                 220
Ala Ala Cys Ala Arg Leu Ala Glu Ala Ser Leu Leu Val Thr Leu
225                 230                 235                 240
Asp Pro Arg Leu Cys His Pro Leu Ala Arg Pro Arg Arg Asp Ala Glu
                    245                 250                 255
Pro Val Leu Gly Gly Pro Gly Gly Ala Cys Arg Ala Arg Arg Leu
                260                 265                 270
Tyr Val Ser Phe Arg Glu Val Gly Trp His Arg Trp Val Ile Ala Pro
            275                 280                 285
Arg Gly Phe Leu Ala Asn Tyr Cys Gln Gly Gln Cys Ala Leu Pro Val
        290                 295                 300
Ala Leu Ser Gly Ser Gly Gly Pro Pro Ala Leu Asn His Ala Val Leu
305                 310                 315                 320
Arg Ala Leu Met His Ala Ala Pro Gly Ala Ala Asp Leu Pro Cys
                    325                 330                 335
Cys Val Pro Ala Arg Leu Ser Pro Ile Ser Val Leu Phe Phe Asp Asn
                340                 345                 350
Ser Asp Asn Val Val Leu Arg Gln Tyr Glu Asp Met Val Val Asp Glu
            355                 360                 365
Cys Gly Cys Arg
    370

<210> SEQ ID NO 57
<211> LENGTH: 429
<212> TYPE: PRT
<213> ORGANISM: Homo sapiens

<400> SEQUENCE: 57

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
```

```
                     20                  25                  30
Ala Gly Gly Asn Ala His Ser Pro Leu Gly Val Pro Gly Gly Leu
            35                  40                  45
Pro Glu His Thr Phe Asn Leu Lys Met Phe Leu Glu Asn Val Lys Val
 50                  55                  60
Asp Phe Leu Arg Ser Leu Asn Leu Ser Gly Val Pro Ser Gln Asp Lys
 65                  70                  75                  80
Thr Arg Val Glu Pro Pro Gln Tyr Met Ile Asp Leu Tyr Asn Arg Tyr
                 85                  90                  95
Thr Ser Asp Lys Ser Thr Thr Pro Ala Ser Asn Ile Val Arg Ser Phe
                100                 105                 110
Ser Met Glu Asp Ala Ile Ser Ile Thr Ala Thr Glu Asp Phe Pro Phe
            115                 120                 125
Gln Lys His Ile Leu Leu Phe Asn Ile Ser Ile Pro Arg His Glu Gln
            130                 135                 140
Ile Thr Arg Ala Glu Leu Arg Leu Tyr Val Ser Cys Gln Asn His Val
145                 150                 155                 160
Asp Pro Ser His Asp Leu Lys Gly Ser Val Ile Tyr Asp Val Leu
                165                 170                 175
Asp Gly Thr Asp Ala Trp Asp Ser Ala Thr Glu Thr Lys Thr Phe Leu
                180                 185                 190
Val Ser Gln Asp Ile Gln Asp Glu Gly Trp Glu Thr Leu Glu Val Ser
                195                 200                 205
Ser Ala Val Lys Arg Trp Val Arg Ser Asp Ser Thr Lys Ser Lys Asn
            210                 215                 220
Lys Leu Glu Val Thr Val Glu Ser His Arg Lys Gly Cys Asp Thr Leu
225                 230                 235                 240
Asp Ile Ser Val Pro Pro Gly Ser Arg Asn Leu Pro Phe Phe Val Val
                245                 250                 255
Phe Ser Asn Asp His Ser Ser Gly Thr Lys Glu Thr Arg Leu Glu Leu
                260                 265                 270
Arg Glu Met Ile Ser His Glu Gln Glu Ser Val Leu Lys Lys Leu Ser
            275                 280                 285
Lys Asp Gly Ser Thr Glu Ala Gly Glu Ser Ser His Glu Glu Asp Thr
            290                 295                 300
Asp Gly His Val Ala Ala Gly Ser Thr Leu Ala Arg Arg Lys Arg Ser
305                 310                 315                 320
Ala Gly Ala Gly Ser His Cys Gln Lys Thr Ser Leu Arg Val Asn Phe
                325                 330                 335
Glu Asp Ile Gly Trp Asp Ser Trp Ile Ile Ala Pro Lys Glu Tyr Glu
            340                 345                 350
Ala Tyr Glu Cys Lys Gly Gly Cys Phe Phe Pro Leu Ala Asp Asp Val
            355                 360                 365
Thr Pro Thr Lys His Ala Ile Val Gln Thr Leu Val His Leu Lys Phe
            370                 375                 380
Pro Thr Lys Val Gly Lys Ala Cys Cys Val Pro Thr Lys Leu Ser Pro
385                 390                 395                 400
Ile Ser Val Leu Tyr Lys Asp Asp Met Gly Val Pro Thr Leu Lys Tyr
                405                 410                 415
His Tyr Glu Gly Met Ser Val Ala Glu Cys Gly Cys Arg
            420                 425

<210> SEQ ID NO 58
<211> LENGTH: 364
```

```
<212> TYPE: PRT
<213> ORGANISM: Homo sapiens

<400> SEQUENCE: 58
```

| | | | | | | | | | | | | | | |
|---|---|---|---|---|---|---|---|---|---|---|---|---|---|---|
| Met | Leu | Arg | Phe | Leu | Pro | Asp | Leu | Ala | Phe | Ser | Phe | Leu | Leu | Ile | Leu |
| 1 | | | | 5 | | | | | 10 | | | | | 15 | |

Ala Leu Gly Gln Ala Val Gln Phe Gln Glu Tyr Val Phe Leu Gln Phe
            20                  25                  30

Leu Gly Leu Asp Lys Ala Pro Ser Pro Gln Lys Phe Gln Pro Val Pro
        35                  40                  45

Tyr Ile Leu Lys Lys Ile Phe Gln Asp Arg Glu Ala Ala Thr Thr
    50                  55                  60

Gly Val Ser Arg Asp Leu Cys Tyr Val Lys Glu Leu Gly Val Arg Gly
65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
            100                 105                 110

Leu Ser Ala Ile Lys Glu Arg Glu Gln Leu Thr Leu Ala Gln Leu Gly
        115                 120                 125

Leu Asp Leu Gly Pro Asn Ser Tyr Tyr Asn Leu Gly Pro Glu Leu Glu
130                 135                 140

Leu Ala Leu Phe Leu Val Gln Glu Pro His Val Trp Gly Gln Thr Thr
145                 150                 155                 160

Pro Lys Pro Gly Lys Met Phe Val Leu Arg Ser Val Pro Trp Pro Gln
                165                 170                 175

Gly Ala Val His Phe Asn Leu Leu Asp Val Ala Lys Asp Trp Asn Asp
            180                 185                 190

Asn Pro Arg Lys Asn Phe Gly Leu Phe Leu Glu Ile Leu Val Lys Glu
        195                 200                 205

Asp Arg Asp Ser Gly Val Asn Phe Gln Pro Glu Asp Thr Cys Ala Arg
    210                 215                 220

Leu Arg Cys Ser Leu His Ala Ser Leu Leu Val Val Thr Leu Asn Pro
225                 230                 235                 240

Asp Gln Cys His Pro Ser Arg Lys Arg Arg Ala Ala Ile Pro Val Pro
                245                 250                 255

Lys Leu Ser Cys Lys Asn Leu Cys His Arg His Gln Leu Phe Ile Asn
            260                 265                 270

Phe Arg Asp Leu Gly Trp His Lys Trp Ile Ile Ala Pro Lys Gly Phe
        275                 280                 285

Met Ala Asn Tyr Cys His Gly Glu Cys Pro Phe Ser Leu Thr Ile Ser
290                 295                 300

Leu Asn Ser Ser Asn Tyr Ala Phe Met Gln Ala Leu Met His Ala Val
305                 310                 315                 320

Asp Pro Glu Ile Pro Gln Ala Val Cys Ile Pro Thr Lys Leu Ser Pro
                325                 330                 335

Ile Ser Met Leu Tyr Gln Asp Asn Asn Asp Asn Val Ile Leu Arg His
            340                 345                 350

Tyr Glu Asp Met Val Val Asp Glu Cys Gly Cys Gly
        355                 360

```
<210> SEQ ID NO 59
<211> LENGTH: 501
<212> TYPE: PRT
<213> ORGANISM: Homo sapiens
```

<400> SEQUENCE: 59

```
Met Arg Leu Pro Lys Leu Leu Thr Phe Leu Leu Trp Tyr Leu Ala Trp
 1               5                  10                  15

Leu Asp Leu Glu Phe Ile Cys Thr Val Leu Gly Ala Pro Asp Leu Gly
            20                  25                  30

Gln Arg Pro Gln Gly Ser Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Val Pro Arg
                245                 250                 255

Ser Arg Arg Ala Ala Gln Leu Lys Leu Ser Ser Cys Pro Ser Gly Arg
            260                 265                 270

Gln Pro Ala Ala Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Thr Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Ser
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415
```

```
Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
            450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 60
<211> LENGTH: 321
<212> TYPE: PRT
<213> ORGANISM: Homo sapiens

<400> SEQUENCE: 60

Asn Ser Asp Leu Ser His Thr Pro Leu Arg Arg Gln Lys Tyr Leu Phe
1               5                   10                  15

Asp Val Ser Met Leu Ser Asp Lys Glu Glu Leu Val Gly Ala Glu Leu
            20                  25                  30

Arg Leu Phe Arg Gln Ala Pro Ser Ala Pro Trp Gly Pro Pro Ala Gly
            35                  40                  45

Pro Leu His Val Gln Leu Phe Pro Cys Leu Ser Pro Leu Leu Leu Asp
        50                  55                  60

Ala Arg Thr Leu Asp Pro Gln Gly Ala Pro Pro Ala Gly Trp Glu Val
65              70                  75                  80

Phe Asp Val Trp Gln Gly Leu Arg His Gln Pro Trp Lys Gln Leu Cys
                85                  90                  95

Leu Glu Leu Arg Ala Ala Trp Gly Glu Leu Asp Ala Gly Glu Ala Glu
            100                 105                 110

Ala Arg Ala Arg Gly Pro Gln Gln Pro Pro Pro Asp Leu Arg Ser
            115                 120                 125

Leu Gly Phe Gly Arg Arg Val Arg Pro Pro Gln Glu Arg Ala Leu Leu
        130                 135                 140

Val Val Phe Thr Arg Ser Gln Arg Lys Asn Leu Phe Ala Glu Met Arg
145                 150                 155                 160

Glu Gln Leu Gly Ser Ala Glu Ala Ala Gly Pro Gly Ala Gly Ala Glu
                165                 170                 175

Gly Ser Trp Pro Pro Pro Ser Gly Ala Pro Asp Ala Arg Pro Trp Leu
            180                 185                 190

Pro Ser Pro Gly Arg Arg Arg Arg Arg Thr Ala Phe Ala Ser Arg His
        195                 200                 205

Gly Lys Arg His Gly Lys Lys Ser Arg Leu Arg Cys Ser Lys Lys Pro
        210                 215                 220

Leu His Val Asn Phe Lys Glu Leu Gly Trp Asp Asp Trp Ile Ile Ala
225                 230                 235                 240

Pro Leu Glu Tyr Glu Ala Tyr His Cys Glu Gly Val Cys Asp Phe Pro
                245                 250                 255

Leu Arg Ser His Leu Glu Pro Thr Asn His Ala Ile Ile Gln Thr Leu
            260                 265                 270

Met Asn Ser Met Asp Pro Gly Ser Thr Pro Pro Ser Cys Cys Val Pro
            275                 280                 285
```

```
Thr Lys Leu Thr Pro Ile Ser Ile Leu Tyr Ile Asp Ala Gly Asn Asn
            290                 295                 300
Val Val Tyr Lys Gln Tyr Glu Asp Met Val Val Glu Ser Cys Gly Cys
305                 310                 315                 320
Arg

<210> SEQ ID NO 61
<211> LENGTH: 388
<212> TYPE: PRT
<213> ORGANISM: Homo sapiens

<400> SEQUENCE: 61

Pro Gly Arg Arg Arg Pro Leu Leu Trp Ala Arg Leu Ala Ala Phe Arg
  1               5                  10                  15
Leu Gly Gln Arg Arg Gly Val Gly Arg Trp Leu Gln Gln Ala Trp Leu
                 20                  25                  30
Pro His Arg Arg Gln Leu Gly His Leu Leu Leu Gly Gly Pro Ala Leu
             35                  40                  45
Thr Val Cys Arg Ile Cys Ser Tyr Thr Ala Leu Ser Leu Cys Pro Cys
         50                  55                  60
Arg Ser Pro Ala Asp Glu Ser Ala Ala Glu Thr Gly Gln Ser Phe Leu
 65                  70                  75                  80
Phe Asp Val Ser Ser Leu Asn Asp Ala Asp Glu Val Val Gly Ala Glu
                 85                  90                  95
Leu Arg Val Leu Arg Arg Gly Ser Pro Glu Ser Gly Pro Gly Ser Trp
            100                 105                 110
Thr Ser Pro Pro Leu Leu Leu Ser Thr Cys Pro Gly Ala Ala Arg
            115                 120                 125
Ala Pro Arg Leu Leu Tyr Ser Arg Ala Ala Glu Pro Leu Val Gly Gln
        130                 135                 140
Arg Trp Glu Ala Phe Asp Val Ala Asp Ala Met Arg Arg His Arg Arg
145                 150                 155                 160
Glu Pro Arg Pro Pro Arg Ala Phe Cys Leu Leu Leu Arg Ala Val Ala
                165                 170                 175
Gly Pro Val Pro Ser Pro Leu Ala Leu Arg Arg Leu Gly Phe Gly Trp
            180                 185                 190
Pro Gly Gly Gly Gly Ser Ala Ala Glu Glu Arg Ala Val Leu Val Val
        195                 200                 205
Ser Ser Arg Thr Gln Arg Lys Glu Ser Leu Phe Arg Glu Ile Arg Ala
210                 215                 220
Gln Ala Arg Ala Leu Gly Ala Ala Leu Ala Ser Glu Pro Leu Pro Asp
225                 230                 235                 240
Pro Gly Thr Gly Thr Ala Ser Pro Arg Ala Val Ile Gly Gly Arg Arg
                245                 250                 255
Arg Arg Arg Thr Ala Leu Ala Gly Thr Arg Thr Ala Gln Gly Ser Gly
            260                 265                 270
Gly Gly Ala Gly Arg Gly His Gly Arg Gly Arg Ser Arg Cys Ser
        275                 280                 285
Arg Lys Pro Leu His Val Asp Phe Lys Glu Leu Gly Trp Asp Asp Trp
290                 295                 300
Ile Ile Ala Pro Leu Asp Tyr Glu Ala Tyr His Cys Glu Gly Leu Cys
305                 310                 315                 320
Asp Phe Pro Leu Arg Ser His Leu Glu Pro Thr Asn His Ala Ile Ile
                325                 330                 335
Gln Thr Leu Leu Asn Ser Met Ala Pro Asp Ala Ala Pro Ala Ser Cys
```

```
            340             345             350
Cys Val Pro Ala Arg Leu Ser Pro Ile Ser Ile Leu Tyr Ile Asp Ala
            355                 360                 365
Ala Asn Asn Val Val Tyr Lys Gln Tyr Glu Asp Met Val Val Glu Ala
            370                 375                 380
Cys Gly Cys Arg
385

<210> SEQ ID NO 62
<211> LENGTH: 375
<212> TYPE: PRT
<213> ORGANISM: Homo sapiens

<400> SEQUENCE: 62

Met Gln Lys Leu Gln Leu Cys Val Tyr Ile Tyr Leu Phe Met Leu Ile
1               5                   10                  15
Val Ala Gly Pro Val Asp Leu Asn Glu Asn Ser Glu Gln Lys Glu Asn
            20                  25                  30
Val Glu Lys Glu Gly Leu Cys Asn Ala Cys Thr Trp Arg Gln Asn Thr
        35                  40                  45
Lys Ser Ser Arg Ile Glu Ala Ile Lys Ile Gln Ile Leu Ser Lys Leu
50                  55                  60
Arg Leu Glu Thr Ala Pro Asn Ile Ser Lys Asp Val Ile Arg Gln Leu
65                  70                  75                  80
Leu Pro Lys Ala Pro Pro Leu Arg Glu Leu Ile Asp Gln Tyr Asp Val
                85                  90                  95
Gln Arg Asp Asp Ser Ser Asp Gly Ser Leu Glu Asp Asp Tyr His
            100                 105                 110
Ala Thr Thr Glu Thr Ile Ile Thr Met Pro Thr Glu Ser Asp Phe Leu
        115                 120                 125
Met Gln Val Asp Gly Lys Pro Lys Cys Cys Phe Phe Lys Phe Ser Ser
130                 135                 140
Lys Ile Gln Tyr Asn Lys Val Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
            180                 185                 190
Lys Leu Asp Met Asn Pro Gly Thr Gly Ile Trp Gln Ser Ile Asp Val
        195                 200                 205
Lys Thr Val Leu Gln Asn Trp Leu Lys Gln Pro Glu Ser Asn Leu Gly
210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
            260                 265                 270
Asp Glu His Ser Thr Glu Ser Arg Cys Cys Arg Tyr Pro Leu Thr Val
        275                 280                 285
Asp Phe Glu Ala Phe Gly Trp Asp Trp Ile Ile Ala Pro Lys Arg Tyr
        290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
```

Gly Pro Cys Cys Thr Pro Thr Lys Met Ser Pro Ile Asn Met Leu Tyr
                325                 330                 335
                        340                 345                 350

Phe Asn Gly Lys Glu Gln Ile Ile Tyr Gly Lys Ile Pro Ala Met Val
            355                 360                 365

Val Asp Arg Cys Gly Cys Ser
        370             375

<210> SEQ ID NO 63
<211> LENGTH: 478
<212> TYPE: PRT
<213> ORGANISM: Homo sapiens

<400> SEQUENCE: 63

Met Ala His Val Pro Ala Arg Thr Ser Pro Gly Pro Gly Pro Gln Leu
 1               5                  10                  15

Leu Leu Leu Leu Leu Pro Leu Phe Leu Leu Leu Arg Asp Val Ala
            20                  25                  30

Gly Ser His Arg Ala Pro Ala Trp Ser Ala Leu Pro Ala Ala Ala Asp
            35                  40                  45

Gly Leu Gln Gly Asp Arg Asp Leu Gln Arg His Pro Gly Asp Ala Ala
 50                  55                  60

Ala Thr Leu Gly Pro Ser Ala Gln Asp Met Val Ala Val His Met His
 65                  70                  75                  80

Arg Leu Tyr Glu Lys Tyr Ser Arg Gln Gly Ala Arg Pro Gly Gly Gly
                85                  90                  95

Asn Thr Val Arg Ser Phe Arg Ala Arg Leu Glu Val Val Asp Gln Lys
            100                 105                 110

Ala Val Tyr Phe Phe Asn Leu Thr Ser Met Gln Asp Ser Glu Met Ile
            115                 120                 125

Leu Thr Ala Thr Phe His Phe Tyr Ser Glu Pro Pro Arg Trp Pro Arg
130                 135                 140

Ala Leu Glu Val Leu Cys Lys Pro Arg Ala Lys Asn Ala Ser Gly Arg
145                 150                 155                 160

Pro Leu Pro Leu Gly Pro Pro Thr Arg Gln His Leu Leu Phe Arg Ser
                165                 170                 175

Leu Ser Gln Asn Thr Ala Thr Gln Gly Leu Leu Arg Gly Ala Met Ala
            180                 185                 190

Leu Ala Pro Pro Pro Arg Gly Leu Trp Gln Ala Lys Asp Ile Ser Pro
            195                 200                 205

Ile Val Lys Ala Ala Arg Arg Asp Gly Glu Leu Leu Leu Ser Ala Gln
210                 215                 220

Leu Asp Ser Glu Glu Arg Asp Pro Gly Val Pro Arg Pro Ser Pro Tyr
225                 230                 235                 240

Ala Pro Tyr Ile Leu Val Tyr Ala Asn Asp Leu Ala Ile Ser Glu Pro
                245                 250                 255

Asn Ser Val Ala Val Thr Leu Gln Arg Tyr Asp Pro Phe Pro Ala Gly
            260                 265                 270

Asp Pro Glu Pro Arg Ala Ala Pro Asn Asn Ser Ala Asp Pro Arg Val
            275                 280                 285

Arg Arg Ala Ala Gln Ala Thr Gly Pro Leu Gln Asp Asn Glu Leu Pro
            290                 295                 300

Gly Leu Asp Glu Arg Pro Pro Arg Ala His Ala Gln His Phe His Lys
305                 310                 315                 320

His Gln Leu Trp Pro Ser Pro Phe Arg Ala Leu Lys Pro Arg Pro Gly

```
                    325                 330                 335
Arg Lys Asp Arg Arg Lys Lys Gly Gln Glu Val Phe Met Ala Ala Ser
                340                 345                 350

Gln Val Leu Asp Phe Asp Glu Lys Thr Met Gln Lys Ala Arg Arg Lys
            355                 360                 365

Gln Trp Asp Glu Pro Arg Val Cys Ser Arg Arg Tyr Leu Lys Val Asp
        370                 375                 380

Phe Ala Asp Ile Gly Trp Asn Glu Trp Ile Ile Ser Pro Lys Ser Phe
385                 390                 395                 400

Asp Ala Tyr Tyr Cys Ala Gly Ala Cys Glu Phe Pro Met Pro Lys Ile
                405                 410                 415

Val Arg Pro Ser Asn His Ala Thr Ile Gln Ser Ile Val Arg Ala Val
            420                 425                 430

Gly Ile Ile Pro Gly Ile Pro Glu Pro Cys Cys Val Pro Asp Lys Met
        435                 440                 445

Asn Ser Leu Gly Val Leu Phe Leu Asp Glu Asn Arg Asn Val Val Leu
    450                 455                 460

Lys Val Tyr Pro Asn Met Ser Val Asp Thr Cys Ala Cys Arg
465                 470                 475

<210> SEQ ID NO 64
<211> LENGTH: 407
<212> TYPE: PRT
<213> ORGANISM: Homo sapiens

<400> SEQUENCE: 64

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
```

```
                225                 230                 235                 240
Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
                260                 265                 270

Ser Leu Gly Pro Gly Ala Glu Gly Leu His Pro Phe Met Glu Leu Arg
                275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
                355                 360                 365

Gly Pro Cys Cys Thr Pro Thr Lys Met Ser Pro Ile Asn Met Leu Tyr
                370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 65
<211> LENGTH: PRT
<212> TYPE: PRT
<213> ORGANISM: Homo sapiens

<400> SEQUENCE: 65

Met Pro Gly Gln Glu Leu Arg Thr Leu Asn Gly Ser Gln Met Leu Leu
1               5                   10                  15

Val Leu Val Leu Ser Trp Leu Pro His Gly Gly Ala Leu Ser Leu
            20                  25                  30

Ala Glu Ala Ser Arg Ala Ser Phe Pro Gly Pro Ser Glu Glu Leu His
            35                  40                  45

Thr Glu Asp Ser Phe Arg Arg Glu Leu Arg Lys Arg Tyr Glu Asp Leu
        50                  55                  60

Leu Thr Arg Leu Arg Ala Asn Gln Ser Trp Glu Asp Ser Asn Thr Asp
65                  70                  75                  80

Leu Val Pro Ala Pro Ala Val Arg Ile Leu Thr Pro Glu Val Arg Leu
                85                  90                  95

Gly Ser Gly Gly His Leu His Leu Arg Ile Ser Arg Ala Ala Leu Pro
                100                 105                 110

Glu Gly Leu Pro Glu Ala Ser Arg Leu His Arg Ala Leu Phe Arg Leu
            115                 120                 125

Ser Pro Thr Ala Ser Arg Ser Trp Asp Val Thr Arg Pro Leu Arg Arg
        130                 135                 140

Gln Leu Ser Leu Ala Arg Pro Gln Ala Pro Ala Leu His Leu Arg Leu
145                 150                 155                 160

Ser Pro Pro Pro Ser Gln Ser Asp Gln Leu Leu Ala Glu Ser Ser Ser
                165                 170                 175

Ala Arg Pro Gln Leu Glu Leu His Leu Arg Pro Gln Ala Ala Arg Gly
                180                 185                 190

Arg Arg Arg Ala Arg Ala Arg Asn Gly Asp His Cys Pro Leu Gly Pro
```

```
                    195                 200                 205
Gly Arg Cys Cys Arg Leu His Thr Val Arg Ala Ser Leu Glu Asp Leu
210                 215                 220

Gly Trp Ala Asp Trp Val Leu Ser Pro Arg Glu Val Gln Val Thr Met
225                 230                 235                 240

Cys Ile Gly Ala Cys Pro Ser Gln Phe Arg Ala Ala Asn Met His Ala
                    245                 250                 255

Gln Ile Lys Thr Ser Leu His Arg Leu Lys Pro Asp Thr Val Pro Ala
                260                 265                 270

Pro Cys Cys Val Pro Ala Ser Tyr Asn Pro Met Val Leu Ile Gln Lys
            275                 280                 285

Thr Asp Thr Gly Val Ser Leu Gln Thr Tyr Asp Leu Leu Ala Lys
    290                 295                 300

Asp Cys His Cys Ile
305

<210> SEQ ID NO 66
<211> LENGTH: 426
<212> TYPE: PRT
<213> ORGANISM: Homo sapiens

<400> SEQUENCE: 66

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
```

```
            260                 265                 270
Gly Gly Gly Glu Gly Gly Ala Gly Ala Asp Glu Glu Lys Glu Gln Ser
            275                 280                 285
His Arg Pro Phe Leu Met Leu Gln Ala Arg Gln Ser Glu Asp His Pro
            290                 295                 300
His Arg Arg Arg Arg Gly Leu Glu Cys Asp Gly Lys Val Asn Ile
305                 310                 315                 320
Cys Cys Lys Lys Gln Phe Phe Val Ser Phe Lys Asp Ile Gly Trp Asn
                325                 330                 335
Asp Trp Ile Ile Ala Pro Ser Gly Tyr His Ala Asn Tyr Cys Glu Gly
            340                 345                 350
Glu Cys Pro Ser His Ile Ala Gly Thr Ser Gly Ser Ser Leu Ser Phe
            355                 360                 365
His Ser Thr Val Ile Asn His Tyr Arg Met Arg Gly His Ser Pro Phe
            370                 375                 380
Ala Asn Leu Lys Ser Cys Cys Val Pro Thr Lys Leu Arg Pro Met Ser
385                 390                 395                 400
Met Leu Tyr Tyr Asp Asp Gly Gln Asn Ile Ile Lys Lys Asp Ile Gln
                405                 410                 415
Asn Met Ile Val Glu Glu Cys Gly Cys Ser
                420                 425

<210> SEQ ID NO 67
<211> LENGTH: 407
<212> TYPE: PRT
<213> ORGANISM: Homo sapiens

<400> SEQUENCE: 67

Met Asp Gly Leu Pro Gly Arg Ala Leu Gly Ala Ala Cys Leu Leu Leu
1               5                   10                  15
Leu Ala Ala Gly Trp Leu Gly Pro Glu Ala Trp Gly Ser Pro Thr Pro
            20                  25                  30
Pro Pro Thr Pro Ala Ala Pro Pro Pro Pro Pro Gly Ala Pro
            35                  40                  45
Gly Gly Ser Gln Asp Thr Cys Thr Ser Cys Gly Gly Phe Arg Arg Pro
        50                  55                  60
Glu Glu Leu Gly Arg Val Asp Gly Asp Phe Leu Glu Ala Val Lys Arg
65                  70                  75                  80
His Ile Leu Ser Arg Leu Gln Met Arg Gly Arg Pro Asn Ile Thr His
                85                  90                  95
Ala Val Pro Lys Ala Ala Met Val Thr Ala Leu Arg Lys Leu His Ala
            100                 105                 110
Gly Lys Val Arg Glu Asp Gly Arg Val Glu Ile Pro His Leu Asp Gly
            115                 120                 125
His Ala Ser Pro Gly Ala Asp Gly Gln Glu Arg Val Ser Glu Ile Ile
        130                 135                 140
Ser Phe Ala Glu Thr Asp Gly Leu Ala Ser Ser Arg Val Arg Leu Tyr
145                 150                 155                 160
Phe Phe Ile Ser Asn Glu Gly Asn Gln Asn Leu Phe Val Val Gln Ala
                165                 170                 175
Ser Leu Trp Leu Tyr Leu Lys Leu Leu Pro Tyr Val Leu Glu Lys Gly
            180                 185                 190
Ser Arg Arg Lys Val Arg Val Lys Val Tyr Phe Gln Glu Gln Gly His
            195                 200                 205
Gly Asp Arg Trp Asn Met Val Glu Lys Arg Val Asp Leu Lys Arg Ser
```

-continued

```
                210                 215                 220
Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Val Gln Ala Arg Leu Gly Asp Ser Arg His Arg
            275                 280                 285

Ile Arg Lys Arg Gly Leu Glu Cys Asp Gly Arg Thr Asn Leu Cys Cys
290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
            340                 345                 350

Ala Val Val Asn Gln Tyr Arg Met Arg Gly Leu Asn Pro Gly Thr Val
            355                 360                 365

Asn Ser Cys Cys Ile Pro Thr Lys Leu Ser Thr Met Ser Met Leu Tyr
370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 68
<211> LENGTH: 352
<212> TYPE: PRT
<213> ORGANISM: Homo sapiens

<400> SEQUENCE: 68

Met Thr Ser Ser Leu Leu Leu Ala Phe Leu Leu Leu Ala Pro Thr Thr
1               5                   10                  15

Val Ala Thr Pro Arg Ala Gly Gly Gln Cys Pro Ala Cys Gly Gly Pro
                20                  25                  30

Thr Leu Glu Leu Glu Ser Gln Arg Glu Leu Leu Leu Asp Leu Ala Lys
            35                  40                  45

Arg Ser Ile Leu Asp Lys Leu His Leu Thr Gln Arg Pro Thr Leu Asn
50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
                85                  90                  95

Glu Ile Ile Ser Phe Ala Glu Thr Gly Leu Ser Thr Ile Asn Gln Thr
            100                 105                 110

Arg Leu Asp Phe His Phe Ser Ser Asp Arg Thr Ala Gly Asp Arg Glu
            115                 120                 125

Val Gln Gln Ala Ser Leu Met Phe Phe Val Gln Leu Pro Ser Asn Thr
130                 135                 140

Thr Trp Thr Leu Lys Val Arg Val Leu Val Leu Gly Pro His Asn Thr
145                 150                 155                 160

Asn Leu Thr Leu Ala Thr Gln Tyr Leu Leu Glu Val Asp Ala Ser Gly
                165                 170                 175

Trp His Gln Leu Pro Leu Gly Pro Glu Ala Gln Ala Ala Cys Ser Gln
```

```
                180                 185                 190
Gly His Leu Thr Leu Glu Leu Val Leu Glu Gly Gln Val Ala Gln Ser
            195                 200                 205

Ser Val Ile Leu Gly Gly Ala Ala His Arg Pro Phe Val Ala Ala Arg
        210                 215                 220

Val Arg Val Gly Gly Lys His Gln Ile His Arg Gly Ile Asp Cys
225                 230                 235                 240

Gln Gly Gly Ser Arg Met Cys Cys Arg Gln Glu Phe Phe Val Asp Phe
                245                 250                 255

Arg Glu Ile Gly Trp His Asp Trp Ile Ile Gln Pro Glu Gly Tyr Ala
            260                 265                 270

Met Asn Phe Cys Ile Gly Gln Cys Pro Leu His Ile Ala Gly Met Pro
        275                 280                 285

Gly Ile Ala Ala Ser Phe His Thr Ala Val Leu Asn Leu Leu Lys Ala
    290                 295                 300

Asn Thr Ala Ala Gly Thr Thr Gly Gly Gly Ser Cys Cys Val Pro Thr
305                 310                 315                 320

Ala Arg Arg Pro Leu Ser Leu Leu Tyr Tyr Asp Arg Asp Ser Asn Ile
                325                 330                 335

Val Lys Thr Asp Ile Pro Asp Met Val Val Glu Ala Cys Gly Cys Ser
            340                 345                 350

<210> SEQ ID NO 69
<211> LENGTH: 350
<212> TYPE: PRT
<213> ORGANISM: Mus musculus

<400> SEQUENCE: 69

Met Lys Leu Pro Lys Ala Gln Leu Trp Leu Ile Leu Leu Trp Ala Leu
1               5                   10                  15

Val Trp Val Gln Ser Arg Arg Ser Ala Cys Pro Ser Cys Gly Gly Pro
            20                  25                  30

Thr Leu Ala Pro Gln Gly Glu Arg Ala Leu Val Leu Glu Leu Ala Lys
        35                  40                  45

Gln Gln Ile Leu Glu Gly Leu His Leu Thr Ser Arg Pro Arg Ile Thr
    50                  55                  60

Arg Pro Leu Pro Gln Ala Ala Leu Thr Arg Ala Leu Arg Arg Leu Gln
65                  70                  75                  80

Pro Lys Ser Met Val Pro Gly Asn Arg Glu Lys Val Ile Ser Phe Ala
                85                  90                  95

Thr Ile Ile Asp Lys Ser Thr Ser Thr Tyr Arg Ser Met Leu Thr Phe
            100                 105                 110

Gln Leu Ser Pro Leu Trp Ser His His Leu Tyr His Ala Arg Leu Trp
        115                 120                 125

Leu His Val Pro Pro Ser Phe Pro Gly Thr Leu Tyr Leu Arg Ile Phe
    130                 135                 140

Arg Cys Gly Thr Thr Arg Cys Arg Gly Phe Arg Thr Phe Leu Ala Glu
145                 150                 155                 160

His Gln Thr Thr Ser Ser Gly Trp His Ala Leu Thr Leu Pro Ser Ser
                165                 170                 175

Gly Leu Arg Ser Glu Asp Ser Gly Val Val Lys Leu Gln Leu Glu Phe
            180                 185                 190

Arg Pro Leu Asp Leu Asn Ser Thr Ala Ala Gly Leu Pro Arg Leu Leu
        195                 200                 205

Leu Asp Thr Ala Gly Gln Gln Arg Pro Phe Leu Glu Leu Lys Ile Arg
```

```
                210                 215                 220
Ala Asn Glu Pro Gly Ala Gly Arg Ala Arg Arg Thr Pro Thr Cys
225                 230                 235                 240

Glu Pro Glu Thr Pro Leu Cys Cys Arg Arg Asp His Tyr Val Asp Phe
                245                 250                 255

Gln Glu Leu Gly Trp Arg Asp Trp Ile Leu Gln Pro Glu Gly Tyr Gln
                260                 265                 270

Leu Asn Tyr Cys Ser Gly Gln Cys Pro Pro His Leu Ala Gly Ser Pro
            275                 280                 285

Gly Ile Ala Ala Ser Phe His Ser Ala Val Phe Ser Leu Leu Lys Ala
        290                 295                 300

Asn Asn Pro Trp Pro Ala Gly Ser Ser Cys Cys Val Pro Thr Ala Arg
305                 310                 315                 320

Arg Pro Leu Ser Leu Leu Tyr Leu Asp His Asn Gly Asn Val Val Lys
                325                 330                 335

Thr Asp Val Pro Asp Met Val Val Glu Ala Cys Gly Cys Ser
                340                 345                 350

<210> SEQ ID NO 70
<211> LENGTH: 351
<212> TYPE: PRT
<213> ORGANISM: Homo sapiens

<400> SEQUENCE: 70

Gly Val Ser Ser Gln Gly Leu Glu Leu Ala Arg Glu Leu Val Leu Ala
1               5                   10                  15

Lys Val Arg Ala Leu Phe Leu Asp Ala Leu Gly Pro Pro Ala Val Thr
                20                  25                  30

Arg Glu Gly Gly Asp Pro Gly Val Arg Arg Leu Pro Arg Arg His Ala
            35                  40                  45

Leu Gly Gly Phe Thr His Arg Gly Ser Glu Pro Glu Glu Glu Glu Asp
        50                  55                  60

Val Ser Gln Ala Ile Leu Phe Pro Ala Thr Asp Ala Ser Cys Glu Asp
65                  70                  75                  80

Lys Ser Ala Ala Arg Gly Leu Ala Gln Glu Ala Glu Glu Gly Leu Phe
                85                  90                  95

Arg Tyr Met Phe Arg Pro Ser Gln His Thr Arg Ser Arg Gln Val Thr
                100                 105                 110

Ser Ala Gln Leu Trp Phe His Thr Gly Leu Asp Arg Gln Gly Thr Ala
            115                 120                 125

Ala Ser Asn Ser Ser Glu Pro Leu Leu Gly Leu Leu Ala Leu Ser Pro
        130                 135                 140

Gly Gly Pro Val Ala Val Pro Met Ser Leu Gly His Ala Pro Pro His
145                 150                 155                 160

Trp Ala Val Leu His Leu Ala Thr Ser Ala Leu Ser Leu Leu Thr His
                165                 170                 175

Pro Val Leu Val Leu Leu Leu Arg Cys Pro Leu Cys Thr Cys Ser Ala
                180                 185                 190

Arg Pro Glu Ala Thr Pro Phe Leu Val Ala His Thr Arg Thr Arg Pro
            195                 200                 205

Pro Ser Gly Gly Glu Arg Ala Arg Arg Ser Thr Pro Leu Met Ser Trp
        210                 215                 220

Pro Trp Ser Pro Ser Ala Leu Arg Leu Leu Gln Arg Pro Pro Glu Glu
225                 230                 235                 240

Pro Ala Ala His Ala Asn Cys His Arg Val Ala Leu Asn Ile Ser Phe
```

```
                    245                 250                 255
Gln Glu Leu Gly Trp Glu Arg Trp Ile Val Tyr Pro Pro Ser Phe Ile
                260                 265                 270

Phe His Tyr Cys His Gly Gly Cys Gly Leu His Ile Pro Pro Asn Leu
            275                 280                 285

Ser Leu Pro Val Pro Gly Ala Pro Pro Thr Pro Ala Gln Pro Tyr Ser
        290                 295                 300

Leu Leu Pro Gly Ala Gln Pro Cys Cys Ala Ala Leu Pro Gly Thr Met
305                 310                 315                 320

Arg Pro Leu His Val Arg Thr Thr Ser Asp Gly Gly Tyr Ser Phe Lys
                325                 330                 335

Tyr Glu Thr Val Pro Asn Leu Leu Thr Gln His Cys Ala Cys Ile
                340                 345                 350

<210> SEQ ID NO 71
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Bovine enterokinase cleavage site

<400> SEQUENCE: 71

Asp Asp Asp Asp Lys
1               5

<210> SEQ ID NO 72
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 72

Glu Asn Leu Tyr Phe Gln Gly
1               5

<210> SEQ ID NO 73
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 73

Glu Asn Leu Tyr Phe Gln Ser
1               5

<210> SEQ ID NO 74
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 74

Glu Asn Ile Tyr Thr Gln Gly
1               5
```

```
<210> SEQ ID NO 75
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 75

Glu Asn Ile Tyr Thr Gln Ser
 1               5

<210> SEQ ID NO 76
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 76

Glu Asn Ile Tyr Leu Gln Gly
 1               5

<210> SEQ ID NO 77
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 77

Glu Asn Ile Tyr Leu Gln Ser
 1               5

<210> SEQ ID NO 78
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 78

Glu Asn Val Tyr Phe Gln Gly
 1               5

<210> SEQ ID NO 79
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 79

Glu Asn Val Tyr Ser Gln Ser
 1               5

<210> SEQ ID NO 80
<211> LENGTH: 7
<212> TYPE: PRT
<213> ORGANISM: Artificial Sequence
```

```
<220> FEATURE:
<221> NAME/KEY: SITE
<222> LOCATION: (1)...(7)
<223> OTHER INFORMATION: Tobacco Etch Virus cleavage site

<400> SEQUENCE: 80

Glu Asn Val Tyr Ser Gln Gly
1               5

<210> SEQ ID NO 81
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 81

Glu Asn Val Tyr Ser Gln Ser
1               5

<210> SEQ ID NO 82
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 82

Glu Ala Leu Phe Gln Gly Pro
1               5

<210> SEQ ID NO 83
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 83

Glu Val Leu Phe Gln Gly Pro
1               5

<210> SEQ ID NO 84
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 84

Glu Leu Leu Phe Gln Gly Pro
1               5

<210> SEQ ID NO 85
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site
```

```
<400> SEQUENCE: 85

Asp Ala Leu Phe Gln Gly Pro
 1               5

<210> SEQ ID NO 86
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 86

Asp Val Leu Phe Gln Gly Pro
 1               5

<210> SEQ ID NO 87
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 87

Asp Leu Leu Phe Gln Gly Pro
 1               5

<210> SEQ ID NO 88
<211> LENGTH: 98
<212> TYPE: PRT
<213> ORGANISM: Artificial Sequence
<220> FEATURE:
<221> NAME/KEY: SITE
<222> LOCATION: (1)...(98)
<223> OTHER INFORMATION: SUMO/ULP-1 cleavage site

<400> SEQUENCE: 88

Met Ala Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
             20                  25                  30

Ser Glu Ile Phe Phe Lys Ile Lys Lys Thr Thr Pro Leu Arg Arg Leu
         35                  40                  45

Met Glu Ala Phe Ala Lys Arg Gln Gly Lys Glu Met Asp Ser Leu Arg
     50                  55                  60

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly

<210> SEQ ID NO 89
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 89

Gly Val Arg Gly
```

```
<210> SEQ ID NO 90
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 90

Ser Ala Arg Gly
 1

<210> SEQ ID NO 91
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 91

Ser Leu Arg Gly
 1

<210> SEQ ID NO 92
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 92

Asp Gly Arg Ile
 1

<210> SEQ ID NO 93
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 93

Gln Gly Lys Ile
 1

<210> SEQ ID NO 94
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 94

Leu Val Pro Arg Gly Ser
 1               5

<210> SEQ ID NO 95
<211> LENGTH: 6
```

```
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 95

Leu Val Pro Lys Gly Ser
 1               5

<210> SEQ ID NO 96
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 96

Phe Ile Pro Arg Thr Phe
 1               5

<210> SEQ ID NO 97
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 97

Val Leu Pro Arg Ser Phe
 1               5

<210> SEQ ID NO 98
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 98

Ile Val Pro Arg Ser Phe
 1               5

<210> SEQ ID NO 99
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 99

Ile Val Pro Arg Gly Tyr
 1               5

<210> SEQ ID NO 100
<211> LENGTH: 6
<212> TYPE: PRT
<213> ORGANISM: Artificial Sequence
<220> FEATURE:
<221> NAME/KEY: SITE
<222> LOCATION: (1)...(6)
```

<223> OTHER INFORMATION: Thrombin cleavage site

<400> SEQUENCE: 100

Val Val Pro Arg Gly Val
1               5

<210> SEQ ID NO 101
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 101

Val Leu Pro Arg Leu Ile
1               5

<210> SEQ ID NO 102
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 102

Val Met Pro Arg Ser Leu
1               5

<210> SEQ ID NO 103
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 103

Met Phe Pro Arg Ser Leu
1               5

<210> SEQ ID NO 104
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Coagulation Factor Xa cleavage site

<400> SEQUENCE: 104

Ile Asp Gly Arg
1

<210> SEQ ID NO 105
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Coagulation Factor Xa cleavage site

<400> SEQUENCE: 105

Ile Glu Gly Arg
1

```
<210> SEQ ID NO 106
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: Flexible spacer

<400> SEQUENCE: 106

Gly Gly Gly Gly Ser
 1               5

<210> SEQ ID NO 107
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: Flexible spacer

<400> SEQUENCE: 107

Glu Ala Ala Ala Lys
 1               5

<210> SEQ ID NO 108
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: FLAG epitope-binding region

<400> SEQUENCE: 108

Asp Tyr Lys Asp Asp Asp Asp Lys
 1               5

<210> SEQ ID NO 109
<211> LENGTH: 9
<212> TYPE: PRT
<213> ORGANISM: Artificial Sequence
<220> FEATURE:
<221> NAME/KEY: PEPTIDE
<222> LOCATION: (1)...(9)
<223> OTHER INFORMATION: Human Influenza virus hemagluttinin (HA)
      epitope-binding region

<400> SEQUENCE: 109

Tyr Pro Tyr Asp Val Pro Asp Tyr Ala
 1               5

<210> SEQ ID NO 110
<211> LENGTH: 10
<212> TYPE: PRT
<213> ORGANISM: Artificial Sequence
<220> FEATURE:
<221> NAME/KEY: PEPTIDE
<222> LOCATION: (1)...(10)
<223> OTHER INFORMATION: Human p62 c-Myc epitope-binding region

<400> SEQUENCE: 110

Glu Gln Lys Leu Ile Ser Glu Glu Asp Leu
 1               5                  10

<210> SEQ ID NO 111
<211> LENGTH: 11
<212> TYPE: PRT
```

```
<213> ORGANISM: Artificial Sequence
<220> FEATURE:
<221> NAME/KEY: PEPTIDE
<222> LOCATION: (1)...(11)
<223> OTHER INFORMATION: Vesicular Stomatitis Virus Glycoprotein (VSV-G)
      epitope-binding region

<400> SEQUENCE: 111

Tyr Thr Asp Ile Glu Met Asn Arg Leu Gly Lys
1               5                   10

<210> SEQ ID NO 112
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Substance P epitope-binding region

<400> SEQUENCE: 112

Gln Phe Phe Gly Leu Met
1               5

<210> SEQ ID NO 113
<211> LENGTH: 11
<212> TYPE: PRT
<213> ORGANISM: Artificial Sequence
<220> FEATURE:
<221> NAME/KEY: PEPTIDE
<222> LOCATION: (1)...(11)
<223> OTHER INFORMATION: Glycoprotein-D precursor of Herpes simplex
      virus epitope-binding region

<400> SEQUENCE: 113

Gln Pro Glu Leu Ala Pro Glu Asp Pro Glu Asp
1               5                   10

<210> SEQ ID NO 114
<211> LENGTH: 14
<212> TYPE: PRT
<213> ORGANISM: Artificial Sequence
<220> FEATURE:
<221> NAME/KEY: PEPTIDE
<222> LOCATION: (1)...(14)
<223> OTHER INFORMATION: V5 epitope-binding region

<400> SEQUENCE: 114

Gly Lys Pro Ile Pro Asn Pro Leu Leu Gly Leu Asp Ser Thr
1               5                   10

<210> SEQ ID NO 115
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: AU1 epitope-binding region

<400> SEQUENCE: 115

Asp Thr Tyr Arg Tyr Ile
1               5

<210> SEQ ID NO 116
<211> LENGTH: 6
<212> TYPE: PRT
<213> ORGANISM: Artificial Sequence
<220> FEATURE:
<221> NAME/KEY: PEPTIDE
```

```
<222> LOCATION: (1)...(6)
<223> OTHER INFORMATION: AU5 epitope-binding region

<400> SEQUENCE: 116

Thr Asp Phe Tyr Leu Lys
 1               5

<210> SEQ ID NO 117
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: HIS epitope-binding region

<400> SEQUENCE: 117

His His His His His His
 1               5

<210> SEQ ID NO 118
<211> LENGTH: 1139
<212> TYPE: PRT
<213> ORGANISM: Artificial Sequence
<220> FEATURE:
<223> OTHER INFORMATION: BoNT/A-AP4A-GRPP

<400> SEQUENCE: 118

Met Arg Ser Leu Gln Asp Thr Glu Glu Lys Ser Arg Ser Phe Ser Ala
 1               5                  10                  15

Ser Gln Ala Asp Pro Leu Ser Asp Pro Asp Gln Met Asn Glu Asp Ala
            20                  25                  30

Leu Asn Asp Leu Cys Ile Lys Val Asn Asn Trp Asp Leu Phe Phe Ser
        35                  40                  45

Pro Ser Glu Asp Asn Phe Thr Asn Asp Leu Asn Lys Gly Glu Glu Ile
    50                  55                  60

Thr Ser Asp Thr Asn Ile Glu Ala Ala Glu Glu Asn Ile Ser Leu Asp
65                  70                  75                  80

Leu Ile Gln Gln Tyr Tyr Leu Thr Phe Asn Phe Asp Asn Glu Pro Glu
                85                  90                  95

Asn Ile Ser Ile Glu Asn Leu Ser Ser Asp Ile Ile Gly Gln Leu Glu
            100                 105                 110

Leu Met Pro Asn Ile Glu Arg Phe Pro Asn Gly Lys Lys Tyr Glu Leu
        115                 120                 125

Asp Lys Tyr Thr Met Phe His Tyr Leu Arg Ala Gln Glu Phe Glu His
    130                 135                 140

Gly Lys Ser Arg Ile Ala Leu Thr Asn Ser Val Asn Glu Ala Leu Leu
145                 150                 155                 160

Asn Pro Ser Arg Val Tyr Thr Phe Phe Ser Ser Asp Tyr Val Lys Lys
                165                 170                 175

Val Asn Lys Ala Thr Glu Ala Ala Met Phe Leu Gly Trp Val Glu Gln
            180                 185                 190

Leu Val Tyr Asp Phe Thr Asp Glu Thr Ser Glu Val Ser Thr Thr Asp
        195                 200                 205

Lys Ile Ala Asp Ile Thr Ile Ile Ile Pro Tyr Ile Gly Pro Ala Leu
    210                 215                 220

Asn Ile Gly Asn Met Leu Tyr Lys Asp Asp Phe Val Gly Ala Leu Ile
225                 230                 235                 240

Phe Ser Gly Ala Val Ile Leu Leu Glu Phe Ile Pro Glu Ile Ala Ile
                245                 250                 255
```

```
Pro Val Leu Gly Thr Phe Ala Leu Val Ser Tyr Ile Ala Asn Lys Val
            260                 265                 270

Leu Thr Val Gln Thr Ile Asp Asn Ala Leu Ser Lys Arg Asn Glu Lys
            275                 280                 285

Trp Asp Glu Val Tyr Lys Tyr Ile Val Thr Asn Trp Leu Ala Lys Val
290                 295                 300

Asn Thr Gln Ile Asp Leu Ile Arg Lys Lys Met Lys Glu Ala Leu Glu
305                 310                 315                 320

Asn Gln Ala Glu Ala Thr Lys Ala Ile Ile Asn Tyr Gln Tyr Asn Gln
                325                 330                 335

Tyr Thr Glu Glu Glu Lys Asn Asn Ile Asn Phe Asn Ile Asp Asp Leu
            340                 345                 350

Ser Ser Lys Leu Asn Glu Ser Ile Asn Lys Ala Met Ile Asn Ile Asn
            355                 360                 365

Lys Phe Leu Asn Gln Cys Ser Val Ser Tyr Leu Met Asn Ser Met Ile
            370                 375                 380

Pro Tyr Gly Val Lys Arg Leu Glu Asp Phe Asp Ala Ser Leu Lys Asp
385                 390                 395                 400

Ala Leu Leu Lys Tyr Ile Tyr Asp Asn Arg Gly Thr Leu Ile Gly Gln
                405                 410                 415

Val Asp Arg Leu Lys Asp Lys Val Asn Asn Thr Leu Ser Thr Asp Ile
            420                 425                 430

Pro Phe Gln Leu Ser Lys Tyr Val Asp Asn Gln Arg Leu Leu Ser Thr
            435                 440                 445

Phe Thr Glu Tyr Ile Lys Asn Ile Ile Asn Thr Ser Ile Leu Asn Leu
            450                 455                 460

Arg Tyr Glu Ser Asn His Leu Ile Asp Leu Ser Arg Tyr Ala Ser Lys
465                 470                 475                 480

Ile Asn Ile Gly Ser Lys Val Asn Phe Asp Pro Ile Asp Lys Asn Gln
                485                 490                 495

Ile Gln Leu Phe Asn Leu Glu Ser Ser Lys Ile Glu Val Ile Leu Lys
            500                 505                 510

Asn Ala Ile Val Tyr Asn Ser Met Tyr Glu Asn Phe Ser Thr Ser Phe
            515                 520                 525

Trp Ile Arg Ile Pro Lys Tyr Phe Asn Ser Ile Ser Leu Asn Asn Glu
            530                 535                 540

Tyr Thr Ile Ile Asn Cys Met Glu Asn Asn Ser Gly Trp Lys Val Ser
545                 550                 555                 560

Leu Asn Tyr Gly Glu Ile Ile Trp Thr Leu Gln Asp Thr Gln Glu Ile
                565                 570                 575

Lys Gln Arg Val Val Phe Lys Tyr Ser Gln Met Ile Asn Ile Ser Asp
            580                 585                 590

Tyr Ile Asn Arg Trp Ile Phe Val Thr Ile Thr Asn Asn Arg Leu Asn
            595                 600                 605

Asn Ser Lys Ile Tyr Ile Asn Gly Arg Leu Ile Asp Gln Lys Pro Ile
            610                 615                 620

Ser Asn Leu Gly Asn Ile His Ala Ser Asn Asn Ile Met Phe Lys Leu
625                 630                 635                 640

Asp Gly Cys Arg Asp Thr His Arg Tyr Ile Trp Ile Lys Tyr Phe Asn
                645                 650                 655

Leu Phe Asp Lys Glu Leu Asn Glu Lys Glu Ile Lys Asp Leu Tyr Asp
            660                 665                 670

Asn Gln Ser Asn Ser Gly Ile Leu Lys Asp Phe Trp Gly Asp Tyr Leu
```

```
                675                 680                 685
Gln Tyr Asp Lys Pro Asp Asp Asp Lys Pro Phe Val Asn Lys Gln
690                 695                 700
Phe Asn Tyr Lys Asp Pro Val Asn Gly Val Asp Ile Ala Tyr Ile Lys
705                 710                 715                 720
Ile Pro Asn Ala Gly Gln Met Gln Pro Val Lys Ala Phe Lys Ile His
                725                 730                 735
Asn Lys Ile Trp Val Ile Pro Glu Arg Asp Thr Phe Thr Asn Pro Glu
                740                 745                 750
Glu Gly Asp Leu Asn Pro Pro Glu Ala Lys Gln Val Pro Val Ser
        755                 760                 765
Tyr Tyr Asp Ser Thr Tyr Leu Ser Thr Asp Asn Glu Lys Asp Asn Tyr
        770                 775                 780
Leu Lys Gly Val Thr Lys Leu Phe Glu Arg Ile Tyr Ser Thr Asp Leu
785                 790                 795                 800
Gly Arg Met Leu Leu Thr Ser Ile Val Arg Gly Ile Pro Phe Trp Gly
                805                 810                 815
Gly Ser Thr Ile Asp Thr Glu Leu Lys Val Ile Asp Thr Asn Cys Ile
                820                 825                 830
Asn Val Ile Gln Pro Asp Gly Ser Tyr Arg Ser Glu Glu Leu Asn Leu
        835                 840                 845
Val Ile Ile Gly Pro Ser Ala Asp Ile Ile Gln Phe Glu Cys Lys Ser
850                 855                 860
Phe Gly His Glu Val Leu Asn Leu Thr Arg Asn Gly Tyr Gly Ser Thr
865                 870                 875                 880
Gln Tyr Ile Arg Phe Ser Pro Asp Phe Thr Phe Gly Phe Glu Glu Ser
                885                 890                 895
Leu Glu Val Asp Thr Asn Pro Leu Leu Gly Ala Gly Lys Phe Ala Thr
                900                 905                 910
Asp Pro Ala Val Thr Leu Ala His Glu Leu Ile His Ala Gly His Arg
                915                 920                 925
Leu Tyr Gly Ile Ala Ile Asn Pro Asn Arg Val Phe Lys Val Asn Thr
        930                 935                 940
Asn Ala Tyr Tyr Glu Met Ser Gly Leu Glu Val Ser Phe Glu Glu Leu
945                 950                 955                 960
Arg Thr Phe Gly Gly His Asp Ala Lys Phe Ile Asp Ser Leu Gln Glu
                965                 970                 975
Asn Glu Phe Arg Leu Tyr Tyr Tyr Asn Lys Phe Lys Asp Ile Ala Ser
                980                 985                 990
Thr Leu Asn Lys Ala Lys Ser Ile Val Gly Thr Thr Ala Ser Leu Gln
        995                 1000                1005
Tyr Met Lys Asn Val Phe Lys Glu Lys Tyr Leu Leu Ser Glu Asp Thr
        1010                1015                1020
Ser Gly Lys Phe Ser Val Asp Lys Leu Lys Phe Asp Lys Leu Tyr Lys
1025                1030                1035                1040
Met Leu Thr Glu Ile Tyr Thr Glu Asp Asn Phe Val Lys Phe Phe Lys
                1045                1050                1055
Val Leu Asn Arg Lys Thr Tyr Leu Asn Phe Asp Lys Ala Val Phe Lys
                1060                1065                1070
Ile Asn Ile Val Pro Lys Val Asn Tyr Thr Ile Tyr Asp Gly Phe Asn
        1075                1080                1085
Leu Arg Asn Thr Asn Leu Ala Ala Asn Phe Asn Gly Gln Asn Thr Glu
        1090                1095                1100
```

-continued

```
Ile Asn Asn Met Asn Phe Thr Lys Leu Lys Asn Phe Thr Gly Leu Phe
1105                1110                1115                1120

Glu Phe Tyr Lys Leu Leu Cys Val Arg Gly Ile Ile Thr Ser Lys Thr
            1125                1130                1135

Lys Ser Leu
```

<210> SEQ ID NO 119
<211> LENGTH: 1139
<212> TYPE: PRT
<213> ORGANISM: Artificial Sequence
<220> FEATURE:
<223> OTHER INFORMATION: BoNT/A-AP4B-GRPP

<400> SEQUENCE: 119

```
Met Arg Ser Leu Gln Asp Thr Glu Glu Lys Ser Arg Ser Phe Ser Ala
 1               5                  10                  15

Ser Gln Ala Asp Pro Leu Ser Asp Pro Asp Gln Met Asn Glu Asp Pro
            20                  25                  30

Phe Val Asn Lys Gln Phe Asn Tyr Lys Asp Pro Val Asn Gly Val Asp
        35                  40                  45

Ile Ala Tyr Ile Lys Ile Pro Asn Ala Gly Gln Met Gln Pro Val Lys
 50                  55                  60

Ala Phe Lys Ile His Asn Lys Ile Trp Val Ile Pro Glu Arg Asp Thr
65                  70                  75                  80

Phe Thr Asn Pro Glu Glu Gly Asp Leu Asn Pro Pro Glu Ala Lys
                85                  90                  95

Gln Val Pro Val Ser Tyr Tyr Asp Ser Thr Tyr Leu Ser Thr Asp Asn
            100                 105                 110

Glu Lys Asp Asn Tyr Leu Lys Gly Val Thr Lys Leu Phe Glu Arg Ile
        115                 120                 125

Tyr Ser Thr Asp Leu Gly Arg Met Leu Leu Thr Ser Ile Val Arg Gly
130                 135                 140

Ile Pro Phe Trp Gly Gly Ser Thr Ile Asp Thr Glu Leu Lys Val Ile
145                 150                 155                 160

Asp Thr Asn Cys Ile Asn Val Ile Gln Pro Asp Gly Ser Tyr Arg Ser
                165                 170                 175

Glu Glu Leu Asn Leu Val Ile Ile Gly Pro Ser Ala Asp Ile Ile Gln
            180                 185                 190

Phe Glu Cys Lys Ser Phe Gly His Glu Val Leu Asn Leu Thr Arg Asn
        195                 200                 205

Gly Tyr Gly Ser Thr Gln Tyr Ile Arg Phe Ser Pro Asp Phe Thr Phe
210                 215                 220

Gly Phe Glu Glu Ser Leu Glu Val Asp Thr Asn Pro Leu Leu Gly Ala
225                 230                 235                 240

Gly Lys Phe Ala Thr Asp Pro Ala Val Thr Leu Ala His Glu Leu Ile
                245                 250                 255

His Ala Gly His Arg Leu Tyr Gly Ile Ala Ile Asn Pro Asn Arg Val
            260                 265                 270

Phe Lys Val Asn Thr Asn Ala Tyr Tyr Glu Met Ser Gly Leu Glu Val
        275                 280                 285

Ser Phe Glu Glu Leu Arg Thr Phe Gly Gly His Asp Ala Lys Phe Ile
290                 295                 300

Asp Ser Leu Gln Glu Asn Glu Phe Arg Leu Tyr Tyr Tyr Asn Lys Phe
305                 310                 315                 320

Lys Asp Ile Ala Ser Thr Leu Asn Lys Ala Lys Ser Ile Val Gly Thr
                325                 330                 335
```

-continued

Thr Ala Ser Leu Gln Tyr Met Lys Asn Val Phe Lys Glu Lys Tyr Leu
            340                 345                 350

Leu Ser Glu Asp Thr Ser Gly Lys Phe Ser Val Asp Lys Leu Lys Phe
            355                 360                 365

Asp Lys Leu Tyr Lys Met Leu Thr Glu Ile Tyr Thr Glu Asp Asn Phe
            370                 375                 380

Val Lys Phe Phe Lys Val Leu Asn Arg Lys Thr Tyr Leu Asn Phe Asp
385                 390                 395                 400

Lys Ala Val Phe Lys Ile Asn Ile Val Pro Lys Val Asn Tyr Thr Ile
            405                 410                 415

Tyr Asp Gly Phe Asn Leu Arg Asn Thr Asn Leu Ala Ala Asn Phe Asn
            420                 425                 430

Gly Gln Asn Thr Glu Ile Asn Asn Met Asn Phe Thr Lys Leu Lys Asn
            435                 440                 445

Phe Thr Gly Leu Phe Glu Phe Tyr Lys Leu Leu Cys Val Arg Gly Ile
            450                 455                 460

Ile Thr Ser Lys Thr Lys Ser Leu Asp Asp Asp Lys Ala Leu Asn
465                 470                 475                 480

Asp Leu Cys Ile Lys Val Asn Asn Trp Asp Leu Phe Phe Ser Pro Ser
            485                 490                 495

Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
            515                 520                 525

Gln Gln Tyr Tyr Leu Thr Phe Asn Phe Asp Asn Glu Pro Glu Asn Ile
            530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
            565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
            595                 600                 605

Ser Arg Val Tyr Thr Phe Phe Ser Ser Asp Tyr Val Lys Lys Val Asn
            610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
            645                 650                 655

Ala Asp Ile Thr Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
            675                 680                 685

Gly Ala Val Ile Leu Leu Glu Phe Ile Pro Glu Ile Ala Ile Pro Val
            690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
            725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln

```
                755                 760                 765
Ala Glu Ala Thr Lys Ala Ile Ile Asn Tyr Gln Tyr Asn Gln Tyr Thr
770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
            805                 810                 815

Leu Asn Gln Cys Ser Val Ser Tyr Leu Met Asn Ser Met Ile Pro Tyr
        820                 825                 830

Gly Val Lys Arg Leu Glu Asp Phe Asp Ala Ser Leu Lys Asp Ala Leu
    835                 840                 845

Leu Lys Tyr Ile Tyr Asp Asn Arg Gly Thr Leu Ile Gly Gln Val Asp
850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Phe Thr
            885                 890                 895

Glu Tyr Ile Lys Asn Ile Ile Asn Thr Ser Ile Leu Asn Leu Arg Tyr
        900                 905                 910

Glu Ser Asn His Leu Ile Asp Leu Ser Arg Tyr Ala Ser Lys Ile Asn
    915                 920                 925

Ile Gly Ser Lys Val Asn Phe Asp Pro Ile Asp Lys Asn Gln Ile Gln
930                 935                 940

Leu Phe Asn Leu Glu Ser Ser Lys Ile Glu Val Ile Leu Lys Asn Ala
945                 950                 955                 960

Ile Val Tyr Asn Ser Met Tyr Glu Asn Phe Ser Thr Ser Phe Trp Ile
            965                 970                 975

Arg Ile Pro Lys Tyr Phe Asn Ser Ile Ser Leu Asn Asn Glu Tyr Thr
        980                 985                 990

Ile Ile Asn Cys Met Glu Asn Asn Ser Gly Trp Lys Val Ser Leu Asn
    995                 1000                1005

Tyr Gly Glu Ile Ile Trp Thr Leu Gln Asp Thr Gln Glu Ile Lys Gln
1010                1015                1020

Arg Val Val Phe Lys Tyr Ser Gln Met Ile Asn Ile Ser Asp Tyr Ile
1025                1030                1035                1040

Asn Arg Trp Ile Phe Val Thr Ile Thr Asn Asn Arg Leu Asn Asn Ser
            1045                1050                1055

Lys Ile Tyr Ile Asn Gly Arg Leu Ile Asp Gln Lys Pro Ile Ser Asn
        1060                1065                1070

Leu Gly Asn Ile His Ala Ser Asn Asn Ile Met Phe Lys Leu Asp Gly
    1075                1080                1085

Cys Arg Asp Thr His Arg Tyr Ile Trp Ile Lys Tyr Phe Asn Leu Phe
1090                1095                1100

Asp Lys Glu Leu Asn Glu Lys Glu Ile Lys Asp Leu Tyr Asp Asn Gln
1105                1110                1115                1120

Ser Asn Ser Gly Ile Leu Lys Asp Phe Trp Gly Asp Tyr Leu Gln Tyr
            1125                1130                1135

Asp Lys Pro

<210> SEQ ID NO 120
<211> LENGTH: 1157
<212> TYPE: PRT
<213> ORGANISM: Artificial Sequence
<220> FEATURE:
<223> OTHER INFORMATION: BoNT/A-CP5A-GRPP
```

<400> SEQUENCE: 120

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415
```

```
Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Asp Asp Lys Arg
            435                 440                 445

Ser Leu Gln Asp Thr Glu Glu Lys Ser Arg Ser Phe Ser Ala Ser Gln
450                 455                 460

Ala Asp Pro Leu Ser Asp Pro Asp Gln Met Asn Glu Asp Ala Leu Ala
465                 470                 475                 480

Gly Gly Gly Gly Ser Gly Gly Gly Ser Gly Gly Gly Ser Ala
                485                 490                 495

Leu Asn Asp Leu Cys Ile Lys Val Asn Asn Trp Asp Leu Phe Phe Ser
            500                 505                 510

Pro Ser Glu Asp Asn Phe Thr Asn Asp Leu Asn Lys Gly Glu Glu Ile
            515                 520                 525

Thr Ser Asp Thr Asn Ile Glu Ala Ala Glu Asn Ile Ser Leu Asp
            530                 535                 540

Leu Ile Gln Gln Tyr Tyr Leu Thr Phe Asn Phe Asp Asn Glu Pro Glu
545                 550                 555                 560

Asn Ile Ser Ile Glu Asn Leu Ser Ser Asp Ile Ile Gly Gln Leu Glu
                565                 570                 575

Leu Met Pro Asn Ile Glu Arg Phe Pro Asn Gly Lys Lys Tyr Glu Leu
            580                 585                 590

Asp Lys Tyr Thr Met Phe His Tyr Leu Arg Ala Gln Glu Phe Glu His
            595                 600                 605

Gly Lys Ser Arg Ile Ala Leu Thr Asn Ser Val Asn Glu Ala Leu Leu
            610                 615                 620

Asn Pro Ser Arg Val Tyr Thr Phe Phe Ser Ser Asp Tyr Val Lys Lys
625                 630                 635                 640

Val Asn Lys Ala Thr Glu Ala Ala Met Phe Leu Gly Trp Val Glu Gln
                645                 650                 655

Leu Val Tyr Asp Phe Thr Asp Glu Thr Ser Glu Val Ser Thr Thr Asp
            660                 665                 670

Lys Ile Ala Asp Ile Thr Ile Ile Pro Tyr Ile Gly Pro Ala Leu
            675                 680                 685

Asn Ile Gly Asn Met Leu Tyr Lys Asp Asp Phe Val Gly Ala Leu Ile
            690                 695                 700

Phe Ser Gly Ala Val Ile Leu Leu Glu Phe Ile Pro Glu Ile Ala Ile
705                 710                 715                 720

Pro Val Leu Gly Thr Phe Ala Leu Val Ser Tyr Ile Ala Asn Lys Val
                725                 730                 735

Leu Thr Val Gln Thr Ile Asp Asn Ala Leu Ser Lys Arg Asn Glu Lys
            740                 745                 750

Trp Asp Glu Val Tyr Lys Tyr Ile Val Thr Asn Trp Leu Ala Lys Val
            755                 760                 765

Asn Thr Gln Ile Asp Leu Ile Arg Lys Lys Met Lys Glu Ala Leu Glu
            770                 775                 780

Asn Gln Ala Glu Ala Thr Lys Ala Ile Ile Asn Tyr Gln Tyr Asn Gln
785                 790                 795                 800

Tyr Thr Glu Glu Glu Lys Asn Asn Ile Asn Phe Asn Ile Asp Asp Leu
                805                 810                 815

Ser Ser Lys Leu Asn Glu Ser Ile Asn Lys Ala Met Ile Asn Ile Asn
            820                 825                 830

Lys Phe Leu Asn Gln Cys Ser Val Ser Tyr Leu Met Asn Ser Met Ile
```

-continued

```
            835                 840                 845
Pro Tyr Gly Val Lys Arg Leu Glu Asp Phe Asp Ala Ser Leu Lys Asp
850                 855                 860

Ala Leu Leu Lys Tyr Ile Tyr Asp Asn Arg Gly Thr Leu Ile Gly Gln
865                 870                 875                 880

Val Asp Arg Leu Lys Asp Lys Val Asn Asn Thr Leu Ser Thr Asp Ile
                885                 890                 895

Pro Phe Gln Leu Ser Lys Tyr Val Asp Asn Gln Arg Leu Leu Ser Thr
                900                 905                 910

Phe Thr Glu Tyr Ile Lys Asn Ile Ile Asn Thr Ser Ile Leu Asn Leu
            915                 920                 925

Arg Tyr Glu Ser Asn His Leu Ile Asp Leu Ser Arg Tyr Ala Ser Lys
        930                 935                 940

Ile Asn Ile Gly Ser Lys Val Asn Phe Asp Pro Ile Asp Lys Asn Gln
945                 950                 955                 960

Ile Gln Leu Phe Asn Leu Glu Ser Ser Lys Ile Glu Val Ile Leu Lys
                965                 970                 975

Asn Ala Ile Val Tyr Asn Ser Met Tyr Glu Asn Phe Ser Thr Ser Phe
                980                 985                 990

Trp Ile Arg Ile Pro Lys Tyr Phe Asn Ser Ile Ser Leu Asn Asn Glu
            995                 1000                1005

Tyr Thr Ile Ile Asn Cys Met Glu Asn Asn Ser Gly Trp Lys Val Ser
1010                1015                1020

Leu Asn Tyr Gly Glu Ile Ile Trp Thr Leu Gln Asp Thr Gln Glu Ile
1025                1030                1035                1040

Lys Gln Arg Val Val Phe Lys Tyr Ser Gln Met Ile Asn Ile Ser Asp
                1045                1050                1055

Tyr Ile Asn Arg Trp Ile Phe Val Thr Ile Thr Asn Asn Arg Leu Asn
                1060                1065                1070

Asn Ser Lys Ile Tyr Ile Asn Gly Arg Leu Ile Asp Gln Lys Pro Ile
            1075                1080                1085

Ser Asn Leu Gly Asn Ile His Ala Ser Asn Asn Ile Met Phe Lys Leu
            1090                1095                1100

Asp Gly Cys Arg Asp Thr His Arg Tyr Ile Trp Ile Lys Tyr Phe Asn
1105                1110                1115                1120

Leu Phe Asp Lys Glu Leu Asn Glu Lys Glu Ile Lys Asp Leu Tyr Asp
                1125                1130                1135

Asn Gln Ser Asn Ser Gly Ile Leu Lys Asp Phe Trp Gly Asp Tyr Leu
            1140                1145                1150

Gln Tyr Asp Lys Pro
        1155

<210> SEQ ID NO 121
<211> LENGTH: 1158
<212> TYPE: PRT
<213> ORGANISM: Artificial Sequence
<220> FEATURE:
<223> OTHER INFORMATION: BoNT/A-CP5B-GRPP

<400> SEQUENCE: 121

Met Asp Asp Asp Lys Ala Leu Asn Asp Leu Cys Ile Lys Val Asn
1               5                   10                  15

Asn Trp Asp Leu Phe Phe Ser Pro Ser Glu Asp Asn Phe Thr Asn Asp
            20                  25                  30

Leu Asn Lys Gly Glu Glu Ile Thr Ser Asp Thr Asn Ile Glu Ala Ala
        35                  40                  45
```

```
Glu Glu Asn Ile Ser Leu Asp Leu Ile Gln Gln Tyr Tyr Leu Thr Phe
 50                  55                  60

Asn Phe Asp Asn Glu Pro Glu Asn Ile Ser Ile Glu Asn Leu Ser Ser
 65                  70                  75                  80

Asp Ile Ile Gly Gln Leu Glu Leu Met Pro Asn Ile Glu Arg Phe Pro
                 85                  90                  95

Asn Gly Lys Lys Tyr Glu Leu Asp Lys Tyr Thr Met Phe His Tyr Leu
            100                 105                 110

Arg Ala Gln Glu Phe Glu His Gly Lys Ser Arg Ile Ala Leu Thr Asn
            115                 120                 125

Ser Val Asn Glu Ala Leu Leu Asn Pro Ser Arg Val Tyr Thr Phe Phe
    130                 135                 140

Ser Ser Asp Tyr Val Lys Lys Val Asn Lys Ala Thr Glu Ala Ala Met
145                 150                 155                 160

Phe Leu Gly Trp Val Glu Gln Leu Val Tyr Asp Phe Thr Asp Glu Thr
                165                 170                 175

Ser Glu Val Ser Thr Thr Asp Lys Ile Ala Asp Ile Thr Ile Ile Ile
            180                 185                 190

Pro Tyr Ile Gly Pro Ala Leu Asn Ile Gly Asn Met Leu Tyr Lys Asp
            195                 200                 205

Asp Phe Val Gly Ala Leu Ile Phe Ser Gly Ala Val Ile Leu Leu Glu
    210                 215                 220

Phe Ile Pro Glu Ile Ala Ile Pro Val Leu Gly Thr Phe Ala Leu Val
225                 230                 235                 240

Ser Tyr Ile Ala Asn Lys Val Leu Thr Val Gln Thr Ile Asp Asn Ala
                245                 250                 255

Leu Ser Lys Arg Asn Glu Lys Trp Asp Glu Val Tyr Lys Tyr Ile Val
            260                 265                 270

Thr Asn Trp Leu Ala Lys Val Asn Thr Gln Ile Asp Leu Ile Arg Lys
            275                 280                 285

Lys Met Lys Glu Ala Leu Glu Asn Gln Ala Glu Ala Thr Lys Ala Ile
    290                 295                 300

Ile Asn Tyr Gln Tyr Asn Gln Tyr Thr Glu Glu Lys Asn Asn Ile
305                 310                 315                 320

Asn Phe Asn Ile Asp Asp Leu Ser Ser Lys Leu Asn Glu Ser Ile Asn
                325                 330                 335

Lys Ala Met Ile Asn Ile Asn Lys Phe Leu Asn Gln Cys Ser Val Ser
            340                 345                 350

Tyr Leu Met Asn Ser Met Ile Pro Tyr Gly Val Lys Arg Leu Glu Asp
            355                 360                 365

Phe Asp Ala Ser Leu Lys Asp Ala Leu Leu Lys Tyr Ile Tyr Asp Asn
    370                 375                 380

Arg Gly Thr Leu Ile Gly Gln Val Asp Arg Leu Lys Asp Lys Val Asn
385                 390                 395                 400

Asn Thr Leu Ser Thr Asp Ile Pro Phe Gln Leu Ser Lys Tyr Val Asp
                405                 410                 415

Asn Gln Arg Leu Leu Ser Thr Phe Thr Glu Tyr Ile Lys Asn Ile Ile
            420                 425                 430

Asn Thr Ser Ile Leu Asn Leu Arg Tyr Glu Ser Asn His Leu Ile Asp
            435                 440                 445

Leu Ser Arg Tyr Ala Ser Lys Ile Asn Ile Gly Ser Lys Val Asn Phe
    450                 455                 460

Asp Pro Ile Asp Lys Asn Gln Ile Gln Leu Phe Asn Leu Glu Ser Ser
```

```
                465                 470                 475                 480
Lys Ile Glu Val Ile Leu Lys Asn Ala Ile Val Tyr Asn Ser Met Tyr
                        485                 490                 495
Glu Asn Phe Ser Thr Ser Phe Trp Ile Arg Ile Pro Lys Tyr Phe Asn
                500                 505                 510
Ser Ile Ser Leu Asn Asn Glu Tyr Thr Ile Ile Asn Cys Met Glu Asn
            515                 520                 525
Asn Ser Gly Trp Lys Val Ser Leu Asn Tyr Gly Glu Ile Ile Trp Thr
        530                 535                 540
Leu Gln Asp Thr Gln Glu Ile Lys Gln Arg Val Val Phe Lys Tyr Ser
545                 550                 555                 560
Gln Met Ile Asn Ile Ser Asp Tyr Ile Asn Arg Trp Ile Phe Val Thr
                565                 570                 575
Ile Thr Asn Asn Arg Leu Asn Asn Ser Lys Ile Tyr Ile Asn Gly Arg
                        580                 585                 590
Leu Ile Asp Gln Lys Pro Ile Ser Asn Leu Gly Asn Ile His Ala Ser
                595                 600                 605
Asn Asn Ile Met Phe Lys Leu Asp Gly Cys Arg Asp Thr His Arg Tyr
            610                 615                 620
Ile Trp Ile Lys Tyr Phe Asn Leu Phe Asp Lys Glu Leu Asn Glu Lys
625                 630                 635                 640
Glu Ile Lys Asp Leu Tyr Asp Asn Gln Ser Asn Ser Gly Ile Leu Lys
                    645                 650                 655
Asp Phe Trp Gly Asp Tyr Leu Gln Tyr Asp Lys Pro Asp Asp Asp Asp
                660                 665                 670
Lys Arg Ser Leu Gln Asp Thr Glu Glu Lys Ser Arg Ser Phe Ser Ala
            675                 680                 685
Ser Gln Ala Asp Pro Leu Ser Asp Pro Asp Gln Met Asn Glu Asp Ala
        690                 695                 700
Leu Ala Gly Gly Gly Ser Gly Gly Gly Ser Gly Gly Gly Gly
705                 710                 715                 720
Ser Pro Phe Val Asn Lys Gln Phe Asn Tyr Lys Asp Pro Val Asn Gly
                    725                 730                 735
Val Asp Ile Ala Tyr Ile Lys Ile Pro Asn Ala Gly Gln Met Gln Pro
                740                 745                 750
Val Lys Ala Phe Lys Ile His Asn Lys Ile Trp Val Ile Pro Glu Arg
                    755                 760                 765
Asp Thr Phe Thr Asn Pro Glu Glu Gly Asp Leu Asn Pro Pro Pro Glu
            770                 775                 780
Ala Lys Gln Val Pro Val Ser Tyr Tyr Asp Ser Thr Tyr Leu Ser Thr
785                 790                 795                 800
Asp Asn Glu Lys Asp Asn Tyr Leu Lys Gly Val Thr Lys Leu Phe Glu
                    805                 810                 815
Arg Ile Tyr Ser Thr Asp Leu Gly Arg Met Leu Leu Thr Ser Ile Val
                820                 825                 830
Arg Gly Ile Pro Phe Trp Gly Gly Ser Thr Ile Asp Thr Glu Leu Lys
            835                 840                 845
Val Ile Asp Thr Asn Cys Ile Asn Val Ile Gln Pro Asp Gly Ser Tyr
        850                 855                 860
Arg Ser Glu Glu Leu Asn Leu Val Ile Ile Gly Pro Ser Ala Asp Ile
865                 870                 875                 880
Ile Gln Phe Glu Cys Lys Ser Phe Gly His Glu Val Leu Asn Leu Thr
                    885                 890                 895
```

-continued

```
Arg Asn Gly Tyr Gly Ser Thr Gln Tyr Ile Arg Phe Ser Pro Asp Phe
                900                 905                 910

Thr Phe Gly Phe Glu Glu Ser Leu Glu Val Asp Thr Asn Pro Leu Leu
            915                 920                 925

Gly Ala Gly Lys Phe Ala Thr Asp Pro Ala Val Thr Leu Ala His Glu
        930                 935                 940

Leu Ile His Ala Gly His Arg Leu Tyr Gly Ile Ala Ile Asn Pro Asn
945                 950                 955                 960

Arg Val Phe Lys Val Asn Thr Asn Ala Tyr Tyr Glu Met Ser Gly Leu
                965                 970                 975

Glu Val Ser Phe Glu Glu Leu Arg Thr Phe Gly Gly His Asp Ala Lys
            980                 985                 990

Phe Ile Asp Ser Leu Gln Glu Asn Glu Phe Arg Leu Tyr Tyr Tyr Asn
        995                 1000                1005

Lys Phe Lys Asp Ile Ala Ser Thr Leu Asn Lys Ala Lys Ser Ile Val
        1010                1015                1020

Gly Thr Thr Ala Ser Leu Gln Tyr Met Lys Asn Val Phe Lys Glu Lys
1025                1030                1035                1040

Tyr Leu Leu Ser Glu Asp Thr Ser Gly Lys Phe Ser Val Asp Lys Leu
                1045                1050                1055

Lys Phe Asp Lys Leu Tyr Lys Met Leu Thr Glu Ile Tyr Thr Glu Asp
            1060                1065                1070

Asn Phe Val Lys Phe Phe Lys Val Leu Asn Arg Lys Thr Tyr Leu Asn
        1075                1080                1085

Phe Asp Lys Ala Val Phe Lys Ile Asn Ile Val Pro Lys Val Asn Tyr
        1090                1095                1100

Thr Ile Tyr Asp Gly Phe Asn Leu Arg Asn Thr Asn Leu Ala Ala Asn
1105                1110                1115                1120

Phe Asn Gly Gln Asn Thr Glu Ile Asn Asn Met Asn Phe Thr Lys Leu
                1125                1130                1135

Lys Asn Phe Thr Gly Leu Phe Glu Phe Tyr Lys Leu Leu Cys Val Arg
            1140                1145                1150

Gly Ile Ile Thr Ser Lys
        1155

<210> SEQ ID NO 122
<211> LENGTH: 1157
<212> TYPE: PRT
<213> ORGANISM: Artificial Sequence
<220> FEATURE:
<223> OTHER INFORMATION: BoNT/A-XP6A-GRPP

<400> SEQUENCE: 122

Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
```

```
                100             105             110
Arg Gly Ile Pro Phe Trp Gly Gly Ser Thr Ile Asp Thr Glu Leu Lys
            115                 120             125
Val Ile Asp Thr Asn Cys Ile Asn Val Ile Gln Pro Asp Gly Ser Tyr
130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
    210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Asp Asp Lys Ala
    435                 440                 445
Leu Asn Asp Leu Cys Ile Lys Val Asn Asn Trp Asp Leu Phe Phe Ser
    450                 455                 460
Pro Ser Glu Asp Asn Phe Thr Asn Asp Leu Asn Lys Gly Glu Glu Ile
465                 470                 475                 480
Thr Ser Asp Thr Asn Ile Glu Ala Ala Glu Glu Asn Ile Ser Leu Asp
                485                 490                 495
Leu Ile Gln Gln Tyr Tyr Leu Thr Phe Asn Phe Asp Asn Glu Pro Glu
            500                 505                 510
Asn Ile Ser Ile Glu Asn Leu Ser Ser Asp Ile Ile Gly Gln Leu Glu
        515                 520                 525
```

-continued

Leu Met Pro Asn Ile Glu Arg Phe Pro Asn Gly Lys Lys Tyr Glu Leu
        530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
            580                 585                 590

Val Asn Lys Ala Thr Glu Ala Ala Met Phe Leu Gly Trp Val Glu Gln
        595                 600                 605

Leu Val Tyr Asp Phe Thr Asp Glu Thr Ser Glu Val Ser Thr Thr Asp
    610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655

Phe Ser Gly Ala Val Ile Leu Leu Glu Phe Ile Pro Glu Ile Ala Ile
            660                 665                 670

Pro Val Leu Gly Thr Phe Ala Leu Val Ser Tyr Ile Ala Asn Lys Val
        675                 680                 685

Leu Thr Val Gln Thr Ile Asp Asn Ala Leu Ser Lys Arg Asn Glu Lys
    690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
            740                 745                 750

Tyr Thr Glu Glu Glu Lys Asn Asn Ile Asn Phe Asn Ile Asp Asp Leu
        755                 760                 765

Ser Ser Lys Leu Asn Glu Ser Ile Asn Lys Ala Met Ile Asn Ile Asn
    770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
            820                 825                 830

Val Asp Arg Leu Lys Asp Lys Val Asn Asn Thr Leu Ser Thr Asp Ile
        835                 840                 845

Pro Phe Gln Leu Ser Lys Tyr Val Asp Asn Gln Arg Leu Leu Ser Thr
    850                 855                 860

Phe Thr Glu Tyr Ile Lys Asn Ile Ile Asn Thr Ser Ile Leu Asn Leu
865                 870                 875                 880

Arg Tyr Glu Ser Asn His Leu Ile Asp Leu Ser Arg Tyr Ala Ser Lys
                885                 890                 895

Ile Asn Ile Gly Ser Lys Val Asn Phe Asp Pro Ile Asp Lys Asn Gln
            900                 905                 910

Ile Gln Leu Phe Asn Leu Glu Ser Ser Lys Ile Glu Val Ile Leu Lys
        915                 920                 925

Asn Ala Ile Val Tyr Asn Ser Met Tyr Glu Asn Phe Ser Thr Ser Phe
    930                 935                 940

Trp Ile Arg Ile Pro Lys Tyr Phe Asn Ser Ile Ser Leu Asn Asn Glu
945                 950                 955                 960

```
Tyr Thr Ile Ile Asn Cys Met Glu Asn Ser Gly Trp Lys Val Ser
                965                 970                 975

Leu Asn Tyr Gly Glu Ile Ile Trp Thr Leu Gln Asp Thr Gln Glu Ile
            980                 985                 990

Lys Gln Arg Val Val Phe Lys Tyr Ser Gln Met Ile Asn Ile Ser Asp
        995                 1000                1005

Tyr Ile Asn Arg Trp Ile Phe Val Thr Ile Thr Asn Asn Arg Leu Asn
    1010                1015                1020

Asn Ser Lys Ile Tyr Ile Asn Gly Arg Leu Ile Asp Gln Lys Pro Ile
1025                1030                1035                1040

Ser Asn Leu Gly Asn Ile His Ala Ser Asn Asn Ile Met Phe Lys Leu
            1045                1050                1055

Asp Gly Cys Arg Asp Thr His Arg Tyr Ile Trp Ile Lys Tyr Phe Asn
            1060                1065                1070

Leu Phe Asp Lys Glu Leu Asn Glu Lys Glu Ile Lys Asp Leu Tyr Asp
        1075                1080                1085

Asn Gln Ser Asn Ser Gly Ile Leu Lys Asp Phe Trp Gly Asp Tyr Leu
    1090                1095                1100

Gln Tyr Asp Lys Pro Ala Leu Ala Gly Gly Gly Ser Gly Gly Gly
1105                1110                1115                1120

Gly Ser Gly Gly Gly Ser Arg Ser Leu Gln Asp Thr Glu Glu Lys
            1125                1130                1135

Ser Arg Ser Phe Ser Ala Ser Gln Ala Asp Pro Leu Ser Asp Pro Asp
            1140                1145                1150

Gln Met Asn Glu Asp
        1155

<210> SEQ ID NO 123
<211> LENGTH: 1153
<212> TYPE: PRT
<213> ORGANISM: Artificial Sequence
<220> FEATURE:
<223> OTHER INFORMATION: BoNT/A-XP6B-GRPP

<400> SEQUENCE: 123

Met Asp Asp Asp Lys Ala Leu Asn Asp Leu Cys Ile Lys Val Asn
 1              5                  10                  15

Asn Trp Asp Leu Phe Phe Ser Pro Ser Glu Asp Asn Phe Thr Asn Asp
            20                  25                  30

Leu Asn Lys Gly Glu Glu Ile Thr Ser Asp Thr Asn Ile Glu Ala Ala
        35                  40                  45

Glu Glu Asn Ile Ser Leu Asp Leu Ile Gln Gln Tyr Tyr Leu Thr Phe
 50                  55                  60

Asn Phe Asp Asn Glu Pro Glu Asn Ile Ser Ile Glu Asn Leu Ser Ser
 65                 70                  75                  80

Asp Ile Ile Gly Gln Leu Glu Leu Met Pro Asn Ile Glu Arg Phe Pro
                85                  90                  95

Asn Gly Lys Lys Tyr Glu Leu Asp Lys Tyr Thr Met Phe His Tyr Leu
            100                 105                 110

Arg Ala Gln Glu Phe Glu His Gly Lys Ser Arg Ile Ala Leu Thr Asn
        115                 120                 125

Ser Val Asn Glu Ala Leu Leu Asn Pro Ser Arg Val Tyr Thr Phe Phe
    130                 135                 140

Ser Ser Asp Tyr Val Lys Lys Val Asn Lys Ala Thr Glu Ala Ala Met
145                 150                 155                 160
```

```
Phe Leu Gly Trp Val Glu Gln Leu Val Tyr Asp Phe Thr Asp Glu Thr
                165                 170                 175

Ser Glu Val Ser Thr Thr Asp Lys Ile Ala Asp Ile Thr Ile Ile Ile
            180                 185                 190

Pro Tyr Ile Gly Pro Ala Leu Asn Ile Gly Asn Met Leu Tyr Lys Asp
        195                 200                 205

Asp Phe Val Gly Ala Leu Ile Phe Ser Gly Ala Val Ile Leu Leu Glu
    210                 215                 220

Phe Ile Pro Glu Ile Ala Ile Pro Val Leu Gly Thr Phe Ala Leu Val
225                 230                 235                 240

Ser Tyr Ile Ala Asn Lys Val Leu Thr Val Gln Thr Ile Asp Asn Ala
                245                 250                 255

Leu Ser Lys Arg Asn Glu Lys Trp Asp Glu Val Tyr Lys Tyr Ile Val
            260                 265                 270

Thr Asn Trp Leu Ala Lys Val Asn Thr Gln Ile Asp Leu Ile Arg Lys
        275                 280                 285

Lys Met Lys Glu Ala Leu Glu Asn Gln Ala Glu Ala Thr Lys Ala Ile
    290                 295                 300

Ile Asn Tyr Gln Tyr Asn Gln Tyr Thr Glu Glu Glu Lys Asn Asn Ile
305                 310                 315                 320

Asn Phe Asn Ile Asp Asp Leu Ser Ser Lys Leu Asn Glu Ser Ile Asn
                325                 330                 335

Lys Ala Met Ile Asn Ile Asn Lys Phe Leu Asn Gln Cys Ser Val Ser
            340                 345                 350

Tyr Leu Met Asn Ser Met Ile Pro Tyr Gly Val Lys Arg Leu Glu Asp
        355                 360                 365

Phe Asp Ala Ser Leu Lys Asp Ala Leu Leu Lys Tyr Ile Tyr Asp Asn
    370                 375                 380

Arg Gly Thr Leu Ile Gly Gln Val Asp Arg Leu Lys Asp Lys Val Asn
385                 390                 395                 400

Asn Thr Leu Ser Thr Asp Ile Pro Phe Gln Leu Ser Lys Tyr Val Asp
                405                 410                 415

Asn Gln Arg Leu Leu Ser Thr Phe Thr Glu Tyr Ile Lys Asn Ile Ile
            420                 425                 430

Asn Thr Ser Ile Leu Asn Leu Arg Tyr Glu Ser Asn His Leu Ile Asp
        435                 440                 445

Leu Ser Arg Tyr Ala Ser Lys Ile Asn Ile Gly Ser Lys Val Asn Phe
    450                 455                 460

Asp Pro Ile Asp Lys Asn Gln Ile Gln Leu Phe Asn Leu Glu Ser Ser
465                 470                 475                 480

Lys Ile Glu Val Ile Leu Lys Asn Ala Ile Val Tyr Asn Ser Met Tyr
                485                 490                 495

Glu Asn Phe Ser Thr Ser Phe Trp Ile Arg Ile Pro Lys Tyr Phe Asn
            500                 505                 510

Ser Ile Ser Leu Asn Asn Glu Tyr Thr Ile Ile Asn Cys Met Glu Asn
        515                 520                 525

Asn Ser Gly Trp Lys Val Ser Leu Asn Tyr Gly Glu Ile Ile Trp Thr
    530                 535                 540

Leu Gln Asp Thr Gln Glu Ile Lys Gln Arg Val Val Phe Lys Tyr Ser
545                 550                 555                 560

Gln Met Ile Asn Ile Ser Asp Tyr Ile Asn Arg Trp Ile Phe Val Thr
                565                 570                 575

Ile Thr Asn Asn Arg Leu Asn Asn Ser Lys Ile Tyr Ile Asn Gly Arg
            580                 585                 590
```

Leu Ile Asp Gln Lys Pro Ile Ser Asn Leu Gly Asn Ile His Ala Ser
            595                 600                 605

Asn Asn Ile Met Phe Lys Leu Asp Gly Cys Arg Asp Thr His Arg Tyr
    610                 615                 620

Ile Trp Ile Lys Tyr Phe Asn Leu Phe Asp Lys Glu Leu Asn Glu Lys
625                 630                 635                 640

Glu Ile Lys Asp Leu Tyr Asp Asn Gln Ser Asn Ser Gly Ile Leu Lys
                645                 650                 655

Asp Phe Trp Gly Asp Tyr Leu Gln Tyr Asp Lys Pro Asp Asp Asp
            660                 665                 670

Lys Pro Phe Val Asn Lys Gln Phe Asn Tyr Lys Asp Pro Val Asn Gly
        675                 680                 685

Val Asp Ile Ala Tyr Ile Lys Ile Pro Asn Ala Gly Gln Met Gln Pro
    690                 695                 700

Val Lys Ala Phe Lys Ile His Asn Lys Ile Trp Val Ile Pro Glu Arg
705                 710                 715                 720

Asp Thr Phe Thr Asn Pro Glu Glu Gly Asp Leu Asn Pro Pro Glu
            725                 730                 735

Ala Lys Gln Val Pro Val Ser Tyr Tyr Asp Ser Thr Tyr Leu Ser Thr
        740                 745                 750

Asp Asn Glu Lys Asp Asn Tyr Leu Lys Gly Val Thr Lys Leu Phe Glu
    755                 760                 765

Arg Ile Tyr Ser Thr Asp Leu Gly Arg Met Leu Leu Thr Ser Ile Val
    770                 775                 780

Arg Gly Ile Pro Phe Trp Gly Gly Ser Thr Ile Asp Thr Glu Leu Lys
785                 790                 795                 800

Val Ile Asp Thr Asn Cys Ile Asn Val Ile Gln Pro Asp Gly Ser Tyr
            805                 810                 815

Arg Ser Glu Glu Leu Asn Leu Val Ile Ile Gly Pro Ser Ala Asp Ile
        820                 825                 830

Ile Gln Phe Glu Cys Lys Ser Phe Gly His Glu Val Leu Asn Leu Thr
    835                 840                 845

Arg Asn Gly Tyr Gly Ser Thr Gln Tyr Ile Arg Phe Ser Pro Asp Phe
    850                 855                 860

Thr Phe Gly Phe Glu Glu Ser Leu Glu Val Asp Thr Asn Pro Leu Leu
865                 870                 875                 880

Gly Ala Gly Lys Phe Ala Thr Asp Pro Ala Val Thr Leu Ala His Glu
            885                 890                 895

Leu Ile His Ala Gly His Arg Leu Tyr Gly Ile Ala Ile Asn Pro Asn
        900                 905                 910

Arg Val Phe Lys Val Asn Thr Asn Ala Tyr Tyr Glu Met Ser Gly Leu
    915                 920                 925

Glu Val Ser Phe Glu Glu Leu Arg Thr Phe Gly Gly His Asp Ala Lys
    930                 935                 940

Phe Ile Asp Ser Leu Gln Glu Asn Glu Phe Arg Leu Tyr Tyr Tyr Asn
945                 950                 955                 960

Lys Phe Lys Asp Ile Ala Ser Thr Leu Asn Lys Ala Lys Ser Ile Val
            965                 970                 975

Gly Thr Thr Ala Ser Leu Gln Tyr Met Lys Asn Val Phe Lys Glu Lys
        980                 985                 990

Tyr Leu Leu Ser Glu Asp Thr Ser Gly Lys Phe Ser Val Asp Lys Leu
    995                 1000                1005

Lys Phe Asp Lys Leu Tyr Lys Met Leu Thr Glu Ile Tyr Thr Glu Asp

-continued

```
              1010                1015                1020
Asn Phe Val Lys Phe Phe Lys Val Leu Asn Arg Lys Thr Tyr Leu Asn
1025                1030                1035                1040

Phe Asp Lys Ala Val Phe Lys Ile Asn Ile Val Pro Lys Val Asn Tyr
                1045                1050                1055

Thr Ile Tyr Asp Gly Phe Asn Leu Arg Asn Thr Asn Leu Ala Ala Asn
                1060                1065                1070

Phe Asn Gly Gln Asn Thr Glu Ile Asn Asn Met Asn Phe Thr Lys Leu
            1075                1080                1085

Lys Asn Phe Thr Gly Leu Phe Glu Phe Tyr Lys Leu Leu Cys Val Arg
        1090                1095                1100

Gly Ile Ile Thr Gly Gly Gly Ser Gly Gly Gly Gly Ser Gly Gly
1105                1110                1115                1120

Gly Gly Ser Arg Ser Leu Gln Asp Thr Glu Glu Lys Ser Arg Ser Phe
                1125                1130                1135

Ser Ala Ser Gln Ala Asp Pro Leu Ser Asp Pro Asp Gln Met Asn Glu
            1140                1145                1150

Asp
```

What is claimed is:

1. A modified Clostridial toxin comprising:
   a) a Clostridial toxin enzymatic domain capable of executing an enzymatic target modification step of a Clostridial toxin intoxication process;
   b) a Clostridial toxin translocation domain capable of executing a translocation step of a Clostridial toxin intoxication process;
   c) a targeting domain comprising a polypeptide consisting of a neuroregulatory cytokine capable of executing a cell binding step of a Clostridial toxin intoxication process, wherein the neuroregulatory cytokine is glycophorin-A (GPA), onostatin M, cardiotrophin-1 (CT-1), cardiotrophin-like cytokine (CLC), a neuroleukin, or Vascular Endothelial Growth Factor (VEGF); and
   d) a protease cleavage site,
   wherein cleavage of the protease cleavage site converts the single-chain form of the modified Clostridial toxin into the di-chain form.

2. The modified Clostridial toxin according to claim 1, wherein the modified Clostridial toxin comprises, in a linear amino-to-carboxyl single polypeptide order, the Clostridial toxin enzymatic domain, the protease cleavage site, the Clostridial toxin translocation domain and the targeting domain.

3. The modified Clostridial toxin according to claim 1, wherein the modified Clostridial toxin comprises, in a linear amino-to-carboxyl single polypeptide order, the Clostridial toxin enzymatic domain, the protease cleavage site, the targeting domain and the Clostridial toxin translocation domain.

4. The modified Clostridial toxin according to claim 1, wherein the modified Clostridial toxin comprises, in a linear amino-to-carboxyl single polypeptide order, the targeting domain, the Clostridial toxin translocation domain, the protease cleavage site and the Clostridial toxin enzymatic domain.

5. The modified Clostridial toxin according to claim 1, wherein the modified Clostridial toxin comprises, in a linear amino-to-carboxyl single polypeptide order, the targeting domain, the Clostridial toxin enzymatic domain, the protease cleavage site and the Clostridial toxin translocation domain.

6. The modified Clostridial toxin according to claim 1, wherein the modified Clostridial toxin comprises, in a linear amino-to-carboxyl single polypeptide order, the Clostridial toxin translocation domain, the protease cleavage site, the Clostridial toxin enzymatic domain and the targeting domain.

7. The modified Clostridial toxin according to claim 1, wherein the modified Clostridial toxin comprises, in a linear amino-to-carboxyl single polypeptide order, the Clostridial toxin translocation domain, the protease cleavage site, the targeting domain and the Clostridial toxin enzymatic domain.

8. The modified Clostridial toxin according to claim 1, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.

9. The modified Clostridial toxin according to claim 1, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.

10. The modified Clostridial toxin according to claim 1, wherein the protease cleavage site is an endogenous Clostridial toxin di-chain loop protease cleavage site or an exogenous cleavage site.

11. The modified Clostridial toxin according to claim 10, wherein the endogenous Clostridial toxin di-chain loop protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

12. The modified Clostridial toxin according to claim 10, wherein the exogenous protease cleavage site is selected from the group consisting of an enterokinase cleavage site, a Thrombin cleavage site, a Factor Xa cleavage site, a human rhinovirus 3C protease cleavage site, a tobacco etch virus protease cleavage site, a dipeptidyl aminopeptidase cleavage site, a small ubiquitin-like modifier (SUMO)/ubiquitin-like protein-1(ULP-1) protease cleavage site, and a Clostridial toxin substrate cleavage site.

13. The modified Clostridial toxin according to claim 12, wherein the Clostridial toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site and a TeNT substrate cleavage site.

* * * * *

UNITED STATES PATENT AND TRADEMARK OFFICE
CERTIFICATE OF CORRECTION

| | |
|---|---|
| PATENT NO. | : 8,021,859 B2 |
| APPLICATION NO. | : 12/192934 |
| DATED | : June 15, 2010 |
| INVENTOR(S) | : Lance E. Steward et al. |

It is certified that error appears in the above-identified patent and that said Letters Patent is hereby corrected as shown below:

In column 85, line 34, delete "persephrin" and insert -- persephin --, therefor.

In column 87, line 59, delete "Persephrin." and insert -- Persephin. --, therefor.

In column 87, line 60, delete "Persephrin" and insert -- Persephin --, therefor.

In column 87, line 62, delete "Persephrin" and insert -- Persephin --, therefor.

In column 87, line 64, delete "Persephrin" and insert -- Persephin --, therefor.

In column 88, line 7, delete "Persephrin" and insert -- Persephin --, therefor.

In column 87, line 16, delete "Persephrin" and insert -- Persephin --, therefor.

In column 88, line 20, delete "Persephrin" and insert -- Persephin --, therefor.

In column 88, line 25, delete "Persephrin" and insert -- Persephin --, therefor.

In column 88, line 29, delete "Persephrin" and insert -- Persephin --, therefor.

In column 88, line 33, delete "Persephrin" and insert -- Persephin --, therefor.

In column 88, line 37, delete "Persephrin" and insert -- Persephin --, therefor.

In column 88, line 41, delete "Persephrin" and insert -- Persephin --, therefor.

In column 88, line 45, delete "Persephrin" and insert -- Persephin --, therefor.

In column 88, line 49, delete "Persephrin" and insert -- Persephin --, therefor.

In column 88, line 53, delete "Persephrin" and insert -- Persephin --, therefor.

In column 88, line 57, delete "Persephrin" and insert -- Persephin --, therefor.

In column 88, line 61, delete "Persephrin" and insert -- Persephin --, therefor.

In column 120, line 48, delete "synonomous" and insert -- synonymous --, therefor.

In column 120, line 63, delete "the a" and insert -- the --, therefor.

In column 128, line 29, after "can" insert -- be --.

In column 133, line 51, delete "hemagluttinin" and insert -- hemagglutinin --, therefor.

In column 134, line 51, delete "hemagluttinin" and insert -- hemagglutinin --, therefor.

Signed and Sealed this
Fourteenth Day of February, 2012

David J. Kappos
*Director of the United States Patent and Trademark Office*

CERTIFICATE OF CORRECTION (continued)
U.S. Pat. No. 8,021,859 B2

In column 135, line 3, delete "hemagluttinin" and insert -- hemagglutinin --, therefor.

In column 135, line 24, delete "hemagluttinin" and insert -- hemagglutinin --, therefor.

In column 136, line 24, delete "hemagluttinin" and insert -- hemagglutinin --, therefor.

In column 136, line 43, delete "hemagluttinin" and insert -- hemagglutinin --, therefor.

In column 140, line 38, delete "semaphroring" and insert -- semaphoring --, therefor.

In column 140, line 40, delete "onostatin" and insert -- oncostatin --, therefor.

In column 143, line 50, delete "tranfection," and insert -- transfection, --, therefor.

In column 144, line 39, delete "Greschet al.," and insert -- Gresch et al., --, therefor.

In column 146, line 28, delete "Clonetech," and insert -- Clontech, --, therefor.

In column 146, line 30, delete "Clonetech," and insert -- Clontech, --, therefor.

In column 147, line 34, delete "SPECTRA™" and insert -- SpECTRA™ --, therefor.

In column 147, line 39, delete "Pharmigen," and insert -- Pharmingen, --, therefor.

In column 154, line 59, delete "enterokinse" and insert -- enterokinase --, therefor.

In column 155, line 32, delete "(CP5Aplied" and insert -- (CP5 Applied --, therefor.

In column 155, line 34, delete "(CP5Aplied" and insert -- (CP5 Applied --, therefor.

In column 158, line 10, delete "enterokinse" and insert -- enterokinase --, therefor.

In column 168, line 12, delete "$C^{2+}$" and insert -- $Co^{2+}$ --, therefor.

In column 170, line 8, delete "monolaureate," and insert -- monolaurate, --, therefor.

In column 170, line 12, delete "monolaureate," and insert -- monolaurate, --, therefor.

In column 329-330, line 32, below "<220> FEATURE:"

<221> NAME/KEY: SITE insert --
<222> LOCATION: (1) . . . (6) --.

In column 331-332, line 41, delete "hemagluttinin" and insert -- hemagglutinin --, therefor.

In column 369, line 39, in claim 1, delete "onostatin" and insert -- oncostatin --, therefor.